(12) United States Patent
Muramatsu et al.

(10) Patent No.: US 9,340,793 B2
(45) Date of Patent: May 17, 2016

(54) RECOMBINANT YEAST AND SUBSTANCE PRODUCTION METHOD USING THE SAME

(75) Inventors: Masayoshi Muramatsu, Miyoshi (JP); Masakazu Ito, Toyota (JP)

(73) Assignee: TOYOTA JIDOSHA KABUSHIKI KAISHA, Aichi (JP)

( * ) Notice: Subject to any disclaimer, the term of this patent is extended or adjusted under 35 U.S.C. 154(b) by 0 days.

(21) Appl. No.: 13/979,537

(22) PCT Filed: Jan. 20, 2011

(86) PCT No.: PCT/JP2011/050974
§ 371 (c)(1),
(2), (4) Date: Jul. 12, 2013

(87) PCT Pub. No.: WO2012/098662
PCT Pub. Date: Jul. 26, 2012

(65) Prior Publication Data
US 2013/0295616 A1  Nov. 7, 2013

(51) Int. Cl.
| | |
|---|---|
| *C12N 1/12* | (2006.01) |
| *C12N 15/00* | (2006.01) |
| *C12N 1/20* | (2006.01) |
| *C12N 9/04* | (2006.01) |
| *C12N 9/88* | (2006.01) |
| *C12N 9/90* | (2006.01) |
| *C12P 7/00* | (2006.01) |
| *C12P 7/54* | (2006.01) |
| *C12P 7/04* | (2006.01) |
| *C07H 21/04* | (2006.01) |
| *C12N 15/81* | (2006.01) |
| *C12P 7/02* | (2006.01) |
| *C12N 9/12* | (2006.01) |
| *C12N 15/52* | (2006.01) |
| *C12P 19/32* | (2006.01) |
| *C12P 7/62* | (2006.01) |

(52) U.S. Cl.
CPC .............. *C12N 15/81* (2013.01); *C12N 9/0006* (2013.01); *C12N 9/1205* (2013.01); *C12N 9/88* (2013.01); *C12N 9/90* (2013.01); *C12N 15/52* (2013.01); *C12P 7/02* (2013.01); *C12P 7/04* (2013.01); *C12P 7/54* (2013.01); *C12P 7/62* (2013.01); *C12P 19/32* (2013.01); *Y02P 20/52* (2015.11)

(58) Field of Classification Search
CPC ......... C12N 9/88; C12N 15/80; C12N 9/0006; C12N 9/90; C12N 15/81; C12P 7/02; C12P 7/04; C12P 7/54
See application file for complete search history.

(56) References Cited

U.S. PATENT DOCUMENTS

| | | | |
|---|---|---|---|
| 6,033,883 A | 3/2000 | Barr et al. | |
| 7,785,858 B2 * | 8/2010 | Kozlov et al. | 435/243 |
| 2006/0040365 A1 * | 2/2006 | Kozlov et al. | 435/106 |
| 2006/0148052 A1 | 7/2006 | Barr et al. | |
| 2008/0293125 A1 | 11/2008 | Subbian et al. | |
| 2009/0087887 A1 | 4/2009 | Kataoka et al. | |
| 2010/0311136 A1 | 12/2010 | Yoneda et al. | |

FOREIGN PATENT DOCUMENTS

| | | |
|---|---|---|
| CN | 101090964 A | 12/2007 |
| JP | 63-287491 A | 11/1988 |
| JP | 2003-180371 A | 7/2003 |
| JP | 2008-022865 A | 2/2008 |
| JP | 2008-509661 A | 4/2008 |
| JP | 2009-060791 A | 3/2009 |
| JP | 2010-279290 A | 12/2010 |
| WO | 03/078643 A1 | 9/2003 |
| WO | 2006/016705 A1 | 2/2006 |
| WO | 2008/045555 A3 | 4/2008 |
| WO | 2008/137406 A1 | 11/2008 |

OTHER PUBLICATIONS

Sonderegger et al., Metabolic Engineering of a Phosphoketolase Pathway for Pentose Catabolism in *Saccharomyces cerevisiae*. Applied and environmental microbiology, p. 2892-2897, 70: 5, 2004.*
Meile et al. Characterization of the D-xylulose 5-phosphate/D-fructose 6-phosphate phosphoketolase gene (xfp) from Bifidobacterium lactis. J. Bacteriol. 183:2929-2936(2001).*
Matsufuji et al. 1. Acetaldehyde tolerance in *Saccharomyces cerevisiae* involves the pentose phosphate pathway and oleic acid biosynthesis. Yeast 2008; 25; 825-833.*
Stewart et al Biotechnology and Genetic Engineering Reviews, 14:67-143, 1997.*
Chinese Office Action 201180065501.2 dated Mar. 3, 2014.
Document 2 cited in Chinese Office Action of Mar. 3, 2014.
Document 3 cited in Chinese Office Action of Mar. 3, 2014.
Chinese Office Action 201180065501.2 dated Mar. 3, 2014.
Meile et al., Accession No. Q9AEM9.1, "Full=Xylulose-5-phosphate/fructose-6-phosphate phosphoketolase," Database NCBI/GenBank (online), 2014, retrieved from http://www.ncbi.nlm.nih.gov/protein/Q9AEM9.1?report=gpwithparts&log$=seqview on Oct. 29, 2014, 2 pages total.
Ratledge, et al., "Pathways of Glucose Metabolism in Candida 107, a Lipid-accumulating Year", Journal of General Microbiology, Oct. 1, 1977, pp. 391-395, XP055090336, England.

(Continued)

*Primary Examiner* — Yong Pak
(74) *Attorney, Agent, or Firm* — Sughrue Mion, PLLC

(57) ABSTRACT

Substance productivity is improved by introducing a metabolic pathway for synthesis of acetyl-CoA or acetic acid from glucose-6-phosphate into yeast. Acetic acid productivity, acetyl-CoA productivity, and productivity of a substance made from acetyl-CoA-derived are improved by attenuating genes involved in the glycolytic system of yeast and introducing a phosphoketolase gene into the yeast.

3 Claims, 14 Drawing Sheets

(56) References Cited

OTHER PUBLICATIONS

Sonderegger, et al., "Metabolic Engineering of a Phosphoketolase Pathway for Pentose Catabolism in *Saccharomyces cerevisiae*", Applied and Environmental Microbiology, American Society for Microbiology, US, vol. 70, No. 5, May 1, 2004, pp. 2892-2897, XP002603126.

Whitworth, et al., "Phosphoketolase in Rhodotorula graminis and Other Yeasts", Journal of General Microbiology, vol. 102, No. 2, Oct. 1, 1977, pp. 397-401, XP055090321.

Chikara Oto et al., "Kumikae Kobo ni yoru Prenyl Alcohol Seisan", Japan Society for Bioscience, Biotechnolgy, and Agrochemistry 2003 Nendo Taikai Koen Yoshishu, Mar. 5, 2003, p. 154, 3A05a02.

Masayoshi Muramatsu et al., "Microbial production on prenyl alcohols", Dai 47 Kai Koryo Terpene Oyobi Seiyu Kagaku ni Kansuru Toronkai, Oct. 30, 2003, pp. 145-147.

T. Hannai et al., "Engineered Synthetic Pathway for Isopropanol Production in *Escherichia coli*", Applied and Environmental Microbiology, Dec. 2007, pp. 7814-7818, vol. 73, No. 24.

Lourdes L. Bermejo et al., "Expression of Clostridium Acetobutylicum ATCC 824 Genes in *Escherichia coli* for Acetone Production and Acetate Detoxification", Applied and Environmental Microbiology, Mar. 1998, pp. 1079-1085, vol. 65, No. 3.

Myong-Ok Park, "New Pathway for Long-Chain n-Alkane Synthesis via 1-Alcohol in Vibrio Furnissii Ml", Journal of Bacteriology, Feb. 2005, pp. 1426-1429, vol. 187, No. 4.

Emanuel Merdinger et al., "Lipids of Debaryomyces Hansenii", Journal of Bacteriology, Jun. 1965, pp. 1488-1493, vol. 89, No. 6.

James T. Kealey et al., "Production of a Polyketide Natural Product in Nonpolyketide-Producing Prokaryotic and Eukaryotic Hosts", Proc. Natl. Acad. Sci., Jan. 1998, pp. 505-509, vol. 95.

Rosaura Rodicio et al., "Single Point Mutations in Either Gene Encoding the Subunits of the Heterooctameric Yeast Phosphofructokinase Abolish Allosteric Inhibition by ATP", The Journal of Biological Chemistry, Dec. 2000, pp. 40952-40960, vol. 275, No. 52.

\* cited by examiner

```
                              SEQUENCE LISTING

<160> NUMBER OF SEQ ID NOS: 100

<210> SEQ ID NO 1
<211> LENGTH: 825
<212> TYPE: PRT
<213> ORGANISM: Bifidobacterium animalis

<400> SEQUENCE: 1

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270
```

-continued

Glu Ile Cys Asp Ile Lys Ala Ala Gln Thr Asp Met Thr Arg
            275                 280             285

Pro Phe Tyr Pro Met Leu Ile Phe Arg Thr Pro Lys Gly Trp Thr Cys
    290                 295                 300

Pro Lys Phe Ile Asp Gly Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
                340                 345                 350

Asp Gly Ser Ile Lys Glu Asp Val Thr Ala Phe Met Pro Lys Gly Glu
            355                 360                 365

Leu Arg Ile Gly Ala Asn Pro Asn Ala Asn Gly Gly Arg Ile Arg Glu
    370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Val
            420                 425                 430

Phe Gly Pro Asp Glu Thr Ala Ser Asn Arg Leu Asn Ala Thr Tyr Glu
    435                 440                 445

Val Thr Lys Lys Gln Trp Asp Asn Gly Tyr Leu Ser Ala Leu Val Asp
    450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
    515                 520                 525

Arg Lys Pro Ile Ser Ser Val Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
            580                 585                 590

Lys Ser Thr Asn Lys Ile Asn Ala Ile Phe Ala Gly Lys Gln Pro Ala
    595                 600                 605

Ala Thr Trp Ile Thr Leu Asp Glu Val Arg Ala Glu Leu Glu Ala Gly
    610                 615                 620

Ala Ala Glu Trp Lys Trp Ala Ser Ala Lys Ser Asn Asp Glu Val
625                 630                 635                 640

Gln Val Val Leu Ala Ala Gly Asp Val Pro Thr Gln Glu Ile Met
                645                 650                 655

Ala Ala Ser Asp Ala Leu Asn Lys Met Gly Ile Lys Phe Lys Val Val
            660                 665                 670

Asn Val Val Asp Leu Ile Lys Leu Gln Ser Ser Lys Glu Asn Asp Glu
    675                 680                 685

Ala Met Ser Asp Glu Asp Phe Ala Asp Leu Phe Thr Ala Asp Lys Pro

```
            690                 695                 700
Val Leu Phe Ala Tyr His Ser Tyr Ala Gln Asp Val Arg Gly Leu Ile
705                 710                 715                 720

Tyr Asp Arg Pro Asn His Asp Asn Phe Thr Val Val Gly Tyr Lys Glu
                725                 730                 735

Gln Gly Ser Thr Thr Pro Phe Asp Met Val Arg Val Asn Asp Met
            740                 745                 750

Asp Arg Tyr Ala Leu Gln Ala Lys Ala Leu Glu Leu Ile Asp Ala Asp
                755                 760                 765

Lys Tyr Ala Asp Lys Ile Asn Glu Leu Asn Glu Phe Arg Lys Thr Ala
            770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Ser Met Leu Ser Ala
                805                 810                 815

Thr Ala Ala Thr Ala Gly Asp Asn Glu
            820                 825

<210> SEQ ID NO 2
<211> LENGTH: 825
<212> TYPE: PRT
<213> ORGANISM: Bifidobacterium longum

<400> SEQUENCE: 2

Met Thr Ser Pro Val Ile Gly Thr Pro Trp Lys Lys Leu Asn Ala Pro
1               5                   10                  15

Val Ser Glu Glu Ala Leu Glu Gly Val Asp Lys Tyr Trp Arg Val Ala
                20                  25                  30

Asn Tyr Leu Ser Ile Gly Gln Ile Tyr Leu Arg Ser Asn Pro Leu Met
            35                  40                  45

Lys Glu Pro Phe Thr Arg Glu Asp Val Lys His Arg Leu Val Gly His
        50                  55                  60

Trp Gly Thr Thr Pro Gly Leu Asn Phe Leu Ile Gly His Ile Asn Arg
65              70                  75                  80

Phe Ile Ala Asp His Gly Gln Asn Thr Val Ile Met Gly Pro Gly
                85                  90                  95

His Gly Gly Pro Ala Gly Thr Ser Gln Ser Tyr Leu Asp Gly Thr Tyr
                100                 105                 110

Thr Glu Thr Phe Pro Lys Ile Thr Lys Asp Glu Ala Gly Leu Gln Lys
            115                 120                 125

Phe Phe Arg Gln Phe Ser Tyr Pro Gly Gly Ile Pro Ser His Phe Ala
130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Ala Ile Val Gly Asp Gly Glu Ala Glu Thr Gly Pro Leu Ala Thr
                180                 185                 190

Gly Trp Gln Ser Asn Lys Leu Val Asn Pro Arg Thr Asp Gly Ile Val
            195                 200                 205

Leu Pro Ile Leu His Leu Asn Gly Tyr Lys Ile Ala Asn Pro Thr Ile
        210                 215                 220

Leu Ser Arg Ile Ser Asp Glu Glu Leu His Glu Phe Phe His Gly Met
225                 230                 235                 240
```

```
Gly Tyr Glu Pro Tyr Glu Phe Val Ala Gly Phe Asp Asp Glu Asp His
                245                 250                 255

Met Ser Ile His Arg Arg Phe Ala Glu Leu Trp Glu Thr Ile Trp Asp
            260                 265                 270

Glu Ile Cys Asp Ile Lys Ala Thr Ala Gln Thr Asp Asn Val His Arg
        275                 280                 285

Pro Phe Tyr Pro Met Leu Ile Phe Arg Thr Pro Lys Gly Trp Thr Cys
    290                 295                 300

Pro Lys Tyr Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Ala
            340                 345                 350

Asn Gly Ala Val Lys Asp Val Leu Ala Phe Met Pro Lys Gly Glu
        355                 360                 365

Leu Arg Ile Gly Ala Asn Pro Asn Ala Asn Gly Val Ile Arg Asn
    370                 375                 380

Asp Leu Lys Leu Pro Asn Leu Glu Asp Tyr Glu Val Lys Glu Val Ala
385                 390                 395                 400

Glu Tyr Gly His Gly Trp Gly Gln Leu Glu Ala Thr Arg Thr Leu Gly
                405                 410                 415

Ala Tyr Thr Arg Asp Ile Ile Lys Asn Asn Pro Arg Asp Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Ala Gly Tyr Ile Ser Asp Glu Val Asp
    450                 455                 460

Glu His Met His Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ala Ser Met Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Cys Phe His Asn Asp His Val Ile Gly Ile Tyr
                565                 570                 575

Phe Ala Thr Asp Ala Asn Met Leu Leu Ala Ile Ala Glu Lys Cys Tyr
            580                 585                 590

Lys Ser Thr Asn Lys Ile Asn Ala Ile Ile Ala Gly Lys Gln Pro Ala
        595                 600                 605

Ala Thr Trp Leu Thr Leu Asp Glu Ala Arg Ala Glu Leu Glu Lys Gly
    610                 615                 620

Ala Ala Ala Trp Asp Trp Ala Ser Thr Ala Lys Asn Asn Asp Glu Ala
625                 630                 635                 640

Glu Val Val Leu Ala Ala Ala Gly Asp Val Pro Thr Gln Glu Ile Met
                645                 650                 655

Ala Ala Ser Asp Lys Leu Lys Glu Leu Gly Ile Lys Phe Lys Val Val
```

```
                    660                 665                 670
Asn Val Ala Asp Leu Leu Ser Leu Gln Ser Ala Lys Glu Asn Asp Glu
            675                 680                 685

Ala Leu Thr Asp Glu Glu Phe Ala Asp Ile Phe Thr Ala Asp Lys Pro
        690                 695                 700

Val Leu Phe Ala Tyr His Ser Tyr Ala His Asp Val Arg Gly Leu Ile
705                 710                 715                 720

Tyr Asp Arg Pro Asn His Asp Asn Phe Asn Val His Gly Tyr Glu Glu
                725                 730                 735

Glu Gly Ser Thr Thr Thr Pro Tyr Asp Met Val Arg Val Asn Arg Ile
            740                 745                 750

Asp Arg Tyr Glu Leu Thr Ala Glu Ala Leu Arg Met Ile Asp Ala Asp
        755                 760                 765

Lys Tyr Ala Asp Lys Ile Asp Glu Leu Glu Lys Phe Arg Asp Glu Ala
    770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asp Lys Lys Gly Ala Val Thr Ala
                805                 810                 815

Thr Ala Thr Ala Gly Asp Asn Glu
            820                 825

<210> SEQ ID NO 3
<211> LENGTH: 825
<212> TYPE: PRT
<213> ORGANISM: Bifidobacterium adolescentis

<400> SEQUENCE: 3

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Met Gly Pro Gly
            85                  90                  95

His Gly Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125

Phe Phe Arg Gln Phe Ser Tyr Pro Gly Gly Ile Pro Ser His Tyr Ala
130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
            165                 170                 175

Pro Ala Ile Val Gly Asp Gly Glu Ala Glu Thr Gly Pro Leu Ala Thr
        180                 185                 190

Gly Trp Gln Ser Asn Lys Leu Ile Asn Pro Arg Thr Asp Gly Ile Val
    195                 200                 205
```

```
Leu Pro Ile Leu His Leu Asn Gly Tyr Lys Ile Ala Asn Pro Thr Ile
210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asn Glu Asp His
            245                 250                 255

Leu Ser Ile His Arg Arg Phe Ala Glu Leu Phe Glu Thr Val Phe Asp
        260                 265                 270

Glu Ile Cys Asp Ile Lys Ala Ala Gln Thr Asp Asp Met Thr Arg
        275                 280                 285

Pro Phe Tyr Pro Met Ile Ile Phe Arg Thr Pro Lys Gly Trp Thr Cys
290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Glu
            340                 345                 350

Asn Gly Ala Val Lys Pro Glu Val Thr Ala Phe Met Pro Thr Gly Glu
            355                 360                 365

Leu Arg Ile Gly Glu Asn Pro Asn Ala Asn Gly Gly Arg Ile Arg Glu
370                 375                 380

Glu Leu Lys Leu Pro Lys Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Asp Ser Phe Arg Ile
                420                 425                 430

Phe Gly Pro Asp Glu Thr Ala Ser Asn Arg Leu Gln Ala Ala Tyr Asp
        435                 440                 445

Val Thr Asn Lys Gln Trp Asp Ala Gly Tyr Leu Ser Ala Gln Val Asp
        450                 455                 460

Glu His Met Ala Val Thr Gly Gln Val Thr Glu Gln Leu Ser Glu His
465                 470                 475                 480

Gln Met Glu Gly Phe Leu Glu Gly Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Met Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
            565                 570                 575

Phe Pro Val Asp Ser Asn Met Leu Leu Ala Val Ala Glu Lys Cys Tyr
        580                 585                 590

Lys Ser Thr Asn Lys Ile Asn Ala Ile Ile Ala Gly Lys Gln Pro Ala
        595                 600                 605

Ala Thr Trp Leu Thr Leu Asp Glu Ala Arg Ala Glu Leu Glu Lys Gly
610                 615                 620

Ala Ala Glu Trp Lys Trp Ala Ser Asn Val Lys Ser Asn Asp Glu Ala
```

```
            625                 630                 635                 640
    Gln Ile Val Leu Ala Ala Thr Gly Asp Val Pro Thr Gln Glu Ile Met
                        645                 650                 655

Ala Ala Ala Asp Lys Leu Asp Ala Met Gly Ile Lys Phe Lys Val Val
                        660                 665                 670

Asn Val Val Asp Leu Val Lys Leu Gln Ser Ala Lys Glu Asn Asn Glu
                        675                 680                 685

Ala Leu Ser Asp Glu Glu Phe Ala Glu Leu Phe Thr Glu Asp Lys Pro
                        690                 695                 700

Val Leu Phe Ala Tyr His Ser Tyr Ala Arg Asp Val Arg Gly Leu Ile
    705                 710                 715                 720

Tyr Asp Arg Pro Asn His Asp Asn Phe Asn Val His Gly Tyr Glu Glu
                        725                 730                 735

Gln Gly Ser Thr Thr Thr Pro Tyr Asp Met Val Arg Val Asn Asn Ile
                        740                 745                 750

Asp Arg Tyr Glu Leu Gln Ala Glu Ala Leu Arg Met Ile Asp Ala Asp
                        755                 760                 765

Lys Tyr Ala Asp Lys Ile Asn Glu Leu Glu Ala Phe Arg Gln Glu Ala
                        770                 775                 780

Phe Gln Phe Ala Val Asp Asn Gly Tyr Asp His Pro Asp Tyr Thr Asp
    785                 790                 795                 800

Trp Val Tyr Ser Gly Val Asn Thr Asn Lys Gln Gly Ala Ile Ser Ala
                        805                 810                 815

Thr Ala Thr Ala Gly Asp Asn Glu
                        820                 825

<210> SEQ ID NO 4
<211> LENGTH: 825
<212> TYPE: PRT
<213> ORGANISM: Bifidobacterium pullorum

<400> SEQUENCE: 4

Met Thr Ser Pro Val Ile Gly Thr Pro Trp Lys Lys Leu Asp Ala Pro
1               5                   10                  15

Val Ser Glu Glu Ala Leu Glu Gly Val Asp Lys Tyr Trp Arg Ala Ser
                20                  25                  30

Asn Tyr Leu Ser Ile Gly Gln Ile Tyr Leu Arg Ser Asn Pro Leu Met
            35                  40                  45

Lys Glu Pro Phe Thr Arg Asn Asp Val Lys His Arg Leu Val Gly His
        50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Met Gly Pro Gly
                85                  90                  95

His Gly Gly Pro Ala Gly Thr Ser Gln Ser Tyr Leu Asp Gly Thr Tyr
                100                 105                 110

Thr Glu Tyr Phe Pro Asn Ile Thr Lys Asp Glu Ala Gly Leu Gln Lys
            115                 120                 125

Phe Phe Arg Gln Phe Ser Tyr Pro Gly Gly Ile Pro Ser His Tyr Ala
        130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175
```

-continued

```
Pro Ala Ile Val Gly Asp Gly Glu Ala Glu Thr Gly Pro Leu Ala Thr
            180                 185                 190
Gly Trp Gln Ser Asn Lys Leu Ile Asn Pro Arg Thr Asp Gly Ile Val
        195                 200                 205
Leu Pro Ile Leu His Leu Asn Gly Tyr Lys Ile Ala Asn Pro Thr Ile
    210                 215                 220
Leu Ala Arg Ile Ser Asp Glu Glu Leu His Glu Phe Phe His Gly Met
225                 230                 235                 240
Gly Tyr Gln Pro Tyr Glu Phe Val Ala Gly Phe Asp Glu Asp His
            245                 250                 255
Met Ser Ile His Arg Arg Phe Ala Asp Leu Phe Glu Thr Val Phe Asp
        260                 265                 270
Glu Ile Cys Asp Ile Lys Ala Ala Gln Thr Asp Asp Met Thr Arg
    275                 280                 285
Pro Phe Tyr Pro Met Ile Ile Phe Arg Thr Pro Lys Gly Trp Thr Cys
290                 295                 300
Pro Lys Tyr Ile Asp Gly Lys Lys Thr Glu Gly Ser Trp Arg Ser His
305                 310                 315                 320
Gln Val Pro Leu Ala Ser Ala Arg Asp Thr Glu Glu His Phe Gln Val
            325                 330                 335
Leu Lys Asn Trp Leu Glu Ser Tyr Lys Pro Glu Glu Leu Phe Asp Glu
        340                 345                 350
Asn Gly Ala Val Lys Pro Glu Val Thr Ala Phe Met Pro Thr Gly Glu
    355                 360                 365
Leu Arg Ile Gly Glu Asn Pro Asn Ala Asn Gly Arg Ile Arg Glu
370                 375                 380
Asp Leu Val Leu Pro Leu Asp Asn Tyr Glu Val Lys Glu Val Ala
385                 390                 395                 400
Lys Phe Gly His Gly Trp Gln Leu Glu Ala Thr Arg Arg Leu Gly
            405                 410                 415
Val Tyr Thr Arg Asp Ile Ile Lys Leu Asn Pro Asp Ser Phe Arg Ile
        420                 425                 430
Phe Gly Pro Asp Glu Thr Ala Ser Asn Arg Leu Gln Ala Ala Tyr Glu
    435                 440                 445
Val Thr Asn Lys Gln Trp Asp Ala Gly Tyr Leu Ser Glu Leu Thr Asp
450                 455                 460
Glu His Met Ala Val Thr Gly Gln Val Thr Glu Gln Leu Ser Glu His
465                 470                 475                 480
Gln Met Glu Gly Phe Ile Glu Gly Tyr Leu Leu Thr Gly Arg His Gly
            485                 490                 495
Ile Trp Ser Ser Tyr Glu Ser Phe Val His Val Ile Asp Ser Met Leu
        500                 505                 510
Asn Gln His Ala Lys Trp Leu Glu Ala Thr Val Arg Glu Ile Pro Trp
    515                 520                 525
Arg Lys Pro Ile Ser Ser Met Asn Leu Leu Val Ser Ser His Val Trp
530                 535                 540
Arg Gln Asp His Asn Gly Phe Ser His Gln Asp Pro Gly Val Thr Ser
545                 550                 555                 560
Val Leu Leu Asn Lys Thr Phe Asn Asn Asp His Val Val Asn Ile Tyr
            565                 570                 575
Phe Pro Cys Asp Ser Asn Met Leu Leu Ala Val Ala Glu Lys Cys Tyr
        580                 585                 590
Lys Ser Thr Asn Gln Ile Asn Ala Ile Ile Ala Gly Lys Gln Pro Ala
```

```
                 595                 600                 605
Ala Thr Trp Met Thr Leu Asp Glu Ala Arg Ala Glu Leu Glu Lys Gly
610                 615                 620

Ala Ala Glu Trp Lys Trp Ala Ser Thr Ala Ala Ser Asn Asp Glu Ala
625                 630                 635                 640

Gln Ile Val Leu Ala Cys Ala Gly Asp Val Pro Thr Gln Glu Ile Met
                645                 650                 655

Ala Ala Ala Asp Lys Leu Asn Glu Met Gly Ile Lys Phe Lys Val Val
                660                 665                 670

Asn Val Val Asp Leu Ile Lys Leu Gln Ser Ala Lys Glu Asn Asp Glu
                675                 680                 685

Ala Leu Thr Asp Glu Glu Phe Ala Glu Ile Phe Thr Ala Asp Lys Pro
690                 695                 700

Val Leu Phe Ala Tyr His Ser Tyr Ala His Asp Val Arg Gly Leu Ile
705                 710                 715                 720

Phe Asp Arg Pro Asn His Asp Asn Phe Asn Val His Gly Tyr Lys Glu
                725                 730                 735

Gln Gly Ser Thr Thr Thr Pro Phe Asp Met Val Arg Val Asn Asp Ile
                740                 745                 750

Asp Arg Tyr Glu Leu Val Ala Glu Ala Leu Arg Met Ile Asp Ala Asp
                755                 760                 765

Lys Tyr Ala Asp Lys Ile Asp Glu Leu Glu Ala Phe Arg Thr Glu Ala
                770                 775                 780

Phe Gln Phe Ala Val Asp Asn Gly Tyr Asp His Pro Asp Tyr Thr Asp
785                 790                 795                 800

Trp Val Tyr Ser Asp Val Lys Thr Asp Val Gln Gly Ala Val Thr Ala
                    805                 810                 815

Thr Ala Thr Ala Gly Asp Asn Glu
                820                 825

<210> SEQ ID NO 5
<211> LENGTH: 788
<212> TYPE: PRT
<213> ORGANISM: Lactobacillus plantarum

<400> SEQUENCE: 5

Met Thr Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
                20                  25                  30

Asp Asn Pro Leu Leu Gln Arg Pro Leu Lys Ala Ser Asp Val Lys Val
                35                  40                  45

His Pro Ile Gly His Trp Gly Thr Ile Ala Gly Gln Asn Phe Ile Tyr
                50                  55                  60

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
                85                  90                  95

Leu Asp Gly Thr Tyr Thr Asp Ile Tyr Pro Glu Ile Thr Gln Asp Val
                100                 105                 110

Glu Gly Met Gln Lys Leu Phe Lys Gln Phe Ser Phe Pro Gly Gly Val
                115                 120                 125

Ala Ser His Ala Ala Pro Glu Thr Pro Gly Ser Ile His Glu Gly Gly
                130                 135                 140
```

-continued

Glu Leu Gly Tyr Ser Ile Ser His Gly Val Gly Ala Ile Leu Asp Asn
145                 150                 155                 160

Pro Asp Glu Ile Ala Ala Val Val Gly Asp Gly Glu Ser Glu Thr
            165                 170                 175

Gly Pro Leu Ala Thr Ser Trp Gln Ser Thr Lys Phe Ile Asn Pro Ile
                180                 185                 190

Asn Asp Gly Ala Val Leu Pro Ile Leu Asn Leu Asn Gly Phe Lys Ile
            195                 200                 205

Ser Asn Pro Thr Ile Phe Gly Arg Thr Ser Asp Ala Lys Ile Lys Glu
    210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255

Glu Lys Ile Lys Ala Ile Gln Lys His Ala Arg Glu Asn Asn Asp Ala
            260                 265                 270

Thr Leu Pro Val Trp Pro Met Ile Val Phe Arg Ala Pro Lys Gly Trp
        275                 280                 285

Thr Gly Pro Lys Ser Trp Asp Gly Asp Lys Ile Glu Gly Ser Phe Arg
    290                 295                 300

Ala His Gln Ile Pro Ile Pro Val Asp Gln Asn Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Ile Lys Glu Ile Ile Pro Thr
            340                 345                 350

Gly Asp Ser Arg Met Ala Ala Asn Pro Ile Thr Asn Gly Gly Val Asp
        355                 360                 365

Pro Lys Ala Leu Asn Leu Pro Asn Phe Arg Asp Tyr Ala Val Asp Thr
    370                 375                 380

Ser Lys Glu Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
        435                 440                 445

Glu Ala Pro Ala Gly Arg Val Leu Asp Ala Gln Leu Ser Glu His Gln
    450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
            500                 505                 510

Lys Tyr Pro Ser Leu Asn Ile Ile Ala Ala Ser Thr Val Phe Gln Gln
        515                 520                 525

Asp His Asn Gly Tyr Thr His Gln Asp Pro Gly Ala Leu Thr His Leu
    530                 535                 540

Ala Glu Lys Lys Pro Glu Tyr Ile Arg Glu Tyr Leu Pro Ala Asp Ala
545                 550                 555                 560

Asn Thr Leu Leu Ala Val Gly Asp Val Ile Phe Arg Ser Gln Glu Lys

```
                    565                 570                 575
Ile Asn Tyr Val Val Thr Ser Lys His Pro Arg Gln Gln Trp Phe Ser
            580                 585                 590

Ile Glu Glu Ala Lys Gln Leu Val Asp Asn Gly Leu Gly Ile Ile Asp
            595                 600                 605

Trp Ala Ser Thr Asp Gln Gly Ser Glu Pro Asp Ile Val Phe Ala Ala
            610                 615                 620

Ala Gly Thr Glu Pro Thr Leu Glu Thr Leu Ala Ala Ile Gln Leu Leu
625                 630                 635                 640

His Asp Ser Phe Pro Glu Met Lys Ile Arg Phe Val Asn Val Val Asp
                    645                 650                 655

Ile Leu Lys Leu Arg Ser Pro Glu Lys Asp Pro Arg Gly Leu Ser Asp
            660                 665                 670

Ala Glu Phe Asp His Tyr Phe Thr Lys Asp Lys Pro Val Val Phe Ala
            675                 680                 685

Phe His Gly Tyr Glu Asp Leu Val Arg Asp Ile Phe Phe Asp Arg His
            690                 695                 700

Asn His Asn Leu Tyr Val His Gly Tyr Arg Glu Asn Gly Asp Ile Thr
705                 710                 715                 720

Thr Pro Phe Asp Val Arg Val Met Asn Gln Met Asp Arg Phe Asp Leu
                    725                 730                 735

Ala Lys Ser Ala Ile Ala Ala Gln Pro Ala Met Glu Asn Thr Gly Ala
            740                 745                 750

Ala Phe Val Gln Ser Met Asp Asn Met Leu Ala Lys His Asn Ala Tyr
            755                 760                 765

Ile Arg Asp Ala Gly Thr Asp Leu Pro Glu Val Asn Asp Trp Gln Trp
            770                 775                 780

Lys Gly Leu Lys
785

<210> SEQ ID NO 6
<211> LENGTH: 803
<212> TYPE: PRT
<213> ORGANISM: Lactobacillus plantarum

<400> SEQUENCE: 6

Met Gln Arg Ser Cys Lys Ile Met Ser Glu Ala Ile Lys Ser Lys Thr
1               5                   10                  15

Val Asp Tyr Ser Ser Asp Glu Tyr Leu Lys Arg Val Asp Glu Tyr Trp
            20                  25                  30

Arg Ala Ala Asn Tyr Ile Ser Val Gly Gln Leu Tyr Leu Leu Asn Asn
            35                  40                  45

Pro Leu Leu Arg Glu Pro Leu Lys Ala Thr Asp Val Lys Val His Pro
50                  55                  60

Ile Gly His Trp Gly Thr Ile Ala Gly Gln Asn Phe Ile Tyr Ala His
65                  70                  75                  80

Leu Asn Arg Ala Ile Asn Lys Tyr Gly Leu Asn Met Phe Tyr Ile Glu
                    85                  90                  95

Gly Pro Gly His Gly Gly Gln Val Met Val Ser Asn Ser Tyr Leu Asp
            100                 105                 110

Gly Thr Tyr Thr Glu Thr Tyr Pro Lys Ile Thr Gln Asp Lys Ala Gly
            115                 120                 125

Met Lys Arg Leu Phe Lys Gln Phe Ser Phe Pro Gly Gly Val Ala Ser
            130                 135                 140
```

-continued

His Ala Asp Pro Lys Thr Pro Gly Ser Ile His Glu Gly Gly Glu Leu
145                 150                 155                 160

Gly Tyr Ser Ile Leu His Gly Ala Gly Ala Val Leu Asp Asn Pro Gly
            165                 170                 175

Leu Ile Ala Ala Thr Val Val Gly Asp Gly Glu Ser Glu Thr Gly Pro
        180                 185                 190

Leu Ala Thr Ser Trp Gln Val Asn Lys Phe Leu Asn Pro Ile Thr Asp
    195                 200                 205

Gly Thr Val Leu Pro Ile Leu Asn Leu Asn Gly Phe Lys Ile Ser Asn
210                 215                 220

Pro Thr Val Leu Ser Arg Glu Ser His Glu Glu Leu Glu Asp Tyr Phe
225                 230                 235                 240

Lys Gly Leu Gly Trp Asp Pro His Phe Val Glu Gly Thr Asp Pro Ala
                245                 250                 255

Lys Met His Lys Ile Met Ala Glu Glu Leu Asp Lys Val Ile Glu Glu
            260                 265                 270

Ile His Ala Ile Arg Lys Asn Ala Lys Asp Asn Asn Asp Glu Ser Arg
        275                 280                 285

Pro Lys Trp Pro Met Ile Val Phe Arg Ala Pro Lys Gly Trp Thr Gly
290                 295                 300

Pro Lys Ser Trp Asp Gly Glu Pro Ile Glu Gly Ser Phe Arg Ala His
305                 310                 315                 320

Gln Ile Pro Ile Pro Val Asp Arg Asn His Met Glu His Ala Asp Lys
                325                 330                 335

Leu Val Asp Trp Leu Lys Ser Tyr Lys Pro Glu Glu Leu Phe Asp Glu
            340                 345                 350

Asn Gly Thr Leu Lys Pro Glu Ile Ala Ala Ile Ile Pro Glu Gly Gln
        355                 360                 365

Ala Arg Met Ala Ala Asn Pro Val Thr Asn Gly Gly Lys Leu Thr Lys
    370                 375                 380

Asp Leu Ile Thr Pro Asn Ile Asp Asp Tyr Ala Leu Asp Asn Lys Ser
385                 390                 395                 400

His Gly Lys Glu Asp Gly Ser Asp Met Thr Glu Leu Gly Lys Tyr Ile
                405                 410                 415

Arg Asp Leu Ile Glu Leu Asn Lys Asp Asn Lys Asn Phe Arg Gly Trp
            420                 425                 430

Gly Pro Asp Glu Thr Leu Ser Asn Lys Leu Gly Ala Ala Phe Glu Asp
        435                 440                 445

Thr Lys Arg Gln Trp Met Glu Pro Ile His Glu Pro Asn Asp Ala Leu
    450                 455                 460

Leu Ala Pro Gln Gly Arg Ile Ile Asp Ser Met Leu Ser Glu His Met
465                 470                 475                 480

Asp Glu Gly Met Leu Glu Ala Tyr Asn Leu Thr Gly Arg Tyr Gly Phe
                485                 490                 495

Phe Ala Ser Tyr Glu Ser Phe Leu Arg Val Val Asp Ser Met Leu Thr
            500                 505                 510

Gln His Phe Lys Trp Leu Arg Asn Ser His Glu Glu Thr Pro Trp Arg
        515                 520                 525

Ala Asp Val Pro Ser Leu Asn Val Ile Ala Ser Ser Thr Ala Phe Gln
    530                 535                 540

Gln Asp His Asn Gly Tyr Ser His Gln Asp Pro Gly Ile Ile Ser His
545                 550                 555                 560

Leu Ala Glu Lys Lys Thr Glu Tyr Val Arg Ala Tyr Leu Pro Gly Asp

```
                    565                 570                 575

Ala Asn Thr Leu Ile Ala Thr Phe Asp Lys Ala Ile Gln Ser Lys Gln
            580                 585                 590

Leu Ile Asn Leu Ile Ile Ala Ser Lys His Pro Arg Pro Gln Trp Phe
            595                 600                 605

Thr Met Asp Glu Ala Lys Arg Leu Val Arg Asp Gly Leu Gly Val Val
            610                 615                 620

Asp Trp Ala Ser Thr Asp His Gly Glu Pro Asp Val Val Phe Ala
625                 630                 635                 640

Thr Ala Gly Ser Glu Pro Thr Thr Glu Ser Leu Ala Ala Val Ser Ile
            645                 650                 655

Leu His Ala Arg Phe Pro Glu Met Lys Ile Arg Phe Ile Asn Val Val
            660                 665                 670

Asp Leu Leu Lys Leu Lys Lys Asp Asp Pro Arg Gly Leu Ser Asp Ala
            675                 680                 685

Glu Phe Asp Ala Phe Phe Thr Lys Asp Lys Pro Val Ile Phe Ala Tyr
            690                 695                 700

His Ala Tyr Asp Asp Leu Val Lys Thr Ile Phe Phe Asp Arg His Asn
705                 710                 715                 720

His Asn Leu His Val His Gly Tyr Arg Glu Glu Gly Asp Ile Thr Thr
                    725                 730                 735

Pro Phe Asp Met Arg Val Arg Asn Glu Leu Asp Arg Phe His Leu Val
            740                 745                 750

Lys Ala Ala Leu Leu Ala Thr Pro Ala Tyr Ala Glu Lys Gly Ala His
            755                 760                 765

Val Ile Gln Glu Met Asn Ser Ile Leu Asp Lys His His Asp Tyr Ile
            770                 775                 780

Arg Ala Glu Gly Thr Asp Ile Pro Glu Val Glu Asn Trp Lys Trp Thr
785                 790                 795                 800

Ala Leu Lys

<210> SEQ ID NO 7
<211> LENGTH: 788
<212> TYPE: PRT
<213> ORGANISM: Lactobacillus pentosus

<400> SEQUENCE: 7

Met Ser Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
            35                  40                  45

His Pro Ile Gly His Trp Gly Thr Ile Ala Gly Gln Asn Phe Ile Tyr
        50                  55                  60

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
            85                  90                  95

Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
            115                 120                 125

Ala Ser His Ala Ala Pro Glu Thr Pro Gly Ser Ile His Glu Gly Gly
```

```
            130             135             140
Glu Leu Gly Tyr Ser Ile Ser His Gly Val Gly Ala Ile Leu Asp Asn
145                 150                 155                 160

Pro Asp Glu Ile Ala Ala Val Val Gly Asp Gly Glu Ser Glu Thr
                165                 170                 175

Gly Pro Leu Ala Thr Ser Trp Gln Ser Thr Lys Phe Ile Asn Pro Ile
                180                 185                 190

Asn Asp Gly Ala Val Leu Pro Ile Leu Asn Leu Asn Gly Phe Lys Ile
            195                 200                 205

Ser Asn Pro Thr Ile Phe Gly Arg Thr Ser Asp Glu Lys Ile Lys Gln
210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255

Glu Lys Ile Lys Ala Ile Gln Lys Asn Ala Arg Glu Asn Asp Asp Ala
                260                 265                 270

Thr Leu Pro Val Trp Pro Met Ile Val Phe Arg Ala Pro Lys Gly Trp
            275                 280                 285

Thr Gly Pro Lys Ser Trp Asp Gly Asp Lys Ile Glu Gly Ser Phe Arg
            290                 295                 300

Ala His Gln Ile Pro Ile Pro Val Asp Gln Thr Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Asp Ile Lys Glu Ile Ile Pro Thr
                340                 345                 350

Gly Asp Ala Arg Met Ala Ala Asn Pro Ile Thr Asn Gly Gly Val Asp
            355                 360                 365

Pro Lys Ala Leu Asn Leu Pro Asn Phe Arg Asp Tyr Ala Val Asp Thr
370                 375                 380

Ser Lys His Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Arg Leu Tyr Gly Val Phe Glu Thr
                420                 425                 430

Thr Asn Arg Gln Trp Met Glu Asp Ile His Pro Asp Ser Asp Gln Tyr
            435                 440                 445

Glu Ala Pro Ala Gly Arg Val Leu Asp Ala Gln Leu Ser Glu His Gln
            450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
                500                 505                 510

Lys Tyr Pro Ser Leu Asn Ile Ile Ala Ala Ser Thr Val Phe Gln Gln
            515                 520                 525

Asp His Asn Gly Tyr Thr His Gln Asp Pro Gly Ala Leu Thr His Leu
            530                 535                 540

Ala Glu Lys Lys Pro Glu Tyr Ile Arg Glu Tyr Leu Pro Ala Asp Ala
545                 550                 555                 560
```

```
Asn Ser Leu Leu Ala Val Gly Asp Val Ile Phe Arg Ser Gln Glu Lys
                565                 570                 575
Ile Asn Tyr Val Val Thr Ser Lys His Pro Arg Gln Gln Trp Phe Ser
            580                 585                 590
Ile Glu Glu Ala Lys Gln Leu Val Asp Asn Gly Leu Gly Ile Ile Asp
        595                 600                 605
Trp Ala Ser Thr Asp Gln Gly Ser Glu Pro Asp Ile Val Phe Ala Ala
    610                 615                 620
Ala Gly Thr Glu Pro Thr Leu Glu Thr Leu Ala Ala Ile Gln Leu Leu
625                 630                 635                 640
His Asp Ser Phe Pro Asp Met Lys Ile Arg Phe Val Asn Val Val Asp
                645                 650                 655
Ile Leu Lys Leu Arg Ser Pro Glu Lys Asp Pro Arg Gly Leu Ser Asp
            660                 665                 670
Ala Glu Phe Asp His Tyr Phe Thr Lys Asp Lys Pro Val Val Phe Ala
        675                 680                 685
Phe His Gly Tyr Glu Asp Leu Val Arg Asp Ile Phe Phe Asp Arg His
    690                 695                 700
Asn His Asn Leu His Val His Gly Tyr Arg Glu Asn Gly Asp Ile Thr
705                 710                 715                 720
Thr Pro Phe Asp Val Arg Val Met Asn Gln Met Asp Arg Phe Asp Leu
                725                 730                 735
Ala Lys Ser Ala Ile Ala Ala Gln Pro Ala Met Glu Asn Thr Gly Ala
            740                 745                 750
Ala Phe Val Gln Asp Met Asp Asn Met Leu Ala Lys His Asn Ala Tyr
        755                 760                 765
Ile Arg Asp Ala Gly Thr Asp Leu Pro Glu Val Asn Asp Trp Gln Trp
    770                 775                 780
Lys Gly Leu Lys
785

<210> SEQ ID NO 8
<211> LENGTH: 787
<212> TYPE: PRT
<213> ORGANISM: Lactobacillus sakei

<400> SEQUENCE: 8

Met Thr Asp Tyr Ser Ser Lys Glu Tyr Leu Ala Lys Val Asp Ala Phe
1               5                   10                  15
Trp Arg Ala Ala Asn Tyr Ile Ser Val Gly Gln Leu Tyr Leu Lys Asp
            20                  25                  30
Asn Pro Leu Leu Gln Arg Pro Leu Glu Ala Lys Asp Val Lys Val Lys
        35                  40                  45
Pro Ile Gly His Trp Gly Thr Ile Ser Gly Gln Asn Phe Leu Tyr Ala
    50                  55                  60
His Leu Asn Arg Ala Ile Asn Lys Tyr Asp Leu Asn Met Phe Tyr Val
65                  70                  75                  80
Glu Gly Pro Gly His Gly Gly Gln Val Met Val Ser Asn Ser Tyr Leu
                85                  90                  95
Asp Gly Ser Tyr Thr Glu Ile Tyr Pro Glu Ile Ser Gln Asp Val Asp
            100                 105                 110
Gly Met Lys Lys Leu Phe Lys Gln Phe Ser Phe Pro Gly Gly Val Ala
        115                 120                 125
Ser His Ala Ala Pro Glu Thr Pro Gly Ser Ile His Glu Gly Gly Glu
```

```
        130                 135                 140
Leu Gly Tyr Ser Leu Ser His Gly Val Gly Ala Ile Leu Asp Asn Pro
145                 150                 155                 160

Asp Val Ile Ala Ala Val Val Gly Asp Gly Glu Ala Glu Thr Gly
            165                 170                 175

Pro Leu Ala Ala Ser Trp Leu Ser Ser Thr Phe Ile Asn Pro Lys Asn
            180                 185                 190

Asp Gly Ala Val Leu Pro Ile Leu Asn Leu Asn Gly Phe Lys Ile Ser
            195                 200                 205

Asn Pro Thr Ile Leu Ser Arg Lys Ser Asp Glu Glu Leu Thr Lys Tyr
            210                 215                 220

Phe Glu Gly Asn Gly Trp Ala Pro Ile Phe Val Gly Asp Asp Pro
225                 230                 235                 240

Glu Lys Met His Pro Ala Thr Ala Ala Met Asp Glu Ala Ile Glu
            245                 250                 255

Lys Ile Gln Ala Ile Gln Lys Ala Ala Arg Glu Asn Gly Asp Thr Ser
            260                 265                 270

Arg Pro Val Trp Pro Met Ile Val Phe Arg Ala Pro Lys Gly Trp Thr
            275                 280                 285

Gly Pro Lys Thr Trp Asp Gly Val Pro Ile Glu Asn Ser Phe Arg Ala
            290                 295                 300

His Gln Ile Pro Val Pro Ile Asp Ser Thr Asp Met Gln His Ala Asp
305                 310                 315                 320

Ala Leu Val Asp Trp Met Lys Ser Tyr Arg Pro Glu Glu Leu Phe Thr
            325                 330                 335

Ala Glu Gly Gln Leu Lys Pro Glu Ile Ala Ala Met Ala Pro Lys Gly
            340                 345                 350

Asp Lys Arg Met Ala Ala Asn Pro Ile Thr Asn Gly Gly Ile Asp Pro
            355                 360                 365

Lys Pro Leu Arg Leu Pro Asp Tyr Arg Asp Tyr Ala Val Asp Asn Thr
            370                 375                 380

Glu His Gly Lys Val Val Ala Gln Asp Met Ile Val Leu Gly Glu Tyr
385                 390                 395                 400

Val Arg Asp Ile Ile Lys Asp Asn Asp Gln Asn Lys Asn Phe Arg Ile
            405                 410                 415

Phe Gly Pro Asp Glu Thr Met Ser Asn Arg Leu Asn His Ile Phe Asp
            420                 425                 430

Val Thr Asn Arg Gln Trp Met Glu Pro Ile Lys Glu Pro Asn Asp Gln
            435                 440                 445

Phe Met Ala Thr Glu Gly Arg Val Leu Asp Ser Gln Leu Ser Glu His
450                 455                 460

Gln Ala Glu Gly Trp Leu Glu Gly Tyr Val Leu Thr Gly Arg His Gly
465                 470                 475                 480

Phe Phe Ala Ser Tyr Glu Ser Phe Leu Arg Val Val Asp Ser Met Leu
            485                 490                 495

Thr Gln His Phe Lys Trp Leu Arg Lys Ala Asp Glu Gln Ala Trp Arg
            500                 505                 510

Asn Lys Tyr Pro Ser Leu Asn Val Ile Ala Thr Ser Thr Val Phe Gln
            515                 520                 525

Gln Asp His Asn Gly Tyr Thr His Gln Asp Pro Gly Val Leu Thr His
            530                 535                 540

Leu Ala Glu Lys Lys Pro Glu Phe Ile Arg Glu Tyr Leu Pro Ala Asp
545                 550                 555                 560
```

```
Ala Asn Thr Leu Leu Ala Thr Met Asn Thr Val Phe Gln Ser Gln Glu
            565                 570                 575

Lys Ile Asn Leu Val Ile Ala Ser Lys His Pro Arg Gln Gln Trp Phe
            580                 585                 590

Ser Ile Asp Glu Ala Thr Val Leu Val Lys Asn Gly Leu Lys Ile Ile
            595                 600                 605

Asp Trp Ala Ser Thr Asp Gln Asp Ala Glu Pro Asp Val Val Ile Ala
            610                 615                 620

Ala Ala Gly Thr Glu Pro Thr Leu Glu Ser Leu Ala Ala Ile Ser Ile
625                 630                 635                 640

Leu His Lys Gln Tyr Pro Asp Met Lys Ile Arg Phe Ile Asn Val Val
            645                 650                 655

Asp Leu Leu Lys Leu Arg Ser Pro Lys Val Asp Pro Arg Gly Leu Thr
            660                 665                 670

Asp Glu Glu Phe Asp Met Tyr Phe Thr Lys Asp Lys Pro Val Val Phe
            675                 680                 685

Ala Phe His Gly Phe Glu Gly Leu Val Arg Asp Ile Phe Phe Asp Arg
            690                 695                 700

His Asn His Asn Leu His Val His Gly Tyr Arg Glu Asn Gly Asp Ile
705                 710                 715                 720

Thr Thr Pro Phe Asp Met Arg Val Leu Asn Gln Met Asp Arg Tyr Asn
            725                 730                 735

Leu Ser Lys Glu Val Ala Ile Asp Val Leu Gly Asp Gln Ala Gly Gln
            740                 745                 750

Phe Ala Gln Ser Met Asp Asp Met Val Ala Lys His Asn Gln Tyr Ile
            755                 760                 765

Arg Asp Glu Gly Thr Asp Leu Pro Glu Val Glu Trp Gln Trp Thr
            770                 775                 780

Pro Leu Arg
785

<210> SEQ ID NO 9
<211> LENGTH: 786
<212> TYPE: PRT
<213> ORGANISM: Lactobacillus salivarius

<400> SEQUENCE: 9

Met Thr Asp Tyr Ser Ser Gln Glu Tyr Leu Asp Lys Leu Asp Ala Tyr
1               5                   10                  15

Trp Arg Ala Ala Asn Tyr Val Ser Val Gly Gln Leu Tyr Leu Lys Asp
            20                  25                  30

Asn Pro Leu Leu Arg Arg Pro Leu Lys Ala Lys Asp Val Lys Val Lys
            35                  40                  45

Pro Ile Gly His Trp Gly Thr Ile Ala Gly Gln Asn Phe Ile Tyr Asp
        50                  55                  60

His Leu Asn Arg Val Ile Asn Lys Tyr Asp Leu Asn Met Phe Tyr Val
65                  70                  75                  80

Glu Gly Pro Gly His Gly Gly Gln Val Met Val Ser Asn Ser Tyr Leu
                85                  90                  95

Asp Gly Ser Tyr Ser Glu Ile Tyr Pro Glu Ile Ser Gln Asp Glu Gln
            100                 105                 110

Gly Met Lys Arg Leu Phe Lys Arg Phe Ser Phe Pro Gly Gly Val Ala
            115                 120                 125

Ser His Ala Ala Pro Glu Thr Pro Gly Ser Ile His Glu Gly Gly Glu
```

```
            130                 135                 140
Leu Gly Tyr Ser Ile Ser His Ser Val Gly Ala Val Leu Asp Asn Pro
145                 150                 155                 160

Asp Leu Ile Val Ala Val Val Gly Asp Gly Glu Ala Glu Thr Gly
                165                 170                 175

Pro Leu Ala Ala Ser Trp Gln Ser Asn Lys Phe Ile Asn Pro Ile His
            180                 185                 190

Asp Gly Ala Val Leu Pro Ile Leu Asp Leu Asn Gly Phe Lys Ile Ser
                195                 200                 205

Asn Pro Thr Ile Leu Ser Arg Glu Ser Asp Glu Thr Leu Thr Lys Tyr
            210                 215                 220

Phe Glu Gly Met Gly Trp His Pro Ile Phe Val Gly Asp Asp Pro
225                 230                 235                 240

Lys Leu Met His Pro Ala Met Ala Lys Ala Met Asp Glu Ala Ile Glu
                245                 250                 255

Glu Ile Lys Ala Ile Gln Lys Asn Ala Arg Glu Asn Asn Asp Pro Ser
                260                 265                 270

Leu Pro Ala Trp Pro Val Ile Ile Phe Arg Ala Pro Lys Gly Trp Thr
            275                 280                 285

Gly Pro Lys Glu Trp Asp Gly Glu Pro Ile Glu Lys Ser Phe Arg Ala
            290                 295                 300

His Gln Ile Pro Ile Pro Val Asp Gln Asn Asp Met Gln His Ala Asp
305                 310                 315                 320

Ala Leu Val Asp Trp Leu Glu Ser Tyr Lys Pro Glu Glu Leu Phe Asp
                325                 330                 335

Glu Asn Gly Lys Leu Lys Ala Glu Ile Ala Glu Ile Thr Pro Lys Gly
                340                 345                 350

Asp Lys Arg Met Ala Ala Asn Pro His Thr Asn Pro Gly Lys Leu Ile
            355                 360                 365

Arg Glu Val Ile Lys Pro Asp Phe Arg Asp Phe Ala Val Asp Thr Ser
            370                 375                 380

Val Pro Gly Lys Glu Val Ala Gln Asp Met Thr Val Leu Gly Lys Tyr
385                 390                 395                 400

Leu Glu Lys Val Leu Ser Asp Asn Arg His Asn Tyr Arg Val Phe Gly
                405                 410                 415

Pro Asp Glu Thr Met Ser Asn Arg Leu Ala Pro Ile Phe Asp Val Thr
            420                 425                 430

Lys Arg Gln Trp Leu Ala Glu Ile Lys Glu Pro Asn Asp Gln Tyr Leu
            435                 440                 445

Ala Pro Ser Gly Gln Val Ile Asp Ser Gln Leu Ser Glu His Gln Ala
450                 455                 460

Glu Gly Phe Leu Glu Gly Tyr Val Leu Thr Gly Arg His Gly Phe Phe
465                 470                 475                 480

Ala Ser Tyr Glu Ser Phe Leu Arg Val Val Asp Ser Met Leu Thr Gln
                485                 490                 495

His Phe Lys Trp Leu Arg Lys Ala Thr Glu Gln Pro Trp Arg Thr Ser
            500                 505                 510

Ile Pro Ser Leu Asn Val Ile Ala Thr Ser Thr Val Phe Gln Gln Asp
            515                 520                 525

His Asn Gly Tyr Thr His Gln Asp Pro Gly Ile Leu Gly His Leu Ala
            530                 535                 540

Asp Lys Lys Pro Glu Tyr Ile Arg Glu Tyr Leu Pro Ala Asp Ala Asn
545                 550                 555                 560
```

```
Ser Leu Leu Ala Val Phe Asp Lys Thr Ile Asn Asp Arg Asp Lys Ile
                565                 570                 575

Asn Leu Ile Val Ala Ser Lys His Pro Arg Gln Gln Phe Tyr Ser Ala
            580                 585                 590

Ala Glu Ala Lys Glu Leu Val Asp Lys Gly Leu Lys Ile Ile Asp Trp
        595                 600                 605

Ala Ser Thr Asp Lys Asn Ala Glu Pro Asp Val Val Ile Ala Ala Ala
    610                 615                 620

Gly Thr Glu Pro Asn Leu Glu Ala Leu Ala Ala Ile Ser Ile Leu His
625                 630                 635                 640

Glu Lys Leu Pro Asp Leu Lys Ile Arg Phe Ile Asn Val Val Asp Ile
                645                 650                 655

Leu Lys Leu Arg Ser Pro Lys Val Asp Pro Arg Gly Leu Ser Asp Asp
            660                 665                 670

Glu Phe Asp Ala Tyr Phe Thr Lys Asp Lys Pro Val Ile Phe Ala Phe
        675                 680                 685

His Gly Tyr Glu Gly Leu Leu Arg Asp Ile Phe Tyr Tyr Arg His Asn
    690                 695                 700

His Asn Val Ala Phe His Gly Tyr Arg Glu Asn Gly Asp Ile Thr Thr
705                 710                 715                 720

Pro Phe Asp Met Arg Val Leu Ser Gln Met Asp Arg Phe Asp Leu Val
                725                 730                 735

Lys Ser Val Ala Leu Ser Leu Pro Asp Ala Asp Lys Tyr Gly Gln Leu
            740                 745                 750

Val Ala Glu Met Asp Ala Lys Val Ala Lys His His Gln Tyr Ile Arg
        755                 760                 765

Asp Glu Gly Thr Asp Leu Pro Glu Val Lys Asn Trp Glu Trp Lys Pro
    770                 775                 780

Leu Asp
785

<210> SEQ ID NO 10
<211> LENGTH: 803
<212> TYPE: PRT
<213> ORGANISM: Lactobacillus reuteri

<400> SEQUENCE: 10

Met Ala Val Asp Tyr Asp Ser Lys Lys Tyr Leu Glu Ser Val Asp Ala
1               5                   10                  15

Tyr Trp Arg Ala Ala Asn Tyr Leu Ser Val Gly Thr Leu Phe Leu Met
            20                  25                  30

Gly Asp Pro Leu Leu Arg Gln Pro Leu Lys Ala Glu Asp Val Lys Pro
        35                  40                  45

Lys Pro Ile Gly His Trp Gly Thr Ile Val Pro Gln Asn Phe Ile Tyr
    50                  55                  60

Ala His Leu Asn Arg Val Ile Lys Tyr Asp Leu Asp Met Phe Tyr
65                  70                  75                  80

Ile Glu Gly Ser Gly His Gly Gly Gln Val Met Val Asn Asn Ser Tyr
            85                  90                  95

Leu Asp Gly Ser Tyr Thr Glu Ile Tyr Pro Glu Tyr Thr Gln Asp Thr
        100                 105                 110

Lys Gly Met Ala Lys Leu Phe Lys His Phe Ser Phe Pro Gly Gly Thr
    115                 120                 125

Ala Ser His Ala Ala Pro Glu Thr Pro Gly Ser Ile His Glu Gly Gly
```

```
            130                 135                 140
Glu Leu Gly Tyr Ser Leu Ser His Gly Val Gly Ala Ile Leu Asp Asn
145                 150                 155                 160

Pro Asp Val Ile Ala Val Glu Ile Gly Asp Gly Glu Ala Glu Thr
                165                 170                 175

Gly Pro Leu Met Ala Ser Trp Phe Ser Asp Lys Phe Ile Asn Pro Ile
            180                 185                 190

Lys Asp Gly Ala Val Leu Pro Ile Ile Gln Val Asn Gly Phe Lys Ile
                195                 200                 205

Ser Asn Pro Thr Ile Leu Ser Arg Met Ser Asp Glu Glu Leu Thr Lys
        210                 215                 220

Tyr Phe Glu Gly Met Gly Trp Lys Pro Tyr Phe Val Ser Ala Tyr Lys
225                 230                 235                 240

Glu Ala Asp Arg Asp Gly Glu Phe Asp Gly Tyr Lys Pro His Met Glu
                245                 250                 255

Val His Glu Gln Met Ala Lys Thr Met Asp Lys Ala Val Glu Glu Ile
            260                 265                 270

Lys Ala Ile Gln Lys Asn Ala Arg Glu Asn Asn Asp Asp Ser Leu Pro
        275                 280                 285

Gln Trp Pro Leu Ile Ile Phe Arg Ala Pro Lys Gly Trp Thr Gly Pro
290                 295                 300

Thr Lys Asp Leu Asp Gly Asn Pro Ile Glu Asn Ser Phe Arg Ala His
305                 310                 315                 320

Gln Ile Pro Ile Pro Val Ser Gln Asp Met Glu His Lys Asp Met
                325                 330                 335

Leu Ile Asn Trp Met Lys Ser Tyr Lys Pro Glu Glu Leu Phe Asp Glu
            340                 345                 350

Asn Gly His Pro Val Ala Leu Val Glu Glu Asn Thr Pro Glu Gly Asn
                355                 360                 365

Arg Arg Met Ala Met Asn Pro Ile Thr Asn Gly Gly Ile Asp Pro Lys
        370                 375                 380

Pro Leu Val Leu Pro Asn Tyr Arg Asp Phe Ala Val Asp Val Gln Thr
385                 390                 395                 400

Pro Gly Ser Val Val Lys Gln Asp Met Leu Glu Trp Gly Lys Tyr Leu
                405                 410                 415

Ser Lys Met Ala Glu Leu Asn Pro Thr Asn Phe Arg Gly Phe Gly Pro
            420                 425                 430

Asp Glu Ser Lys Ser Asn Arg Leu Tyr Ala Phe Leu Asp Asn Gln Lys
                435                 440                 445

Arg Gln Trp Met Glu Gly Ile His Glu Pro Asn Asp Glu Asn Val Ala
        450                 455                 460

Pro Gln Gly Arg Met Ile Asp Ser Gln Leu Ser His Gln Ala Glu
465                 470                 475                 480

Gly Phe Leu Glu Gly Tyr Thr Leu Thr Gly Arg His Gly Phe Ala
                485                 490                 495

Thr Tyr Glu Ala Phe Gly Arg Val Val Asp Ser Met Leu Thr Gln His
            500                 505                 510

Met Lys Trp Leu Arg Lys Ala Lys Asp Leu Tyr Trp Arg Arg Gln Tyr
        515                 520                 525

Pro Ala Leu Asn Phe Val Asp Thr Ser Thr Val Phe Gln Gln Asp His
530                 535                 540

Asn Gly Tyr Thr His Gln Asp Pro Gly Leu Leu Thr His Leu Phe Glu
545                 550                 555                 560
```

```
Lys Glu Arg Pro Asp Leu Val Lys Glu Tyr Leu Pro Ala Asp Thr Asn
            565                 570                 575
Ser Leu Met Ala Val Ser Asn Lys Ala Phe Arg Asn Gln Glu Cys Ile
        580                 585                 590
Asn Leu Phe Val Thr Ser Lys His Pro Arg Ala Gln Trp Phe Ser Ile
            595                 600                 605
Asp Glu Ala Thr Glu Leu Val Asp Asn Gly Leu Gly Tyr Ile Asn Trp
        610                 615                 620
Ala Ser Thr Asp Gln Gly Ser Glu Pro Asp Val Val Phe Ala Ser Ala
625                 630                 635                 640
Gly Thr Glu Pro Thr Glu Glu Ala Leu Ala Ile Asp Ile Leu His
                645                 650                 655
Asp Asn Phe Pro Glu Leu Lys Ile Arg Tyr Ile Asn Ile Ile Glu Ile
            660                 665                 670
Met Lys Leu Met Lys Gln Asp Lys Asn Pro Glu Gly Leu Ser Asp Ala
        675                 680                 685
Glu Phe Asn Arg Tyr Phe Thr Thr Asp Lys Pro Val Ile Phe Ala Trp
    690                 695                 700
His Gly Phe Arg Asp Met Ile Gln Ala Leu Phe Phe Asp Arg Ala Asn
705                 710                 715                 720
Arg Asn Val His Ile His Ser Tyr Glu Glu Asn Gly Asp Ile Thr Thr
                725                 730                 735
Pro Phe Asp Met Arg Val Leu Asn Glu Leu Asp Arg Phe His Leu Ala
            740                 745                 750
Lys Asp Ala Ile Gln Ser Val Pro Gly Tyr Glu Gln Lys Ser Ala Ala
        755                 760                 765
Phe Val Ala Lys Met Asp Asn Met Ile Asn Lys His Asn His Tyr Ile
    770                 775                 780
Arg Ser Glu Gly Lys Asp Leu Pro Glu Val Thr Asn Trp Thr Trp Lys
785                 790                 795                 800

Gly Leu Lys

<210> SEQ ID NO 11
<211> LENGTH: 801
<212> TYPE: PRT
<213> ORGANISM: Lactobacillus johnsonii

<400> SEQUENCE: 11

Met Ala Val Asn Tyr Asp Ser Gln Glu Tyr Leu Lys Ser Val Asp Ala
1               5                   10                  15
Tyr Trp Arg Ala Ala Asn Tyr Leu Ser Val Gly Gln Leu Phe Leu Met
            20                  25                  30
Asn Asn Pro Leu Leu Lys Arg Glu Leu Lys Ala Glu Asp Val Lys Pro
        35                  40                  45
Lys Pro Ile Gly His Trp Gly Thr Ile Val Pro Gln Asn Phe Ile Tyr
    50                  55                  60
Gly His Leu Asn Arg Ala Ile Lys Lys Tyr Asp Leu Asn Met Phe Tyr
65                  70                  75                  80
Ile Glu Gly Ser Gly His Gly Gly Gln Val Met Val Ser Asn Ser Tyr
            85                  90                  95
Leu Asp Gly Ser Tyr Thr Glu Arg Tyr Pro Glu Ile Thr Gln Asp Glu
        100                 105                 110
Lys Gly Met Ala Lys Leu Phe Lys Gln Phe Ser Phe Pro Gly Gly Val
    115                 120                 125
```

```
Ala Ser His Ala Ala Pro Glu Thr Pro Gly Ser Ile His Glu Gly Gly
    130                 135                 140

Glu Leu Gly Tyr Ser Leu Ser His Gly Val Gly Ala Ile Leu Asp Asn
145                 150                 155                 160

Pro Asp Val Ile Ala Ala Val Glu Ile Gly Asp Gly Glu Ser Glu Thr
                165                 170                 175

Gly Pro Leu Ala Thr Ser Trp Phe Ser Ser Lys Phe Ile Asn Pro Ile
                180                 185                 190

Lys Asp Gly Ala Val Ile Pro Ile Leu Gln Ile Asn Gly Phe Lys Ile
                195                 200                 205

Ser Asn Pro Thr Ile Val Ser Arg Met Ser Asp Glu Asp Leu Thr Lys
    210                 215                 220

Tyr Phe Glu Gly Met Gly Trp Lys Pro Tyr Phe Val Ser Ala Tyr Lys
225                 230                 235                 240

Asp Gly Glu Phe Asn Gly Tyr Lys Asp His Met Glu Val His Gln Glu
                245                 250                 255

Met Ala Lys Thr Met Asp Glu Val Val Glu Glu Ile Lys Ala Ile Gln
                260                 265                 270

Lys His Ala Arg Glu Asn Asn Asp Asp Ser Leu Val Lys Trp Pro Met
    275                 280                 285

Ile Val Phe Arg Val Pro Lys Gly Trp Thr Gly Pro Lys Phe Asp Leu
    290                 295                 300

Asp Gly Asn Pro Ile Glu Asn Ser Phe Arg Ala His Gln Ile Pro Ile
305                 310                 315                 320

Pro Val Ala Gln Asp Asp Met Asn His Lys Glu Met Leu Thr Asp Trp
                325                 330                 335

Met Glu Ser Tyr Lys Pro Glu Glu Leu Phe Asn Glu Asp Gly Ser Pro
                340                 345                 350

Lys Asp Ile Val Lys Glu Asn Thr Leu Ser Gly Asp Gln Arg Met Ala
                355                 360                 365

Met Asn Pro Val Thr Asn Gly Gly Ile Asp Pro Lys Val Leu Asn Met
    370                 375                 380

Pro Asp Tyr Arg Asp Phe Ala Ile Lys Phe Asp Lys Pro Gly Ser Val
385                 390                 395                 400

Glu Lys Gln Asp Met Ala Glu Trp Ala Lys Tyr Leu Asp Lys Met Ser
                405                 410                 415

Glu Leu Asn Pro Thr Asn Phe Arg Gly Phe Gly Pro Asp Glu Thr Lys
                420                 425                 430

Ser Asn Arg Leu Phe Gln Leu Leu Asp Asn Gln Lys Arg Gln Trp Met
    435                 440                 445

Glu Ser Ile His Thr Pro Asn Asp Glu Asn Leu Ala His Glu Gly Arg
    450                 455                 460

Val Ile Asp Ser Gln Leu Ser Glu His Gln Asp Glu Gly Trp Leu Glu
465                 470                 475                 480

Gly Tyr Val Leu Thr Gly Arg His Gly Phe Phe Ala Thr Tyr Glu Ala
                485                 490                 495

Phe Gly Arg Val Val Asp Ser Met Leu Thr Gln His Met Lys Trp Leu
                500                 505                 510

Arg Lys Ala Lys Glu Gln Ala Trp Arg His Asp Tyr Pro Ala Leu Asn
    515                 520                 525

Leu Val Asp Thr Ser Thr Val Phe Gln Gln Asp His Asn Gly Tyr Thr
    530                 535                 540
```

His Gln Asp Pro Gly Met Leu Thr His Leu Tyr Glu Lys Asn Arg Pro
545                 550                 555                 560

Asp Leu Ile His Glu Tyr Leu Pro Ala Asp Thr Asn Ser Leu Leu Ala
                565                 570                 575

Val Ser Asp Lys Ala Phe Arg Asp Arg Glu Cys Ile Asn Val Leu Val
            580                 585                 590

Thr Ser Lys Gln Pro Arg Pro Gln Trp Phe Ser Ile Glu Glu Ala Lys
        595                 600                 605

Lys Leu Val Asp Lys Gly Leu Gly Tyr Val Asp Trp Ala Ser Thr Asp
    610                 615                 620

Lys Gly Ala Lys Pro Asp Val Val Phe Ala Ser Thr Gly Thr Glu Pro
625                 630                 635                 640

Thr Ile Glu Ser Leu Ala Ala Ile Asp Leu Leu His Lys Lys Phe Pro
                645                 650                 655

Asp Leu Lys Ile Arg Tyr Ile Asn Val Ile Asp Val Met Lys Leu Met
                660                 665                 670

Ser Pro Glu Lys Asn Pro Asn Ala Ile Ser Asn Glu Glu Phe Asn Arg
            675                 680                 685

Leu Phe Pro Lys Gly Thr Pro Val Ile Phe Ala Trp His Gly Phe Lys
        690                 695                 700

Pro Met Met Glu Ser Ile Trp Phe Asp Arg Gly Arg Gly Lys Asp Asp
705                 710                 715                 720

Val His Ile His Gly Tyr Glu Glu Asn Gly Asp Ile Thr Thr Pro Phe
                725                 730                 735

Asp Met Arg Val Leu Asn His Met Asp Arg Tyr Asp Leu Ala Lys Asp
                740                 745                 750

Val Val Glu Ser Ile Pro Glu Leu Asn Glu Lys Asn Ala Asp Phe Ile
            755                 760                 765

Asp Glu Met Asp Ser Leu Leu Ala Lys His His Gln Tyr Ile Arg Asp
        770                 775                 780

Asn Gly Lys Asp Met Pro Glu Val Thr Glu Trp Gln Trp Asn Gly Leu
785                 790                 795                 800

Lys

<210> SEQ ID NO 12
<211> LENGTH: 793
<212> TYPE: PRT
<213> ORGANISM: Lactobacillus casei

<400> SEQUENCE: 12

Met Asp Thr Lys Val Lys Thr Val Asp Tyr Ser Ser Lys Glu Tyr Phe
1               5                   10                  15

Asp Lys Met Thr Ala Tyr Trp Arg Ala Ala Asn Tyr Ile Ser Val Gly
                20                  25                  30

Gln Leu Tyr Leu Lys Asp Asn Pro Leu Leu Glu Arg Pro Leu Lys Ser
            35                  40                  45

Glu Asp Val Lys Pro His Pro Ile Gly His Trp Gly Thr Ile Ala Gly
        50                  55                  60

Gln Asn Phe Ile Tyr Thr His Leu Asn Arg Val Ile Asn Lys Tyr Asp
65                  70                  75                  80

Leu Asn Met Phe Tyr Ile Glu Gly Pro Gly His Gly Gly Gln Val Met
                85                  90                  95

Val Ser Asn Ser Tyr Leu Asp Gly Ser Tyr Ser Glu Ile Tyr Pro Arg
            100                 105                 110

-continued

```
Val Ser Gln Asp Lys Glu Gly Met Lys Asn Leu Phe Thr Gln Phe Ser
            115                 120                 125
Trp Pro Gly Gly Val Ala Ser His Ala Ser Ala Gln Thr Pro Gly Ser
130                 135                 140
Ile His Glu Gly Gly Glu Leu Gly Tyr Ala Leu Ser His Ala Thr Gly
145                 150                 155                 160
Ala Ile Leu Asp Asn Pro Glu Val Ile Ala Val Val Thr Gly Asp
                165                 170                 175
Gly Glu Thr Glu Thr Gly Pro Leu Ala Ala Ser Trp Phe Ser Asn Thr
            180                 185                 190
Phe Ile Asn Pro Ile Thr Asp Gly Ala Ile Leu Pro Ile Val His Met
            195                 200                 205
Asn Gly Phe Lys Ile Ser Asn Pro Thr Ile Leu Ser Arg Lys Ser Asp
210                 215                 220
Glu Asp Leu Asp Lys Tyr Phe Ser Gly Met Gly Trp Lys Pro Phe Phe
225                 230                 235                 240
Val Glu Gly Asp Pro Glu Lys Leu Asn Pro Glu Met Ala Lys Val
                245                 250                 255
Leu Asp Glu Ala Ile Glu Asp Ile Lys Ala Ile Gln Lys His Ala Arg
            260                 265                 270
Glu Thr Gly Asp Thr Thr Met Pro His Trp Pro Val Ile Phe Arg
            275                 280                 285
Ser Pro Lys Gly Trp Thr Gly Pro Lys Ser Trp Asn Gly Glu Pro Ile
290                 295                 300
Glu Gly Ser Phe Arg Ala His Gln Ile Pro Ile Pro Val Asp Ala Glu
305                 310                 315                 320
Asp Met Glu His Ala Asp Ser Leu Ala Gly Trp Leu Lys Ser Tyr His
                325                 330                 335
Pro Glu Glu Leu Phe Asp Glu Asn Gly Lys Leu Ile Pro Glu Leu Ala
            340                 345                 350
Ala Leu Pro Pro Lys Gly Glu Gln Arg Met Ala Ala Asn Pro Ile Thr
            355                 360                 365
Asn Gly Gly Ile Asp Pro Lys Pro Leu Val Leu Pro Asp Tyr Arg Lys
370                 375                 380
Tyr Ala Leu Asp Asn Lys Glu His Gly Lys Gln Ile Lys Gln Asp Met
385                 390                 395                 400
Ile Val Trp Ser Asp Tyr Leu Arg Asp Leu Ile Lys Leu Asn Pro His
                405                 410                 415
Asn Phe Arg Ile Phe Gly Pro Asp Glu Thr Met Ser Asn Arg Leu Tyr
            420                 425                 430
Ser Leu Phe Glu Val Thr Asn Arg Gln Trp Leu Glu Pro Ile Lys Glu
            435                 440                 445
Pro Ala Asp Gln Tyr Leu Ala Pro Ala Gly Arg Ile Ile Asp Ser Gln
450                 455                 460
Leu Ser Glu His Gln Ala Glu Gly Phe Asn Gly Tyr Thr Leu Thr
465                 470                 475                 480
Gly Arg His Gly Leu Phe Thr Ser Tyr Glu Ala Phe Leu Arg Val Val
                485                 490                 495
Asp Ser Met Leu Thr Gln His Phe Lys Trp Ile Arg Lys Ala His Glu
            500                 505                 510
Glu Pro Trp His Lys Ala Tyr Pro Ser Leu Asn Val Val Ser Thr Ser
            515                 520                 525
Thr Ser Phe Gln Gln Asp His Asn Gly Tyr Thr His Gln Asp Pro Gly
```

```
            530                 535                 540
Ile Leu Thr His Met Ala Glu Lys Lys Ala Glu Tyr Ile Arg Glu Tyr
545                 550                 555                 560

Leu Pro Ala Asp Ala Asn Ser Leu Leu Ala Ile Ser Pro Lys Leu Phe
                565                 570                 575

Ser Ser Gln Asn Thr Val Asn Val Leu Ile Thr Ser Lys Gln Pro Arg
                580                 585                 590

Pro Gln Phe Tyr Ser Ile Asp Glu Ala Thr Val Leu Ala Asn Ser Gly
            595                 600                 605

Leu Lys Arg Ile Asp Trp Ala Ser Asn Asp Asp Gly Val Glu Pro Asp
        610                 615                 620

Val Val Ile Ala Ala Gly Thr Glu Pro Asn Met Glu Ser Leu Ala
625                 630                 635                 640

Ala Ile Asn Leu Leu His Asp Ala Phe Pro Asp Leu Lys Ile Arg Phe
                645                 650                 655

Ile Asn Val Val Asp Leu Leu Lys Leu Arg Ser Pro Glu Ile Asp Pro
                660                 665                 670

Arg Gly Leu Ser Asp Ala Glu Phe Asn Ser Tyr Phe Thr Thr Asp Lys
            675                 680                 685

Pro Ile Leu Phe Ala Tyr His Gly Phe Glu Gly Leu Ile Arg Asp Ile
        690                 695                 700

Phe Phe Thr Arg Pro Asn Arg Asn Val Leu Ile His Gly Tyr Arg Glu
705                 710                 715                 720

Glu Gly Asp Ile Thr Thr Pro Phe Asp Met Arg Val Leu Asn Glu Leu
                725                 730                 735

Asp Arg Tyr His Leu Ala Lys Asp Val Ile Gln His Val Pro Ala Tyr
            740                 745                 750

Ala Glu Lys Ala Ala Phe Val Gln Lys Met Asp Asp Thr Leu Gln
        755                 760                 765

Tyr His His Asp Phe Ile Arg Ala Asn Gly Asp Ile Pro Glu Val
770                 775                 780

Gln Glu Trp Thr Trp Lys Pro Ile Lys
785                 790

<210> SEQ ID NO 13
<211> LENGTH: 794
<212> TYPE: PRT
<213> ORGANISM: Bacillus coagulans

<400> SEQUENCE: 13

Met Glu Met Ala Ala Ser Gln Val Ala Tyr Ser Ser Pro Ala Tyr Leu
1               5                   10                  15

Lys Asn Leu Asp Val Tyr Trp Arg Ala Ala Asn Tyr Ile Ser Val Gly
            20                  25                  30

Gln Leu Tyr Leu Lys Asp Asn Pro Leu Leu Lys Glu Pro Val Lys Pro
        35                  40                  45

Ser Asp Leu Lys Ala Lys Pro Ile Gly His Trp Gly Thr Ile Ser Gly
    50                  55                  60

Gln Asn Phe Ile Tyr Ala His Leu Asn Arg Val Ile Asn Lys Tyr Asp
65                  70                  75                  80

Leu Asn Met Phe Tyr Ile Glu Gly Pro Gly His Gly Gly Gln Val Met
                85                  90                  95

Val Ser Asn Ser Tyr Leu Asp Gly Ser Tyr Thr Glu Ile Tyr Pro Asn
            100                 105                 110
```

```
Val Thr Gln Asp Ile Glu Gly Met Lys Arg Leu Phe Lys Gln Phe Ser
        115                 120                 125

Phe Pro Gly Gly Ile Ala Ser His Ala Ala Pro Glu Thr Pro Gly Ser
130                 135                 140

Ile His Glu Gly Gly Glu Leu Gly Tyr Ser Leu Ser His Gly Thr Gly
145                 150                 155                 160

Ala Ile Leu Asp Gln Pro Asp Leu Met Ala Val Val Gly Asp
                165                 170                 175

Gly Glu Ala Glu Thr Gly Pro Leu Ala Thr Ser Trp Leu Ser Asn Arg
            180                 185                 190

Phe Ile Asn Pro Val Thr Asp Gly Ala Val Leu Pro Ile Leu Leu Leu
        195                 200                 205

Asn Gly Phe Lys Ile Ser Asn Pro Thr Met Leu Ser Arg Met Ser Asp
210                 215                 220

Glu Gln Leu Ala Leu Tyr Phe Glu Gly Ile Gly Trp Arg Pro Tyr Phe
225                 230                 235                 240

Val Glu Gly Glu Asp Pro Glu Glu Met His Arg Asp Met Ala Tyr Val
                245                 250                 255

Met Asp Gln Met Ile Glu Gln Ile Gln Ala Ile Gln Ser His Ala Arg
            260                 265                 270

Lys Thr Gly Asp Thr Thr Arg Pro Ala Trp Pro Met Leu Val Phe Arg
        275                 280                 285

Ala Pro Lys Gly Trp Thr Gly Pro Lys Glu Trp Asp Glu Lys Pro Val
290                 295                 300

Glu His Ser Phe Arg Ala His Gln Ile Pro Val Pro Val Asp Gln Asp
305                 310                 315                 320

His Met Glu His Leu Asp Val Leu Ile Asn Trp Met Lys Ser Tyr Arg
                325                 330                 335

Pro Glu Glu Leu Phe Asn Glu Asn Gly Arg Leu Arg Pro Glu Ile Ala
            340                 345                 350

Lys Ile Ala Pro Lys Gly Ser Lys Arg Met Ala Met Asn Pro Ala Thr
        355                 360                 365

Asn Ala Gly Phe His Ile Lys Asp Leu Asp Leu Pro Asp Phe Arg Asp
370                 375                 380

Tyr Ala Leu Asp Asn Lys Glu His Gly Lys Gln Met Ala Gln Asp Met
385                 390                 395                 400

Thr Val Leu Gly Thr Tyr Leu Lys Asp Val Ile Leu Lys Asn Glu Ala
                405                 410                 415

Lys Arg Asn Phe Arg Ile Phe Gly Pro Asp Glu Thr Met Ser Asn Arg
            420                 425                 430

Leu Ala Pro Val Phe Glu Ala Thr Lys Arg Gln Trp Val Gly Lys Ile
        435                 440                 445

Lys Glu Pro Asn Asp Glu Phe Leu Ala Pro Asp Gly Arg Val Ile Asp
450                 455                 460

Ser Gln Leu Ser Glu His Gln Ala Glu Gly Phe Leu Glu Gly Tyr Val
465                 470                 475                 480

Leu Thr Gly Arg His Gly Phe Phe Ala Ser Tyr Glu Ala Phe Leu Arg
                485                 490                 495

Val Val Asp Ser Met Ile Thr Gln His Phe Lys Trp Leu Arg Lys Ala
            500                 505                 510

Ala Glu Gln Lys Trp Arg Ala Asp Ile Pro Ser Leu Asn Val Val Ala
        515                 520                 525

Thr Ser Thr Val Phe Gln Gln Asp His Asn Gly Tyr Thr His Gln Asp
```

```
            530                 535                 540
Pro Gly Ile Leu Gly His Leu Ala Asp Lys Lys Pro Glu Phe Ile Arg
545                 550                 555                 560

Glu Tyr Leu Pro Ala Asp Ala Asn Thr Leu Leu Ala Val Phe Asp Lys
                565                 570                 575

Ile Leu Asn Asp Arg Gly Lys Ile Asn Leu Ile Val Ser Ser Lys His
            580                 585                 590

Pro Arg Pro Gln Trp Phe Thr Val Glu Glu Ala Glu Glu Leu Ala Asp
        595                 600                 605

Arg Gly Leu Lys Ile Ile Asp Trp Ala Ser Thr Asp Glu Gly Gly Asn
    610                 615                 620

Pro Asp Ile Val Ile Ala Ala Cys Gly Thr Glu Pro Leu Leu Glu Ser
625                 630                 635                 640

Leu Ala Ala Val Ser Ile Leu His Glu Lys Leu Pro Lys Leu Lys Ile
                645                 650                 655

Arg Met Ile Asn Val Leu Asp Ile Leu Lys Leu Arg Ser Pro Ala Leu
            660                 665                 670

Asp Pro Arg Gly Leu Ser Asp Glu Ala Phe Asp Ala Tyr Phe Thr Lys
        675                 680                 685

Asp Lys Pro Val Val Phe Ala Phe His Gly Tyr Glu Gly Leu Ile Lys
    690                 695                 700

Asp Leu Phe Phe Asp Arg Ala Asn His Asn Leu His Val His Gly Tyr
705                 710                 715                 720

Arg Glu Asn Gly Asp Ile Thr Thr Pro Phe Asp Met Arg Val Met Asn
                725                 730                 735

Gln Met Asp Arg Phe Asp Leu Val Lys Glu Val Val Ser Ser Leu Pro
            740                 745                 750

Asp Thr Ala Arg His Ala Ala Leu Ile Ser Glu Met Asp Ser Met Leu
        755                 760                 765

Gln Lys His His Ala Tyr Ile Arg Glu Glu Gly Thr Asp Leu Pro Glu
    770                 775                 780

Ile Glu Asn Trp Gln Trp Gln Ala Ile Lys
785                 790

<210> SEQ ID NO 14
<211> LENGTH: 788
<212> TYPE: PRT
<213> ORGANISM: Leuconostoc mesenteroides

<400> SEQUENCE: 14

Met Asn Ile Asp Ser Thr Asp Tyr Leu Asn Asn Leu Asp Ala Tyr Trp
1               5                   10                  15

Arg Ala Thr Asn Tyr Leu Ser Val Gly Gln Leu Tyr Leu Leu Asp Asn
                20                  25                  30

Pro Leu Leu Lys Glu Lys Leu Thr Ala Glu Gln Val Lys Ile His Pro
            35                  40                  45

Ile Gly His Trp Gly Thr Ile Pro Ser Gln Asn Phe Ile Tyr Ala His
        50                  55                  60

Leu Asn Arg Ala Ile Asn Lys Phe Asn Leu Asn Met Phe Tyr Ile Glu
65                  70                  75                  80

Gly Pro Gly His Gly Gly Gln Val Met Ile Ser Asn Ala Tyr Leu Asp
                85                  90                  95

Gly Ser Tyr Thr Glu Ala Phe Pro Glu Ile Thr Gln Asp Glu Ala Gly
            100                 105                 110
```

-continued

Met Gln Lys Met Phe Lys Arg Phe Ser Phe Pro Gly Val Ala Ser
115                 120                 125

His Ala Asp Pro Lys Val Pro Gly Ser Ile His Glu Gly Gly Ala Leu
130                 135                 140

Gly Tyr Ser Ile Leu His Gly Ala Gly Ala Val Leu Asp Asn Pro Asp
145                 150                 155                 160

Leu Ile Ala Ala Val Val Gly Asp Gly Glu Ala Glu Thr Ala Pro
                165                 170                 175

Leu Ala Thr Ser Trp His Val Asn Lys Phe Leu Asn Pro Lys Asn Asp
                180                 185                 190

Gly Thr Val Leu Pro Ile Leu Asn Leu Asn Gly Phe Lys Ile Ala Asn
                195                 200                 205

Pro Thr Val Leu Ser Arg Glu Ser Asp Glu Thr Leu Thr Asp Tyr Phe
210                 215                 220

His Ser Leu Gly Trp His Pro Tyr Phe Val Ser Ser Phe Asp Lys Pro
225                 230                 235                 240

Ile Met Gln Val His Glu Glu Met Ala Lys Thr Met Asp Thr Val Phe
                245                 250                 255

Thr Glu Ile Lys Asp Ile Arg Glu Lys Ala Val Gln Gln Thr Asn Glu
                260                 265                 270

Glu Ile Thr Arg Pro Leu Trp Pro Met Ile Val Leu Arg Ser Pro Lys
                275                 280                 285

Gly Trp Thr Gly Pro Lys Thr Trp Asp Asp Lys Pro Ile Glu Asn Ser
                290                 295                 300

Phe Arg Ala His Gln Ile Pro Ile Pro Ala Asp Gln Asn His Pro Glu
305                 310                 315                 320

Tyr Ile Pro Gln Leu Val Asp Trp Leu Gln Ser Tyr Lys Pro Asp Glu
                325                 330                 335

Leu Phe Asp Glu Asn Gly Gln Leu Thr Gln Ser Ile Gln Glu Val Leu
                340                 345                 350

Pro Lys Lys Glu Leu Arg Met Ala Asn Asn Ser Val Thr Asn Ala Gly
                355                 360                 365

Ile Ile Lys Pro Leu Ile Leu Pro Asp Ile Asp Asn Tyr Leu Val Glu
370                 375                 380

Asn Asn Gln Pro Asp Asn Asn Leu Ala Gln Asp Ala Ile Leu Leu Gly
385                 390                 395                 400

Asp Tyr Leu Arg Asp Ile Ile Lys Leu Asn Pro Thr Asn Phe Arg Gly
                405                 410                 415

Phe Gly Pro Asp Glu Thr Ala Ser Asn Arg Phe Gln Asp Ile Phe Glu
                420                 425                 430

Thr Thr Asn Arg Gln Trp Leu Leu Pro Ile Lys Glu Pro Asn Asp Gln
                435                 440                 445

Phe Met Ala Pro Glu Gly Arg Ile Ile Asp Ser Met Leu Ser Glu His
450                 455                 460

Tyr Asp Glu Gly Met Leu Glu Ala Tyr Thr Leu Thr Gly Arg His Gly
465                 470                 475                 480

Phe Phe Ala Ser Tyr Glu Val Phe Ile Arg Glu Val Asp Asp Met Ile
                485                 490                 495

Val Gln His Phe Lys Trp Leu Asn His Ser His Asp Val Ser Trp Arg
                500                 505                 510

Lys Asp Val Pro Ala Leu Asn Ile Ile Ala Asp Ser Thr Val Phe Gln
                515                 520                 525

Gln Asp His Asn Gly Tyr Ser His Gln Asp Pro Gly Val Thr Thr Met

```
              530                 535                 540
Leu Tyr Glu Lys Gln Pro Asp Phe Ile Arg Glu Phe Pro Ala Asp
545                 550                 555                 560

Ala Asn Ser Leu Val Ala Thr Phe Glu His Ala Ala Gln Ala Thr Gln
                565                 570                 575

Gln Ile Asn Tyr Ile Val Ala Ser Lys His Pro Arg Leu Gln Trp Phe
                580                 585                 590

Ser Pro Thr Glu Ala Lys Gln Leu Val Thr Gln Gly Leu Arg Val Ile
            595                 600                 605

Asp Trp Ala Ser Thr Asp Lys Gly Glu Lys Pro Asp Ile Ile Thr
        610                 615                 620

Ser Ala Gly Ser Glu Pro Thr Thr Glu Ser Leu Ala Ala Ile Gln Ile
625                 630                 635                 640

Leu His Glu His Ile Pro Ser Leu Lys Ile Arg Tyr Ile Asn Val Leu
                645                 650                 655

Asp Leu Phe Lys Leu Arg Ala Asp Ala Ser Tyr Gly Leu Ser Asp Asp
                660                 665                 670

Glu Phe Asp Ala Tyr Phe Thr Thr Asp Thr Pro Val Leu Phe Ala Phe
            675                 680                 685

His Gly Tyr Glu Pro Met Ile Glu Ser Ile Phe Phe Lys Arg His Asn
        690                 695                 700

His His Leu Ala Val His Gly Tyr Arg Glu Val Gly Asp Ile Thr Thr
705                 710                 715                 720

Pro Phe Asp Met Arg Val Leu Asn Lys Ile Asp Arg Phe Asn Leu Val
                725                 730                 735

Lys Ala Ala Ile Asn Leu Leu Pro Glu Asn Ile Arg Thr Lys Gln Ala
                740                 745                 750

Ala Leu Val Gln Glu Met Thr Asp Lys Leu Asp Leu His Val Ala Tyr
            755                 760                 765

Thr Arg Ser Lys Gly Thr Asp Leu Pro Glu Val Glu Asp Trp Arg Trp
        770                 775                 780

Arg Pro Leu Lys
785

<210> SEQ ID NO 15
<211> LENGTH: 813
<212> TYPE: PRT
<213> ORGANISM: Leuconostoc mesenteroides

<400> SEQUENCE: 15

Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
                20                  25                  30

Asn Pro Leu Phe Ser Val Thr Asn Thr Pro Ile Lys Ala Glu Asp Val
            35                  40                  45

Lys Val Lys Pro Ile Gly His Trp Gly Thr Ile Ser Gly Gln Thr Phe
        50                  55                  60

Leu Tyr Ala His Ala Asn Arg Leu Ile Asn Lys Tyr Gly Leu Asn Met
65                  70                  75                  80

Phe Tyr Val Gly Gly Pro Gly His Gly Gly Gln Val Met Val Thr Asn
                85                  90                  95

Ala Tyr Leu Asp Gly Ala Tyr Thr Glu Asp Tyr Pro Glu Ile Thr Gln
            100                 105                 110
```

-continued

```
Asp Ile Glu Gly Met Ser His Leu Phe Lys Arg Phe Ser Phe Pro Gly
            115                 120                 125
Gly Ile Gly Ser His Met Thr Ala Gln Thr Pro Gly Ser Leu His Glu
        130                 135                 140
Gly Gly Glu Leu Gly Tyr Ser Leu Ser His Ala Phe Gly Ala Val Leu
145                 150                 155                 160
Asp Asn Pro Asp Gln Val Ala Phe Ala Val Val Gly Asp Gly Glu Ala
                165                 170                 175
Glu Thr Gly Pro Ser Met Ala Ser Trp His Ser Ile Lys Phe Leu Asn
            180                 185                 190
Ala Lys Asn Asp Gly Ala Val Leu Pro Val Leu Asp Leu Asn Gly Phe
        195                 200                 205
Lys Ile Ser Asn Pro Thr Ile Phe Ser Arg Met Ser Asp Glu Glu Ile
210                 215                 220
Thr Lys Phe Phe Glu Gly Leu Gly Tyr Ser Pro Arg Phe Ile Glu Asn
225                 230                 235                 240
Asp Asp Ile His Asp Tyr Ala Thr Tyr His Gln Leu Ala Ala Asn Ile
                245                 250                 255
Leu Asp Gln Ala Ile Glu Asp Ile Gln Ala Ile Gln Asn Asp Ala Arg
            260                 265                 270
Glu Asn Gly Lys Tyr Gln Asp Gly Glu Ile Pro Ala Trp Pro Val Ile
        275                 280                 285
Ile Ala Arg Leu Pro Lys Gly Trp Gly Gly Pro Thr His Asp Ala Ser
290                 295                 300
Asn Asn Pro Ile Glu Asn Ser Phe Arg Ala His Gln Val Pro Leu Pro
305                 310                 315                 320
Leu Glu Gln His Asp Leu Ala Thr Leu Pro Glu Phe Glu Asp Trp Met
                325                 330                 335
Asn Ser Tyr Lys Pro Glu Glu Leu Phe Asn Ala Asp Gly Ser Leu Lys
            340                 345                 350
Asp Glu Leu Lys Ala Ile Ala Pro Lys Gly Asp Lys Arg Met Ser Ala
        355                 360                 365
Asn Pro Ile Thr Asn Gly Gly Ala Asp Arg Ser Asp Leu Lys Leu Pro
370                 375                 380
Asn Trp Arg Glu Phe Ala Asn Asp Ile Asn Asp Asp Thr Arg Gly Lys
385                 390                 395                 400
Glu Phe Ala Asp Ser Lys Arg Asn Met Asp Met Ala Thr Leu Ser Asn
                405                 410                 415
Tyr Leu Gly Ala Val Ser Gln Leu Asn Pro Thr Arg Phe Arg Phe Phe
            420                 425                 430
Gly Pro Asp Glu Thr Met Ser Asn Arg Leu Trp Gly Leu Phe Asn Val
        435                 440                 445
Thr Pro Arg Gln Trp Met Glu Glu Ile Lys Glu Pro Gln Asp Gln Leu
450                 455                 460
Leu Ser Pro Thr Gly Arg Ile Ile Asp Ser Gln Leu Ser Glu His Gln
465                 470                 475                 480
Ala Glu Gly Trp Leu Glu Gly Tyr Thr Leu Thr Gly Arg Val Gly Ile
                485                 490                 495
Phe Ala Ser Tyr Glu Ser Phe Leu Arg Val Val Asp Thr Met Val Thr
            500                 505                 510
Gln His Phe Lys Trp Leu Arg His Ala Ser Glu Gln Ala Trp Arg Asn
        515                 520                 525
Asp Tyr Pro Ser Leu Asn Leu Ile Ala Thr Ser Thr Ala Phe Gln Gln
```

```
               530                 535                 540
Asp His Asn Gly Tyr Thr His Gln Asp Pro Gly Met Leu Thr His Leu
545                 550                 555                 560

Ala Glu Lys Lys Ser Asn Phe Ile Arg Glu Tyr Leu Pro Ala Asp Gly
                565                 570                 575

Asn Ser Leu Leu Ala Val Gln Glu Arg Ala Phe Ser Glu Arg His Lys
            580                 585                 590

Val Asn Leu Leu Ile Ala Ser Lys Gln Pro Arg Gln Gln Trp Phe Thr
        595                 600                 605

Val Glu Glu Ala Glu Val Leu Ala Asn Glu Gly Leu Lys Ile Ile Asp
    610                 615                 620

Trp Ala Ser Thr Ala Pro Ser Ser Asp Val Asp Ile Thr Phe Ala Ser
625                 630                 635                 640

Ala Gly Thr Glu Pro Thr Ile Glu Thr Leu Ala Ala Leu Trp Leu Ile
                645                 650                 655

Asn Gln Ala Phe Pro Asp Val Lys Phe Arg Tyr Val Asn Val Val Glu
            660                 665                 670

Leu Leu Arg Leu Gln Lys Lys Ser Glu Pro Asn Met Asn Asp Glu Arg
        675                 680                 685

Glu Leu Ser Ala Glu Glu Phe Asn Lys Tyr Phe Gln Ala Asp Thr Pro
    690                 695                 700

Val Ile Phe Gly Phe His Ala Tyr Glu Asn Leu Ile Glu Ser Phe Phe
705                 710                 715                 720

Phe Glu Arg Lys Phe Thr Gly Asp Val Tyr Val His Gly Tyr Arg Glu
                725                 730                 735

Asp Gly Asp Ile Thr Thr Thr Tyr Asp Met Arg Val Tyr Ser His Leu
            740                 745                 750

Asp Arg Phe His Gln Ala Lys Glu Ala Ala Glu Ile Leu Ser Ala Asn
        755                 760                 765

Gly Lys Ile Asp Gln Ala Ala Ala Asp Thr Phe Ile Ala Lys Met Asp
    770                 775                 780

Asp Thr Leu Ala Lys His Phe Gln Val Thr Arg Asn Glu Gly Arg Asp
785                 790                 795                 800

Ile Glu Glu Phe Thr Asp Trp Thr Trp Ser Pro Leu Lys
                805                 810

<210> SEQ ID NO 16
<211> LENGTH: 794
<212> TYPE: PRT
<213> ORGANISM: Streptococcus gordonii

<400> SEQUENCE: 16

Met Thr Thr Asp Tyr Asn Ser Lys Ala Tyr Leu Glu Lys Val Asp Ala
1               5                   10                  15

Trp Trp Arg Ala Ala Asn Tyr Ile Ser Ala Ala Gln Met Tyr Leu Lys
                20                  25                  30

Asp Asn Pro Leu Leu Lys Arg Asp Val Val Ala Asn Asp Leu Lys Ala
            35                  40                  45

His Pro Ile Gly His Trp Gly Thr Val Pro Gly Gln Asn Phe Ile Tyr
        50                  55                  60

Ala His Leu Asn Arg Thr Ile Asn Lys Tyr Asp Leu Asp Met Phe Tyr
65                  70                  75                  80

Ile Glu Gly Pro Gly His Gly Gly Gln Val Met Val Ser Asn Ser Tyr
                85                  90                  95
```

```
Leu Asp Gly Ser Tyr Thr Glu Leu Asn Pro Asn Ile Pro Gln Asn Glu
                100                 105                 110

Glu Gly Phe Lys His Leu Cys Lys Ile Phe Ser Phe Pro Gly Gly Ile
            115                 120                 125

Ala Ser His Ala Ala Pro Glu Thr Pro Gly Ser Ile His Glu Gly Gly
        130                 135                 140

Glu Leu Gly Tyr Ala Leu Ser His Ala Ala Gly Ala Ile Leu Asp Asn
145                 150                 155                 160

Pro Asp Val Ile Ala Ala Thr Val Ile Gly Asp Gly Glu Gly Glu Thr
                165                 170                 175

Gly Pro Leu Met Ala Gly Trp Leu Ser Asn Thr Phe Ile Asn Pro Val
            180                 185                 190

Asn Asp Gly Ala Ile Leu Pro Ile Phe Tyr Leu Asn Gly Gly Lys Ile
        195                 200                 205

His Asn Pro Thr Ile Phe Glu Arg Lys Thr Asp Glu Glu Leu Thr Leu
    210                 215                 220

Phe Phe Glu Gly Leu Gly Trp Lys Pro Ile Phe Ala Asp Val Thr Ala
225                 230                 235                 240

Ile Ser Glu Asn His Glu Ala Ala His Ala Leu Phe Ala Ala Lys Leu
                245                 250                 255

Asp Glu Ala Ile Glu Glu Ile Lys Lys Val Gln Ala Glu Ala Arg Lys
            260                 265                 270

Gly Ser Ala Glu Glu Ala Thr Gln Ala Ile Phe Pro Val Leu Val Ala
        275                 280                 285

Arg Ile Pro Lys Gly Trp Thr Gly Pro Lys Ser Trp Glu Gly Thr Pro
    290                 295                 300

Ile Glu Gly Gly Phe Arg Ala His Gln Val Pro Ile Pro Val Asp Ala
305                 310                 315                 320

His His Met Glu His Val Asp Ala Leu Leu Asn Trp Leu Lys Ser Tyr
                325                 330                 335

Arg Pro Glu Glu Leu Phe Asp Glu Ser Gly Lys Val Leu Pro Glu Ile
            340                 345                 350

Ala Ala Ile Gly Pro Lys Gly Asp Arg Arg Met Ala Met Asn Pro Ile
        355                 360                 365

Thr Asn Ala Gly Val Ile Lys Pro Met Asp Thr Ala Asp Trp Lys Lys
    370                 375                 380

His Ala Leu Lys Phe Gly Thr Pro Gly Glu Ile Val Ala Gln Asp Met
385                 390                 395                 400

Ile Glu Phe Gly Lys Tyr Ala Thr Asp Leu Val Asp Ala Asn Pro Asp
                405                 410                 415

Asn Phe Arg Ile Phe Gly Pro Asp Glu Thr Lys Ser Asn Arg Leu Gln
            420                 425                 430

Glu Val Phe Thr Arg Thr Ser Arg Gln Trp Leu Gly Arg Met Arg Pro
        435                 440                 445

Glu Tyr Asp Glu Ala Leu Ser Pro Ala Gly Arg Val Ile Asp Ser Gln
    450                 455                 460

Leu Ser Glu His Gln Ala Glu Gly Met Leu Glu Gly Tyr Val Leu Thr
465                 470                 475                 480

Gly Arg His Gly Phe Ala Ser Tyr Glu Ser Phe Leu Arg Val Val
                485                 490                 495

Asp Ser Met Val Thr Gln His Phe Lys Trp Leu Arg Lys Cys Lys Thr
            500                 505                 510

His Thr Thr Trp Arg Lys Asn Tyr Pro Ala Leu Asn Leu Ile Ala Thr
```

```
            515                 520                 525
Ser Thr Val Phe Gln Gln Asp His Asn Gly Tyr Thr His Gln Asp Pro
530                 535                 540

Gly Ile Leu Thr His Leu Ala Glu Lys Thr Pro Glu Phe Ile Arg Glu
545                 550                 555                 560

Tyr Leu Pro Ala Asp Thr Asn Ser Leu Leu Ala Val Met Asp Lys Ala
                565                 570                 575

Phe Lys Ala Glu Asp Lys Val Asn Leu Ile Val Thr Ser Lys His Pro
                580                 585                 590

Arg Pro Gln Phe Tyr Ser Ala Glu Ala Glu Glu Leu Val Arg Glu
                595                 600                 605

Gly Tyr Lys Val Ile Asp Trp Ala Ser Thr Val Ser Asn Asn Glu Glu
610                 615                 620

Pro Asp Val Val Phe Ala Ala Ala Gly Thr Glu Pro Asn Leu Glu Ala
625                 630                 635                 640

Leu Ala Ala Val Ser Ile Leu His Lys Ala Phe Pro Glu Leu Lys Ile
                645                 650                 655

Arg Phe Val Asn Val Val Asp Ile Leu Lys Leu Arg His Pro Ser Val
                660                 665                 670

Asp Ala Arg Gly Leu Ser Asp Glu Glu Phe Asp Gln Val Phe Thr Thr
                675                 680                 685

Asp Lys Pro Val Ile Phe Ala Phe His Gly Tyr Glu Gly Met Ile Arg
                690                 695                 700

Asp Ile Phe Phe Asn Arg His Asn His Asn Leu Arg Val His Gly Tyr
705                 710                 715                 720

Arg Glu Asn Gly Asp Ile Thr Thr Pro Phe Asp Met Arg Val Met Ser
                725                 730                 735

Glu Leu Asp Arg Phe His Leu Ala Gln Asp Ala Ala Asn Ala Ala Leu
                740                 745                 750

Gly Glu Asp Ala Ala Val Phe Ser Ala Lys Met Asp Glu Thr Val Ala
                755                 760                 765

Tyr His Asn Ala Tyr Ile Arg Glu Asn Gly Asp Asp Ile Pro Glu Val
                770                 775                 780

Gln Asn Trp Lys Trp Glu Asn Ile Asn Lys
785                 790

<210> SEQ ID NO 17
<211> LENGTH: 796
<212> TYPE: PRT
<213> ORGANISM: Clostridium acetobutylicum

<400> SEQUENCE: 17

Met Gln Ser Ile Ile Gly Lys His Lys Asp Glu Gly Lys Ile Thr Pro
1               5                   10                  15

Glu Tyr Leu Lys Lys Ile Asp Ala Tyr Trp Arg Ala Ala Asn Phe Ile
                20                  25                  30

Ser Val Gly Gln Leu Tyr Leu Asp Asn Pro Leu Leu Arg Glu Pro
                35                  40                  45

Leu Lys Pro Glu His Leu Lys Arg Lys Val Val Gly His Trp Gly Thr
                50                  55                  60

Ile Pro Gly Gln Asn Phe Ile Tyr Ala His Leu Asn Arg Val Ile Lys
65                  70                  75                  80

Lys Tyr Asp Leu Asp Met Ile Tyr Val Ser Gly Pro Gly His Gly Gly
                85                  90                  95
```

```
Gln Val Met Val Ser Asn Ser Tyr Leu Asp Gly Thr Tyr Ser Glu Val
                100                 105                 110

Tyr Pro Asn Val Ser Arg Asp Leu Asn Gly Leu Lys Lys Leu Cys Lys
            115                 120                 125

Gln Phe Ser Phe Pro Gly Gly Ile Ser Ser His Met Ala Pro Glu Thr
        130                 135                 140

Pro Gly Ser Ile Asn Glu Gly Glu Leu Gly Tyr Ser Leu Ala His
145                 150                 155                 160

Ser Phe Gly Ala Val Phe Asp Asn Pro Asp Leu Ile Thr Ala Cys Val
                165                 170                 175

Val Gly Asp Gly Glu Ala Glu Thr Gly Pro Leu Ala Thr Ser Trp Gln
            180                 185                 190

Ala Asn Lys Phe Leu Asn Pro Val Thr Asp Gly Ala Val Leu Pro Ile
        195                 200                 205

Leu His Leu Asn Gly Tyr Lys Ile Ser Asn Pro Thr Val Leu Ser Arg
    210                 215                 220

Ile Pro Lys Asp Glu Leu Glu Lys Phe Glu Gly Asn Gly Trp Lys
225                 230                 235                 240

Pro Tyr Phe Val Glu Gly Glu Asp Pro Glu Thr Met His Lys Leu Met
                245                 250                 255

Ala Glu Thr Leu Asp Ile Val Thr Glu Glu Ile Leu Asn Ile Gln Lys
            260                 265                 270

Asn Ala Arg Glu Asn Asn Asp Cys Ser Arg Pro Lys Trp Pro Met Ile
        275                 280                 285

Val Leu Arg Thr Pro Lys Gly Trp Thr Gly Pro Lys Phe Val Asp Gly
    290                 295                 300

Val Pro Asn Glu Gly Ser Phe Arg Ala His Gln Val Pro Leu Ala Val
305                 310                 315                 320

Asp Arg Tyr His Thr Glu Asn Leu Asp Gln Leu Glu Glu Trp Leu Lys
                325                 330                 335

Ser Tyr Lys Pro Glu Glu Leu Phe Asp Glu Asn Tyr Arg Leu Ile Pro
            340                 345                 350

Glu Leu Glu Glu Leu Thr Pro Lys Gly Asn Lys Arg Met Ala Ala Asn
        355                 360                 365

Leu His Ala Asn Gly Gly Leu Leu Arg Glu Leu Arg Thr Pro Asp
    370                 375                 380

Phe Arg Asp Tyr Ala Val Asp Val Pro Thr Pro Gly Ser Thr Val Lys
385                 390                 395                 400

Gln Asp Met Ile Glu Leu Gly Lys Tyr Val Arg Asp Val Val Lys Leu
                405                 410                 415

Asn Glu Asp Thr Arg Asn Phe Arg Ile Phe Gly Pro Asp Glu Thr Met
            420                 425                 430

Ser Asn Arg Leu Trp Ala Val Phe Glu Gly Thr Lys Arg Gln Trp Leu
        435                 440                 445

Ser Glu Ile Lys Glu Pro Asn Asp Glu Phe Leu Ser Asn Asp Gly Arg
    450                 455                 460

Ile Val Asp Ser Met Leu Ser Glu His Leu Cys Glu Gly Trp Leu Glu
465                 470                 475                 480

Gly Tyr Leu Leu Thr Gly Arg His Gly Phe Ala Ser Tyr Glu Ala
                485                 490                 495

Phe Leu Arg Ile Val Asp Ser Met Ile Thr Gln His Gly Lys Trp Leu
            500                 505                 510

Lys Val Thr Ser Gln Leu Pro Trp Arg Lys Asp Ile Ala Ser Leu Asn
```

```
            515                 520                 525
Leu Ile Ala Thr Ser Asn Val Trp Gln Gln Asp His Asn Gly Tyr Thr
            530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
                565                 570                 575

Phe Asp Lys Cys Leu His Thr Lys His Lys Ile Asn Leu Leu Val Thr
            580                 585                 590

Ser Lys His Pro Arg Gln Gln Trp Leu Thr Met Asp Gln Ala Val Lys
        595                 600                 605

His Val Glu Gln Gly Ile Ser Ile Trp Asp Trp Ala Ser Asn Asp Lys
    610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                645                 650                 655

Leu Lys Val Arg Phe Val Asn Val Val Asp Met Met Lys Leu Leu Pro
            660                 665                 670

Glu Asn Glu His Pro His Gly Leu Ser Asp Lys Asp Tyr Asn Ala Leu
        675                 680                 685

Phe Thr Thr Asp Lys Pro Val Ile Phe Ala Phe His Gly Phe Ala His
    690                 695                 700

Leu Ile Asn Gln Leu Thr Tyr His Arg Glu Asn Arg Asn Leu His Val
705                 710                 715                 720

His Gly Tyr Met Glu Glu Gly Thr Ile Thr Thr Pro Phe Asp Met Arg
                725                 730                 735

Val Gln Asn Lys Leu Asp Arg Phe Asn Leu Val Lys Asp Val Val Glu
            740                 745                 750

Asn Leu Pro Gln Leu Gly Asn Arg Gly Ala His Leu Val Gln Leu Met
        755                 760                 765

Asn Asp Lys Leu Val Glu His Asn Gln Tyr Ile Arg Glu Val Gly Glu
    770                 775                 780

Asp Leu Pro Glu Ile Thr Asn Trp Gln Trp His Val
785                 790                 795

<210> SEQ ID NO 18
<211> LENGTH: 791
<212> TYPE: PRT
<213> ORGANISM: Clostridium butyricum

<400> SEQUENCE: 18

Met Thr Asn Ile Asn Tyr Ser Ser Glu Ser Tyr Leu Lys Lys Val Asp
1               5                   10                  15

Ala Tyr Trp Arg Ala Thr Asn Tyr Ile Ser Val Gly Gln Leu Tyr Leu
            20                  25                  30

Lys Gly Asn Pro Leu Leu Arg Glu Pro Leu Lys Pro Glu His Val Lys
        35                  40                  45

Asn Ala Val Phe Gly His Trp Gly Thr Ile Ala Gly Gln Asn Phe Ile
    50                  55                  60

Tyr Ala His Leu Asn Arg Val Ile Asn Lys Tyr Asp Leu Ser Met Leu
65                  70                  75                  80

Tyr Ile Ser Gly Pro Gly His Gly Gly Gln Val Met Val Ser Asn Ser
                85                  90                  95
```

```
Tyr Leu Asp Gly Ser Tyr Ser Glu Val Tyr Pro Glu Ile Thr Gln Asp
                100                 105                 110

Leu Glu Gly Leu Ser Lys Leu Tyr Lys Gln Phe Ser Phe Ser Gly Gly
            115                 120                 125

Ile Gly Ser His Ala Thr Pro Gln Ala Pro Gly Ser Ile His Glu Gly
        130                 135                 140

Gly Glu Leu Gly Tyr Ser Leu Val His Gly Phe Gly Ala Ile Leu Asp
145                 150                 155                 160

Asn Pro Asp Leu Ile Ala Thr Val Val Gly Asp Gly Glu Ala Glu
                165                 170                 175

Thr Gly Pro Leu Ala Thr Ser Trp Gln Leu Asn Lys Phe Ile Asn Pro
                180                 185                 190

Val Thr Asp Gly Val Val Leu Pro Ile Leu Tyr Leu Asn Gly Phe Lys
            195                 200                 205

Ile Ser Asn Pro Thr Ile Met Ala Lys Met Thr Asp Glu Glu Leu Gln
        210                 215                 220

Lys Tyr Phe Glu Gly Leu Gly Trp Asp Pro Ile Phe Val Glu Gly Asp
225                 230                 235                 240

Glu Pro Glu Val Met His Gln Leu Met Ala Glu Lys Met Asp Glu Ala
                245                 250                 255

Ile Glu Lys Ile Leu Thr Ile Lys Lys Arg Ala Val Glu Glu Asn Asp
            260                 265                 270

Met Ser Arg Pro Lys Trp Pro Val Ile Leu Asn Arg Thr Pro Lys Gly
        275                 280                 285

Trp Thr Gly Pro Lys Glu Leu Asp Gly Lys Pro Ile Glu Gly Ser Phe
290                 295                 300

Arg Ala His Gln Val Pro Ile Pro Phe Asp Ser Lys His Met Glu Cys
305                 310                 315                 320

Ala Asp Asp Phe Val Lys Trp Met Asn Thr Tyr Gly Pro Glu Glu Leu
                325                 330                 335

Phe Thr Glu Asp Gly Lys Leu Val Glu Glu Ile Ala Glu Ile Ile Pro
            340                 345                 350

Lys Gly Asp Arg Arg Met Ser Cys Asn Pro Ala Thr Asn Gly Gly Lys
        355                 360                 365

Ile Met Lys Gly Leu Arg Leu Pro Asp Tyr Arg Glu Tyr Ala Ile Asp
370                 375                 380

Asn Lys Glu Lys Gly Lys Asn Val Ala Gln Asp Met Leu Ile Leu Gly
385                 390                 395                 400

Lys Tyr Val Arg Asp Val Met Lys Leu Asn Asp Lys Glu Arg Asn Phe
                405                 410                 415

Arg Val Phe Ser Pro Asp Glu Ala Ser Asn Arg Leu Tyr Ala Met
            420                 425                 430

Phe Glu Glu Thr Lys Arg Gln Trp Val Gly Glu Ile Asp Glu Pro Tyr
        435                 440                 445

Asp Glu Phe Leu Ala Pro Asp Gly Arg Ile Leu Asp Ser Met Leu Ser
450                 455                 460

Glu His Ile Ala Glu Gly Ala Leu Glu Ala Tyr Leu Leu Thr Gly Arg
465                 470                 475                 480

His Gly Phe Ile His Ser Tyr Glu Ser Phe Leu Arg Val Val Asp Ser
                485                 490                 495

Met Ile Thr Gln His Phe Lys Trp Leu Asn Gln Cys Glu Asp Ile Pro
            500                 505                 510

Trp Arg Ala Asp Ile Pro Ser Leu Asn Leu Ile Asn Thr Ser His Ile
```

```
        515                 520                 525

Trp Gln Gln Asp His Asn Gly Tyr Thr His Gln Asp Pro Gly Met Leu
    530                 535                 540

Gly His Leu Ala Asp Lys Asn Ser Gly Leu Ile His Glu Tyr Leu Pro
545                 550                 555                 560

Ala Asp Ala Asn Thr Leu Leu Val Thr Phe Asp Lys Cys Ile Arg Ser
                565                 570                 575

Ile Asn Gln Val Asn Val Met Thr Ala Ser Lys His Pro Arg Gln Gln
            580                 585                 590

Trp Phe Thr Ile Glu Glu Ala Glu Tyr Leu Val Asn Lys Gly Leu Gly
        595                 600                 605

Ile Val Asp Trp Ala Ser Thr Asp Lys Asn Gly Glu Thr Asp Ile Val
    610                 615                 620

Phe Ala Met Ala Gly Asp Thr Pro Thr Leu Glu Gly Leu Ala Ala Val
625                 630                 635                 640

Gln Leu Leu His Asp Tyr Leu Pro Asp Leu Lys Ile Arg Phe Val Asn
                645                 650                 655

Ile Val Asp Leu Leu Lys Leu Gln Ser Pro Glu Val Tyr Glu His Gly
            660                 665                 670

Ile Ser Asp Glu Glu Phe Asn Met Ile Phe Thr Lys Asp Lys Pro Ile
        675                 680                 685

Ile Phe Gly Phe His Gly Tyr Glu Asn Leu Val Asp Thr Leu Phe Phe
    690                 695                 700

Lys Arg Asp Asn His Asn Val Ser Val His Gly Tyr Arg Asp Lys Gly
705                 710                 715                 720

Glu Ile Thr Thr Gly Phe Asp Met Arg Val Met Asn Glu Leu Asp Arg
                725                 730                 735

Phe Asn Leu Val Lys Asp Ala Ile Tyr His Leu Pro Gln Leu Ala Asn
            740                 745                 750

Lys Gly Ala His Ile Ile Arg Glu Met Asn Glu Lys Leu Glu Ile His
        755                 760                 765

Thr Lys Phe Val His Glu Asn Gly Ile Asp Leu Pro Glu Ile Ala Asn
    770                 775                 780

Trp Arg Trp Lys Gly Leu Lys
785                 790

<210> SEQ ID NO 19
<211> LENGTH: 795
<212> TYPE: PRT
<213> ORGANISM: Mycoplasma agalactiae

<400> SEQUENCE: 19

Met Lys Lys Ser His Asp Phe Asp Ser Lys Glu Tyr Leu Asn Leu Val
1               5                   10                  15

Asp Ala Trp Trp Arg Ala Ala Asn Tyr Leu Ser Val Gly Gln Met Tyr
            20                  25                  30

Leu Arg Asn Asn Pro Leu Leu Lys Ile Pro Leu Thr Ser Asn Asp Val
        35                  40                  45

Lys Ile Tyr Pro Ile Gly His Trp Gly Thr Val Pro Gly Gln Asn Phe
    50                  55                  60

Ile Tyr Ala His Leu Asn Arg Ile Ile Asn Lys Tyr Asp Leu Asn Met
65                  70                  75                  80

Phe Phe Ile Ser Gly Pro Gly His Gly Gly Gln Val Ile Ala Ser Asn
                85                  90                  95
```

```
Thr Tyr Leu Asp Gly Ser Tyr Thr Glu Leu Phe Pro His Val Thr Lys
                100                 105                 110

Asp Ile Lys Gly Met Thr His Leu Phe Lys Tyr Phe Ser Phe Pro Gly
            115                 120                 125

Gly Thr Ala Ser His Ala Ala Pro Glu Cys Pro Gly Ser Ile His Glu
        130                 135                 140

Gly Gly Glu Leu Gly Tyr Ser Leu Ser His Ala Ala Gly Ala Val Leu
145                 150                 155                 160

Asp Asn Pro Asp Val Ile Ala Ala Thr Val Ile Gly Asp Gly Glu Ser
                165                 170                 175

Glu Thr Gly Pro Leu Ser Ala Gly Trp Phe Ile Asn Ser Phe Ile Asn
                180                 185                 190

Pro Ala Asn Asp Gly Ala Val Leu Pro Ile Leu His Val Asn Gly Gly
            195                 200                 205

Lys Ile Ser Asn Pro Thr Ile Trp Ser Arg Arg Ser Asn Glu Glu Leu
        210                 215                 220

Val Ser Tyr Phe Thr Gly Ala Gly Trp Lys Pro Phe Ile Val Glu Gly
225                 230                 235                 240

Asn Glu Pro Glu Tyr Met His His Glu Met Ala Lys Ala Leu Asp Ala
                245                 250                 255

Ser Val Glu Leu Ile Lys Gln Tyr Gln Ala Glu Ala Arg Lys Asn Gly
                260                 265                 270

Ala Asn Lys Ala Lys Arg Pro Gln Trp Pro Met Ile Val Leu Lys Ser
            275                 280                 285

Pro Lys Gly Trp Thr Gly Pro Lys Glu Trp Asn His Glu Ala Ile Glu
290                 295                 300

Gly Ser Phe Arg Ala His Gln Val Pro Val Pro Val Ser Ala Glu Lys
305                 310                 315                 320

Met Gln His Ile Asp Ala Leu Glu Asn Trp Leu Arg Ser Tyr Arg Pro
                325                 330                 335

Glu Glu Leu Phe Asp Glu Asn Ala Gln Leu Lys Pro Glu Ile Ala Ala
                340                 345                 350

Ile Ala Pro Lys Gly Asp Arg Arg Met Gly Lys Asn Pro Ile Ala Asn
            355                 360                 365

Gly Gly Ile Asn Pro Arg Ala Ile Asn Val Gly Asp Trp Thr Lys Phe
        370                 375                 380

Ala Leu Asp Ile Lys Gln Pro Gly Lys Val Ile Asn Gln Asp Met Val
385                 390                 395                 400

Thr Leu Gly Ser Tyr Leu Gly Glu Leu Ser Leu Leu Asn Lys Asp Asn
                405                 410                 415

Phe Arg Val Trp Gly Pro Asp Glu His Lys Ser Asn Arg Leu Tyr Glu
                420                 425                 430

Met Phe Lys Val Thr Asp Arg Gln Trp Leu Asp Arg Ile Asp Glu Lys
            435                 440                 445

Tyr Asp Glu Phe Leu Ser Ser Val Gly Arg Ile Ile Asp Ser Gln Leu
        450                 455                 460

Ser Glu His Gln Ala Glu Gly Met Leu Glu Gly Tyr Val Leu Thr Gly
465                 470                 475                 480

Arg His Gly Val Phe Ala Ser Tyr Glu Ser Phe Leu Arg Val Val Asp
                485                 490                 495

Ser Met Leu Thr Gln His Met Lys Trp Val Lys Lys Ala Leu Asp Ile
                500                 505                 510

Pro Trp Arg Asn Asp Tyr Pro Ser Leu Asn Val Ile Ala Thr Ser Asn
```

```
            515                 520                 525
Ala Phe Gln Gln Asp His Asn Gly Tyr Thr His Gln Asp Pro Gly Leu
    530                 535                 540

Ile Gly His Leu Ala Asp Lys Arg Pro Glu Leu Ile Arg Glu Tyr Leu
545                 550                 555                 560

Pro Ala Asp Thr Asn Thr Leu Leu Ala Thr Met Ala Lys Ala Leu Gln
                565                 570                 575

Asp Arg Asn Val Ile Asn Leu Ile Ile Ser Ser Lys Gln Pro Arg His
            580                 585                 590

Gln Phe Phe Ser Ile Glu Glu Ala Thr Glu Leu Val Glu Lys Gly Ile
        595                 600                 605

Lys Ile Ile Asp Trp Ala Ser Asn Ile Lys Pro Asn Glu Glu Pro Asp
    610                 615                 620

Leu Val Val Ala Ala Ser Gly Thr Glu Ser Thr Ile Glu Ser Leu Ala
625                 630                 635                 640

Thr Ile Thr Tyr Leu Arg Ala His Phe Pro Glu Leu Lys Ile Arg Phe
                645                 650                 655

Val Asn Val Leu Asp Leu Leu Lys Leu Arg His Pro Ser Ile Asp Pro
            660                 665                 670

Arg Gly Leu Ser Asp Ser Glu Phe Asp Ser Ile Phe Thr Lys Asp Lys
        675                 680                 685

Pro Ile Leu Phe Ala Phe His Gly Tyr Glu Ala Ile Leu Arg Asp Ile
    690                 695                 700

Phe Phe Leu Arg Ser Asn His Asn Ile Ile Thr His Gly Tyr Arg Glu
705                 710                 715                 720

Asn Gly Asp Ile Thr Thr Ala Phe Asp Ile Arg Leu Leu Ser Glu Met
                725                 730                 735

Asp Arg Phe His Met Thr Ala Asn Val Ala Lys Lys Leu Ala Pro Val
            740                 745                 750

Val Gly Glu Ser Lys Ala Asn Glu Leu Val Lys Leu Met Gly Asp Lys
        755                 760                 765

Ile Lys Glu His Arg Ala Tyr Ile Lys Glu Tyr Gly Thr Asp Leu Pro
    770                 775                 780

Glu Val Lys Glu Trp Glu Trp Thr Pro Tyr Lys
785                 790                 795

<210> SEQ ID NO 20
<211> LENGTH: 323
<212> TYPE: PRT
<213> ORGANISM: Bacillus subtilis

<400> SEQUENCE: 20

Met Ala Asp Leu Phe Ser Thr Val Gln Glu Lys Val Ala Gly Lys Asp
1               5                   10                  15

Val Lys Ile Val Phe Pro Glu Gly Leu Asp Glu Arg Ile Leu Glu Ala
            20                  25                  30

Val Ser Lys Leu Ala Gly Asn Lys Val Leu Asn Pro Ile Val Ile Gly
        35                  40                  45

Asn Glu Asn Glu Ile Gln Ala Lys Ala Lys Glu Leu Asn Leu Thr Leu
    50                  55                  60

Gly Gly Val Lys Ile Tyr Asp Pro His Thr Tyr Glu Gly Met Glu Asp
65                  70                  75                  80

Leu Val Gln Ala Phe Val Glu Arg Arg Lys Gly Lys Ala Thr Glu Glu
                85                  90                  95
```

Gln Ala Arg Lys Ala Leu Leu Asp Glu Asn Tyr Phe Gly Thr Met Leu
            100                 105                 110

Val Tyr Lys Gly Leu Ala Asp Gly Leu Val Ser Gly Ala Ala His Ser
        115                 120                 125

Thr Ala Asp Thr Val Arg Pro Ala Leu Gln Ile Ile Lys Thr Lys Glu
    130                 135                 140

Gly Val Lys Lys Thr Ser Gly Val Phe Ile Met Ala Arg Gly Glu Glu
145                 150                 155                 160

Gln Tyr Val Phe Ala Asp Cys Ala Ile Asn Ile Ala Pro Asp Ser Gln
                165                 170                 175

Asp Leu Ala Glu Ile Ala Ile Glu Ser Ala Asn Thr Ala Lys Met Phe
            180                 185                 190

Asp Ile Glu Pro Arg Val Ala Met Leu Ser Phe Ser Thr Lys Gly Ser
        195                 200                 205

Ala Lys Ser Asp Glu Thr Glu Lys Val Ala Asp Ala Val Lys Ile Ala
    210                 215                 220

Lys Glu Lys Ala Pro Glu Leu Thr Leu Asp Gly Glu Phe Gln Phe Asp
225                 230                 235                 240

Ala Ala Phe Val Pro Ser Val Ala Glu Lys Lys Ala Pro Asp Ser Glu
                245                 250                 255

Ile Lys Gly Asp Ala Asn Val Phe Val Phe Pro Ser Leu Glu Ala Gly
            260                 265                 270

Asn Ile Gly Tyr Lys Ile Ala Gln Arg Leu Gly Asn Phe Glu Ala Val
        275                 280                 285

Gly Pro Ile Leu Gln Gly Leu Asn Met Pro Val Asn Asp Leu Ser Arg
    290                 295                 300

Gly Cys Asn Ala Glu Asp Val Tyr Asn Leu Ala Leu Ile Thr Ala Ala
305                 310                 315                 320

Gln Ala Leu

<210> SEQ ID NO 21
<211> LENGTH: 323
<212> TYPE: PRT
<213> ORGANISM: Bacillus amyloliquefaciens

<400> SEQUENCE: 21

Met Ala Asp Leu Phe Thr Lys Val Gln Glu Lys Val Ala Gly Lys Asp
1               5                   10                  15

Val Lys Ile Val Phe Pro Glu Gly Leu Asp Glu Arg Ile Leu Val Ala
            20                  25                  30

Val Asn Asn Leu Ala Gly Asn Lys Val Leu Lys Pro Ile Val Val Gly
        35                  40                  45

Asn Lys Glu Asp Ile Gln Ala Lys Ala Lys Glu Leu Asn Leu Thr Leu
    50                  55                  60

Asp Gly Val Asp Ile Phe Asp Pro His Thr Tyr Glu Gly Met Glu Glu
65                  70                  75                  80

Leu Val Gln Ala Phe Val Glu Arg Arg Lys Gly Lys Ala Thr Glu Glu
                85                  90                  95

Gln Ala Arg Lys Ala Leu Leu Asp Glu Asn Tyr Phe Gly Thr Met Leu
            100                 105                 110

Val Tyr Lys Gly Leu Ala Asp Gly Leu Val Ser Gly Ala Ala His Ser
        115                 120                 125

Thr Ala Asp Thr Val Arg Pro Ala Leu Gln Ile Ile Lys Thr Lys Glu
    130                 135                 140

```
Gly Val Lys Lys Thr Ser Gly Val Phe Ile Met Ala Arg Gly Asp Glu
145                 150                 155                 160

Gln Tyr Val Phe Ala Asp Cys Ala Ile Asn Ile Ala Pro Asp Ser Gln
                165                 170                 175

Asp Leu Ala Glu Ile Ala Ile Glu Ser Ala Asn Thr Ala Gln Met Phe
            180                 185                 190

Asp Ile Asp Pro Arg Val Ala Met Leu Ser Phe Ser Thr Lys Gly Ser
        195                 200                 205

Ala Lys Ser Asp Glu Thr Asp Lys Val Ala Glu Ala Val Lys Ile Ala
    210                 215                 220

Lys Glu Lys Ala Pro Glu Leu Thr Leu Asp Gly Glu Phe Gln Phe Asp
225                 230                 235                 240

Ala Ala Phe Val Pro Ser Val Ala Glu Lys Lys Ala Pro Asp Ser Asp
                245                 250                 255

Ile Lys Gly Asp Ala Asn Val Phe Val Phe Pro Ser Leu Glu Ala Gly
            260                 265                 270

Asn Ile Gly Tyr Lys Ile Ala Gln Arg Leu Gly Phe Glu Ala Val
        275                 280                 285

Gly Pro Ile Leu Gln Gly Leu Asn Met Pro Val Asn Asp Leu Ser Arg
    290                 295                 300

Gly Cys Asn Ala Glu Asp Val Tyr Asn Leu Ala Leu Ile Thr Ala Ala
305                 310                 315                 320

Gln Ala Leu

<210> SEQ ID NO 22
<211> LENGTH: 323
<212> TYPE: PRT
<213> ORGANISM: Bacillus licheniformis

<400> SEQUENCE: 22

Met Ala Asp Leu Phe Thr Thr Val Gln Gly Lys Val Ala Gly Lys Gly
1               5                   10                  15

Val Lys Ile Val Phe Pro Glu Gly Leu Asp Glu Arg Ile Leu Thr Ala
                20                  25                  30

Val Asn Lys Leu Ala Gly Asn Asn Val Leu Lys Pro Ile Leu Val Gly
            35                  40                  45

Asn Glu Gln Glu Ile Lys Asp Lys Ala Asn Gly Leu Asn Leu Thr Leu
        50                  55                  60

Asp Gly Val Asp Ile Tyr Asp Pro His Thr Tyr Glu Gly Met Glu Asp
65                  70                  75                  80

Leu Val Gln Ala Phe Val Glu Arg Arg Lys Gly Lys Ala Thr Glu Glu
                85                  90                  95

Gln Ala Arg Gln Ile Leu Leu Asp Glu Asn Tyr Phe Gly Thr Met Leu
            100                 105                 110

Val Tyr Lys Gly Leu Ala Asp Gly Leu Val Ser Gly Ala Ala His Ser
        115                 120                 125

Thr Ala Asp Thr Val Arg Pro Ala Leu Gln Ile Ile Lys Thr Lys Glu
    130                 135                 140

Gly Val Lys Lys Thr Ser Gly Val Phe Ile Met Ala Arg Gly Asp Glu
145                 150                 155                 160

Gln Tyr Val Phe Ala Asp Cys Ala Ile Asn Ile Ala Pro Asp Ser Gln
                165                 170                 175

Asp Leu Ala Glu Ile Ala Ile Glu Ser Ala Asn Thr Ala Lys Met Phe
            180                 185                 190
```

```
Asp Ile Glu Pro Arg Val Ala Met Leu Ser Phe Ser Thr Lys Gly Ser
            195                 200                 205

Ala Lys Ser Asp Glu Thr Glu Lys Val Ala Asn Ala Val Ala Ile Ala
            210                 215                 220

Lys Glu Lys Ala Pro Glu Leu Thr Leu Asp Gly Glu Phe Gln Phe Asp
225                 230                 235                 240

Ala Ala Phe Val Pro Ser Val Ala Glu Lys Lys Ala Pro Asp Ser Val
                245                 250                 255

Ile Lys Gly Asp Ala Asn Val Phe Val Phe Pro Ser Leu Glu Ala Gly
            260                 265                 270

Asn Ile Gly Tyr Lys Ile Ala Gln Arg Leu Gly Asn Phe Glu Ala Val
            275                 280                 285

Gly Pro Ile Leu Gln Gly Leu Asn Met Pro Val Asn Asp Leu Ser Arg
290                 295                 300

Gly Cys Asn Ala Glu Asp Val Tyr Asn Leu Ala Leu Ile Thr Ala Ala
305                 310                 315                 320

Gln Ala Leu

<210> SEQ ID NO 23
<211> LENGTH: 324
<212> TYPE: PRT
<213> ORGANISM: Geobacillus thermodenitrificans

<400> SEQUENCE: 23

Met Ala Asn Asp Leu Phe Thr Ala Leu Lys Glu Lys Val Val Gly Thr
1               5                   10                  15

Gly Arg Lys Ile Val Phe Pro Glu Gly Thr Asp Asp Arg Ile Leu Thr
            20                  25                  30

Ala Ala Ser Arg Leu Ala Ala Glu Gln Val Leu Leu Pro Ile Val Leu
            35                  40                  45

Gly Asp Glu Gln Ala Ile Lys Ala Arg Ala Ala Glu Leu Gly Leu Pro
        50                  55                  60

Phe Asp Gly Val Asp Ile Ile Asn Pro Arg Asp Tyr Ala Glu Phe Asp
65                  70                  75                  80

Gln Leu Val Ser Ala Phe Val Glu Arg Arg Lys Gly Lys Val Thr Glu
                85                  90                  95

Glu Ala Ala Arg Lys Leu Leu Leu Asp Glu Asn Tyr Phe Gly Thr Met
            100                 105                 110

Leu Val Tyr Thr Gly Ala Ala Asp Gly Leu Val Ser Gly Ala Ala His
            115                 120                 125

Ser Thr Ala Asp Thr Val Arg Pro Ala Leu Gln Ile Ile Lys Thr Lys
130                 135                 140

Pro Gly Val Arg Lys Thr Ser Gly Val Phe Ile Met Val Arg Gly Glu
145                 150                 155                 160

Glu Lys Tyr Val Phe Ala Asp Cys Ala Ile Asn Ile Ala Pro Asp Ser
                165                 170                 175

Gln Asp Leu Ala Glu Ile Ala Ile Glu Ser Ala Arg Thr Ala Ala Met
            180                 185                 190

Phe Gly Leu His Pro Arg Val Ala Met Leu Ser Phe Ser Thr Lys Gly
            195                 200                 205

Ser Ala Ser Ser Pro Glu Thr Glu Lys Val Ala Glu Ala Val Arg Leu
            210                 215                 220

Ala Lys Glu Met Ala Pro Asp Leu Val Leu Asp Gly Glu Phe Gln Phe
225                 230                 235                 240
```

```
Asp Ala Ala Phe Val Pro Glu Val Ala Lys Lys Ala Pro Asp Ser
            245                 250                 255

Val Ile Gln Gly Asp Ala Asn Val Phe Ile Phe Pro Ser Leu Glu Ala
        260                 265                 270

Gly Asn Ile Gly Tyr Lys Ile Ala Gln Arg Leu Gly Gly Phe Glu Ala
        275                 280                 285

Val Gly Pro Ile Leu Gln Gly Leu Asn Lys Pro Val Asn Asp Leu Ser
        290                 295                 300

Arg Gly Cys Ser Ala Glu Asp Ala Tyr Lys Leu Ala Leu Ile Thr Ala
305                 310                 315                 320

Ala Gln Ser Leu

<210> SEQ ID NO 24
<211> LENGTH: 325
<212> TYPE: PRT
<213> ORGANISM: Listeria innocua

<400> SEQUENCE: 24

Met Ser Glu Leu Phe Thr Thr Ile Lys Gly Gln Val Thr Gly Lys Asn
1               5                   10                  15

Val Arg Ile Val Leu Pro Glu Gly Thr Asp Glu Arg Ile Val Gly Ala
            20                  25                  30

Ala Ala Arg Leu Gln Lys Glu Asn Ile Val Thr Pro Ile Leu Leu Gly
        35                  40                  45

Asn Lys Ala Glu Ile Glu Ala Lys Ala Lys Glu Ile Gly Val Ser Val
    50                  55                  60

Glu Gly Ile Thr Ile His Asp Pro Ala Thr Asp Pro Leu Phe Asp Glu
65                  70                  75                  80

Leu Val Ala Ala Phe Val Glu Arg Arg Lys Gly Lys Ala Thr Glu Glu
                85                  90                  95

Ala Ala Arg Lys Met Leu Val Asp Pro Asn Tyr Phe Gly Thr Met Leu
            100                 105                 110

Val Tyr Thr Gly Lys Ala Glu Gly Leu Val Ser Gly Ala Ala His Ser
        115                 120                 125

Thr Gly Asp Thr Val Arg Pro Ala Leu Gln Ile Ile Lys Thr Lys Pro
130                 135                 140

Gly Val Ser Lys Val Ala Gly Ala Met Ile Met Val Arg Gly Glu Glu
145                 150                 155                 160

Arg Tyr Leu Phe Ser Asp Val Ala Ile Asn Ile Ala Pro Val Ala Ala
                165                 170                 175

Asp Leu Ala Glu Asn Ala Ile Val Ser Ala Glu Thr Ala Glu Ile Phe
            180                 185                 190

Gly Ile Asp Pro Arg Val Ala Met Leu Ser Phe Ser Thr Lys Gly Ser
        195                 200                 205

Ala Lys Ser Asp Glu Thr Glu Lys Val Val Glu Ala Thr Ala Leu Ala
    210                 215                 220

Lys Glu Lys Ala Pro Glu Leu Thr Leu Asp Gly Glu Phe Gln Phe Asp
225                 230                 235                 240

Ala Ala Phe Val Pro Thr Val Ala Glu Lys Lys Ala Pro Gly Ser Val
                245                 250                 255

Ile Lys Gly Asp Ala Asn Val Phe Ile Phe Pro Ser Leu Glu Ala Gly
            260                 265                 270

Asn Ile Gly Tyr Lys Ile Ala Gln Arg Leu Gly Asn Phe Glu Ala Val
        275                 280                 285
```

Gly Pro Ile Leu Gln Gly Leu Asn Ala Pro Val Asn Asp Leu Ser Arg
            290                 295                 300

Gly Cys Asn Thr Asp Asp Val Tyr Asn Leu Thr Leu Ile Thr Ala Ala
305                 310                 315                 320

Gln Ala Val Asn Lys
                325

<210> SEQ ID NO 25
<211> LENGTH: 328
<212> TYPE: PRT
<213> ORGANISM: Staphylococcus aureus

<400> SEQUENCE: 25

Met Ala Asp Leu Leu Asn Val Leu Lys Asp Lys Leu Ser Gly Lys Asn
1               5                   10                  15

Val Lys Ile Val Leu Pro Glu Gly Glu Asp Glu Arg Val Leu Thr Ala
                20                  25                  30

Ala Thr Gln Leu Gln Ala Thr Asp Tyr Val Thr Pro Ile Val Leu Gly
            35                  40                  45

Asp Glu Thr Lys Val Gln Ser Leu Ala Gln Lys Leu Asp Leu Asp Ile
        50                  55                  60

Ser Asn Ile Glu Leu Ile Asn Pro Ala Thr Ser Glu Leu Lys Ala Glu
65                  70                  75                  80

Leu Val Gln Ser Phe Val Glu Arg Arg Lys Gly Lys Ala Thr Glu Glu
                85                  90                  95

Gln Ala Gln Glu Leu Leu Asn Asn Val Asn Tyr Phe Gly Thr Met Leu
            100                 105                 110

Val Tyr Ala Gly Lys Ala Asp Gly Leu Val Ser Gly Ala Ala His Ser
        115                 120                 125

Thr Gly Asp Thr Val Arg Pro Ala Leu Gln Ile Ile Lys Thr Lys Pro
130                 135                 140

Gly Val Ser Arg Thr Ser Gly Ile Phe Phe Met Ile Lys Gly Asp Glu
145                 150                 155                 160

Gln Tyr Ile Phe Gly Asp Cys Ala Ile Asn Pro Glu Leu Asp Ser Gln
                165                 170                 175

Gly Leu Ala Glu Ile Ala Val Glu Ser Ala Lys Ser Ala Leu Ser Phe
            180                 185                 190

Gly Met Asp Pro Lys Val Ala Met Leu Ser Phe Ser Thr Lys Gly Ser
        195                 200                 205

Ala Lys Ser Asp Asp Val Thr Lys Val Gln Glu Ala Val Lys Leu Ala
210                 215                 220

Gln Gln Lys Ala Glu Glu Lys Leu Glu Ala Ile Ile Asp Gly Glu
225                 230                 235                 240

Phe Gln Phe Asp Ala Ala Ile Val Pro Gly Val Ala Glu Lys Lys Ala
                245                 250                 255

Pro Gly Ala Lys Leu Gln Gly Asp Ala Asn Val Phe Val Phe Pro Ser
            260                 265                 270

Leu Glu Ala Gly Asn Ile Gly Tyr Lys Ile Ala Gln Arg Leu Gly Gly
        275                 280                 285

Tyr Asp Ala Val Gly Pro Val Leu Gln Gly Leu Asn Ser Pro Val Asn
290                 295                 300

Asp Leu Ser Arg Gly Cys Ser Ile Glu Asp Val Tyr Asn Leu Ser Ile
305                 310                 315                 320

Ile Thr Ala Ala Gln Ala Leu Gln
                325

<210> SEQ ID NO 26
<211> LENGTH: 326
<212> TYPE: PRT
<213> ORGANISM: Lactococcus lactis

<400> SEQUENCE: 26

| Met | Glu | Leu | Phe | Glu | Ser | Leu | Lys | Gln | Lys | Ile | Ser | Gly | Lys | Asp | Leu |
|---|---|---|---|---|---|---|---|---|---|---|---|---|---|---|---|
| 1 | | | | 5 | | | | | 10 | | | | | 15 | |

| Lys | Ile | Val | Phe | Pro | Glu | Gly | Thr | Asp | Thr | Arg | Ile | Leu | Gly | Ala | Ala |
|---|---|---|---|---|---|---|---|---|---|---|---|---|---|---|---|
| | | | 20 | | | | | 25 | | | | | 30 | | |

| Asn | Arg | Leu | Asn | Ala | Asp | Gly | Leu | Ile | Thr | Pro | Val | Phe | Ile | Gly | Asn |
|---|---|---|---|---|---|---|---|---|---|---|---|---|---|---|---|
| | | 35 | | | | | 40 | | | | | 45 | | | |

| Val | Lys | Glu | Val | Thr | Glu | Thr | Leu | Ile | Ser | Arg | Gly | Ile | Asn | Pro | Glu |
|---|---|---|---|---|---|---|---|---|---|---|---|---|---|---|---|
| 50 | | | | | 55 | | | | | 60 | | | | | |

| Gly | Phe | Glu | Ile | Tyr | Asp | Pro | Glu | Asn | Cys | Gly | Arg | Phe | Glu | Thr | Met |
|---|---|---|---|---|---|---|---|---|---|---|---|---|---|---|---|
| 65 | | | | | 70 | | | | | 75 | | | | | 80 |

| Thr | Glu | Thr | Phe | Val | Glu | Arg | Arg | Lys | Gly | Lys | Val | Thr | Glu | Glu | Gln |
|---|---|---|---|---|---|---|---|---|---|---|---|---|---|---|---|
| | | | | 85 | | | | | 90 | | | | | 95 | |

| Ala | Lys | Glu | Ile | Leu | Lys | Asp | Pro | Asn | Tyr | Phe | Gly | Thr | Met | Leu | Val |
|---|---|---|---|---|---|---|---|---|---|---|---|---|---|---|---|
| | | | 100 | | | | | 105 | | | | | 110 | | |

| Tyr | Met | Gly | Ile | Ala | Asp | Gly | Met | Val | Ser | Gly | Ala | Ile | His | Ser | Thr |
|---|---|---|---|---|---|---|---|---|---|---|---|---|---|---|---|
| | | 115 | | | | | 120 | | | | | 125 | | | |

| Ala | Asp | Thr | Val | Arg | Pro | Ala | Leu | Gln | Ile | Ile | Lys | Thr | Lys | Pro | Gly |
|---|---|---|---|---|---|---|---|---|---|---|---|---|---|---|---|
| 130 | | | | | 135 | | | | | 140 | | | | | |

| Val | Lys | Ser | Val | Ser | Gly | Ala | Phe | Ile | Met | Val | Arg | Gly | Arg | Asp | Asp |
|---|---|---|---|---|---|---|---|---|---|---|---|---|---|---|---|
| 145 | | | | | 150 | | | | | 155 | | | | | 160 |

| Asn | Glu | Lys | Tyr | Ile | Phe | Gly | Asp | Cys | Ala | Ile | Asn | Ile | Lys | Pro | Asp |
|---|---|---|---|---|---|---|---|---|---|---|---|---|---|---|---|
| | | | | 165 | | | | | 170 | | | | | 175 | |

| Ala | Pro | Thr | Leu | Ala | Asp | Ile | Ala | Val | Ala | Ser | Ala | Glu | Thr | Ala | Arg |
|---|---|---|---|---|---|---|---|---|---|---|---|---|---|---|---|
| | | | 180 | | | | | 185 | | | | | 190 | | |

| Leu | Phe | Asp | Ile | Asp | Pro | Lys | Ile | Ala | Met | Leu | Ser | Phe | Ser | Thr | Lys |
|---|---|---|---|---|---|---|---|---|---|---|---|---|---|---|---|
| | | 195 | | | | | 200 | | | | | 205 | | | |

| Gly | Ser | Gly | Lys | Ser | Glu | Asp | Val | Asp | Lys | Val | Val | Glu | Ala | Thr | Thr |
|---|---|---|---|---|---|---|---|---|---|---|---|---|---|---|---|
| 210 | | | | | 215 | | | | | 220 | | | | | |

| Leu | Val | Lys | Glu | Gly | His | Pro | Glu | Val | Glu | Ile | Asp | Gly | Glu | Leu | Gln |
|---|---|---|---|---|---|---|---|---|---|---|---|---|---|---|---|
| 225 | | | | | 230 | | | | | 235 | | | | | 240 |

| Phe | Asp | Ala | Ala | Phe | Val | Pro | Ala | Val | Ala | Arg | Gln | Lys | Ala | Pro | Asp |
|---|---|---|---|---|---|---|---|---|---|---|---|---|---|---|---|
| | | | | 245 | | | | | 250 | | | | | 255 | |

| Ser | Glu | Val | Ala | Gly | Arg | Ala | Asn | Val | Phe | Ile | Phe | Pro | Asp | Ile | Gln |
|---|---|---|---|---|---|---|---|---|---|---|---|---|---|---|---|
| | | | 260 | | | | | 265 | | | | | 270 | | |

| Ser | Gly | Asn | Ile | Gly | Tyr | Lys | Ile | Ala | Gln | Arg | Leu | Gly | Asn | Phe | Glu |
|---|---|---|---|---|---|---|---|---|---|---|---|---|---|---|---|
| | | 275 | | | | | 280 | | | | | 285 | | | |

| Ala | Ile | Gly | Pro | Ile | Leu | Gln | Gly | Leu | Asn | Ala | Pro | Val | Ser | Asp | Leu |
|---|---|---|---|---|---|---|---|---|---|---|---|---|---|---|---|
| 290 | | | | | 295 | | | | | 300 | | | | | |

| Ser | Arg | Gly | Cys | Asn | Glu | Glu | Asp | Val | Tyr | Lys | Leu | Ala | Ile | Ile | Thr |
|---|---|---|---|---|---|---|---|---|---|---|---|---|---|---|---|
| 305 | | | | | 310 | | | | | 315 | | | | | 320 |

| Ala | Ala | Gln | Ala | Leu | Lys |
|---|---|---|---|---|---|
| | | | | 325 | |

<210> SEQ ID NO 27
<211> LENGTH: 326
<212> TYPE: PRT
<213> ORGANISM: Carnobacterium sp.

<400> SEQUENCE: 27

```
Met Glu Leu Ile Glu Ser Leu Ser Ser Lys Ile Lys Gly Lys Lys Val
1               5                   10                  15

Arg Ile Val Phe Pro Glu Gly Ser Glu Pro Arg Ile Leu Gly Ala Val
            20                  25                  30

Val Arg Leu Ala Ser Glu Asp Leu Val Gln Pro Val Leu Ile Gly Asn
        35                  40                  45

Pro Glu Val Val Lys Glu Ala Ala Lys Asn Arg Gly Phe Asn Val Glu
    50                  55                  60

Asn Ile Glu Ile Val Asp Pro Ala Asn Tyr Ala Lys Ile Asp Glu Met
65                  70                  75                  80

Val Ala Ser Phe Val Glu Arg Arg Lys Gly Lys Val Ser Glu Glu Lys
                85                  90                  95

Ala Ile Glu Leu Leu Lys Asp Glu Asn Tyr Phe Gly Thr Met Leu Thr
            100                 105                 110

Tyr Met Gly Leu Val Asp Gly Leu Val Ser Gly Ala Ile His Ser Thr
        115                 120                 125

Gly Asp Thr Val Arg Pro Ala Leu Gln Ile Ile Lys Thr Lys Pro Gly
    130                 135                 140

Val Ser Arg Thr Ser Gly Ala Phe Ile Met Met Arg Gly Arg Gly Gln
145                 150                 155                 160

Glu Lys Tyr Leu Phe Ser Asp Cys Ala Ile Asn Val Asn Pro Asn Ala
                165                 170                 175

Gln Glu Leu Ala Glu Ile Ala Val Glu Ser Ala Lys Thr Ala Glu Met
            180                 185                 190

Phe Gly Ile Glu Pro Lys Val Ala Met Leu Ser Phe Ser Thr Arg Gly
        195                 200                 205

Ser Ala Val Ala Glu Glu Ala Thr Lys Val Ala Glu Ala Thr Lys Ile
    210                 215                 220

Ala Gln Glu Leu Ala Pro Gln Tyr Asp Ile Asp Gly Glu Met Gln Phe
225                 230                 235                 240

Asp Ala Ala Phe Val Ala Ser Val Ala Glu Gln Lys Ala Pro Asp Ser
                245                 250                 255

Asn Val Ala Gly Gln Ala Ser Val Phe Val Phe Pro Glu Leu Gln Ser
            260                 265                 270

Gly Asn Ile Gly Tyr Lys Ile Ala Gln Arg Phe Gly Asn Phe Glu Ala
        275                 280                 285

Ile Gly Pro Ile Leu Gln Gly Leu Asn Lys Pro Ile Ser Asp Leu Ser
    290                 295                 300

Arg Gly Cys Asn Glu Glu Asp Val Tyr Lys Leu Thr Ile Ile Thr Ala
305                 310                 315                 320

Asn Gln Thr Leu Met Asn
                325

<210> SEQ ID NO 28
<211> LENGTH: 692
<212> TYPE: PRT
<213> ORGANISM: Mycobacterium vanbaalenii

<400> SEQUENCE: 28

Met Pro Asp Ala Thr Thr Gly Thr Ser Ser Ile Tyr Leu Ala Ser
1               5                   10                  15

Pro Glu Gly Asp Thr Gly Lys Ser Thr Ile Ala Leu Gly Ile Leu His
            20                  25                  30

Arg Leu Ser Ala Thr Ala Ala Arg Val Gly Val Phe Arg Pro Ile Thr
```

```
                35                  40                  45
Arg Met Gly Glu Ser Arg Asp Tyr Ile Leu Glu Leu Leu Asp His
 50                  55                  60

Thr Thr Ala Gly Leu Pro Tyr Glu Asp Cys Val Gly Val Gly Tyr Gln
 65                  70                  75                  80

Gln Leu His Asp Asp Pro Asp Ala Ala Leu Ala Glu Ile Val Asp Arg
                     85                  90                  95

Phe His Arg Val Ala Asp Arg Cys Asp Ala Val Leu Val Gly Ser
                100                 105                 110

Asp Tyr Thr Asp Val Ala Ala Pro Ser Glu Leu Ser Val Asn Ala Arg
                115                 120                 125

Ile Ala Ala Asn Leu Gly Ala Pro Val Val Leu Ala Val Lys Gly Lys
                130                 135                 140

Gly Arg Thr Pro Glu Gln Ile Leu Gln Val Val Asp Val Cys Ile Asn
145                 150                 155                 160

Glu Ile Ala Ala Gln His Ala His Thr Ala Ala Val Val Val Asn Arg
                165                 170                 175

Cys Asp Pro Ile Leu Leu Val Asp Val Ala Glu Ala Leu Ala Ser Ile
                180                 185                 190

Gly Pro Gln Ser Tyr Val Leu Pro Glu Glu Pro Leu Leu Val Ala Pro
                195                 200                 205

Ser Val Ser Glu Leu Arg Ser Ala Val Glu Gly His Gln Val Gln Gly
210                 215                 220

Asp Pro Ala Leu Leu Asp Arg Glu Val Leu Asp Val Leu Val Ala Gly
225                 230                 235                 240

Met Thr Ala Glu His Val Leu Glu Arg Leu Thr Gly Val Ala Val
                245                 250                 255

Val Thr Pro Gly Asp Arg Ser Asp Val Val Leu Ala Val Leu Ser Ala
                260                 265                 270

His Ala Ala Gly Phe Pro Ser Leu Ser Ala Val Ile Leu Asn Gly
                275                 280                 285

Gly Leu Thr Leu His Pro Ala Ile Gly Ser Leu Val Ala Gly Leu Gly
290                 295                 300

Leu Arg Leu Pro Val Ile Glu Thr Arg Leu Gly Thr Phe Glu Thr Ala
305                 310                 315                 320

Ser Arg Ile Ala Ala Thr Arg Gly Arg Val Thr Ser Lys Ser His Arg
                325                 330                 335

Lys Ile Asp Thr Ala Leu Thr Leu Met Asp Thr Tyr Val Asp Thr Ala
                340                 345                 350

Glu Leu Leu Ala His Leu Ala Ile Pro Ile Pro Thr Val Thr Pro
                355                 360                 365

Gln Met Phe Thr His Gln Leu Ile Glu Gln Ala Arg Ser Asp Arg Lys
                370                 375                 380

Arg Ile Val Leu Pro Glu Gly Asn Asp Arg Ile Leu Lys Ala Ala
385                 390                 395                 400

Gly Arg Leu Leu His Arg Gly Val Ala Asp Leu Thr Ile Leu Gly Glu
                405                 410                 415

Glu Ala Gln Val Arg Ala Arg Ala Ala Glu Leu Gly Leu Asp Leu Ser
                420                 425                 430

Thr Ala Val Val Leu Asp Pro Gln Thr Ser Glu Leu Cys Asp Arg Phe
                435                 440                 445

Ala Glu Gln Tyr Ala Lys Leu Arg Ala His Lys Gly Val Thr Val Glu
                450                 455                 460
```

Gln Ala His Glu Ile Ile His Asp Val Ser Tyr Phe Gly Thr Met Leu
465                 470                 475                 480

Val His Asn Asp Leu Val Asp Gly Met Val Ser Gly Ala Cys His Thr
            485                 490                 495

Thr Ala His Thr Ile Arg Pro Ala Leu Glu Ile Ile Arg Thr Ala Pro
        500                 505                 510

Gly Val Ser Thr Val Ser Ser Ile Phe Leu Met Cys Leu Ala His Glu
            515                 520                 525

Val Leu Ala Tyr Gly Asp Cys Ala Ile Val Pro Asp Pro Thr Ala Glu
530                 535                 540

Gln Leu Ala Asp Ile Ala Ile Ser Ser Ala Arg Thr Ala Ala Gln Phe
545                 550                 555                 560

Gly Ile Glu Pro Lys Val Ala Met Leu Ser Tyr Ser Thr Gly Thr Ser
                565                 570                 575

Gly Thr Gly Ala Asp Val Asp Lys Val Arg Lys Ala Thr Glu Leu Val
            580                 585                 590

Arg Ser Arg Ala Pro Glu Leu Leu Val Glu Gly Pro Ile Gln Tyr Asp
            595                 600                 605

Ala Ala Val Glu Pro Ser Val Ala Met Thr Lys Met Pro Asp Ser Arg
610                 615                 620

Val Ala Gly His Ala Thr Val Leu Ile Phe Pro Asp Leu Asn Thr Gly
625                 630                 635                 640

Asn Asn Thr Tyr Lys Ala Val Gln Arg Ser Ala Gly Ala Ile Ala Ile
                645                 650                 655

Gly Pro Val Leu Gln Gly Leu Asn Lys Pro Val Asn Asp Leu Ser Arg
            660                 665                 670

Gly Ala Leu Val Glu Asp Ile Val Asn Thr Val Ala Ile Thr Ala Ile
            675                 680                 685

Gln Ala Gln Gly
        690

<210> SEQ ID NO 29
<211> LENGTH: 333
<212> TYPE: PRT
<213> ORGANISM: Clostridium perfringens

<400> SEQUENCE: 29

Met Glu Leu Met Lys Gln Ile Trp Glu Ser Ala Lys Asn Asn Arg Lys
1               5                   10                  15

Lys Ile Val Leu Pro Glu Gly Asp Glu Glu Arg Thr Leu Val Ala Ser
            20                  25                  30

Gln Arg Ile Lys Glu Glu Gly Leu Ala Asp Val Tyr Leu Val Gly Ser
        35                  40                  45

Glu Gln Val Ile Arg Glu Lys Ala Glu Ala Leu Gly Val Asn Leu Glu
50                  55                  60

Gly Val Asn Ile Val Asp Pro Glu Thr Ser Asp Lys Leu Asp Thr Tyr
65                  70                  75                  80

Ile Asn Glu Phe Tyr Glu Leu Arg Lys Ala Lys Gly Met Thr Val Glu
                85                  90                  95

Lys Ala Gly Lys Ile Val Arg Asp Pro Leu Tyr Phe Gly Thr Met Met
            100                 105                 110

Val Lys Met Gly Asp Ala Asp Gly Met Val Ser Gly Ala Val His Thr
        115                 120                 125

Thr Gly Asp Leu Leu Arg Pro Gly Leu Gln Ile Ile Lys Thr Ala Pro

```
            130                 135                 140
Gly Val Ser Val Val Ser Ser Phe Phe Ile Met Met Val Pro Gly Ser
145                 150                 155                 160

Gln Tyr Gly Glu Gly Gly Met Leu Leu Phe Ser Asp Cys Ala Val Asn
                165                 170                 175

Pro Asn Pro Asn Ala Asp Gln Leu Ala Ala Ile Ala Ile Ala Thr Ala
            180                 185                 190

Asp Thr Ala Lys Asn Leu Cys Lys Met Asp Pro Lys Val Ala Met Leu
                195                 200                 205

Ser Phe Ser Thr Met Gly Ser Ala Asp His Asp Leu Val Thr Lys Val
            210                 215                 220

Arg Val Ala Thr Glu Lys Ala Lys Glu Leu Arg Pro Asp Leu Asp Ile
225                 230                 235                 240

Asp Gly Glu Leu Gln Leu Asp Ala Ala Ile Val Gly Lys Val Ala Ser
                245                 250                 255

Gln Lys Ala Pro Asn Ser Lys Val Ala Gly Asn Ala Asn Val Leu Val
            260                 265                 270

Phe Pro Asp Leu Gln Ala Gly Asn Ile Gly Tyr Lys Leu Val Gln Arg
                275                 280                 285

Phe Ala Asn Ala Glu Ala Ile Gly Pro Val Cys Gln Gly Phe Ala Lys
            290                 295                 300

Pro Ile Asn Asp Leu Ser Arg Gly Cys Ser Ser Glu Asp Ile Val Asn
305                 310                 315                 320

Val Val Ala Ile Thr Ala Val Gln Ala Gln Ala Thr Lys
                325                 330
```

<210> SEQ ID NO 30
<211> LENGTH: 327
<212> TYPE: PRT
<213> ORGANISM: Enterococcus faecalis

<400> SEQUENCE: 30

```
Met Glu Leu Phe Asp Ser Leu Lys Phe Lys Val Val Arg Arg Asn Ile
1               5                   10                  15

Lys Ile Val Phe Pro Glu Ala Thr Asp Pro Arg Ile Leu Gly Ala Ala
                20                  25                  30

Ala Arg Leu Lys Ser Asp Glu Leu Val Glu Pro Ile Leu Ile Gly Asp
            35                  40                  45

Pro Thr Asp Ile Ala Asn Ala Ala Met Ala Arg Gly Ile Asn Thr Ser
    50                  55                  60

Asn Phe Ile Ile Ile Asn Pro Asn Asp Tyr Glu Lys Trp Asp Glu Met
65                  70                  75                  80

Val Glu Ala Phe Val Glu Arg Arg Asn Gly Lys Ala Thr Lys Glu Asp
                85                  90                  95

Ala Glu Lys Ile Leu Lys Asp Val Asn Tyr Phe Gly Thr Met Leu Thr
            100                 105                 110

Tyr Met Gly Ile Ala Asp Gly Met Val Ser Gly Ala Ile His Ser Thr
        115                 120                 125

Gly Asp Thr Val Arg Pro Ala Leu Gln Ile Ile Lys Thr Lys Pro Gly
    130                 135                 140

Val Ser Arg Thr Ser Gly Ala Phe Leu Met Ile Arg Gly Arg Asp Gln
145                 150                 155                 160

Glu Arg Tyr Leu Phe Ser Asp Cys Ala Ile Asn Val Asn Pro Thr Ala
                165                 170                 175
```

```
Gln Glu Leu Ala Glu Ile Ala Val Asp Ser Ala Lys Thr Ala Glu Leu
                180                 185                 190

Phe Asp Ile Glu Pro Lys Val Ser Leu Leu Ser Phe Ser Thr Lys Gly
            195                 200                 205

Ser Ala Lys Ala Pro Glu Val Thr Lys Val Ala Glu Ala Thr Lys Ile
        210                 215                 220

Ala Gln Glu Leu Ala Pro Glu Tyr Ala Ile Asp Gly Glu Leu Gln Phe
225                 230                 235                 240

Asp Ala Ser Tyr Val Ser Val Ala Gln Leu Lys Ala Pro Asn Ser
                245                 250                 255

Lys Val Ala Gly Glu Ala Thr Val Phe Val Phe Pro Asp Leu Gln Ser
                260                 265                 270

Gly Asn Ile Gly Tyr Lys Ile Ala Gln Arg Leu Gly Asn Phe Glu Ala
            275                 280                 285

Ile Gly Pro Ile Leu Gln Gly Leu Asn Lys Pro Val Ser Asp Leu Ser
        290                 295                 300

Arg Gly Ala Asn Glu Glu Asp Val Tyr Lys Leu Ser Ile Ile Thr Ala
305                 310                 315                 320

Ala Gln Thr Leu Met Asn Asp
                325

<210> SEQ ID NO 31
<211> LENGTH: 326
<212> TYPE: PRT
<213> ORGANISM: Leuconostoc mesenteroides

<400> SEQUENCE: 31

Met Glu Leu Phe Glu Gln Leu Lys Asn Lys Ile Thr Gly Gln Asn Lys
1               5                   10                  15

Thr Ile Val Phe Pro Glu Gly Glu Asp Pro Arg Ile Gln Gly Ala Ala
            20                  25                  30

Ile Arg Leu Ala Ala Asp Asn Leu Ile Glu Pro Ile Leu Leu Gly Asp
        35                  40                  45

Ala Gln Glu Ile Ser Lys Thr Ala Gln Ala His Asn Phe Asp Leu Ser
50                  55                  60

Asn Ile Glu Thr Ile Asp Pro Ala Ser Tyr Asp Glu Asn Glu Leu Ala
65                  70                  75                  80

Lys Leu Asn Ala Thr Leu Val Glu Arg Arg Lys Gly Lys Thr Asp Ala
                85                  90                  95

Glu Thr Ala Ala Lys Trp Leu Gln Asn Val Asn Tyr Phe Gly Thr Met
            100                 105                 110

Leu Val Tyr Thr Gly Lys Ala Asp Gly Met Val Ser Gly Ala Val His
        115                 120                 125

Pro Thr Gly Asp Thr Val Arg Pro Ala Leu Gln Ile Ile Lys Thr Ala
    130                 135                 140

Pro Gly Ser Ser Arg Ile Ser Gly Ala Phe Ile Met Gln Lys Gly Glu
145                 150                 155                 160

Glu Arg Tyr Val Phe Ala Asp Ala Ala Ile Asn Ile Asp Ile Asp Ser
                165                 170                 175

Asp Thr Met Ala Glu Ile Ala Ile Gln Ser Ala His Thr Ala Gln Val
            180                 185                 190

Phe Asp Ile Glu Pro Lys Val Ala Met Leu Ser Phe Ser Thr Lys Gly
        195                 200                 205

Ser Ala Lys Ser Pro Leu Val Asp Lys Val Ala Thr Ala Thr Ala Leu
    210                 215                 220
```

```
Ala Lys Lys Leu Ala Pro Glu Leu Ala Asp Ser Ile Asp Gly Glu Leu
225                 230                 235                 240

Gln Phe Asp Ala Ala Phe Val Glu Ser Val Ala Ala Lys Ala Pro
                245                 250                 255

Asp Ser Lys Val Ala Gly Lys Ala Asn Thr Phe Ile Phe Pro Ser Leu
            260                 265                 270

Glu Ala Gly Asn Ile Gly Tyr Lys Ile Ala Gln Arg Leu Gly Gly Phe
            275                 280                 285

Glu Ala Ile Gly Pro Ile Leu Gln Gly Leu Ala Lys Pro Val Ser Asp
            290                 295                 300

Leu Ser Arg Gly Ala Asn Glu Glu Asp Val Tyr Lys Val Ala Ile Ile
305                 310                 315                 320

Thr Ala Ala Gln Ala Leu
                325

<210> SEQ ID NO 32
<211> LENGTH: 333
<212> TYPE: PRT
<213> ORGANISM: Clostridium acetobutylicum

<400> SEQUENCE: 32

Met Asp Leu Ile Glu Ser Ile Trp Glu Cys Ala Lys Gln Asp Lys Lys
1               5                   10                  15

Arg Ile Ile Leu Ala Glu Gly Glu Glu Lys Arg Asn Leu Ile Ala Ala
                20                  25                  30

Asp Lys Ile Ile Lys Glu Gly Leu Ala Glu Leu Val Leu Val Gly Asp
            35                  40                  45

Glu Asn Lys Ile Lys Glu Lys Ala Ser Glu Leu Asn Leu Asp Ile Ser
        50                  55                  60

Lys Ala Glu Ile Met Asp Pro Glu Thr Ser Leu Lys Thr Glu Thr Tyr
65                  70                  75                  80

Ala Arg Asp Phe Tyr Glu Leu Arg Lys His Lys Gly Met Thr Ile Glu
                85                  90                  95

Lys Ser Glu Lys Met Val Arg Asp Pro Leu Tyr Phe Ala Thr Met Ala
            100                 105                 110

Leu Lys Asp Gly Tyr Val Asp Gly Met Val Ser Gly Ala Val His Thr
        115                 120                 125

Thr Gly Asp Leu Leu Arg Pro Gly Leu Gln Ile Ile Lys Thr Ala Pro
130                 135                 140

Gly Val Lys Ile Val Ser Gly Phe Phe Val Met Ile Ile Pro Asp Cys
145                 150                 155                 160

Asp Tyr Gly Glu Glu Gly Leu Leu Leu Phe Ala Asp Cys Ala Val Asn
                165                 170                 175

Pro Asn Pro Thr Ser Asp Glu Leu Ala Asp Ile Ala Ile Thr Thr Ala
            180                 185                 190

Glu Thr Ala Arg Lys Leu Cys Asn Val Glu Pro Lys Val Ala Met Leu
        195                 200                 205

Ser Phe Ser Thr Met Gly Ser Ala Lys Gly Glu Met Val Asp Lys Val
210                 215                 220

Lys Asn Ala Val Glu Ile Thr Lys Lys Phe Arg Pro Asp Leu Ala Ile
225                 230                 235                 240

Asp Gly Glu Leu Gln Leu Asp Ala Ala Ile Asp Ser Glu Val Ala Ala
                245                 250                 255

Leu Lys Ala Pro Ser Ser Asn Val Ala Gly Asn Ala Asn Val Leu Val
```

```
                260                 265                 270
Phe Pro Asp Leu Gln Thr Gly Asn Ile Gly Tyr Lys Leu Val Gln Arg
            275                 280                 285

Phe Ala Lys Ala Lys Ala Ile Gly Pro Ile Cys Gln Gly Phe Ala Lys
        290                 295                 300

Pro Ile Asn Asp Leu Ser Arg Gly Cys Ser Ser Glu Asp Ile Val Asn
305                 310                 315                 320

Val Val Ala Ile Thr Val Val Gln Ala Gln Arg Gly Ile
                325                 330
```

<210> SEQ ID NO 33
<211> LENGTH: 560
<212> TYPE: PRT
<213> ORGANISM: Bifidobacterium animalis lactis

<400> SEQUENCE: 33

```
Met Ser Leu Lys Asn Val Ser Ile Ile Ser Pro Glu Pro Gly Asp Gly
1               5                   10                  15

Arg Asn Val Val Ala Leu Gly Val Val Asp Met Leu Ala His Thr Ala
            20                  25                  30

Lys Thr Ser Ile Phe Arg Pro Ala Val Gln Ala Asp Glu Asn Leu Thr
        35                  40                  45

Asp Ala Leu Leu Ser Val Ser Val Leu Gln Thr Arg Glu Gln Ala
    50                  55                  60

Val Gly Val Thr Leu His Asp Ala Arg Leu Asp Lys Asp Asn Ala Arg
65                  70                  75                  80

Gln Gln Ile Val Ser Lys Phe Ile Asp Thr Asn Ala Glu Ile Asn Pro
                85                  90                  95

Gln Ile Arg Val Ile Val Gly Ser Asp Arg Thr Asn Val Gly Asp Pro
            100                 105                 110

Glu Arg Phe Thr Phe Asn Ala Asp Val Ser Ala Asp Leu Gln Ser Pro
        115                 120                 125

Val Leu Leu Ser Val Ser Ser Met Gly Arg Thr Pro Asp Glu Ile Arg
    130                 135                 140

Glu Thr Ile Asp Ala Cys Arg Glu Val Val Ala Asn Ala Gly Thr Gln
145                 150                 155                 160

Val Ile Gly Val Phe Ile Thr Asp Cys Thr Asn Ser Ala Leu Pro Thr
                165                 170                 175

Leu Thr Asp Glu Phe Val Ser Tyr Asp Leu Pro Thr Trp Pro Leu Pro
            180                 185                 190

Leu Val Glu Leu Gly Ser Ala Asp Thr Asn Val Lys Ala Ala Leu Asp
        195                 200                 205

Ala Phe Asp Glu His Val Asp Lys Glu Ser Leu Leu Asn Val Leu Asp
    210                 215                 220

Thr Pro Phe Val Pro Pro Thr Thr Pro Phe Ala Phe Gln Tyr Asp Leu
225                 230                 235                 240

Leu Ala Arg Ala Lys Lys Asp Lys Lys Thr Ile Val Leu Pro Glu Gly
                245                 250                 255

Glu Asp Asp Arg Ile Ile Thr Ala Ala Asn Tyr Leu Leu Gln Ser Asn
            260                 265                 270

Val Val Asp Leu Val Ile Ile Gly Asp Arg Asn Glu Ile Leu Ala Arg
        275                 280                 285

Gly Glu Lys Leu Gly Leu Lys Ala Leu Asp Gln Ala Lys Phe Val Ser
    290                 295                 300
```

Ile Asp Asp Lys His Leu Leu Asp Thr Met Val Pro Lys Leu Cys Glu
305                 310                 315                 320

Leu Arg Ala Lys Lys Gly Met Thr Pro Asp Val Ala Leu Lys Thr Leu
            325                 330                 335

Arg Asp Thr Asn Tyr Phe Gly Thr Met Leu Ile Val Leu Gly Met Ala
                340                 345                 350

Asp Gly Leu Val Ser Gly Ala Ile Ser Ser Thr Ala Asn Thr Val Arg
            355                 360                 365

Pro Ala Leu Gln Leu Ile Lys Thr Lys Pro Gly Val Ser Ser Val Ser
370                 375                 380

Gly Ala Phe Leu Met Cys Leu Lys Asp His Val Ser Val Phe Ala Asp
385                 390                 395                 400

Cys Ala Ile Asn Leu Asp Pro Asp Pro Gln Gln Leu Ala Asp Ile Ala
                405                 410                 415

Ile Gln Ser Ala Glu Thr Ala Lys Ala Phe Ser Ile Asp Pro Lys Ile
                420                 425                 430

Gly Leu Leu Ser Tyr Ser Thr Leu Gly Ser Gly Lys Gly Pro Asp Val
            435                 440                 445

Asp Leu Val Val Glu Ala Thr Ser Ile Ala Gln Asn Lys Arg Pro Asp
450                 455                 460

Leu Pro Ile Val Gly Pro Ile Gln Phe Asp Ala Ala Trp Ser Lys Thr
465                 470                 475                 480

Val Ala Arg Val Lys Ala Phe Gly Asn Pro Ile Ala Gly Asn Val Thr
                485                 490                 495

Val Phe Val Phe Pro Asp Leu Asp Ala Gly Asn Ile Cys Tyr Lys Ala
                500                 505                 510

Val Gln Arg Thr Ser Gly Ala Val Ala Ile Gly Pro Val Leu Gln Gly
            515                 520                 525

Leu Asn Arg Pro Val Asn Asp Leu Ser Arg Gly Ala Leu Val Gln Asp
530                 535                 540

Ile Ile Asn Thr Ile Ala Leu Thr Ala Ile Glu Ala Gln Ser Asn Glu
545                 550                 555                 560

<210> SEQ ID NO 34
<211> LENGTH: 461
<212> TYPE: PRT
<213> ORGANISM: Corynebacterium glutamicum

<400> SEQUENCE: 34

Met Ser Asp Thr Pro Thr Ser Ala Leu Ile Thr Thr Val Asn Arg Ser
1               5                   10                  15

Phe Asp Gly Phe Asp Leu Glu Glu Val Ala Ala Asp Leu Gly Val Arg
            20                  25                  30

Leu Thr Tyr Leu Pro Asp Glu Glu Leu Glu Val Ser Lys Val Leu Ala
        35                  40                  45

Ala Asp Leu Leu Ala Glu Gly Pro Ala Leu Ile Gly Val Gly Asn
    50                  55                  60

Thr Phe Phe Asp Ala Gln Val Ala Ala Leu Gly Val Pro Val Leu
65              70                  75                  80

Leu Leu Val Asp Lys Gln Gly Lys His Val Ala Leu Ala Arg Thr Gln
            85                  90                  95

Val Asn Asn Ala Gly Ala Val Val Ala Ala Phe Thr Ala Glu Gln
                100                 105                 110

Glu Pro Met Pro Asp Lys Leu Arg Lys Ala Val Arg Asn His Ser Asn
            115                 120                 125

Leu Glu Pro Val Met Ser Ala Glu Leu Phe Glu Asn Trp Leu Leu Lys
            130                 135                 140

Arg Ala Arg Ala Glu His Ser His Ile Val Leu Pro Glu Gly Asp Asp
145                 150                 155                 160

Asp Arg Ile Leu Met Ala Ala His Gln Leu Leu Asp Gln Asp Ile Cys
                165                 170                 175

Asp Ile Thr Ile Leu Gly Asp Pro Val Lys Ile Lys Glu Arg Ala Thr
            180                 185                 190

Glu Leu Gly Leu His Leu Asn Thr Ala Tyr Leu Val Asn Pro Leu Thr
        195                 200                 205

Asp Pro Arg Leu Glu Glu Phe Ala Glu Gln Phe Ala Glu Leu Arg Lys
    210                 215                 220

Ser Lys Ser Val Thr Ile Asp Glu Ala Arg Glu Ile Met Lys Asp Ile
225                 230                 235                 240

Ser Tyr Phe Gly Thr Met Met Val His Asn Gly Asp Ala Asp Gly Met
                245                 250                 255

Val Ser Gly Ala Ala Asn Thr Thr Ala His Thr Ile Lys Pro Ser Phe
            260                 265                 270

Gln Ile Ile Lys Thr Val Pro Glu Ala Ser Val Val Ser Ser Ile Phe
        275                 280                 285

Leu Met Val Leu Arg Gly Arg Leu Trp Ala Phe Gly Asp Cys Ala Val
    290                 295                 300

Asn Pro Asn Pro Thr Ala Glu Gln Leu Gly Glu Ile Ala Val Val Ser
305                 310                 315                 320

Ala Lys Thr Ala Ala Gln Phe Gly Ile Asp Pro Arg Val Ala Ile Leu
                325                 330                 335

Ser Tyr Ser Thr Gly Asn Ser Gly Gly Gly Ser Asp Val Asp Arg Ala
            340                 345                 350

Ile Asp Ala Leu Ala Glu Ala Arg Arg Leu Asn Pro Glu Leu Cys Val
        355                 360                 365

Asp Gly Pro Leu Gln Phe Asp Ala Ala Val Asp Pro Gly Val Ala Arg
    370                 375                 380

Lys Lys Met Pro Asp Ser Asp Val Ala Gly Gln Ala Asn Val Phe Ile
385                 390                 395                 400

Phe Pro Asp Leu Glu Ala Gly Asn Ile Gly Tyr Lys Thr Ala Gln Arg
                405                 410                 415

Thr Gly His Ala Leu Ala Val Gly Pro Ile Leu Gln Gly Leu Asn Lys
            420                 425                 430

Pro Val Asn Asp Leu Ser Arg Gly Ala Thr Val Pro Asp Ile Val Asn
        435                 440                 445

Thr Val Ala Ile Thr Ala Ile Gln Ala Gly Gly Arg Ser
    450                 455                 460

<210> SEQ ID NO 35
<211> LENGTH: 714
<212> TYPE: PRT
<213> ORGANISM: Escherichia coli K-12

<400> SEQUENCE: 35

Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp

```
                35                  40                  45
Ala Pro Asp Gln Thr Thr Thr Ile Val Arg Ala Asn Ser Ser Thr Thr
 50                  55                  60

Thr Ala Ala Glu Pro Leu Lys Met Ser Tyr Val Glu Gly Leu Leu Ser
 65                  70                  75                  80

Ser Asn Gln Lys Asp Val Leu Met Glu Glu Ile Val Ala Asn Tyr His
                 85                  90                  95

Ala Asn Thr Lys Asp Ala Glu Val Val Leu Val Glu Gly Leu Val Pro
                100                 105                 110

Thr Arg Lys His Gln Phe Ala Gln Ser Leu Asn Tyr Glu Ile Ala Lys
                115                 120                 125

Thr Leu Asn Ala Glu Ile Val Phe Val Met Ser Gln Gly Thr Asp Thr
        130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
                180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
                260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
        290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
                340                 345                 350

Asp Asp His Glu Arg Ile Glu Lys Val Gln Glu Tyr Val Ala Asn Tyr
        355                 360                 365

Ile Asn Ala Asp Trp Ile Glu Ser Leu Thr Ala Thr Ser Glu Arg Ser
        370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ile Cys Ala Glu Arg Gly Ile Ala Thr Cys
                420                 425                 430

Val Leu Leu Gly Asn Pro Ala Glu Ile Asn Arg Val Ala Ala Ser Gln
        435                 440                 445

Gly Val Glu Leu Gly Ala Gly Ile Glu Ile Val Asp Pro Glu Val Val
        450                 455                 460
```

```
Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
            485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
            515                 520                 525

Lys Thr Ala Pro Gly Ser Ser Leu Val Ser Ser Val Phe Phe Met Leu
530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
            565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
            595                 600                 605

Thr Arg Leu Ala Gln Glu Lys Arg Pro Asp Leu Met Ile Asp Gly Pro
610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
            645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
            675                 680                 685

Asp Leu Ser Arg Gly Ala Leu Val Asp Asp Ile Val Tyr Thr Ile Ala
            690                 695                 700

Leu Thr Ala Ile Gln Ser Ala Gln Gln Gln
705                 710

<210> SEQ ID NO 36
<211> LENGTH: 714
<212> TYPE: PRT
<213> ORGANISM: Escherichia coli 53638

<400> SEQUENCE: 36

Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
            35                  40                  45

Ala Pro Asp Gln Thr Thr Thr Ile Val Arg Ala Asn Ser Ser Thr Thr
        50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
```

```
            115                 120                 125
Thr Leu Asn Ala Glu Ile Val Phe Val Met Ser Gln Gly Thr Asp Thr
        130                 135                 140
Pro Glu Gln Leu Lys Glu Arg Ile Glu Leu Thr Arg Asn Ser Phe Gly
145                 150                 155                 160
Gly Ala Lys Asn Thr Asn Ile Thr Gly Val Ile Val Asn Lys Leu Asn
                165                 170                 175
Ala Pro Val Asp Glu Gln Gly Arg Thr Arg Pro Asp Leu Ser Glu Ile
            180                 185                 190
Phe Asp Asp Ser Ser Lys Ala Lys Val Asn Asn Val Asp Pro Ala Lys
        195                 200                 205
Leu Gln Glu Ser Ser Pro Leu Pro Val Leu Gly Ala Val Pro Trp Ser
    210                 215                 220
Phe Asp Leu Ile Ala Thr Arg Ala Ile Asp Met Ala Arg His Leu Asn
225                 230                 235                 240
Ala Thr Ile Ile Asn Glu Gly Asp Ile Asn Thr Arg Arg Val Lys Ser
                245                 250                 255
Val Thr Phe Cys Ala Arg Ser Ile Pro His Met Leu Glu His Phe Arg
            260                 265                 270
Ala Gly Ser Leu Leu Val Thr Ser Ala Asp Arg Pro Asp Val Leu Val
        275                 280                 285
Ala Ala Cys Leu Ala Ala Met Asn Gly Val Glu Ile Gly Ala Leu Leu
    290                 295                 300
Leu Thr Gly Gly Tyr Glu Met Asp Ala Arg Ile Ser Lys Leu Cys Glu
305                 310                 315                 320
Arg Ala Phe Ala Thr Gly Leu Pro Val Phe Met Val Asn Thr Asn Thr
                325                 330                 335
Trp Gln Thr Ser Leu Ser Leu Gln Ser Phe Asn Leu Glu Val Pro Val
            340                 345                 350
Asp Asp His Glu Arg Ile Glu Lys Val Gln Glu Tyr Val Ala Asn Tyr
        355                 360                 365
Ile Asn Ala Asp Trp Ile Glu Ser Leu Thr Ala Thr Ser Glu Arg Ser
    370                 375                 380
Arg Arg Leu Ser Pro Pro Ala Phe Arg Tyr Gln Leu Thr Glu Leu Ala
385                 390                 395                 400
Arg Lys Ala Gly Lys Arg Ile Val Leu Pro Glu Gly Asp Glu Pro Arg
                405                 410                 415
Thr Val Lys Ala Ala Ala Ile Cys Ala Glu Arg Gly Ile Ala Thr Cys
            420                 425                 430
Val Leu Leu Gly Asn Pro Ala Glu Ile Asn Arg Val Ala Ala Ser Gln
        435                 440                 445
Gly Val Glu Leu Gly Ala Gly Ile Glu Ile Val Asp Pro Glu Val Val
    450                 455                 460
Arg Glu Ser Tyr Val Gly Arg Leu Val Glu Leu Arg Lys Asn Lys Gly
465                 470                 475                 480
Met Thr Glu Thr Val Ala Arg Glu Gln Leu Glu Asp Asn Val Val Leu
                485                 490                 495
Gly Thr Leu Met Leu Glu Gln Asp Glu Val Asp Gly Leu Val Ser Gly
            500                 505                 510
Ala Val His Thr Thr Ala Asn Thr Ile Arg Pro Pro Leu Gln Leu Ile
        515                 520                 525
Lys Thr Ala Pro Gly Ser Ser Leu Val Ser Ser Val Phe Phe Met Leu
    530                 535                 540
```

```
Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
            565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
        595                 600                 605

Thr Arg Leu Ala Gln Glu Lys Arg Pro Asp Leu Met Ile Asp Gly Pro
        610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
            645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
            675                 680                 685

Asp Leu Ser Arg Gly Ala Leu Val Asp Asp Ile Val Tyr Thr Ile Ala
            690                 695                 700

Leu Thr Ala Ile Gln Ser Ala Gln Gln Gln
705                 710
```

<210> SEQ ID NO 37
<211> LENGTH: 714
<212> TYPE: PRT
<213> ORGANISM: Vibrio vulnificus

<400> SEQUENCE: 37

```
Met Ser Arg Thr Ile Met Leu Ile Pro Ala Ser Ala Gly Val Gly Leu
1               5                   10                  15

Thr Ser Val Ser Met Gly Val Leu Arg Ala Met Glu Arg Lys Gly Val
            20                  25                  30

Lys Val Ser Phe Tyr Lys Pro Ile Ala Gln Pro Arg Ser Gly Gly Asp
            35                  40                  45

Leu Pro Asp Leu Thr Thr Thr Ile Val Gly Ala Asn Ser Asp Met Lys
50                  55                  60

Ile Gly Glu Pro Leu Leu Met Ser Val Ala Glu Asn Leu Ile Gly Asn
65                  70                  75                  80

Asp Asn Met Asp Glu Leu Leu Glu Thr Val Val Glu Arg Tyr Asn Gln
            85                  90                  95

Ile Asn Lys Asp Ala Asp Val Thr Leu Ile Glu Gly Leu Val Pro Thr
            100                 105                 110

Arg Lys His Pro Phe Ala Asn Gln Val Asn Ala Glu Ile Ala Ala Thr
            115                 120                 125

Leu Gly Ala Glu Ile Val Leu Val Ala Thr Pro Gly Thr Asp Asn Pro
        130                 135                 140

Ala Gln Leu Lys Glu Arg Ile Glu Val Ala Cys Ser Asn Phe Gly Gly
145                 150                 155                 160

Thr Lys Asn Lys Asn Ile Ser Gly Val Ile Asn Lys Leu Asn Ala
            165                 170                 175

Pro Val Asp Glu Ala Gly Arg Thr Arg Pro Asp Leu Ser Glu Ile Phe
            180                 185                 190

Asp Asp Ala Asp Ser Ala Lys Gln Asn Gln Leu Glu Val Met Gln Ile
```

-continued

```
            195                 200                 205
Phe Asn Ser Ser Pro Ile Arg Val Leu Gly Cys Val Pro Trp Ser Ile
210                 215                 220
Asn Leu Ile Ala Thr Arg Ala Ile Asp Met Ala Lys His Leu Lys Ala
225                 230                 235                 240
Glu Val Ile Asn Glu Gly Asp Ile Asn Thr Arg Arg Ile Lys Ser Ile
                245                 250                 255
Thr Phe Cys Ala Arg Ser Leu Pro His Met Ile Glu His Phe Lys Pro
            260                 265                 270
Gly Ser Leu Leu Val Thr Ser Ala Asp Arg Pro Asp Val Ile Val Ala
                275                 280                 285
Ala Ser Leu Ala Ala Met Asn Gly Val Glu Ile Gly Ala Val Leu Leu
290                 295                 300
Thr Gly Gly Tyr Asp Ile Pro Thr Glu Ile Glu Asn Leu Cys Lys Pro
305                 310                 315                 320
Ala Phe Glu Ser Gly Leu Pro Ile Phe Lys Ala Gln Gly Asn Thr Trp
                325                 330                 335
Gln Thr Ser Leu Asn Leu Gln Ser Phe Ser Leu Glu Val Pro Ala Asp
            340                 345                 350
Asp Lys Glu Arg Ile Glu Phe Ile Asn Asp His Val Ala Gly His Ile
                355                 360                 365
Asp Gly Asn Trp Ile Glu Ser Met Thr Glu Thr Glu Arg Ser Arg
370                 375                 380
Arg Leu Ser Pro Pro Ala Phe Arg Tyr Gln Leu Thr Glu Leu Ala Arg
385                 390                 395                 400
Lys Ala Gly Lys Arg Ile Val Leu Pro Glu Gly Asp Glu Pro Arg Thr
                405                 410                 415
Val Lys Ala Ala Ala Ile Cys Ala Glu Arg Gly Ile Ala Glu Cys Val
                420                 425                 430
Leu Leu Gly Asn Pro Glu Glu Ile Lys Arg Val Ala Ala Gln Gln Gly
            435                 440                 445
Val Glu Leu Gly Ala Gly Val Lys Ile Ile Asp Ala Asp Ala Ile Arg
450                 455                 460
Glu Asn Tyr Val Ala Arg Leu Val Glu Leu Arg Gly Ser Lys Gly Met
465                 470                 475                 480
Thr Glu Val Val Ala Arg Glu Lys Leu Gln Asp Ser Val Phe Leu Gly
                485                 490                 495
Thr Met Met Leu Glu Asn Asp Glu Val Asp Gly Leu Val Ser Gly Ala
            500                 505                 510
Val His Thr Thr Ala Asn Thr Ile Val Pro Pro Phe Gln Ile Ile Lys
            515                 520                 525
Thr Ala Pro Asn Ala Ser Ile Val Ser Ser Val Phe Met Leu Leu
530                 535                 540
Pro Asp Gln Val Leu Val Tyr Gly Asp Cys Ala Ile Asn Pro Asp Pro
545                 550                 555                 560
Thr Ala Glu Gln Leu Ala Glu Ile Ala Ile Gln Ser Ala Asp Ser Ala
                565                 570                 575
Ala Ala Phe Gly Ile Asp Pro Arg Val Ala Met Ile Ser Tyr Ser Thr
            580                 585                 590
Gly Glu Ser Gly Lys Gly Ala Asp Val Asp Lys Val Arg Glu Ala Thr
                595                 600                 605
Lys Leu Ala Gln Glu Lys Arg Pro Asp Leu Ile Ile Asp Gly Pro Leu
            610                 615                 620
```

```
Gln Tyr Asp Ala Ala Ile Met Glu Asn Val Ala Ala Ser Lys Ala Pro
625                 630                 635                 640

Asn Ser Pro Val Ala Gly Lys Ala Thr Val Phe Val Phe Pro Asp Leu
            645                 650                 655

Asn Thr Gly Asn Thr Thr Tyr Lys Ala Val Gln Arg Ser Ala Asp Leu
        660                 665                 670

Val Ser Ile Gly Pro Met Leu Gln Gly Met Arg Lys Pro Val Asn Asp
    675                 680                 685

Leu Ser Arg Gly Ala Leu Val Asp Asp Ile Val Tyr Thr Ile Ala Leu
690                 695                 700

Thr Ala Ile Gln Ala Thr Gln Asp Gln Lys
705                 710

<210> SEQ ID NO 38
<211> LENGTH: 712
<212> TYPE: PRT
<213> ORGANISM: Haemophilus somnus

<400> SEQUENCE: 38

Met Ser Arg Thr Ile Ile Leu Ile Pro Ile Ser Thr Gly Val Gly Leu
1               5                   10                  15

Thr Ser Val Ser Leu Gly Leu Ile His Ala Leu Glu Gln Lys Gly Ala
            20                  25                  30

Lys Ile Gly Phe Met Lys Pro Ile Ser Gln Pro Ser Thr Asp Glu Asp
        35                  40                  45

Lys Leu Asp Arg Thr Thr Ser Ile Val Arg Thr Ser Thr Thr Leu Glu
50                  55                  60

Thr Ala Glu Pro Phe Met Leu Ser Val Ala Glu Asn Leu Ile Gly Gln
65                  70                  75                  80

Asn Gln Ser Asp Val Leu Leu Glu Lys Ile Val Glu Asn His Gln Gln
                85                  90                  95

Leu Ala Lys Asn Asn Glu Leu Ile Val Glu Gly Leu Val Pro Thr
            100                 105                 110

Arg Lys His Gly Tyr Ala Asn Ser Ile Asn Tyr Glu Ile Ala Lys Ala
        115                 120                 125

Leu Asp Ala Glu Ile Val Leu Ala Ala Pro Ala Thr Glu Thr Pro
130                 135                 140

Ala Glu Leu Lys Glu Arg Ile Glu Ala Ala Ser Gln Phe Gly Gly
145                 150                 155                 160

Lys Asn Asn Pro Asn Leu Leu Gly Val Ile Ile Asn Lys Phe Asn Ala
                165                 170                 175

Pro Ile Asp Glu Ser Gly Arg Thr Arg Pro Asp Leu Ser Glu Ile Phe
            180                 185                 190

Asp Ala Tyr Gln His Lys Gln Asn Asn Leu Asn Glu Val Tyr Lys Leu
        195                 200                 205

Phe Glu Lys Ser Pro Ile Lys Val Leu Ala Cys Val Pro Trp Asn Ala
    210                 215                 220

Glu Leu Ile Ala Thr Arg Ala Ile Asp Leu Val Asn His Leu Gly Ala
225                 230                 235                 240

Ser Ile Leu His Glu Gly Asp Ile Lys Thr Arg Ile Arg Ser Ile
                245                 250                 255

Thr Phe Cys Ala Arg Ser Leu Gln Asn Met Val Glu His Phe Lys Thr
            260                 265                 270

Gly Ser Leu Leu Val Thr Ser Ala Asp Arg Pro Asp Val Leu Thr Ala
```

```
                275                 280                 285
Ser Ala Leu Ala Ala Thr Asn Gly Ile Glu Leu Gly Gly Ile Leu Leu
    290                 295                 300
Thr Gly Gly Tyr Lys Ile Asp Asn Gln Ile Lys Lys Leu Cys Gln Pro
305                 310                 315                 320
Val Phe Glu Asn Thr Gly Leu Pro Ile Phe Arg Ile Glu Gly Asn Thr
                325                 330                 335
Trp Gln Ser Ala Leu Ala Leu Gln Ser Phe Asn Leu Glu Val Pro Val
                340                 345                 350
Asp Asp Lys Glu Arg Ile Glu Asn Ile Lys Gln Tyr Thr Ser Gln Gln
                355                 360                 365
Phe Lys Ser Ser Phe Ile Glu Asn Leu Val Ala Ala Ser Thr Arg Pro
    370                 375                 380
Arg Arg Leu Ser Pro Pro Ala Phe Arg Phe Gln Leu Thr Glu Leu Ala
385                 390                 395                 400
Arg Ala Ala Lys Lys Arg Ile Val Leu Pro Glu Gly Asp Glu Pro Arg
                405                 410                 415
Thr Val Lys Ala Ala Ser Leu Cys Ala Glu Arg Gly Ile Ala Glu Cys
                420                 425                 430
Ile Leu Leu Ala Asn Pro Asp Asp Val Lys Arg Val Ala Asp Ala Gln
                435                 440                 445
Gly Val Val Leu Gly Lys Gly Ile Thr Ile Ile Asp Pro Val Ser Val
    450                 455                 460
Arg Glu Asn Tyr Val Asp Arg Leu Val Glu Leu Arg Lys Ala Lys Gly
465                 470                 475                 480
Met Thr Glu Thr Ser Ala Arg Glu Gln Leu Glu Asp Thr Val Val Leu
                485                 490                 495
Gly Thr Met Met Leu Glu Ala Asn Glu Val Asp Gly Leu Val Ser Gly
                500                 505                 510
Ala Ile His Thr Thr Ala Asn Thr Ile Arg Pro Pro Met Gln Ile Ile
                515                 520                 525
Lys Thr Ala Pro Gly Asn Ser Ile Val Ser Ser Ile Phe Phe Met Leu
    530                 535                 540
Leu Pro Asp Gln Val Leu Val Tyr Gly Asp Cys Ala Val Asn Pro Asp
545                 550                 555                 560
Pro Thr Ala Glu Gln Leu Ala Glu Ile Ala Ile Gln Ser Ala Asp Ser
                565                 570                 575
Ala Lys Ala Phe Gly Ile Asp Pro Lys Val Ala Met Ile Ser Tyr Ser
                580                 585                 590
Thr Gly Thr Ser Gly Ser Gly Ala Asp Val Glu Lys Val Lys Glu Ala
                595                 600                 605
Thr Arg Ile Ala Gln Glu Lys Arg Pro Asp Leu Leu Ile Asp Gly Pro
                610                 615                 620
Leu Gln Tyr Asp Ala Ala Val Met Glu Asp Val Ala Lys Ser Lys Ala
625                 630                 635                 640
Pro Asn Ser Pro Val Ala Gly Lys Ala Thr Val Phe Val Phe Pro Asp
                645                 650                 655
Leu Asn Thr Gly Asn Thr Thr Tyr Lys Ala Val Gln Arg Ser Ala Asp
                660                 665                 670
Leu Val Ser Ile Gly Pro Met Leu Gln Gly Met Arg Lys Pro Val Asn
                675                 680                 685
Asp Leu Ser Arg Gly Ala Leu Val Asp Asp Ile Val Tyr Thr Ile Ala
                690                 695                 700
```

```
Leu Thr Ala Ile Gln Ala Thr Gln
705                 710

<210> SEQ ID NO 39
<211> LENGTH: 717
<212> TYPE: PRT
<213> ORGANISM: Yersinia pestis

<400> SEQUENCE: 39

Met Ser Arg Thr Ile Met Leu Ile Pro Thr Gly Thr Ser Val Gly Leu
1               5                   10                  15

Thr Ser Val Ser Leu Gly Val Ile Arg Ser Met Glu Gln Lys Gly Val
            20                  25                  30

Ser Leu Ser Val Phe Lys Pro Ile Ala Gln Pro Arg Ala Gly Asn Asp
        35                  40                  45

Ala Pro Asp Gln Thr Thr Thr Ile Ile Arg Ala Asn Ser Ser Ile Thr
    50                  55                  60

Ala Ala Glu Pro Leu Asn Met Asn Tyr Val Glu Thr Leu Leu Ser Ser
65                  70                  75                  80

Asn Gln Gln Asp Val Leu Met Glu Glu Ile Val Ala Arg Tyr His Glu
                85                  90                  95

Asn Thr Lys Asp Ala Glu Val Val Leu Val Glu Gly Leu Val Pro Thr
            100                 105                 110

Arg Lys His Gln Phe Ala Asn Ala Leu Asn Tyr Glu Ile Ala Lys Thr
        115                 120                 125

Leu Asn Ala Glu Ile Val Phe Val Ile Ala Leu Gly Asn Asp Ser Pro
    130                 135                 140

Asp Gln Leu Lys Glu Arg Ile Glu Leu Ala Arg Ser Ser Phe Gly Gly
145                 150                 155                 160

Ser Lys Asn Lys Asn Ile Thr Gly Val Ile Ile Asn Lys Leu Asn Ala
                165                 170                 175

Pro Val Asp Glu Gln Gly Arg Thr Arg Pro Asp Leu Ser Glu Ile Phe
            180                 185                 190

Asp Asp Ser Thr Lys Ala Ser Val Ala Asn Ile Asp Pro Ser Gln Leu
        195                 200                 205

Phe Ala Asn Ser Pro Ile Pro Val Leu Gly Cys Val Pro Trp Ser Phe
    210                 215                 220

Glu Leu Ile Ala Thr Arg Ala Ile Asp Met Ala Lys His Leu Asn Ala
225                 230                 235                 240

Arg Ile Ile Asn Glu Gly Asp Ile Lys Thr Arg Arg Val Lys Ser Val
                245                 250                 255

Thr Phe Cys Ala Arg Ser Ile Pro His Met Leu Glu His Phe Arg Pro
            260                 265                 270

Gly Ser Leu Leu Val Thr Ser Ala Asp Arg Pro Asp Val Leu Val Ser
        275                 280                 285

Ala Cys Leu Ala Ala Met Asn Gly Val Glu Ile Gly Ala Ile Leu Leu
    290                 295                 300

Thr Gly Gly Tyr Ala Ile Asp Asp Arg Ile Asn Asn Leu Cys Glu Arg
305                 310                 315                 320

Ala Phe Gln Thr Gly Leu Pro Val Phe Met Val Asp Thr Asn Thr Trp
                325                 330                 335

Gln Thr Ser Leu Ser Leu Gln Ser Phe Asn Leu Glu Val Pro Ala Asp
            340                 345                 350

Asp His Glu Arg Val Glu Lys Leu Gln Asn Tyr Val Ala Ser His Ile
```

```
            355                 360                 365
Ser Ser Glu Trp Ile Asp Ser Leu Thr Ala Ala Ser Glu Arg Pro Arg
370                 375                 380

Arg Leu Ser Pro Pro Ala Phe Arg Tyr Glu Leu Thr Glu Leu Ala Arg
385                 390                 395                 400

Lys Ala Gly Lys Arg Ile Val Leu Pro Glu Gly Asp Glu Pro Arg Thr
                405                 410                 415

Ile Lys Ala Ala Ser Ile Cys Ala Glu Arg Gly Ile Ala Thr Cys Val
                420                 425                 430

Leu Leu Gly Asn Pro Glu Glu Ile Gln Arg Val Ala Thr Ser Gln Gly
            435                 440                 445

Val Glu Leu Gly Lys Gly Val Glu Ile Ile Asp Pro Val Ala Val Arg
450                 455                 460

Glu Gln Tyr Val Pro Arg Leu Val Glu Leu Arg Lys Ser Lys Gly Met
465                 470                 475                 480

Thr Glu Val Val Ala Arg Glu Gln Leu Glu Asp Asn Val Val Leu Gly
                485                 490                 495

Thr Leu Met Leu Glu Lys Gly Glu Val Asp Gly Leu Val Ser Gly Ala
            500                 505                 510

Val His Thr Thr Ala Asn Thr Ile Arg Pro Pro Leu Gln Leu Ile Lys
            515                 520                 525

Thr Ala Pro Gly Ser Ser Leu Val Ser Val Phe Phe Met Leu Leu
530                 535                 540

Pro Asp Gln Val Leu Val Tyr Gly Asp Cys Ala Ile Asn Pro Asp Pro
545                 550                 555                 560

Thr Ala Glu Gln Leu Ser Glu Ile Ala Ile Gln Ser Ala Asp Ser Ala
                565                 570                 575

Ala Ala Phe Gly Ile Glu Pro Arg Val Ala Met Ile Ser Tyr Ser Thr
            580                 585                 590

Gly Asn Ser Gly Ala Gly Ser Asp Val Glu Lys Val Arg Glu Ala Thr
            595                 600                 605

Arg Leu Ala Gln Glu Lys Arg Pro Asp Leu Ile Ile Asp Gly Pro Leu
610                 615                 620

Gln Tyr Asp Ala Ala Ile Met Ala Asp Val Ala Lys Ser Lys Ala Pro
625                 630                 635                 640

Asn Ser Pro Val Ala Gly Arg Ala Thr Val Phe Ile Phe Pro Asp Leu
                645                 650                 655

Asn Thr Gly Asn Thr Thr Tyr Lys Ala Val Gln Arg Ser Ala Asp Leu
            660                 665                 670

Ile Ser Ile Gly Pro Met Leu Gln Gly Met Arg Lys Pro Val Asn Asp
            675                 680                 685

Leu Ser Arg Gly Ala Leu Val Asp Asp Ile Val Tyr Thr Val Ala Leu
            690                 695                 700

Thr Ala Ile Gln Ser Ala Gln Ala Asp Ser Ala Ala Ser
705                 710                 715

<210> SEQ ID NO 40
<211> LENGTH: 714
<212> TYPE: PRT
<213> ORGANISM: Shigella sonnei

<400> SEQUENCE: 40

Met Ser Arg Ile Ile Met Leu Ile Pro Thr Gly Thr Ser Val Gly Leu
1               5                   10                  15
```

-continued

```
Thr Ser Val Ser Leu Gly Val Ile Arg Ala Met Glu Arg Lys Gly Val
            20                  25                  30
Arg Leu Ser Val Phe Lys Pro Ile Ala Gln Pro Arg Thr Gly Gly Asp
        35                  40                  45
Ala Pro Asp Gln Thr Thr Thr Ile Val Arg Ala Asn Ser Ser Thr Thr
50                  55                  60
Thr Ala Ala Glu Pro Leu Lys Met Ser Tyr Val Gly Leu Leu Ser
65                  70                  75                  80
Ser Asn Gln Lys Asp Val Leu Met Glu Glu Ile Val Ala Asn Tyr His
                85                  90                  95
Ala Asn Thr Lys Asp Ala Glu Val Val Leu Val Glu Gly Leu Val Pro
            100                 105                 110
Thr Arg Lys His Gln Phe Ala Gln Ser Leu Asn Tyr Glu Ile Ala Lys
        115                 120                 125
Thr Leu Asn Ala Glu Ile Val Phe Val Met Ser Gln Gly Thr Asp Thr
130                 135                 140
Pro Glu Gln Leu Lys Glu Arg Ile Glu Leu Thr Arg Asn Ser Phe Gly
145                 150                 155                 160
Gly Ala Lys Asn Thr Asn Ile Thr Gly Val Ile Val Asn Lys Leu Asn
                165                 170                 175
Ala Pro Val Asp Glu Gln Gly Arg Thr Arg Pro Asp Leu Ser Glu Ile
            180                 185                 190
Phe Asp Asp Ser Ser Lys Ala Lys Val Asn Asn Val Asp Pro Ala Lys
        195                 200                 205
Leu Gln Glu Ser Ser Pro Leu Pro Val Leu Gly Ala Val Pro Trp Ser
210                 215                 220
Phe Asp Leu Ile Ala Thr Arg Ala Ile Asp Met Ala Arg His Leu Asn
225                 230                 235                 240
Ala Thr Ile Ile Asn Glu Gly Asp Ile Asn Thr Arg Arg Val Lys Ser
                245                 250                 255
Val Thr Phe Cys Ala Arg Ser Ile Pro His Met Leu Glu His Phe Arg
            260                 265                 270
Ala Gly Ser Leu Leu Val Thr Ser Ala Asp Arg Pro Asp Val Leu Val
        275                 280                 285
Ala Ala Cys Leu Ala Ala Met Asn Gly Val Glu Ile Gly Ala Leu Leu
290                 295                 300
Leu Thr Gly Gly Tyr Glu Met Asp Ala Arg Ile Ser Lys Leu Cys Glu
305                 310                 315                 320
Arg Ala Phe Ala Thr Gly Leu Pro Val Phe Met Val Asn Thr Asn Thr
                325                 330                 335
Trp Gln Thr Ser Leu Ser Leu Gln Ser Phe Asn Leu Glu Val Pro Val
            340                 345                 350
Asp Asp His Glu Arg Ile Glu Lys Val Gln Glu Tyr Val Ala Asn Tyr
        355                 360                 365
Ile Asn Ala Asp Trp Ile Glu Ser Leu Thr Ala Thr Ser Glu Arg Ser
370                 375                 380
Arg Arg Leu Ser Pro Pro Ala Phe Arg Tyr Gln Leu Thr Glu Leu Ala
385                 390                 395                 400
Arg Lys Ala Gly Lys Arg Ile Val Leu Pro Glu Gly Asp Glu Pro Arg
                405                 410                 415
Thr Val Lys Ala Ala Ala Ile Cys Ala Glu Arg Gly Ile Ala Thr Cys
            420                 425                 430
Val Leu Leu Gly Asn Pro Ala Glu Ile Asn Arg Val Ala Ala Ser Gln
```

```
                435                 440                 445
Gly Val Glu Leu Gly Ala Gly Ile Glu Ile Val Asp Pro Glu Val Val
    450                 455                 460
Arg Glu Ser Tyr Val Gly Arg Leu Val Glu Leu Arg Lys Asn Lys Gly
465                 470                 475                 480
Met Thr Glu Thr Val Ala Arg Glu Gln Leu Glu Asp Asn Val Val Leu
                485                 490                 495
Gly Thr Leu Met Leu Glu Gln Asp Glu Val Asp Gly Leu Val Ser Gly
            500                 505                 510
Ala Val His Thr Thr Ala Asn Thr Ile Arg Pro Pro Leu Gln Leu Ile
        515                 520                 525
Lys Thr Ala Pro Gly Ser Ser Leu Val Ser Ser Val Phe Phe Met Leu
    530                 535                 540
Leu Pro Glu Gln Val Tyr Val Tyr Gly Asp Cys Ala Ile Asn Pro Asp
545                 550                 555                 560
Pro Thr Ala Glu Gln Leu Ala Glu Ile Ala Ile Gln Ser Ala Asp Ser
                565                 570                 575
Ala Ala Ala Phe Gly Ile Glu Pro Arg Val Ala Met Leu Ser Tyr Ser
            580                 585                 590
Thr Gly Thr Ser Gly Ala Gly Ser Asp Val Glu Lys Val Arg Glu Ala
        595                 600                 605
Thr Arg Leu Ala Gln Glu Lys Arg Pro Asp Leu Met Ile Asp Gly Pro
    610                 615                 620
Leu Gln Tyr Asp Ala Ala Val Met Ala Asp Val Ala Lys Ser Lys Ala
625                 630                 635                 640
Pro Asn Ser Pro Val Ala Gly Arg Ala Thr Val Phe Ile Phe Pro Asp
                645                 650                 655
Leu Asn Thr Gly Asn Thr Thr Tyr Lys Ala Val Gln Arg Ser Ala Asp
            660                 665                 670
Leu Ile Ser Ile Gly Pro Met Leu Gln Gly Met Arg Lys Pro Val Asn
        675                 680                 685
Asp Leu Ser Arg Gly Ala Leu Val Asp Asp Ile Val Tyr Thr Ile Ala
    690                 695                 700
Leu Thr Ala Ile Gln Ser Ala Gln Gln Gln
705                 710

<210> SEQ ID NO 41
<211> LENGTH: 33
<212> TYPE: DNA
<213> ORGANISM: Artificial
<220> FEATURE:
<223> OTHER INFORMATION: Synthetic DNA

<400> SEQUENCE: 41
cacggaattc cagttcgagt ttatcattat caa                                    33

<210> SEQ ID NO 42
<211> LENGTH: 35
<212> TYPE: DNA
<213> ORGANISM: Artificial
<220> FEATURE:
<223> OTHER INFORMATION: Synthetic DNA

<400> SEQUENCE: 42
ctctggatcc tttgtttgtt tatgtgtgtt tattc                                  35

<210> SEQ ID NO 43
```

<211> LENGTH: 32
<212> TYPE: DNA
<213> ORGANISM: Artificial
<220> FEATURE:
<223> OTHER INFORMATION: Synthetic DNA

<400> SEQUENCE: 43
taggcaattg caagaattac tcgtgagtaa gg                                    32

<210> SEQ ID NO 44
<211> LENGTH: 36
<212> TYPE: DNA
<213> ORGANISM: Artificial
<220> FEATURE:
<223> OTHER INFORMATION: Synthetic DNA

<400> SEQUENCE: 44
ataagaattc tgttttatat ttgttgtaaa aagtag                                36

<210> SEQ ID NO 45
<211> LENGTH: 43
<212> TYPE: DNA
<213> ORGANISM: Artificial
<220> FEATURE:
<223> OTHER INFORMATION: Synthetic DNA

<400> SEQUENCE: 45
cgcggatccg cggggcccat aaggcaagat gagtgaaggc ccc                        43

<210> SEQ ID NO 46
<211> LENGTH: 43
<212> TYPE: DNA
<213> ORGANISM: Artificial
<220> FEATURE:
<223> OTHER INFORMATION: Synthetic DNA

<400> SEQUENCE: 46
ccgctcgagc gggtcgacgt gcttgcattt ttctaattat cct                        43

<210> SEQ ID NO 47
<211> LENGTH: 40
<212> TYPE: DNA
<213> ORGANISM: Artificial
<220> FEATURE:
<223> OTHER INFORMATION: Synthetic DNA

<400> SEQUENCE: 47
ggaattccgc ggccgcaggt aaacacacaa gaaaaaatgg                            40

<210> SEQ ID NO 48
<211> LENGTH: 41
<212> TYPE: DNA
<213> ORGANISM: Artificial
<220> FEATURE:
<223> OTHER INFORMATION: Synthetic DNA

<400> SEQUENCE: 48
ccttaattaa gggactagtc taagaaatgc cgcatatgta c                          41

<210> SEQ ID NO 49
<211> LENGTH: 50
<212> TYPE: DNA
<213> ORGANISM: Artificial
<220> FEATURE:
<223> OTHER INFORMATION: Synthetic DNA

<400> SEQUENCE: 49 tccccccgggg gacgagctcg ctcagtttct tcttgaaatt tagcatcgtg    50

<210> SEQ ID NO 50
<211> LENGTH: 43
<212> TYPE: DNA
<213> ORGANISM: Artificial
<220> FEATURE:
<223> OTHER INFORMATION: Synthetic DNA

<400> SEQUENCE: 50 tccccccgggg gacgagctcg aaacggaaag aaaaaaggcc gac    43

<210> SEQ ID NO 51
<211> LENGTH: 50
<212> TYPE: DNA
<213> ORGANISM: Artificial
<220> FEATURE:
<223> OTHER INFORMATION: Synthetic DNA

<400> SEQUENCE: 51
ctagaggatc cccgggtacc ctcagtttct tcttgaaatt tagcatcgtg    50

<210> SEQ ID NO 52
<211> LENGTH: 43
<212> TYPE: DNA
<213> ORGANISM: Artificial
<220> FEATURE:
<223> OTHER INFORMATION: Synthetic DNA

<400> SEQUENCE: 52
cggccagtga attcgagctc aaacggaaag aaaaaaggcc gac    43

<210> SEQ ID NO 53
<211> LENGTH: 50
<212> TYPE: DNA
<213> ORGANISM: Artificial
<220> FEATURE:
<223> OTHER INFORMATION: Synthetic DNA

<400> SEQUENCE: 53 tccccccgggg gacgagctcg tccggtcttt atctaccatt catttattac    50

<210> SEQ ID NO 54
<211> LENGTH: 61
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (2)..(2)
<223> OTHER INFORMATION: r is g or a
<220> FEATURE:
<221> NAME/KEY: misc_feature
<222> LOCATION: (6)..(6)
<223> OTHER INFORMATION: s is g or c
<220> FEATURE:
<221> NAME/KEY: misc_feature
<222> LOCATION: (7)..(7)
<223> OTHER INFORMATION: y is t or c
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: h is a, c, or t
<220> FEATURE:

```
<221> NAME/KEY: misc_feature
<222> LOCATION: (13)..(13)
<223> OTHER INFORMATION: d is a, g, or t
<220> FEATURE:
<221> NAME/KEY: misc_feature
<222> LOCATION: (14)..(14)
<223> OTHER INFORMATION: n is a, c, g, or t

<400> SEQUENCE: 54
artcasynth tcdnatcccc cgggggacga gctcgggttt catggggtag tacttgtatt    60
a                                                                    61

<210> SEQ ID NO 55
<211> LENGTH: 65
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (2)..(2)
<223> OTHER INFORMATION: r is g or a
<220> FEATURE:
<221> NAME/KEY: misc_feature
<222> LOCATION: (6)..(6)
<223> OTHER INFORMATION: s is g or c
<220> FEATURE:
<221> NAME/KEY: misc_feature
<222> LOCATION: (7)..(7)
<223> OTHER INFORMATION: y is t or c
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: h is a, c, or t
<220> FEATURE:
<221> NAME/KEY: misc_feature
<222> LOCATION: (13)..(13)
<223> OTHER INFORMATION: d is a, g, or t
<220> FEATURE:
<221> NAME/KEY: misc_feature
<222> LOCATION: (14)..(14)
<223> OTHER INFORMATION: n is a, c, g, or t

<400> SEQUENCE: 55
artcasynth tcdnactaga ggatccccgg gtacctccgg tctttatcta ccattcattt    60
attac                                                                65

<210> SEQ ID NO 56
<211> LENGTH: 46
<212> TYPE: DNA
<213> ORGANISM: Artificial
<220> FEATURE:
<223> OTHER INFORMATION: Synthetic DNA

<400> SEQUENCE: 56
cggccagtga attcgagctc ggtttcatgg ggtagtactt gtatta                   46

<210> SEQ ID NO 57
<211> LENGTH: 40
<212> TYPE: DNA
<213> ORGANISM: Artificial
<220> FEATURE:
<223> OTHER INFORMATION: Synthetic DNA

<400> SEQUENCE: 57
tacgactcac tatagggccc tttggcctgg tattgtcatc                          40
```

<210> SEQ ID NO 58
<211> LENGTH: 35
<212> TYPE: DNA
<213> ORGANISM: Artificial
<220> FEATURE:
<223> OTHER INFORMATION: Synthetic DNA

<400> SEQUENCE: 58
tctgttccat gtcgaccgac gattctgacc ctttc                              35

<210> SEQ ID NO 59
<211> LENGTH: 36
<212> TYPE: DNA
<213> ORGANISM: Artificial
<220> FEATURE:
<223> OTHER INFORMATION: Synthetic DNA

<400> SEQUENCE: 59
gggcccgggc gtcgacagca aaaccaaaca tatcaa                             36

<210> SEQ ID NO 60
<211> LENGTH: 37
<212> TYPE: DNA
<213> ORGANISM: Artificial
<220> FEATURE:
<223> OTHER INFORMATION: Synthetic DNA

<400> SEQUENCE: 60
accaagctta ctcgagcaca cgaaaaaaaa aaagtcg                            37

<210> SEQ ID NO 61
<211> LENGTH: 36
<212> TYPE: DNA
<213> ORGANISM: Artificial
<220> FEATURE:
<223> OTHER INFORMATION: Synthetic DNA

<400> SEQUENCE: 61
gggcccgggc gtcgactgtt atacacaaac agaata                             36

<210> SEQ ID NO 62
<211> LENGTH: 38
<212> TYPE: DNA
<213> ORGANISM: Artificial
<220> FEATURE:
<223> OTHER INFORMATION: Synthetic DNA

<400> SEQUENCE: 62
accaagctta ctcgagagaa aaggagcgaa attttatc                           38

<210> SEQ ID NO 63
<211> LENGTH: 1469
<212> TYPE: DNA
<213> ORGANISM: Bifidobacterium animalis
<220> FEATURE:
<221> NAME/KEY: CDS
<222> LOCATION: (45)..(1469)

<400> SEQUENCE: 63
aaggaaaaaa gcggccgcaa aaggaaaagg actagtccta tata atg act aat cca    56
                                             Met Thr Asn Pro
                                             1 gtt att gga act ccc tgg caa aag tta gat agg cca gtt tct gaa gaa   104
Val Ile Gly Thr Pro Trp Gln Lys Leu Asp Arg Pro Val Ser Glu Glu
 5                  10                  15                  20

| | | |
|---|---|---|
| gct ata gaa ggt atg gat aaa tat tgg cgt gtt gct aat tat atg tcc<br>Ala Ile Glu Gly Met Asp Lys Tyr Trp Arg Val Ala Asn Tyr Met Ser<br>                25                     30                 35 | 152 | |
| att gga cag att tac ctt agg tca aat ccc tta atg aaa gag cct ttc<br>Ile Gly Gln Ile Tyr Leu Arg Ser Asn Pro Leu Met Lys Glu Pro Phe<br>            40                     45                 50 | 200 | |
| act cgt gat gat gtg aaa cac aga ttg gtt gga cat tgg gga aca acc<br>Thr Arg Asp Asp Val Lys His Arg Leu Val Gly His Trp Gly Thr Thr<br>          55                     60                 65 | 248 | |
| cca ggt ctg aac ttc ctt ctg gca cac att aat aga ttg att gct gat<br>Pro Gly Leu Asn Phe Leu Leu Ala His Ile Asn Arg Leu Ile Ala Asp<br>70                     75                     80 | 296 | |
| cac cag cag aat acg gtc ttt att atg ggg cca gga cat ggt ggt cct<br>His Gln Gln Asn Thr Val Phe Ile Met Gly Pro Gly His Gly Gly Pro<br>85                     90                     95              100 | 344 | |
| gca ggt act gct cag tcc tat ata gac ggc aca tac acc gaa tac tac<br>Ala Gly Thr Ala Gln Ser Tyr Ile Asp Gly Thr Tyr Thr Glu Tyr Tyr<br>                     105                  110               115 | 392 | |
| cca aat atc aca aaa gat gaa gcg ggc cta caa aag ttc ttc aga caa<br>Pro Asn Ile Thr Lys Asp Glu Ala Gly Leu Gln Lys Phe Phe Arg Gln<br>            120                    125                130 | 440 | |
| ttt tcc tat cct gga ggt att cca agt cac ttc gct cct gaa acc cca<br>Phe Ser Tyr Pro Gly Gly Ile Pro Ser His Phe Ala Pro Glu Thr Pro<br>               135                  140               145 | 488 | |
| ggg tct ata cac gaa ggt ggc gaa tta ggc tat gca cta tcg cat gcc<br>Gly Ser Ile His Glu Gly Gly Glu Leu Gly Tyr Ala Leu Ser His Ala<br>            150                    155                160 | 536 | |
| tat ggt gca att atg gac aat cct tct ttg ttc gtt ccg tgt ata atc<br>Tyr Gly Ala Ile Met Asp Asn Pro Ser Leu Phe Val Pro Cys Ile Ile<br>165                    170                   175              180 | 584 | |
| ggt gac gga gag gcc gaa acc ggt cct ttg gct act gga tgg caa tcc<br>Gly Asp Gly Glu Ala Glu Thr Gly Pro Leu Ala Thr Gly Trp Gln Ser<br>                     185                  190               195 | 632 | |
| aat aag ctg gta aat cct aga acg gat ggg att gta tta ccg ata ctt<br>Asn Lys Leu Val Asn Pro Arg Thr Asp Gly Ile Val Leu Pro Ile Leu<br>            200                    205                210 | 680 | |
| cac ttg aat ggc tac aag att gct aat ccc act ata tta gca aga att<br>His Leu Asn Gly Tyr Lys Ile Ala Asn Pro Thr Ile Leu Ala Arg Ile<br>               215                  220               225 | 728 | |
| tcc gat gaa gag tta cac gat ttc ttt aga ggc atg ggc tat cat ccg<br>Ser Asp Glu Glu Leu His Asp Phe Phe Arg Gly Met Gly Tyr His Pro<br>            230                    235                240 | 776 | |
| tac gaa ttt gtt gca ggt ttt gat aac gaa gac cat ctg tct att cat<br>Tyr Glu Phe Val Ala Gly Phe Asp Asn Glu Asp His Leu Ser Ile His<br>245                    250                   255              260 | 824 | |
| agg aga ttc gca gag tta ttt gag aca atc ttt gac gaa ata tgc gat<br>Arg Arg Phe Ala Glu Leu Phe Glu Thr Ile Phe Asp Glu Ile Cys Asp<br>               265                  270               275 | 872 | |
| att aag gca gcc gct caa acg gac gac atg acc aga cct ttc tac ccg<br>Ile Lys Ala Ala Ala Gln Thr Asp Asp Met Thr Arg Pro Phe Tyr Pro<br>            280                    285                290 | 920 | |
| atg cta atc ttt agg aca cca aag gga tgg act tgt cca aaa ttc ata<br>Met Leu Ile Phe Arg Thr Pro Lys Gly Trp Thr Cys Pro Lys Phe Ile<br>               295                  300               305 | 968 | |
| gac ggt aag aaa aca gaa ggt tca tgg aga gcg cat caa gtc cca ctt<br>Asp Gly Lys Lys Thr Glu Gly Ser Trp Arg Ala His Gln Val Pro Leu<br>310                    315                   320 | 1016 | |
| gcc tca gct aga gac act gaa gca cat ttc gaa gtc ctt aaa ggt tgg<br>Ala Ser Ala Arg Asp Thr Glu Ala His Phe Glu Val Leu Lys Gly Trp | 1064 | |

```
                  325                 330                 335                 340
atg gaa tcc tac aaa cca gaa gaa cta ttt aat gct gat ggt tct atc          1112
Met Glu Ser Tyr Lys Pro Glu Glu Leu Phe Asn Ala Asp Gly Ser Ile
                345                 350                 355 aag gaa gat gtt acg gct ttt atg cct aag gga gaa tta cgt ata ggc          1160
Lys Glu Asp Val Thr Ala Phe Met Pro Lys Gly Glu Leu Arg Ile Gly
                360                 365                 370 gca aat ccc aac gcc aac gga ggg aga att agg gag gac ttg aaa ttg          1208
Ala Asn Pro Asn Ala Asn Gly Gly Arg Ile Arg Glu Asp Leu Lys Leu
                375                 380                 385 cca gaa tta gat cag tac gaa att acg ggc gtt aaa gag tat ggt cat          1256
Pro Glu Leu Asp Gln Tyr Glu Ile Thr Gly Val Lys Glu Tyr Gly His
                390                 395                 400 gga tgg gga caa gtt gaa gca ccg aga agt ctt ggt gcg tat tgt aga          1304
Gly Trp Gly Gln Val Glu Ala Pro Arg Ser Leu Gly Ala Tyr Cys Arg
405                 410                 415                 420 gac atc atc aag aat aac cct gat agt ttc aga gtg ttt ggc cca gat          1352
Asp Ile Ile Lys Asn Asn Pro Asp Ser Phe Arg Val Phe Gly Pro Asp
                425                 430                 435 gaa act gcg tcc aat cgt ttg aat gca act tat gaa gtt aca aag aaa          1400
Glu Thr Ala Ser Asn Arg Leu Asn Ala Thr Tyr Glu Val Thr Lys Lys
                440                 445                 450 caa tgg gat aac ggt tac tta agt gca ttg gtg gat gaa aac atg gca          1448
Gln Trp Asp Asn Gly Tyr Leu Ser Ala Leu Val Asp Glu Asn Met Ala
                455                 460                 465 gta aca ggg caa gtt gtt gag                                              1469
Val Thr Gly Gln Val Val Glu
                470                 475

<210> SEQ ID NO 64
<211> LENGTH: 475
<212> TYPE: PRT
<213> ORGANISM: Bifidobacterium animalis

<400> SEQUENCE: 64

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
                20                  25                  30

Asn Tyr Met Ser Ile Gly Gln Ile Tyr Leu Arg Ser Asn Pro Leu Met
            35                  40                  45

Lys Glu Pro Phe Thr Arg Asp Asp Val Lys His Arg Leu Val Gly His
        50                  55                  60

Trp Gly Thr Thr Pro Gly Leu Asn Phe Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
                100                 105                 110

Thr Glu Tyr Tyr Pro Asn Ile Thr Lys Asp Glu Ala Gly Leu Gln Lys
            115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175
```

-continued

```
Pro Cys Ile Ile Gly Asp Gly Glu Ala Glu Thr Gly Pro Leu Ala Thr
            180                 185                 190
Gly Trp Gln Ser Asn Lys Leu Val Asn Pro Arg Thr Asp Gly Ile Val
        195                 200                 205
Leu Pro Ile Leu His Leu Asn Gly Tyr Lys Ile Ala Asn Pro Thr Ile
    210                 215                 220
Leu Ala Arg Ile Ser Asp Glu Glu Leu His Asp Phe Phe Arg Gly Met
225                 230                 235                 240
Gly Tyr His Pro Tyr Glu Phe Val Ala Gly Phe Asp Asn Glu Asp His
                245                 250                 255
Leu Ser Ile His Arg Arg Phe Ala Glu Leu Phe Glu Thr Ile Phe Asp
            260                 265                 270
Glu Ile Cys Asp Ile Lys Ala Ala Ala Gln Thr Asp Asp Met Thr Arg
        275                 280                 285
Pro Phe Tyr Pro Met Leu Ile Phe Arg Thr Pro Lys Gly Trp Thr Cys
    290                 295                 300
Pro Lys Phe Ile Asp Gly Lys Lys Thr Glu Gly Ser Trp Arg Ala His
305                 310                 315                 320
Gln Val Pro Leu Ala Ser Ala Arg Asp Thr Glu Ala His Phe Glu Val
                325                 330                 335
Leu Lys Gly Trp Met Glu Ser Tyr Lys Pro Glu Glu Leu Phe Asn Ala
            340                 345                 350
Asp Gly Ser Ile Lys Glu Asp Val Thr Ala Phe Met Pro Lys Gly Glu
        355                 360                 365
Leu Arg Ile Gly Ala Asn Pro Asn Ala Asn Gly Arg Ile Arg Glu
    370                 375                 380
Asp Leu Lys Leu Pro Glu Leu Asp Gln Tyr Glu Ile Thr Gly Val Lys
385                 390                 395                 400
Glu Tyr Gly His Gly Trp Gln Val Glu Ala Pro Arg Ser Leu Gly
                405                 410                 415
Ala Tyr Cys Arg Asp Ile Ile Lys Asn Asn Pro Asp Ser Phe Arg Val
            420                 425                 430
Phe Gly Pro Asp Glu Thr Ala Ser Asn Arg Leu Asn Ala Thr Tyr Glu
        435                 440                 445
Val Thr Lys Lys Gln Trp Asp Asn Gly Tyr Leu Ser Ala Leu Val Asp
    450                 455                 460
Glu Asn Met Ala Val Thr Gly Gln Val Val Glu
465                 470                 475

<210> SEQ ID NO 65
<211> LENGTH: 2497
<212> TYPE: DNA
<213> ORGANISM: Aspergillus oryzae
<220> FEATURE:
<221> NAME/KEY: CDS
<222> LOCATION: (45)..(2474)

<400> SEQUENCE: 65
aaggaaaaaa gcggccgcaa aaggaaaagg actagtccta tata atg gca cct agt    56
                                              Met Ala Pro Ser
                                               1 tct gaa tca gac gac aat att tca gcc tat ggt gcg act aga agc acc   104
Ser Glu Ser Asp Asp Asn Ile Ser Ala Tyr Gly Ala Thr Arg Ser Thr
  5              10                  15                  20 att aag gga caa ccc cta gac gcc gac gaa gtg aga aag atg gat gca   152
Ile Lys Gly Gln Pro Leu Asp Ala Asp Glu Val Arg Lys Met Asp Ala
             25                  30                  35
```

```
tat ttc aga gca tct atg tac ttg tgt tta ggt atg ctt tac atg agg    200
Tyr Phe Arg Ala Ser Met Tyr Leu Cys Leu Gly Met Leu Tyr Met Arg
        40                  45                  50 gat aat gtt tta ttg aaa gag cct tta aag gtc gaa cat cta aaa gcc    248
Asp Asn Val Leu Leu Lys Glu Pro Leu Lys Val Glu His Leu Lys Ala
        55                  60                  65 aga cta ctt ggg cat tgg ggt tca gac gct ggt caa tct ttc aca tgg    296
Arg Leu Leu Gly His Trp Gly Ser Asp Ala Gly Gln Ser Phe Thr Trp
    70                  75                  80 tta cac atg aat agg tta atc aag aaa tat gat tta gac gta ttg ttt    344
Leu His Met Asn Arg Leu Ile Lys Lys Tyr Asp Leu Asp Val Leu Phe
85                  90                  95                 100 gtt tca ggc cca ggt cac ggt gct ccg gcc gtt tta tct caa tcg tat    392
Val Ser Gly Pro Gly His Gly Ala Pro Ala Val Leu Ser Gln Ser Tyr
            105                 110                 115 ctt gaa ggt gtt tac agt gaa gtt tac cca gac aaa agt gaa gat gag    440
Leu Glu Gly Val Tyr Ser Glu Val Tyr Pro Asp Lys Ser Glu Asp Glu
            120                 125                 130 aaa ggg cta cag aga ttc ttt aaa cag ttc tcg ttc cct gga ggt att    488
Lys Gly Leu Gln Arg Phe Phe Lys Gln Phe Ser Phe Pro Gly Gly Ile
        135                 140                 145 ggt tcc cat gct acc cct gag aca cct ggg tcc att cat gaa gga gga    536
Gly Ser His Ala Thr Pro Glu Thr Pro Gly Ser Ile His Glu Gly Gly
        150                 155                 160 gaa tta ggc tac tcc att agt cac gca ttt ggg tca gtg ttt gat cat    584
Glu Leu Gly Tyr Ser Ile Ser His Ala Phe Gly Ser Val Phe Asp His
165                 170                 175                 180 ccg aat ttg att acc tta acc atg gta ggt gat ggt gag tcc gaa aca    632
Pro Asn Leu Ile Thr Leu Thr Met Val Gly Asp Gly Glu Ser Glu Thr
                185                 190                 195 gga cct tta gcg act tca tgg cac tca acg aaa ttc cta aat cct tgc    680
Gly Pro Leu Ala Thr Ser Trp His Ser Thr Lys Phe Leu Asn Pro Cys
            200                 205                 210 aca gat ggt gca gtc tta cct gta ttg cac ttg aat gga tat aag ata    728
Thr Asp Gly Ala Val Leu Pro Val Leu His Leu Asn Gly Tyr Lys Ile
            215                 220                 225 aac aac cca acg gta tta gcg aga atc tcg cat gaa gag ttg aaa gcc    776
Asn Asn Pro Thr Val Leu Ala Arg Ile Ser His Glu Glu Leu Lys Ala
        230                 235                 240 ttg ttc gtt ggt tat ggt tgg act cca tac ttt gtg gaa gga aat gat    824
Leu Phe Val Gly Tyr Gly Trp Thr Pro Tyr Phe Val Glu Gly Asn Asp
245                 250                 255                 260 aga gaa tct atg cat caa gcc atg gct gct aca tta gaa cac tgt atc    872
Arg Glu Ser Met His Gln Ala Met Ala Ala Thr Leu Glu His Cys Ile
                265                 270                 275 gtc gaa ata aag aag ata cag aag caa gcc aga gaa tct aat aaa ccg    920
Val Glu Ile Lys Lys Ile Gln Lys Gln Ala Arg Glu Ser Asn Lys Pro
            280                 285                 290 ttt agg cct aga tgg ccc atg att gtg cta cgt tct ccc aaa ggt tgg    968
Phe Arg Pro Arg Trp Pro Met Ile Val Leu Arg Ser Pro Lys Gly Trp
        295                 300                 305 agc gct cca aga gaa ata gac gga aag tta ctg gaa gga ttt tgg aga   1016
Ser Ala Pro Arg Glu Ile Asp Gly Lys Leu Leu Glu Gly Phe Trp Arg
        310                 315                 320 tca cat caa atc cca ata act gat gtg ctg acc aat cca gca cat ttg   1064
Ser His Gln Ile Pro Ile Thr Asp Val Leu Thr Asn Pro Ala His Leu
325                 330                 335                 340 aag ctg tta gag act tgg atg aag agc tac aaa cca gaa gaa ttg ttc   1112
Lys Leu Leu Glu Thr Trp Met Lys Ser Tyr Lys Pro Glu Glu Leu Phe
```

-continued

|  | 345 |  |  |  | 350 |  |  |  | 355 |  |  |  |  |
|---|---|---|---|---|---|---|---|---|---|---|---|---|---|
| gac | aag | aac | ggc | aaa | ctt | gta | gaa | gag | ctt | aag | gcc | ttg | gca | cca | tct | 1160 |
| Asp | Lys | Asn | Gly | Lys | Leu | Val | Glu | Glu | Leu | Lys | Ala | Leu | Ala | Pro | Ser |  |
|  |  |  | 360 |  |  |  |  | 365 |  |  |  |  | 370 |  |  |  |

```
gac aag aac ggc aaa ctt gta gaa gag ctt aag gcc ttg gca cca tct      1160
Asp Lys Asn Gly Lys Leu Val Glu Glu Leu Lys Ala Leu Ala Pro Ser
            360                 365                 370 ggt aat tcc aga atg tct gca aat cca gtt ggc aat ggc ggt att tta      1208
Gly Asn Ser Arg Met Ser Ala Asn Pro Val Gly Asn Gly Gly Ile Leu
        375                 380                 385 aga aga cca ttg caa cta ccc gat ttt cgt gat tac gct ttg aag gat      1256
Arg Arg Pro Leu Gln Leu Pro Asp Phe Arg Asp Tyr Ala Leu Lys Asp
390                 395                 400 att gat cca gga gtt tca gtt agg ggc tct atg act aat atg agt aaa      1304
Ile Asp Pro Gly Val Ser Val Arg Gly Ser Met Thr Asn Met Ser Lys
405                 410                 415                 420 ttt ctg aga gat gtc gta aag gag aac atg acc acg ttt aga gtc ttc      1352
Phe Leu Arg Asp Val Val Lys Glu Asn Met Thr Thr Phe Arg Val Phe
                425                 430                 435 ggt cca gat gag act gaa tcg aat aaa ctt gct gaa att tac aaa gct      1400
Gly Pro Asp Glu Thr Glu Ser Asn Lys Leu Ala Glu Ile Tyr Lys Ala
            440                 445                 450 ggc aag aaa gta tgg ttg ggc gat tat ttt gaa gag gac aaa gat ggt      1448
Gly Lys Lys Val Trp Leu Gly Asp Tyr Phe Glu Glu Asp Lys Asp Gly
        455                 460                 465 gga aac ttg gct ttt gaa gga cgt gtc atg gaa atg cta agc gaa cac      1496
Gly Asn Leu Ala Phe Glu Gly Arg Val Met Glu Met Leu Ser Glu His
470                 475                 480 act tgt gag ggt tgg tta gag ggt tat gtg ttg tcc ggc cgt cat ggt      1544
Thr Cys Glu Gly Trp Leu Glu Gly Tyr Val Leu Ser Gly Arg His Gly
485                 490                 495                 500 att ttg aac tca tat gaa cca ttt ata cat gtt atc gac tca atg gta      1592
Ile Leu Asn Ser Tyr Glu Pro Phe Ile His Val Ile Asp Ser Met Val
                505                 510                 515 aac caa cat tgt aag tgg att gag aaa tgc tta gaa gtc gaa tgg aga      1640
Asn Gln His Cys Lys Trp Ile Glu Lys Cys Leu Glu Val Glu Trp Arg
            520                 525                 530 gct aag gtt gct tct ctt aac atc ttg ctg aca gct act gtt tgg cgt      1688
Ala Lys Val Ala Ser Leu Asn Ile Leu Leu Thr Ala Thr Val Trp Arg
        535                 540                 545 caa gat cat aat ggt ttt acg cat cag gac cca ggt ttt ctg gat gtg      1736
Gln Asp His Asn Gly Phe Thr His Gln Asp Pro Gly Phe Leu Asp Val
550                 555                 560 gtt gca aac aaa tcg cct gaa gtt gtc cgt ata tat cta cca ccg gat      1784
Val Ala Asn Lys Ser Pro Glu Val Val Arg Ile Tyr Leu Pro Pro Asp
565                 570                 575                 580 ggg aat act ctt ttg tcc gtg atg gat cac tgt ttc aga agc gtc aac      1832
Gly Asn Thr Leu Leu Ser Val Met Asp His Cys Phe Arg Ser Val Asn
                585                 590                 595 tac gtt aac gtt gta gtt gct gac aaa caa gaa cat ata cag ttc ttg      1880
Tyr Val Asn Val Val Val Ala Asp Lys Gln Glu His Ile Gln Phe Leu
            600                 605                 610 tct atg gat gaa gcg ata gaa cat tgc aca aaa gga ttg ggt att tgg      1928
Ser Met Asp Glu Ala Ile Glu His Cys Thr Lys Gly Leu Gly Ile Trp
        615                 620                 625 gat tgg gcc tct aac gat caa ggt caa gaa cct gat gtt gtt atg gca      1976
Asp Trp Ala Ser Asn Asp Gln Gly Gln Glu Pro Asp Val Val Met Ala
630                 635                 640 gcg tgt ggt gat gtg cct act cac gaa gcc ttg gct gca acc gcc tta      2024
Ala Cys Gly Asp Val Pro Thr His Glu Ala Leu Ala Ala Thr Ala Leu
645                 650                 655                 660 ttg aac gaa cat ttg cct caa ttg aaa gtt aga ttt gtt aat gtg gta      2072
```

```
                                                                                 2120
gac tta ttc aga ctg att aac gag aaa gac cat cca cat ggt atg ccc
Asp Leu Phe Arg Leu Ile Asn Glu Lys Asp His Pro His Gly Met Pro
            680                 685                 690 gat aga cag tgg aag gct gtc ttt acg gat gat aaa ccc atc atc ttc    2168
Asp Arg Gln Trp Lys Ala Val Phe Thr Asp Asp Lys Pro Ile Ile Phe
        695                 700                 705 aac ttt cac agt tat ccg tgg cta att cac aga ttg aca tat aaa aga    2216
Asn Phe His Ser Tyr Pro Trp Leu Ile His Arg Leu Thr Tyr Lys Arg
    710                 715                 720 cct ggc caa cat aat ctg cat gtg aga ggg tat aga gag aaa ggc aat    2264
Pro Gly Gln His Asn Leu His Val Arg Gly Tyr Arg Glu Lys Gly Asn
725                 730                 735                 740 att gat aca ccc ttt gaa cta gct gtc agg aat cag aca gat agg tat    2312
Ile Asp Thr Pro Phe Glu Leu Ala Val Arg Asn Gln Thr Asp Arg Tyr
                745                 750                 755 tcc ctt gca atc gac gca att gat aga gta ggt agt tta ggc aat act    2360
Ser Leu Ala Ile Asp Ala Ile Asp Arg Val Gly Ser Leu Gly Asn Thr
            760                 765                 770 gca agt cac gtt agg gag aaa ttg atc aac caa caa ctt gct gca aaa    2408
Ala Ser His Val Arg Glu Lys Leu Ile Asn Gln Gln Leu Ala Ala Lys
        775                 780                 785 caa gaa gcc tat gac aat ggg ctg gat gct gaa tac ata agg aat tgg    2456
Gln Glu Ala Tyr Asp Asn Gly Leu Asp Ala Glu Tyr Ile Arg Asn Trp
    790                 795                 800 aag tac cca aag aaa gcg taaggaagat cttcccgagc tcg                  2497
Lys Tyr Pro Lys Lys Ala
805                 810

<210> SEQ ID NO 66
<211> LENGTH: 810
<212> TYPE: PRT
<213> ORGANISM: Aspergillus oryzae

<400> SEQUENCE: 66

Met Ala Pro Ser Ser Glu Ser Asp Asp Asn Ile Ser Ala Tyr Gly Ala
1               5                   10                  15

Thr Arg Ser Thr Ile Lys Gly Gln Pro Leu Asp Ala Asp Glu Val Arg
            20                  25                  30

Lys Met Asp Ala Tyr Phe Arg Ala Ser Met Tyr Leu Cys Leu Gly Met
        35                  40                  45

Leu Tyr Met Arg Asp Asn Val Leu Leu Lys Glu Pro Leu Lys Val Glu
    50                  55                  60

His Leu Lys Ala Arg Leu Leu Gly His Trp Gly Ser Asp Ala Gly Gln
65                  70                  75                  80

Ser Phe Thr Trp Leu His Met Asn Arg Leu Ile Lys Lys Tyr Asp Leu
                85                  90                  95

Asp Val Leu Phe Val Ser Gly Pro Gly His Gly Ala Pro Ala Val Leu
            100                 105                 110

Ser Gln Ser Tyr Leu Glu Gly Val Tyr Ser Glu Val Tyr Pro Asp Lys
        115                 120                 125

Ser Glu Asp Glu Lys Gly Leu Gln Arg Phe Phe Lys Gln Phe Ser Phe
    130                 135                 140

Pro Gly Gly Ile Gly Ser His Ala Thr Pro Glu Thr Pro Gly Ser Ile
145                 150                 155                 160

His Glu Gly Gly Glu Leu Gly Tyr Ser Ile Ser His Ala Phe Gly Ser
                165                 170                 175
```

```
Val Phe Asp His Pro Asn Leu Ile Thr Leu Thr Met Val Gly Asp Gly
            180                 185                 190

Glu Ser Glu Thr Gly Pro Leu Ala Thr Ser Trp His Ser Thr Lys Phe
        195                 200                 205

Leu Asn Pro Cys Thr Asp Gly Ala Val Leu Pro Val Leu His Leu Asn
210                 215                 220

Gly Tyr Lys Ile Asn Asn Pro Thr Val Leu Ala Arg Ile Ser His Glu
225                 230                 235                 240

Glu Leu Lys Ala Leu Phe Val Gly Tyr Gly Trp Thr Pro Tyr Phe Val
                245                 250                 255

Glu Gly Asn Asp Arg Glu Ser Met His Gln Ala Met Ala Ala Thr Leu
            260                 265                 270

Glu His Cys Ile Val Glu Ile Lys Lys Ile Gln Lys Gln Ala Arg Glu
        275                 280                 285

Ser Asn Lys Pro Phe Arg Pro Arg Trp Pro Met Ile Val Leu Arg Ser
290                 295                 300

Pro Lys Gly Trp Ser Ala Pro Arg Glu Ile Asp Gly Lys Leu Leu Glu
305                 310                 315                 320

Gly Phe Trp Arg Ser His Gln Ile Pro Ile Thr Asp Val Leu Thr Asn
                325                 330                 335

Pro Ala His Leu Lys Leu Leu Glu Thr Trp Met Lys Ser Tyr Lys Pro
            340                 345                 350

Glu Glu Leu Phe Asp Lys Asn Gly Lys Leu Val Glu Glu Leu Lys Ala
        355                 360                 365

Leu Ala Pro Ser Gly Asn Ser Arg Met Ser Ala Asn Pro Val Gly Asn
370                 375                 380

Gly Gly Ile Leu Arg Arg Pro Leu Gln Leu Pro Asp Phe Arg Asp Tyr
385                 390                 395                 400

Ala Leu Lys Asp Ile Asp Pro Gly Val Ser Val Arg Gly Ser Met Thr
                405                 410                 415

Asn Met Ser Lys Phe Leu Arg Asp Val Val Lys Glu Asn Met Thr Thr
            420                 425                 430

Phe Arg Val Phe Gly Pro Asp Glu Thr Glu Ser Asn Lys Leu Ala Glu
        435                 440                 445

Ile Tyr Lys Ala Gly Lys Lys Val Trp Leu Gly Asp Tyr Phe Glu Glu
450                 455                 460

Asp Lys Asp Gly Gly Asn Leu Ala Phe Glu Gly Arg Val Met Glu Met
465                 470                 475                 480

Leu Ser Glu His Thr Cys Glu Gly Trp Leu Glu Gly Tyr Val Leu Ser
                485                 490                 495

Gly Arg His Gly Ile Leu Asn Ser Tyr Glu Pro Phe Ile His Val Ile
            500                 505                 510

Asp Ser Met Val Asn Gln His Cys Lys Trp Ile Glu Lys Cys Leu Glu
        515                 520                 525

Val Glu Trp Arg Ala Lys Val Ala Ser Leu Asn Ile Leu Leu Thr Ala
530                 535                 540

Thr Val Trp Arg Gln Asp His Asn Gly Phe Thr His Gln Asp Pro Gly
545                 550                 555                 560

Phe Leu Asp Val Val Ala Asn Lys Ser Pro Glu Val Val Arg Ile Tyr
                565                 570                 575

Leu Pro Pro Asp Gly Asn Thr Leu Leu Ser Val Met Asp His Cys Phe
            580                 585                 590
```

```
Arg Ser Val Asn Tyr Val Asn Val Val Ala Asp Lys Gln Glu His
            595                 600                 605

Ile Gln Phe Leu Ser Met Asp Glu Ala Ile Glu His Cys Thr Lys Gly
        610                 615                 620

Leu Gly Ile Trp Asp Trp Ala Ser Asn Asp Gln Gly Gln Glu Pro Asp
625                 630                 635                 640

Val Val Met Ala Ala Cys Gly Asp Val Pro Thr His Glu Ala Leu Ala
                645                 650                 655

Ala Thr Ala Leu Leu Asn Glu His Leu Pro Gln Leu Lys Val Arg Phe
            660                 665                 670

Val Asn Val Val Asp Leu Phe Arg Leu Ile Asn Glu Lys Asp His Pro
        675                 680                 685

His Gly Met Pro Asp Arg Gln Trp Lys Ala Val Phe Thr Asp Asp Lys
    690                 695                 700

Pro Ile Ile Phe Asn Phe His Ser Tyr Pro Trp Leu Ile His Arg Leu
705                 710                 715                 720

Thr Tyr Lys Arg Pro Gly Gln His Asn Leu His Val Arg Gly Tyr Arg
                725                 730                 735

Glu Lys Gly Asn Ile Asp Thr Pro Phe Glu Leu Ala Val Arg Asn Gln
            740                 745                 750

Thr Asp Arg Tyr Ser Leu Ala Ile Asp Ala Ile Asp Arg Val Gly Ser
        755                 760                 765

Leu Gly Asn Thr Ala Ser His Val Arg Glu Lys Leu Ile Asn Gln Gln
    770                 775                 780

Leu Ala Ala Lys Gln Glu Ala Tyr Asp Asn Gly Leu Asp Ala Glu Tyr
785                 790                 795                 800

Ile Arg Asn Trp Lys Tyr Pro Lys Lys Ala
                805                 810

<210> SEQ ID NO 67
<211> LENGTH: 2521
<212> TYPE: DNA
<213> ORGANISM: Aspergillus oryzae
<220> FEATURE:
<221> NAME/KEY: CDS
<222> LOCATION: (45)..(2498)

<400> SEQUENCE: 67
aaggaaaaaa gcggccgcaa aaggaaaagg actagtccta tata atg ccg ggc gaa      56
                                              Met Pro Gly Glu
                                                1 att ata gac aga cct aat cct aaa gcc gaa cca agc cat atc cca gat     104
Ile Ile Asp Arg Pro Asn Pro Lys Ala Glu Pro Ser His Ile Pro Asp
 5                  10                  15                  20 gtg gta gag caa ttg caa gta caa cta gat caa gca tca ttg gat caa     152
Val Val Glu Gln Leu Gln Val Gln Leu Asp Gln Ala Ser Leu Asp Gln
                 25                  30                  35 agc act tct gat gcc ttc tta aag ttt aga aga gct gcc gct tac atc     200
Ser Thr Ser Asp Ala Phe Leu Lys Phe Arg Arg Ala Ala Ala Tyr Ile
             40                  45                  50 gct gct gac atc cgt agc tgt tcg tta gcc atg atc ttc ttg caa gac     248
Ala Ala Asp Ile Arg Ser Cys Ser Leu Ala Met Ile Phe Leu Gln Asp
         55                  60                  65 aat gtg cta ctg aaa aga gat ttg caa cac gat gac ata aaa ccc aga     296
Asn Val Leu Leu Lys Arg Asp Leu Gln His Asp Asp Ile Lys Pro Arg
     70                  75                  80 tta ttg ggg cat tgg gga acg tgt cca gga ttg ata ctg gtt tat tcg     344
Leu Leu Gly His Trp Gly Thr Cys Pro Gly Leu Ile Leu Val Tyr Ser
 85
```

| | | |
|---|---|---|
| cat ctg aac tac atc gtt cgt aaa cag aac tta gat atg tta tac gta<br>His Leu Asn Tyr Ile Val Arg Lys Gln Asn Leu Asp Met Leu Tyr Val<br>85                                                                   90                                                             95                                              100 | 392 |

```
                  85                  90                  95                 100 cat ctg aac tac atc gtt cgt aaa cag aac tta gat atg tta tac gta         392
His Leu Asn Tyr Ile Val Arg Lys Gln Asn Leu Asp Met Leu Tyr Val
                    105                 110                 115 gta ggg cca gga cat ggt gca cca ggg ttg ttg gcg tct ctg tgg cta         440
Val Gly Pro Gly His Gly Ala Pro Gly Leu Leu Ala Ser Leu Trp Leu
            120                 125                 130 gaa gga tca tta ggg aga ttt tat cct cag tat agt aga gat atg gaa         488
Glu Gly Ser Leu Gly Arg Phe Tyr Pro Gln Tyr Ser Arg Asp Met Glu
        135                 140                 145 ggt ctt aag aac ctt ata tcc aca ttt tct act tct gga ggt tgg cct         536
Gly Leu Lys Asn Leu Ile Ser Thr Phe Ser Thr Ser Gly Gly Leu Pro
    150                 155                 160 aga cta gac gct cca cat cat atc aat gct gaa act cca ggt gcc att         584
Arg Leu Asp Ala Pro His His Ile Asn Ala Glu Thr Pro Gly Ala Ile
165                 170                 175                 180 cac gaa ggt gga gag tta ggc tac gcg ttg gcc gtt tcg ttc ggt gcc         632
His Glu Gly Gly Glu Leu Gly Tyr Ala Leu Ala Val Ser Phe Gly Ala
                185                 190                 195 gtt atg gat aat cct gat ttg ata gtg acc tgt gtg gtt ggt gat ggg         680
Val Met Asp Asn Pro Asp Leu Ile Val Thr Cys Val Val Gly Asp Gly
            200                 205                 210 gaa gcg gaa act ggt cca acc gcc acc agt tgg cac gct atc aag tac         728
Glu Ala Glu Thr Gly Pro Thr Ala Thr Ser Trp His Ala Ile Lys Tyr
        215                 220                 225 ata gat cct gca gaa tca ggt gct gta ttg ccc atc tta cac gtc aat         776
Ile Asp Pro Ala Glu Ser Gly Ala Val Leu Pro Ile Leu His Val Asn
    230                 235                 240 ggc ttc aag att tct gaa agg acc att ttc ggt tgt atg gat aat aaa         824
Gly Phe Lys Ile Ser Glu Arg Thr Ile Phe Gly Cys Met Asp Asn Lys
245                 250                 255                 260 gaa ttg atc tct tta ttt acc ggt tat ggc tat caa gtc aga att gta         872
Glu Leu Ile Ser Leu Phe Thr Gly Tyr Gly Tyr Gln Val Arg Ile Val
                265                 270                 275 gaa aat ctt gat gac att gac acg gat ttg cat tgc tct atg aac tgg         920
Glu Asn Leu Asp Asp Ile Asp Thr Asp Leu His Cys Ser Met Asn Trp
            280                 285                 290 gca gtt ggt gaa att cat aaa att caa caa gca gca aga tca ggc aaa         968
Ala Val Gly Glu Ile His Lys Ile Gln Gln Ala Ala Arg Ser Gly Lys
        295                 300                 305 ccc atc atg aaa ccg aga tgg ccg atg atc gta ctt agg act ccc aaa        1016
Pro Ile Met Lys Pro Arg Trp Pro Met Ile Val Leu Arg Thr Pro Lys
    310                 315                 320 gga tgg tct gga cct aag gag tta cac ggc cag ttt att gaa ggt tcc        1064
Gly Trp Ser Gly Pro Lys Glu Leu His Gly Gln Phe Ile Glu Gly Ser
325                 330                 335                 340 ttt cat tct cat cag gta cct ttg cct aat gca aag aaa gat aag gag        1112
Phe His Ser His Gln Val Pro Leu Pro Asn Ala Lys Lys Asp Lys Glu
                345                 350                 355 gaa ttg caa gct ctt caa aca tgg tta tcg tca tat aac cca cat gag        1160
Glu Leu Gln Ala Leu Gln Thr Trp Leu Ser Ser Tyr Asn Pro His Glu
            360                 365                 370 ctt ttc aca gag aca ggt gat gtc ata gac gaa gtc aag tcc att ata        1208
Leu Phe Thr Glu Thr Gly Asp Val Ile Asp Glu Val Lys Ser Ile Ile
        375                 380                 385 cca tct gac gac tct aag aag tta ggt caa aga ttt gag gcc tat aag        1256
Pro Ser Asp Asp Ser Lys Lys Leu Gly Gln Arg Phe Glu Ala Tyr Lys
    390                 395                 400 gca tat gaa ccg ccc aat tta cca gat tgg agg aca ttt tgc gtt gaa        1304
```

| | | | | | | | | | | | | |
|---|---|---|---|---|---|---|---|---|---|---|---|---|
| Ala | Tyr | Glu | Pro | Pro | Asn | Leu | Pro | Asp | Trp | Arg | Thr | Phe | Cys | Val | Glu |
| 405 | | | | 410 | | | | | 415 | | | | | 420 |

```
aag ggt gca caa gag agt agt atg aaa acg ata ggt aaa ttt att gac    1352
Lys Gly Ala Gln Glu Ser Ser Met Lys Thr Ile Gly Lys Phe Ile Asp
                425                 430                 435 aag gtg ttt act caa aat ccc cat tcc gtg aga ctg ttt tcc cca gat    1400
Lys Val Phe Thr Gln Asn Pro His Ser Val Arg Leu Phe Ser Pro Asp
            440                 445                 450 gaa ctg gaa tca aat aaa cta gat gct gct ctt gct cat aca ggt aga    1448
Glu Leu Glu Ser Asn Lys Leu Asp Ala Ala Leu Ala His Thr Gly Arg
                455                 460                 465 aac ttc cag tgg gat caa tat agc aat gca aaa ggt gga aga gtt att    1496
Asn Phe Gln Trp Asp Gln Tyr Ser Asn Ala Lys Gly Gly Arg Val Ile
        470                 475                 480 gag gtt cta tcc gaa cat atg tgt cag ggt ttt ctt cag ggt tat aca    1544
Glu Val Leu Ser Glu His Met Cys Gln Gly Phe Leu Gln Gly Tyr Thr
485                 490                 495                 500 ttg act ggc aga gtg ggt ctt ttc cct agt tac gaa tct ttc ttg ggg    1592
Leu Thr Gly Arg Val Gly Leu Phe Pro Ser Tyr Glu Ser Phe Leu Gly
                505                 510                 515 ata gtt cat act atg atg gtc caa tat gct aaa ttc atg aag atg gct    1640
Ile Val His Thr Met Met Val Gln Tyr Ala Lys Phe Met Lys Met Ala
            520                 525                 530 aga gaa acc ggt tgg cat aaa gat gta gca tcc ata aac tac att gaa    1688
Arg Glu Thr Gly Trp His Lys Asp Val Ala Ser Ile Asn Tyr Ile Glu
                535                 540                 545 aca tct act tgg aca cgt cag gaa cac aat gga ttt agt cac cag aac    1736
Thr Ser Thr Trp Thr Arg Gln Glu His Asn Gly Phe Ser His Gln Asn
        550                 555                 560 cca tca ttt ata ggc aat gtg cta aaa ctg aaa ccg aat gcc gcc aga    1784
Pro Ser Phe Ile Gly Asn Val Leu Lys Leu Lys Pro Asn Ala Ala Arg
565                 570                 575                 580 gtg tat ttg cca cct gac gct aac act ttc cta aca acc gtt cat cat    1832
Val Tyr Leu Pro Pro Asp Ala Asn Thr Phe Leu Thr Thr Val His His
                585                 590                 595 tgc ttg aag tca aag aac tac att aac ctt atg gtt ggc tcc aaa caa    1880
Cys Leu Lys Ser Lys Asn Tyr Ile Asn Leu Met Val Gly Ser Lys Gln
            600                 605                 610 cca act cct gta tac cta tcg cca gag gaa gcg gaa tcc cac tgt aga    1928
Pro Thr Pro Val Tyr Leu Ser Pro Glu Glu Ala Glu Ser His Cys Arg
                615                 620                 625 gca ggt gcg tca atc tgg aaa ttt tgc tca aca aac gac gga tta gat    1976
Ala Gly Ala Ser Ile Trp Lys Phe Cys Ser Thr Asn Asp Gly Leu Asp
        630                 635                 640 cct gat gtc gtt ttg gta ggg gtt ggt gtg gag gtt atg ttt gag gtt    2024
Pro Asp Val Val Leu Val Gly Val Gly Val Glu Val Met Phe Glu Val
645                 650                 655                 660 att tat gct gca gcc att ttg aga caa aga tgt ccc gaa tta aga gtc    2072
Ile Tyr Ala Ala Ala Ile Leu Arg Gln Arg Cys Pro Glu Leu Arg Val
                665                 670                 675 cgt gtt att aat gtc acg gac tta atg att ttg gaa aac gaa gga gca    2120
Arg Val Ile Asn Val Thr Asp Leu Met Ile Leu Glu Asn Glu Gly Ala
            680                 685                 690 cat ccg cat gct tta acc act gaa agt ttt gat aac ttg ttc act agc    2168
His Pro His Ala Leu Thr Thr Glu Ser Phe Asp Asn Leu Phe Thr Ser
                695                 700                 705 gat aaa cca atc cac ttt aat tat cac gga tac gtt acg gag tta caa    2216
Asp Lys Pro Ile His Phe Asn Tyr His Gly Tyr Val Thr Glu Leu Gln
        710                 715                 720
```

-continued

| | | | | | | | | | | | | | | | |
|---|---|---|---|---|---|---|---|---|---|---|---|---|---|---|---|
| ggc | tta | ttg | ttc | ggt | agg | cca | aga | cta | gag | aga | gtt | tct | att | gca | ggc | 2264 |
| Gly | Leu | Leu | Phe | Gly | Arg | Pro | Arg | Leu | Glu | Arg | Val | Ser | Ile | Ala | Gly |
| 725 | | | | 730 | | | | | 735 | | | | | 740 |

| tat | ata | gaa | gaa | ggt | tca | acg | act | acc | cca | ttc | gat | atg | atg | ttg | gtc | 2312 |
| Tyr | Ile | Glu | Glu | Gly | Ser | Thr | Thr | Thr | Pro | Phe | Asp | Met | Met | Leu | Val |
| | | | | 745 | | | | | 750 | | | | | 755 |

| aat | aag | aca | agt | aga | ttt | cac | gtt | gcg | caa | gct | gct | att | aag | ggt | gct | 2360 |
| Asn | Lys | Thr | Ser | Arg | Phe | His | Val | Ala | Gln | Ala | Ala | Ile | Lys | Gly | Ala |
| | | | 760 | | | | | 765 | | | | | 770 |

| gca | aaa | cgt | aat | gag | aaa | gtc | caa | cta | agg | gaa | caa | gaa | ctg | agc | aca | 2408 |
| Ala | Lys | Arg | Asn | Glu | Lys | Val | Gln | Leu | Arg | Glu | Gln | Glu | Leu | Ser | Thr |
| 775 | | | | | 780 | | | | | 785 |

| gaa | tta | aac | cac | aat | att | gtc | gaa | act | agg | aaa | tac | att | cat | gct | aat | 2456 |
| Glu | Leu | Asn | His | Asn | Ile | Val | Glu | Thr | Arg | Lys | Tyr | Ile | His | Ala | Asn |
| 790 | | | | | 795 | | | | | 800 |

| agg | aaa | gac | cca | gat | gat | atg | tac | gag | atg | cct | cag | ttt | agg | | | 2498 |
| Arg | Lys | Asp | Pro | Asp | Asp | Met | Tyr | Glu | Met | Pro | Gln | Phe | Arg |
| 805 | | | | 810 | | | | | 815 | taaggaagat cttcccgagc tcg   2521

<210> SEQ ID NO 68
<211> LENGTH: 818
<212> TYPE: PRT
<213> ORGANISM: Aspergillus oryzae

<400> SEQUENCE: 68

Met Pro Gly Glu Ile Ile Asp Arg Pro Asn Pro Lys Ala Glu Pro Ser
1               5                   10                  15

His Ile Pro Asp Val Val Glu Gln Leu Gln Val Gln Leu Asp Gln Ala
            20                  25                  30

Ser Leu Asp Gln Ser Thr Ser Asp Ala Phe Leu Lys Phe Arg Arg Ala
        35                  40                  45

Ala Ala Tyr Ile Ala Ala Asp Ile Arg Ser Cys Ser Leu Ala Met Ile
    50                  55                  60

Phe Leu Gln Asp Asn Val Leu Leu Lys Arg Asp Leu Gln His Asp Asp
65                  70                  75                  80

Ile Lys Pro Arg Leu Leu Gly His Trp Gly Thr Cys Pro Gly Leu Ile
                85                  90                  95

Leu Val Tyr Ser His Leu Asn Tyr Ile Val Arg Lys Gln Asn Leu Asp
            100                 105                 110

Met Leu Tyr Val Val Gly Pro Gly His Gly Ala Pro Gly Leu Leu Ala
        115                 120                 125

Ser Leu Trp Leu Glu Gly Ser Leu Gly Arg Phe Tyr Pro Gln Tyr Ser
    130                 135                 140

Arg Asp Met Glu Gly Leu Lys Asn Leu Ile Ser Thr Phe Ser Thr Ser
145                 150                 155                 160

Gly Gly Leu Pro Arg Leu Asp Ala Pro His His Ile Asn Ala Glu Thr
                165                 170                 175

Pro Gly Ala Ile His Glu Gly Gly Glu Leu Gly Tyr Ala Leu Ala Val
            180                 185                 190

Ser Phe Gly Ala Val Met Asp Asn Pro Asp Leu Ile Val Thr Cys Val
        195                 200                 205

Val Gly Asp Gly Glu Ala Glu Thr Gly Pro Thr Ala Thr Ser Trp His
    210                 215                 220

Ala Ile Lys Tyr Ile Asp Pro Ala Glu Ser Gly Ala Val Leu Pro Ile
225                 230                 235                 240

```
Leu His Val Asn Gly Phe Lys Ile Ser Glu Arg Thr Ile Phe Gly Cys
            245                 250                 255

Met Asp Asn Lys Glu Leu Ile Ser Leu Phe Thr Gly Tyr Gly Tyr Gln
        260                 265                 270

Val Arg Ile Val Glu Asn Leu Asp Asp Ile Asp Thr Asp Leu His Cys
        275                 280                 285

Ser Met Asn Trp Ala Val Gly Glu Ile His Lys Ile Gln Gln Ala Ala
290                 295                 300

Arg Ser Gly Lys Pro Ile Met Lys Pro Arg Trp Pro Met Ile Val Leu
305                 310                 315                 320

Arg Thr Pro Lys Gly Trp Ser Gly Pro Lys Glu Leu His Gly Gln Phe
                325                 330                 335

Ile Glu Gly Ser Phe His Ser His Gln Val Pro Leu Pro Asn Ala Lys
            340                 345                 350

Lys Asp Lys Glu Glu Leu Gln Ala Leu Gln Thr Trp Leu Ser Ser Tyr
        355                 360                 365

Asn Pro His Glu Leu Phe Thr Glu Thr Gly Asp Val Ile Asp Glu Val
        370                 375                 380

Lys Ser Ile Ile Pro Ser Asp Asp Ser Lys Lys Leu Gly Gln Arg Phe
385                 390                 395                 400

Glu Ala Tyr Lys Ala Tyr Glu Pro Pro Asn Leu Pro Asp Trp Arg Thr
                405                 410                 415

Phe Cys Val Glu Lys Gly Ala Gln Glu Ser Ser Met Lys Thr Ile Gly
            420                 425                 430

Lys Phe Ile Asp Lys Val Phe Thr Gln Asn Pro His Ser Val Arg Leu
        435                 440                 445

Phe Ser Pro Asp Glu Leu Glu Ser Asn Lys Leu Asp Ala Ala Leu Ala
        450                 455                 460

His Thr Gly Arg Asn Phe Gln Trp Asp Gln Tyr Ser Asn Ala Lys Gly
465                 470                 475                 480

Gly Arg Val Ile Glu Val Leu Ser Glu His Met Cys Gln Gly Phe Leu
                485                 490                 495

Gln Gly Tyr Thr Leu Thr Gly Arg Val Gly Leu Phe Pro Ser Tyr Glu
            500                 505                 510

Ser Phe Leu Gly Ile Val His Thr Met Met Val Gln Tyr Ala Lys Phe
        515                 520                 525

Met Lys Met Ala Arg Glu Thr Gly Trp His Lys Asp Val Ala Ser Ile
        530                 535                 540

Asn Tyr Ile Glu Thr Ser Thr Trp Thr Arg Gln Glu His Asn Gly Phe
545                 550                 555                 560

Ser His Gln Asn Pro Ser Phe Ile Gly Asn Val Leu Lys Leu Lys Pro
                565                 570                 575

Asn Ala Ala Arg Val Tyr Leu Pro Pro Asp Ala Asn Thr Phe Leu Thr
            580                 585                 590

Thr Val His His Cys Leu Lys Ser Lys Asn Tyr Ile Asn Leu Met Val
        595                 600                 605

Gly Ser Lys Gln Pro Thr Pro Val Tyr Leu Ser Pro Glu Glu Ala Glu
        610                 615                 620

Ser His Cys Arg Ala Gly Ala Ser Ile Trp Lys Phe Cys Ser Thr Asn
625                 630                 635                 640

Asp Gly Leu Asp Pro Asp Val Val Leu Val Gly Val Gly Val Glu Val
                645                 650                 655

Met Phe Glu Val Ile Tyr Ala Ala Ala Ile Leu Arg Gln Arg Cys Pro
```

```
                   660                  665                 670
Glu Leu Arg Val Arg Val Ile Asn Val Thr Asp Leu Met Ile Leu Glu
            675                 680                 685

Asn Glu Gly Ala His Pro His Ala Leu Thr Thr Glu Ser Phe Asp Asn
690                 695                 700

Leu Phe Thr Ser Asp Lys Pro Ile His Phe Asn Tyr His Gly Tyr Val
705                 710                 715                 720

Thr Glu Leu Gln Gly Leu Leu Phe Gly Arg Pro Arg Leu Glu Arg Val
            725                 730                 735

Ser Ile Ala Gly Tyr Ile Glu Glu Gly Ser Thr Thr Pro Phe Asp
            740                 745                 750

Met Met Leu Val Asn Lys Thr Ser Arg Phe His Val Ala Gln Ala Ala
            755                 760                 765

Ile Lys Gly Ala Ala Lys Arg Asn Glu Lys Val Gln Leu Arg Glu Gln
            770                 775                 780

Glu Leu Ser Thr Glu Leu Asn His Asn Ile Val Glu Thr Arg Lys Tyr
785                 790                 795                 800

Ile His Ala Asn Arg Lys Asp Pro Asp Asp Met Tyr Glu Met Pro Gln
            805                 810                 815

Phe Arg

<210> SEQ ID NO 69
<211> LENGTH: 2278
<212> TYPE: DNA
<213> ORGANISM: Nostoc punctiforme
<220> FEATURE:
<221> NAME/KEY: CDS
<222> LOCATION: (45)..(2255)

<400> SEQUENCE: 69
aaggaaaaaa gcggccgcaa aaggaaaagg actagtccta tata atg aca gct ata      56
                                                Met Thr Ala Ile
                                                1 agt cca aaa gcg tca tcg gca ttg ccc aac ttt tct gag ggc atc caa     104
Ser Pro Lys Ala Ser Ser Ala Leu Pro Asn Phe Ser Glu Gly Ile Gln
5               10                  15                  20 tac ttc ggc gaa gcc tta cct gat ttt gag aca tat gga gcg aca ccg     152
Tyr Phe Gly Glu Ala Leu Pro Asp Phe Glu Thr Tyr Gly Ala Thr Pro
                25                  30                  35 gct ata gaa tca ggt aag att gcc att gct tca cct acc gat aag gct     200
Ala Ile Glu Ser Gly Lys Ile Ala Ile Ala Ser Pro Thr Asp Lys Ala
            40                  45                  50 gct gtt tac cag aca cta tta gca gct gat gca tta agg tac ctt acg     248
Ala Val Tyr Gln Thr Leu Leu Ala Ala Asp Ala Leu Arg Tyr Leu Thr
        55                  60                  65 ctg caa gtg act gcg tct aaa gca tct gga cat cct ggt ggt ttc gca     296
Leu Gln Val Thr Ala Ser Lys Ala Ser Gly His Pro Gly Gly Phe Ala
70                  75                  80 tct caa gcc gag gca tac gcc tct ctg gtt atg cta gga tat aag aac     344
Ser Gln Ala Glu Ala Tyr Ala Ser Leu Val Met Leu Gly Tyr Lys Asn
85                  90                  95                  100 atc att aca gaa gtt ggt cat cat gca cca ggc ttt tat tcc gca atg     392
Ile Ile Thr Glu Val Gly His His Ala Pro Gly Phe Tyr Ser Ala Met
                105                 110                 115 ttc tta gat agg tcg ctg gaa gat atg ggc ata ttc acc gta cag gag     440
Phe Leu Asp Arg Ser Leu Glu Asp Met Gly Ile Phe Thr Val Gln Glu
            120                 125                 130 tta cgt gat agg ttt aga gaa aag cac gga ctg tta gga cat cta tcc     488
```

```
                Leu Arg Asp Arg Phe Arg Glu Lys His Gly Leu Leu Gly His Leu Ser
                        135                 140                 145 ggt ttt att cca ggt att ttg gcg cca gct gga cca ttg ggg caa gga       536
Gly Phe Ile Pro Gly Ile Leu Ala Pro Ala Gly Pro Leu Gly Gln Gly
        150                 155                 160 caa cat ttt gcc atg gca gct gcc ttg cta cac aaa gac aag cta ttt       584
Gln His Phe Ala Met Ala Ala Ala Leu Leu His Lys Asp Lys Leu Phe
165                 170                 175                 180 cct ttc acg gta ggt gac ggt ggt cta ggc gaa ccc tac att gtc agt       632
Pro Phe Thr Val Gly Asp Gly Gly Leu Gly Glu Pro Tyr Ile Val Ser
                185                 190                 195 gct ata gct cac ttt cat acc gct tat cct gca gtt act aac ttt cta       680
Ala Ile Ala His Phe His Thr Ala Tyr Pro Ala Val Thr Asn Phe Leu
        200                 205                 210 cca gtt cta gtt tgg aat ggc tat tct caa gaa cac cac tca atg gta       728
Pro Val Leu Val Trp Asn Gly Tyr Ser Gln Glu His His Ser Met Val
                215                 220                 225 tcg tta aag act aac gaa caa atg caa gcg tat tgg caa ggc aat ggt       776
Ser Leu Lys Thr Asn Glu Gln Met Gln Ala Tyr Trp Gln Gly Asn Gly
        230                 235                 240 ttt gac gaa gtc gtg ttg gtg gat gcc aaa gac ttt gat gat cgt gat       824
Phe Asp Glu Val Val Leu Val Asp Ala Lys Asp Phe Asp Asp Arg Asp
245                 250                 255                 260 caa ccc ggt gat tat gta gat agt acc gca ttt tct ttc gag aaa aga       872
Gln Pro Gly Asp Tyr Val Asp Ser Thr Ala Phe Ser Phe Glu Lys Arg
                265                 270                 275 ctg gca ttt acg cag gct gta cta tcc ggt gta gac aag gca gcc aga       920
Leu Ala Phe Thr Gln Ala Val Leu Ser Gly Val Asp Lys Ala Ala Arg
        280                 285                 290 tca gct ttg gga ggc aaa ttg aca gtc ttc atc att aaa cag cta aaa       968
Ser Ala Leu Gly Gly Lys Leu Thr Val Phe Ile Ile Lys Gln Leu Lys
                295                 300                 305 ggc gcc ggt gtc cat gca aga ggc gcc aaa agt cac aat tta tac ccg      1016
Gly Ala Gly Val His Ala Arg Gly Ala Lys Ser His Asn Leu Tyr Pro
        310                 315                 320 aaa gac acc ttg gat gca cca cat ata atc agc gct ttg cag acg aga      1064
Lys Asp Thr Leu Asp Ala Pro His Ile Ile Ser Ala Leu Gln Thr Arg
325                 330                 335                 340 gct tta tcg gcc gaa gcc tgg caa tta gtt aga acg aac gct gaa aga      1112
Ala Leu Ser Ala Glu Ala Trp Gln Leu Val Arg Thr Asn Ala Glu Arg
                345                 350                 355 gct ggt gga gga cct gct gcg aaa act gtt gtt act gag ttc gaa tta      1160
Ala Gly Gly Gly Pro Ala Ala Lys Thr Val Val Thr Glu Phe Glu Leu
        360                 365                 370 cct tta cca gag ttg ggc gaa tta cca ttg gaa gaa tat gcc gta ggt      1208
Pro Leu Pro Glu Leu Gly Glu Leu Pro Leu Glu Glu Tyr Ala Val Gly
        375                 380                 385 ggt gag gct aag gtt tca acg act gcc atg gga cgt tta gtt gga att      1256
Gly Glu Ala Lys Val Ser Thr Thr Ala Met Gly Arg Leu Val Gly Ile
        390                 395                 400 gtg ggt aat aaa gat cgt aac ttt ctt gtg aca aat gca gat ggg aat      1304
Val Gly Asn Lys Asp Arg Asn Phe Leu Val Thr Asn Ala Asp Gly Asn
405                 410                 415                 420 gaa gcc tct ggg att gca aac att aat cag gcc ttg aaa atc ata cat      1352
Glu Ala Ser Gly Ile Ala Asn Ile Asn Gln Ala Leu Lys Ile Ile His
                425                 430                 435 ccc aca act gac gac ttg tac aat caa gcc cca aat ggt caa gtg tat      1400
Pro Thr Thr Asp Asp Leu Tyr Asn Gln Ala Pro Asn Gly Gln Val Tyr
                440                 445                 450
```

```
gag cca tta tct gag gat gcc tgt gct ggt ttg gca gct ggt ctt gct    1448
Glu Pro Leu Ser Glu Asp Ala Cys Ala Gly Leu Ala Ala Gly Leu Ala
        455                 460                 465 ctt atg ggt gct aga act ctt tgg tgt tcc tat gaa tca ttc gca ata    1496
Leu Met Gly Ala Arg Thr Leu Trp Cys Ser Tyr Glu Ser Phe Ala Ile
470                 475                 480 aat gga ttg cct att tgg caa acc gtt act caa tct atg gct gaa ttg    1544
Asn Gly Leu Pro Ile Trp Gln Thr Val Thr Gln Ser Met Ala Glu Leu
485                 490                 495                 500 aga aga caa act ccc agt acc atc acc tta ttt aca gca gga gca ttg    1592
Arg Arg Gln Thr Pro Ser Thr Ile Thr Leu Phe Thr Ala Gly Ala Leu
            505                 510                 515 gaa caa ggg aga aat ggc tgg aca cac caa aga cca gaa att gag gcc    1640
Glu Gln Gly Arg Asn Gly Trp Thr His Gln Arg Pro Glu Ile Glu Ala
        520                 525                 530 tac ttt gcg tct ctt atg agg aat ggg aac gtc ttt ccg ctt ttc cca    1688
Tyr Phe Ala Ser Leu Met Arg Asn Gly Asn Val Phe Pro Leu Phe Pro
535                 540                 545 cct gat gct aac tca atc cag gca tgt tac gaa tgg gct tta aag acc    1736
Pro Asp Ala Asn Ser Ile Gln Ala Cys Tyr Glu Trp Ala Leu Lys Thr
550                 555                 560 aag aac aag ggt ata gtg att acc gca agc aaa agc cct ttg ccg atc    1784
Lys Asn Lys Gly Ile Val Ile Thr Ala Ser Lys Ser Pro Leu Pro Ile
565                 570                 575                 580 agg aca act tta gaa caa acc aga cag ggg ttg aga gat ggt gct gtc    1832
Arg Thr Thr Leu Glu Gln Thr Arg Gln Gly Leu Arg Asp Gly Ala Val
            585                 590                 595 tta ctg cat gaa att gct ggc gac aaa cag gtc gta ttc aca gtt att    1880
Leu Leu His Glu Ile Ala Gly Asp Lys Gln Val Val Phe Thr Val Ile
        600                 605                 610 ggt gat atg acg cta atg cca gtg ttc gaa gca gcc gct ttt ctg gag    1928
Gly Asp Met Thr Leu Met Pro Val Phe Glu Ala Ala Ala Phe Leu Glu
                615                 620                 625 act gaa ggg att ggt gct aaa atc atc agc gtc att aat ccc aga caa    1976
Thr Glu Gly Ile Gly Ala Lys Ile Ile Ser Val Ile Asn Pro Arg Gln
        630                 635                 640 ctg tat aga cca cat gac aca gca tgg gat aca tgc tcc gaa cct gaa    2024
Leu Tyr Arg Pro His Asp Thr Ala Trp Asp Thr Cys Ser Glu Pro Glu
645                 650                 655                 660 ggt ggt ttt ctt gat gat gcc aaa ttc gca gaa tta ttc gat ggg gac    2072
Gly Gly Phe Leu Asp Asp Ala Lys Phe Ala Glu Leu Phe Asp Gly Asp
            665                 670                 675 gcg ttg ata gca gtt aca ggt gga gcg gct ggt atg ttg gaa ccg ata    2120
Ala Leu Ile Ala Val Thr Gly Gly Ala Ala Gly Met Leu Glu Pro Ile
        680                 685                 690 ttg ttg agg tcc act gcg aag aga gac act ttt gct tgg aag aga ggt    2168
Leu Leu Arg Ser Thr Ala Lys Arg Asp Thr Phe Ala Trp Lys Arg Gly
                695                 700                 705 gaa act act gct agt gcc ggt gaa ctt atg gcg ttt aat ggt ctt act    2216
Glu Thr Thr Ala Ser Ala Gly Glu Leu Met Ala Phe Asn Gly Leu Thr
        710                 715                 720 gct gag gct ttg act aaa aga gca tca gct ttg gtt cat taaggaagat    2265
Ala Glu Ala Leu Thr Lys Arg Ala Ser Ala Leu Val His
725                 730                 735 cttcccgagc tcg                                                     2278

<210> SEQ ID NO 70
<211> LENGTH: 737
<212> TYPE: PRT
<213> ORGANISM: Nostoc punctiforme
```

<400> SEQUENCE: 70

```
Met Thr Ala Ile Ser Pro Lys Ala Ser Ser Ala Leu Pro Asn Phe Ser
1               5                   10                  15

Glu Gly Ile Gln Tyr Phe Gly Glu Ala Leu Pro Asp Phe Glu Thr Tyr
            20                  25                  30

Gly Ala Thr Pro Ala Ile Glu Ser Gly Lys Ile Ala Ile Ala Ser Pro
        35                  40                  45

Thr Asp Lys Ala Ala Val Tyr Gln Thr Leu Leu Ala Ala Asp Ala Leu
    50                  55                  60

Arg Tyr Leu Thr Leu Gln Val Thr Ala Ser Lys Ala Ser Gly His Pro
65              70                  75                  80

Gly Gly Phe Ala Ser Gln Ala Glu Ala Tyr Ala Ser Leu Val Met Leu
                85                  90                  95

Gly Tyr Lys Asn Ile Ile Thr Glu Val Gly His His Ala Pro Gly Phe
            100                 105                 110

Tyr Ser Ala Met Phe Leu Asp Arg Ser Leu Glu Asp Met Gly Ile Phe
        115                 120                 125

Thr Val Gln Glu Leu Arg Asp Arg Phe Arg Glu Lys His Gly Leu Leu
    130                 135                 140

Gly His Leu Ser Gly Phe Ile Pro Gly Ile Leu Ala Pro Ala Gly Pro
145                 150                 155                 160

Leu Gly Gln Gly Gln His Phe Ala Met Ala Ala Leu Leu His Lys
                165                 170                 175

Asp Lys Leu Phe Pro Phe Thr Val Gly Asp Gly Gly Leu Gly Glu Pro
            180                 185                 190

Tyr Ile Val Ser Ala Ile Ala His Phe His Thr Ala Tyr Pro Ala Val
        195                 200                 205

Thr Asn Phe Leu Pro Val Leu Val Trp Asn Gly Tyr Ser Gln Glu His
    210                 215                 220

His Ser Met Val Ser Leu Lys Thr Asn Glu Gln Met Gln Ala Tyr Trp
225                 230                 235                 240

Gln Gly Asn Gly Phe Asp Glu Val Val Leu Val Asp Ala Lys Asp Phe
                245                 250                 255

Asp Asp Arg Asp Gln Pro Gly Asp Tyr Val Asp Ser Thr Ala Phe Ser
            260                 265                 270

Phe Glu Lys Arg Leu Ala Phe Thr Gln Ala Val Leu Ser Gly Val Asp
        275                 280                 285

Lys Ala Ala Arg Ser Ala Leu Gly Gly Lys Leu Thr Val Phe Ile Ile
    290                 295                 300

Lys Gln Leu Lys Gly Ala Gly Val His Ala Arg Gly Ala Lys Ser His
305                 310                 315                 320

Asn Leu Tyr Pro Lys Asp Thr Leu Asp Ala Pro His Ile Ile Ser Ala
                325                 330                 335

Leu Gln Thr Arg Ala Leu Ser Ala Glu Ala Trp Gln Leu Val Arg Thr
            340                 345                 350

Asn Ala Glu Arg Ala Gly Gly Pro Ala Ala Lys Thr Val Val Thr
        355                 360                 365

Glu Phe Glu Leu Pro Leu Pro Glu Leu Gly Glu Pro Leu Glu Glu
    370                 375                 380

Tyr Ala Val Gly Gly Glu Ala Lys Val Ser Thr Thr Ala Met Gly Arg
385                 390                 395                 400

Leu Val Gly Ile Val Gly Asn Lys Asp Arg Asn Phe Leu Val Thr Asn
```

```
            405                 410                 415
Ala Asp Gly Asn Glu Ala Ser Gly Ile Ala Asn Ile Asn Gln Ala Leu
        420                 425                 430

Lys Ile Ile His Pro Thr Thr Asp Asp Leu Tyr Asn Gln Ala Pro Asn
    435                 440                 445

Gly Gln Val Tyr Glu Pro Leu Ser Glu Asp Ala Cys Ala Gly Leu Ala
450                 455                 460

Ala Gly Leu Ala Leu Met Gly Ala Arg Thr Leu Trp Cys Ser Tyr Glu
465                 470                 475                 480

Ser Phe Ala Ile Asn Gly Leu Pro Ile Trp Gln Thr Val Thr Gln Ser
                485                 490                 495

Met Ala Glu Leu Arg Arg Gln Thr Pro Ser Thr Ile Thr Leu Phe Thr
            500                 505                 510

Ala Gly Ala Leu Glu Gln Gly Arg Asn Gly Trp Thr His Gln Arg Pro
        515                 520                 525

Glu Ile Glu Ala Tyr Phe Ala Ser Leu Met Arg Asn Gly Asn Val Phe
    530                 535                 540

Pro Leu Phe Pro Pro Asp Ala Asn Ser Ile Gln Ala Cys Tyr Glu Trp
545                 550                 555                 560

Ala Leu Lys Thr Lys Asn Lys Gly Ile Val Ile Thr Ala Ser Lys Ser
                565                 570                 575

Pro Leu Pro Ile Arg Thr Thr Leu Glu Gln Thr Arg Gln Gly Leu Arg
            580                 585                 590

Asp Gly Ala Val Leu Leu His Glu Ile Ala Gly Asp Lys Gln Val Val
        595                 600                 605

Phe Thr Val Ile Gly Asp Met Thr Leu Met Pro Val Phe Glu Ala Ala
    610                 615                 620

Ala Phe Leu Glu Thr Glu Gly Ile Gly Ala Lys Ile Ile Ser Val Ile
625                 630                 635                 640

Asn Pro Arg Gln Leu Tyr Arg Pro His Asp Thr Ala Trp Asp Thr Cys
                645                 650                 655

Ser Glu Pro Glu Gly Gly Phe Leu Asp Asp Ala Lys Phe Ala Glu Leu
            660                 665                 670

Phe Asp Gly Asp Ala Leu Ile Ala Val Thr Gly Gly Ala Ala Gly Met
        675                 680                 685

Leu Glu Pro Ile Leu Leu Arg Ser Thr Ala Lys Arg Asp Thr Phe Ala
    690                 695                 700

Trp Lys Arg Gly Glu Thr Thr Ala Ser Ala Gly Glu Leu Met Ala Phe
705                 710                 715                 720

Asn Gly Leu Thr Ala Glu Ala Leu Thr Lys Arg Ala Ser Ala Leu Val
                725                 730                 735

His

<210> SEQ ID NO 71
<211> LENGTH: 2485
<212> TYPE: DNA
<213> ORGANISM: Marinobacter aquaeolei
<220> FEATURE:
<221> NAME/KEY: CDS
<222> LOCATION: (45)..(2462)

<400> SEQUENCE: 71
aaggaaaaaa gcggccgcaa aaggaaaagg actagtccta tata atg tct tct cca      56
                                             Met Ser Ser Pro
                                               1
```

| | | |
|---|---|---|
| aca gag cca gtt cag gct cca aac gaa gcg act cct ggt agc gca ttt<br>Thr Glu Pro Val Gln Ala Pro Asn Glu Ala Thr Pro Gly Ser Ala Phe<br>5                           10                 15                   20 | 104 |
| cat tgc tgg caa caa ggt tat ggc gtt ata cgt cac agt gaa cag act<br>His Cys Trp Gln Gln Gly Tyr Gly Val Ile Arg His Ser Glu Gln Thr<br>                      25                 30                   35 | 152 |
| tca gct aga gta cgt gaa tta gct ggt aaa tta gtt tct gcc ggt cat<br>Ser Ala Arg Val Arg Glu Leu Ala Gly Lys Leu Val Ser Ala Gly His<br>            40                   45                 50 | 200 |
| caa ccc gat gaa gat acc gta tac cgt aaa ttg ata gcc tta gat aga<br>Gln Pro Asp Glu Asp Thr Val Tyr Arg Lys Leu Ile Ala Leu Asp Arg<br>               55                 60                65 | 248 |
| ctg aca tct gcc gga tta tgg ctg gta cac atg aca tat tgt aat<br>Leu Thr Ser Ala Gly Leu Trp Leu Val Val His Met Thr Tyr Cys Asn<br>    70                   75                 80 | 296 |
| aga gtt gat att gct gga gcc ccg ttg gtt gcg caa gac ttt aaa gcg<br>Arg Val Asp Ile Ala Gly Ala Pro Leu Val Ala Gln Asp Phe Lys Ala<br>85                      90                95                  100 | 344 |
| tcc cca gaa ggt cat acc ggt ggc gcc ctg aac atg gtc ccc gct tat<br>Ser Pro Glu Gly His Thr Gly Gly Ala Leu Asn Met Val Pro Ala Tyr<br>                   105                 110               115 | 392 |
| gct gct tat ctt gca ctt aac aat ttg acc ggt aaa act aga tca tgg<br>Ala Ala Tyr Leu Ala Leu Asn Asn Leu Thr Gly Lys Thr Arg Ser Trp<br>          120                  125               130 | 440 |
| ttg atg ggg caa ggt cac tgt gtt gcc gcc gtt gac gcc ttg aac gtc<br>Leu Met Gly Gln Gly His Cys Val Ala Ala Val Asp Ala Leu Asn Val<br>       135                  140               145 | 488 |
| tta act ggt aat ttg cac ccc gaa caa aga gcg cgt tat ctt gca cct<br>Leu Thr Gly Asn Leu His Pro Glu Gln Arg Ala Arg Tyr Leu Ala Pro<br>150                   155                 160 | 536 |
| gaa gga ttg tcc agg ctg gct tct gac ttc tac tct tat aga caa aag<br>Glu Gly Leu Ser Arg Leu Ala Ser Asp Phe Tyr Ser Tyr Arg Gln Lys<br>165                   170                175               180 | 584 |
| cct gat ggt aca atg gct gct cca ctg ggt tct cat gtt aat ccg cac<br>Pro Asp Gly Thr Met Ala Ala Pro Leu Gly Ser His Val Asn Pro His<br>                 185                 190               195 | 632 |
| aca gca gga gga atc atc gag ggt ggt tac tta ggg ttt gct gaa tta<br>Thr Ala Gly Gly Ile Ile Glu Gly Gly Tyr Leu Gly Phe Ala Glu Leu<br>            200                 205               210 | 680 |
| caa tac gca cat atg cct ttg ccc gga gaa agt ttg gtg gca ttt ctt<br>Gln Tyr Ala His Met Pro Leu Pro Gly Glu Ser Leu Val Ala Phe Leu<br>               215                220               225 | 728 |
| agc gat ggc gct gca gaa gag cag aga ggg tcc gat tgg att cct aga<br>Ser Asp Gly Ala Ala Glu Glu Gln Arg Gly Ser Asp Trp Ile Pro Arg<br>230                   235                240 | 776 |
| tgg tgg aga gca gaa gat tgt ggt cta gta ctg ccg gtc atg att gct<br>Trp Trp Arg Ala Glu Asp Cys Gly Leu Val Leu Pro Val Met Ile Ala<br>245                   250                255               260 | 824 |
| aat gga aga aga atc gaa caa aga act gag ctt ggt acc agg gaa ggc<br>Asn Gly Arg Arg Ile Glu Gln Arg Thr Glu Leu Gly Thr Arg Glu Gly<br>                 265                270               275 | 872 |
| tta gaa aga ttc gaa caa cat ttg caa cat tgg ggt ttt gac cct gtt<br>Leu Glu Arg Phe Glu Gln His Leu Gln His Trp Gly Phe Asp Pro Val<br>          280                  285               290 | 920 |
| agg ttt gat ggc aga gat cct gcg gct ttt gtt tgc gct atg tac gac<br>Arg Phe Asp Gly Arg Asp Pro Ala Ala Phe Val Cys Ala Met Tyr Asp<br>               295                300               305 | 968 |
| atg gaa caa gcg ttg gct gcc cat ggc acc gca gct cag caa gga gaa<br>Met Glu Gln Ala Leu Ala Ala His Gly Thr Ala Ala Gln Gln Gly Glu<br>310                   315                320 | 1016 |

```
acc ggg tat cca gtt aga atc cct tac ggt att gca gaa act gtt aag    1064
Thr Gly Tyr Pro Val Arg Ile Pro Tyr Gly Ile Ala Glu Thr Val Lys
325                 330                 335                 340 ggg tat gga ttt tat ggc gcc gga gaa aat gca gct cac aac tta cca    1112
Gly Tyr Gly Phe Tyr Gly Ala Gly Glu Asn Ala Ala His Asn Leu Pro
                345                 350                 355 ttg cct ggg aat cca aga atg gat gct ata tca agg gag ctt ttc aac    1160
Leu Pro Gly Asn Pro Arg Met Asp Ala Ile Ser Arg Glu Leu Phe Asn
            360                 365                 370 gaa tac gct aca ccc tta tgg gtt aag cca caa gag cta aat ttg gcc    1208
Glu Tyr Ala Thr Pro Leu Trp Val Lys Pro Gln Glu Leu Asn Leu Ala
        375                 380                 385 gtt tca gaa cta aat gaa cat tca caa cag gga aga cct ttg gag aga    1256
Val Ser Glu Leu Asn Glu His Ser Gln Gln Gly Arg Pro Leu Glu Arg
    390                 395                 400 gat cat cca cta gct tta cgt aga ccg tcg gag cca gct ata cca gtc    1304
Asp His Pro Leu Ala Leu Arg Arg Pro Ser Glu Pro Ala Ile Pro Val
405                 410                 415                 420 cta cca tgg gca cag aat aaa tgt agt cca atg act gcc gtc gat gag    1352
Leu Pro Trp Ala Gln Asn Lys Cys Ser Pro Met Thr Ala Val Asp Glu
                425                 430                 435 ttc ttt aaa gca ctg gta gct gac aac cca gag ttg agg cct cgt gta    1400
Phe Phe Lys Ala Leu Val Ala Asp Asn Pro Glu Leu Arg Pro Arg Val
            440                 445                 450 gga aat cca gat gaa ttg gcg tct aat cgt ttg aaa ggt gtt ttg gat    1448
Gly Asn Pro Asp Glu Leu Ala Ser Asn Arg Leu Lys Gly Val Leu Asp
        455                 460                 465 tcg tta aaa cat agg gtc aat gat ccg gag aac gag gca gaa agt gtc    1496
Ser Leu Lys His Arg Val Asn Asp Pro Glu Asn Glu Ala Glu Ser Val
    470                 475                 480 cat ggc aag att atc act gcc ctt aat gaa gaa gca gta gtt agc gct    1544
His Gly Lys Ile Ile Thr Ala Leu Asn Glu Glu Ala Val Val Ser Ala
485                 490                 495                 500 tgc ttg gca aac aag gca ggt cta aac tta gtt gct agt tat gaa gcc    1592
Cys Leu Ala Asn Lys Ala Gly Leu Asn Leu Val Ala Ser Tyr Glu Ala
                505                 510                 515 ttt tgt gtg aaa atg tta ggt gct att agg caa gaa cta ata ttc gcg    1640
Phe Cys Val Lys Met Leu Gly Ala Ile Arg Gln Glu Leu Ile Phe Ala
            520                 525                 530 aga cat cag aaa gaa gta ggt aga cca cca caa tgg ctt ggt tta ccc    1688
Arg His Gln Lys Glu Val Gly Arg Pro Pro Gln Trp Leu Gly Leu Pro
        535                 540                 545 gtg ata gct act tcc cat act tgg gaa aac ggt aag aat gaa caa tcg    1736
Val Ile Ala Thr Ser His Thr Trp Glu Asn Gly Lys Asn Glu Gln Ser
550                 555                 560 cac cag gat aca tcg ttc tgt gaa gca ttg tta ggc gaa atg tct gat    1784
His Gln Asp Thr Ser Phe Cys Glu Ala Leu Leu Gly Glu Met Ser Asp
565                 570                 575                 580 gta tcc agg gta att ttc cct gct gac tat aat tcc gcc ttg gca att    1832
Val Ser Arg Val Ile Phe Pro Ala Asp Tyr Asn Ser Ala Leu Ala Ile
                585                 590                 595 tta cca agc gtt tat aga gaa aga ggt aga atc tca tgt ctg gtg atc    1880
Leu Pro Ser Val Tyr Arg Glu Arg Gly Arg Ile Ser Cys Leu Val Ile
            600                 605                 610 cca aag aga gag aga ccg tgc gtg ttt aac ggc tca gag gct gaa gca    1928
Pro Lys Arg Glu Arg Pro Cys Val Phe Asn Gly Ser Glu Ala Glu Ala
        615                 620                 625 tta gca aga cac ggt gca ttg gtg gtg gat gaa gac aca agt gct ggc    1976
Leu Ala Arg His Gly Ala Leu Val Val Asp Glu Asp Thr Ser Ala Gly
```

```
gaa gaa cca ttg cta ttg att gca aat ggt gct tac caa cta tct gaa    2024
Glu Glu Pro Leu Leu Leu Ile Ala Asn Gly Ala Tyr Gln Leu Ser Glu
645                 650                 655                 660 gcc ata aga gca tgt gag agg ctt cgt gaa aca ggt aca ccc ttt aga    2072
Ala Ile Arg Ala Cys Glu Arg Leu Arg Glu Thr Gly Thr Pro Phe Arg
                665                 670                 675 tta gtc tac ctt cag gaa cct ggc aga ttc aga caa ccc aga gac cca    2120
Leu Val Tyr Leu Gln Glu Pro Gly Arg Phe Arg Gln Pro Arg Asp Pro
            680                 685                 690 atg gag gcc acg tcc tgc tta act gag ttc gaa aga gag agg ctt ttc    2168
Met Glu Ala Thr Ser Cys Leu Thr Glu Phe Glu Arg Glu Arg Leu Phe
        695                 700                 705 cct cat aga atg cat agg agg gtt gca cta acg cat atg aga cct gaa    2216
Pro His Arg Met His Arg Arg Val Ala Leu Thr His Met Arg Pro Glu
    710                 715                 720 gtg ttt agg gga cac cta cac acg tta ttt cca caa cct ggt cat tca    2264
Val Phe Arg Gly His Leu His Thr Leu Phe Pro Gln Pro Gly His Ser
725                 730                 735                 740 aga gtc ttg ggg tac att aac aga ggc ggt acg ctg aat gag gcc ggt    2312
Arg Val Leu Gly Tyr Ile Asn Arg Gly Gly Thr Leu Asn Glu Ala Gly
                745                 750                 755 atg ttg ttt gcc aat cgt tgc agt tgg gga cac gca ttg gcg gct tgt    2360
Met Leu Phe Ala Asn Arg Cys Ser Trp Gly His Ala Leu Ala Ala Cys
            760                 765                 770 gct gaa gtc atg gac aag cca ccg ggt gaa tgg ttg tct tca gcg gag    2408
Ala Glu Val Met Asp Lys Pro Pro Gly Glu Trp Leu Ser Ser Ala Glu
        775                 780                 785 tta gcc gct gtt gaa ggg aga ggt gat cct gga gtg att acc aga ggt    2456
Leu Ala Ala Val Glu Gly Arg Gly Asp Pro Gly Val Ile Thr Arg Gly
    790                 795                 800 tta ccc taaggaagat cttcccgagc tcg                                  2485
Leu Pro
805

<210> SEQ ID NO 72
<211> LENGTH: 806
<212> TYPE: PRT
<213> ORGANISM: Marinobacter aquaeolei

<400> SEQUENCE: 72

Met Ser Ser Pro Thr Glu Pro Val Gln Ala Pro Asn Glu Ala Thr Pro
1               5                   10                  15

Gly Ser Ala Phe His Cys Trp Gln Gln Gly Tyr Gly Val Ile Arg His
            20                  25                  30

Ser Glu Gln Thr Ser Ala Arg Val Arg Glu Leu Ala Gly Lys Leu Val
        35                  40                  45

Ser Ala Gly His Gln Pro Asp Glu Asp Thr Val Tyr Arg Lys Leu Ile
    50                  55                  60

Ala Leu Asp Arg Leu Thr Ser Ala Gly Leu Trp Leu Val Val His Met
65                  70                  75                  80

Thr Tyr Cys Asn Arg Val Asp Ile Ala Gly Ala Pro Leu Val Ala Gln
                85                  90                  95

Asp Phe Lys Ala Ser Pro Glu Gly His Thr Gly Gly Ala Leu Asn Met
            100                 105                 110

Val Pro Ala Tyr Ala Ala Tyr Leu Ala Leu Asn Asn Leu Thr Gly Lys
        115                 120                 125

Thr Arg Ser Trp Leu Met Gly Gln Gly His Cys Val Ala Ala Val Asp
```

```
            130                 135                 140
Ala Leu Asn Val Leu Thr Gly Asn Leu His Pro Glu Gln Arg Ala Arg
145                 150                 155                 160

Tyr Leu Ala Pro Glu Gly Leu Ser Arg Leu Ala Ser Asp Phe Tyr Ser
                165                 170                 175

Tyr Arg Gln Lys Pro Asp Gly Thr Met Ala Ala Pro Leu Gly Ser His
            180                 185                 190

Val Asn Pro His Thr Ala Gly Ile Ile Glu Gly Tyr Leu Gly
        195                 200                 205

Phe Ala Glu Leu Gln Tyr Ala His Met Pro Leu Pro Gly Glu Ser Leu
210                 215                 220

Val Ala Phe Leu Ser Asp Gly Ala Ala Glu Glu Gln Arg Gly Ser Asp
225                 230                 235                 240

Trp Ile Pro Arg Trp Arg Ala Glu Asp Cys Gly Leu Val Leu Pro
                245                 250                 255

Val Met Ile Ala Asn Gly Arg Arg Ile Glu Gln Arg Thr Glu Leu Gly
                260                 265                 270

Thr Arg Glu Gly Leu Glu Arg Phe Glu Gln His Leu Gln His Trp Gly
            275                 280                 285

Phe Asp Pro Val Arg Phe Asp Gly Arg Asp Pro Ala Ala Phe Val Cys
        290                 295                 300

Ala Met Tyr Asp Met Glu Gln Ala Leu Ala Ala His Gly Thr Ala Ala
305                 310                 315                 320

Gln Gln Gly Glu Thr Gly Tyr Pro Val Arg Ile Pro Tyr Gly Ile Ala
                325                 330                 335

Glu Thr Val Lys Gly Tyr Gly Phe Tyr Gly Ala Gly Glu Asn Ala Ala
                340                 345                 350

His Asn Leu Pro Leu Pro Gly Asn Pro Arg Met Asp Ala Ile Ser Arg
            355                 360                 365

Glu Leu Phe Asn Glu Tyr Ala Thr Pro Leu Trp Val Lys Pro Gln Glu
        370                 375                 380

Leu Asn Leu Ala Val Ser Glu Leu Asn Glu His Ser Gln Gln Gly Arg
385                 390                 395                 400

Pro Leu Glu Arg Asp His Pro Leu Ala Leu Arg Arg Pro Ser Glu Pro
                405                 410                 415

Ala Ile Pro Val Leu Pro Trp Ala Gln Asn Lys Cys Ser Pro Met Thr
                420                 425                 430

Ala Val Asp Glu Phe Phe Lys Ala Leu Val Ala Asp Asn Pro Glu Leu
            435                 440                 445

Arg Pro Arg Val Gly Asn Pro Asp Glu Leu Ala Ser Asn Arg Leu Lys
        450                 455                 460

Gly Val Leu Asp Ser Leu Lys His Arg Val Asn Asp Pro Glu Asn Glu
465                 470                 475                 480

Ala Glu Ser Val His Gly Lys Ile Ile Thr Ala Leu Asn Glu Glu Ala
                485                 490                 495

Val Val Ser Ala Cys Leu Ala Asn Lys Ala Gly Leu Asn Leu Val Ala
                500                 505                 510

Ser Tyr Glu Ala Phe Cys Val Lys Met Leu Gly Ala Ile Arg Gln Glu
            515                 520                 525

Leu Ile Phe Ala Arg His Gln Lys Glu Val Gly Arg Pro Pro Gln Trp
        530                 535                 540

Leu Gly Leu Pro Val Ile Ala Thr Ser His Thr Trp Glu Asn Gly Lys
545                 550                 555                 560
```

Asn Glu Gln Ser His Gln Asp Thr Ser Phe Cys Glu Ala Leu Leu Gly
            565                 570                 575

Glu Met Ser Asp Val Ser Arg Val Ile Phe Pro Ala Asp Tyr Asn Ser
            580                 585                 590

Ala Leu Ala Ile Leu Pro Ser Val Tyr Arg Glu Arg Gly Arg Ile Ser
            595                 600                 605

Cys Leu Val Ile Pro Lys Arg Glu Arg Pro Cys Val Phe Asn Gly Ser
            610                 615                 620

Glu Ala Glu Ala Leu Ala Arg His Gly Ala Leu Val Val Asp Glu Asp
625                 630                 635                 640

Thr Ser Ala Gly Glu Glu Pro Leu Leu Leu Ile Ala Asn Gly Ala Tyr
            645                 650                 655

Gln Leu Ser Glu Ala Ile Arg Ala Cys Glu Arg Leu Arg Glu Thr Gly
            660                 665                 670

Thr Pro Phe Arg Leu Val Tyr Leu Gln Glu Pro Gly Arg Phe Arg Gln
            675                 680                 685

Pro Arg Asp Pro Met Glu Ala Thr Ser Cys Leu Thr Glu Phe Glu Arg
690                 695                 700

Glu Arg Leu Phe Pro His Arg Met His Arg Val Ala Leu Thr His
705                 710                 715                 720

Met Arg Pro Glu Val Phe Arg Gly His Leu His Thr Leu Phe Pro Gln
            725                 730                 735

Pro Gly His Ser Arg Val Leu Gly Tyr Ile Asn Arg Gly Gly Thr Leu
            740                 745                 750

Asn Glu Ala Gly Met Leu Phe Ala Asn Arg Cys Ser Trp Gly His Ala
            755                 760                 765

Leu Ala Ala Cys Ala Glu Val Met Asp Lys Pro Pro Gly Glu Trp Leu
770                 775                 780

Ser Ser Ala Glu Leu Ala Ala Val Glu Gly Arg Gly Asp Pro Gly Val
785                 790                 795                 800

Ile Thr Arg Gly Leu Pro
            805

<210> SEQ ID NO 73
<211> LENGTH: 1026
<212> TYPE: DNA
<213> ORGANISM: Bacillus subtilis
<220> FEATURE:
<221> NAME/KEY: CDS
<222> LOCATION: (31)..(999)

<400> SEQUENCE: 73
cgcggatccg cgccgctcga gcggtatata atg gcg gac ttg ttt tca acg gtt      54
                                Met Ala Asp Leu Phe Ser Thr Val
                                  1               5 caa gag aaa gta gct ggt aaa gac gtg aag ata gtc ttt cca gaa ggt     102
Gln Glu Lys Val Ala Gly Lys Asp Val Lys Ile Val Phe Pro Glu Gly
         10                  15                  20 ctt gat gag agg att tta gaa gct gtt tcg aaa ttg gca ggc aat aag     150
Leu Asp Glu Arg Ile Leu Glu Ala Val Ser Lys Leu Ala Gly Asn Lys
 25                  30                  35                  40 gtc tta aac cct atc gta atc ggc aat gaa aat gaa ata cag gca aaa     198
Val Leu Asn Pro Ile Val Ile Gly Asn Glu Asn Glu Ile Gln Ala Lys
                 45                  50                  55 gcg aaa gaa ctt aac ctg act cta gga ggt gtc aag att tat gac cct     246
Ala Lys Glu Leu Asn Leu Thr Leu Gly Gly Val Lys Ile Tyr Asp Pro
             60                  65                  70

```
cac acc tat gaa ggc atg gag gat ctt gtg caa gca ttt gtc gaa cgt        294
His Thr Tyr Glu Gly Met Glu Asp Leu Val Gln Ala Phe Val Glu Arg
         75                  80                  85 aga aaa gga aag gca act gag gaa caa gcc agg aaa gcc tta ttg gat        342
Arg Lys Gly Lys Ala Thr Glu Glu Gln Ala Arg Lys Ala Leu Leu Asp
 90                  95                 100 gaa aac tac ttt gga act atg tta gtt tac aag ggt ttg gct gat ggt        390
Glu Asn Tyr Phe Gly Thr Met Leu Val Tyr Lys Gly Leu Ala Asp Gly
105                 110                 115                 120 ttg gta agt gga gct gcg cat tct act gcg gat act gtc aga cca gcc        438
Leu Val Ser Gly Ala Ala His Ser Thr Ala Asp Thr Val Arg Pro Ala
                125                 130                 135 tta cag atc att aaa acg aaa gaa ggg gtt aag aaa aca tct ggc gtt        486
Leu Gln Ile Ile Lys Thr Lys Glu Gly Val Lys Lys Thr Ser Gly Val
            140                 145                 150 ttc atc atg gct aga ggt gaa gaa caa tat gtg ttt gct gac tgt gcc        534
Phe Ile Met Ala Arg Gly Glu Glu Gln Tyr Val Phe Ala Asp Cys Ala
        155                 160                 165 ata aac ata gct cct gat agc caa gat ttg gcc gaa att gca att gaa        582
Ile Asn Ile Ala Pro Asp Ser Gln Asp Leu Ala Glu Ile Ala Ile Glu
170                 175                 180 agt gcc aat aca gct aaa atg ttc gac ata gag cct aga gtg gct atg        630
Ser Ala Asn Thr Ala Lys Met Phe Asp Ile Glu Pro Arg Val Ala Met
185                 190                 195                 200 ctt agc ttc tcc aca aaa gga tct gct aag tct gat gaa acc gag aaa        678
Leu Ser Phe Ser Thr Lys Gly Ser Ala Lys Ser Asp Glu Thr Glu Lys
                205                 210                 215 gta gct gat gca gtc aag att gcc aaa gag aaa gct cca gag tta acc        726
Val Ala Asp Ala Val Lys Ile Ala Lys Glu Lys Ala Pro Glu Leu Thr
            220                 225                 230 ttg gat ggt gag ttt cag ttc gat gca gcg ttt gtt cca tcc gtt gct        774
Leu Asp Gly Glu Phe Gln Phe Asp Ala Ala Phe Val Pro Ser Val Ala
        235                 240                 245 gaa aag aaa gca ccg gat tca gaa atc aag ggt gat gcc aat gtg ttt        822
Glu Lys Lys Ala Pro Asp Ser Glu Ile Lys Gly Asp Ala Asn Val Phe
250                 255                 260 gtt ttc cca tcg cta gaa gct ggc aat att ggg tat aag ata gca caa        870
Val Phe Pro Ser Leu Glu Ala Gly Asn Ile Gly Tyr Lys Ile Ala Gln
265                 270                 275                 280 aga ctg ggt aac ttc gaa gct gtt ggt ccc att ttg caa ggg ttg aac        918
Arg Leu Gly Asn Phe Glu Ala Val Gly Pro Ile Leu Gln Gly Leu Asn
                285                 290                 295 atg ccc gta aat gac cta tca aga ggt tgc aat gca gaa gac gtt tac        966
Met Pro Val Asn Asp Leu Ser Arg Gly Cys Asn Ala Glu Asp Val Tyr
            300                 305                 310 aat cta gca ctg att aca gct gca caa gcc tta taacccaagc ttgggctagc    1019
Asn Leu Ala Leu Ile Thr Ala Ala Gln Ala Leu
                315                 320 tagctag                                                                1026

<210> SEQ ID NO 74
<211> LENGTH: 323
<212> TYPE: PRT
<213> ORGANISM: Bacillus subtilis

<400> SEQUENCE: 74

Met Ala Asp Leu Phe Ser Thr Val Gln Glu Lys Val Ala Gly Lys Asp
1               5                   10                  15

Val Lys Ile Val Phe Pro Glu Gly Leu Asp Glu Arg Ile Leu Glu Ala
```

```
            20                  25                  30
Val Ser Lys Leu Ala Gly Asn Lys Val Leu Asn Pro Ile Val Ile Gly
        35                  40                  45
Asn Glu Asn Glu Ile Gln Ala Lys Ala Lys Glu Leu Asn Leu Thr Leu
 50                  55                  60
Gly Gly Val Lys Ile Tyr Asp Pro His Thr Tyr Glu Gly Met Glu Asp
 65                  70                  75                  80
Leu Val Gln Ala Phe Val Glu Arg Arg Lys Gly Lys Ala Thr Glu Glu
                 85                  90                  95
Gln Ala Arg Lys Ala Leu Leu Asp Glu Asn Tyr Phe Gly Thr Met Leu
            100                 105                 110
Val Tyr Lys Gly Leu Ala Asp Gly Leu Val Ser Gly Ala Ala His Ser
            115                 120                 125
Thr Ala Asp Thr Val Arg Pro Ala Leu Gln Ile Ile Lys Thr Lys Glu
            130                 135                 140
Gly Val Lys Lys Thr Ser Gly Val Phe Ile Met Ala Arg Gly Glu Glu
145                 150                 155                 160
Gln Tyr Val Phe Ala Asp Cys Ala Ile Asn Ile Ala Pro Asp Ser Gln
                165                 170                 175
Asp Leu Ala Glu Ile Ala Ile Glu Ser Ala Asn Thr Ala Lys Met Phe
            180                 185                 190
Asp Ile Glu Pro Arg Val Ala Met Leu Ser Phe Ser Thr Lys Gly Ser
            195                 200                 205
Ala Lys Ser Asp Glu Thr Glu Lys Val Ala Asp Ala Val Lys Ile Ala
            210                 215                 220
Lys Glu Lys Ala Pro Glu Leu Thr Leu Asp Gly Glu Phe Gln Phe Asp
225                 230                 235                 240
Ala Ala Phe Val Pro Ser Val Ala Glu Lys Lys Ala Pro Asp Ser Glu
                245                 250                 255
Ile Lys Gly Asp Ala Asn Val Phe Val Phe Pro Ser Leu Glu Ala Gly
            260                 265                 270
Asn Ile Gly Tyr Lys Ile Ala Gln Arg Leu Gly Asn Phe Glu Ala Val
            275                 280                 285
Gly Pro Ile Leu Gln Gly Leu Asn Met Pro Val Asn Asp Leu Ser Arg
            290                 295                 300
Gly Cys Asn Ala Glu Asp Val Tyr Asn Leu Ala Leu Ile Thr Ala Ala
305                 310                 315                 320
Gln Ala Leu

<210> SEQ ID NO 75
<211> LENGTH: 1737
<212> TYPE: DNA
<213> ORGANISM: Bifidobacterium animalis
<220> FEATURE:
<221> NAME/KEY: CDS
<222> LOCATION: (31)..(1710)

<400> SEQUENCE: 75
cgcggatccg cgccgctcga gcggtatata atg tca tta aag aac gtc agt att     54
                                Met Ser Leu Lys Asn Val Ser Ile
                                  1               5 atc agt cca gaa cct gga gat ggg aga aat gtg gtt gct ttg ggt gtc    102
Ile Ser Pro Glu Pro Gly Asp Gly Arg Asn Val Val Ala Leu Gly Val
         10                  15                  20 gta gat atg ctt gct cat aca gct aag acc agc atc ttc agg cca gct    150
Val Asp Met Leu Ala His Thr Ala Lys Thr Ser Ile Phe Arg Pro Ala
```

```
            25                  30                  35                  40
gtt caa gcc gat gag aat ttg aca gac gca ttg tta tcc gtt gtt tca        198
Val Gln Ala Asp Glu Asn Leu Thr Asp Ala Leu Leu Ser Val Val Ser
                        45                  50                  55 gtc tta caa aca aga gaa caa gcc gtc ggt gtt acg ttg cat gat gct        246
Val Leu Gln Thr Arg Glu Gln Ala Val Gly Val Thr Leu His Asp Ala
                60                  65                  70 agg ctt gat aaa gat aat gcc aga caa cag ata gtt agc aaa ttc atc        294
Arg Leu Asp Lys Asp Asn Ala Arg Gln Gln Ile Val Ser Lys Phe Ile
            75                  80                  85 gac aca aat gcc gaa att aat cca cag att aga gtg att gta ggt tct        342
Asp Thr Asn Ala Glu Ile Asn Pro Gln Ile Arg Val Ile Val Gly Ser
        90                  95                 100 gat agg act aat gtc gga gat ccg gaa cgt ttt acc ttt aat gct gat        390
Asp Arg Thr Asn Val Gly Asp Pro Glu Arg Phe Thr Phe Asn Ala Asp
105                 110                 115                 120 gtc agt gcg gac cta caa tca cca gta ctg ctg tct gtt tcc tcg atg        438
Val Ser Ala Asp Leu Gln Ser Pro Val Leu Leu Ser Val Ser Ser Met
                    125                 130                 135 ggg aga act cca gac gaa atc aga gaa aca att gat gca tgt agg gaa        486
Gly Arg Thr Pro Asp Glu Ile Arg Glu Thr Ile Asp Ala Cys Arg Glu
                140                 145                 150 gta gtc gcg aat gct ggt acc caa gtt ata ggc gtt ttc ata aca gac        534
Val Val Ala Asn Ala Gly Thr Gln Val Ile Gly Val Phe Ile Thr Asp
            155                 160                 165 tgt aca aat tca gcc tta ccc act ctg act gat gag ttt gtt tcc tat        582
Cys Thr Asn Ser Ala Leu Pro Thr Leu Thr Asp Glu Phe Val Ser Tyr
        170                 175                 180 gat ctt cca acg tgg cct ttg ccc ctt gtt gag tta ggt tct gca gac        630
Asp Leu Pro Thr Trp Pro Leu Pro Leu Val Glu Leu Gly Ser Ala Asp
185                 190                 195                 200 act aac gtg aaa gct gcg tta gat gca ttt gac gaa cat gtg gat aag        678
Thr Asn Val Lys Ala Ala Leu Asp Ala Phe Asp Glu His Val Asp Lys
                    205                 210                 215 gaa agt ctg cta aat gtg tta gac acc cca ttt gtc cct cct aca aca        726
Glu Ser Leu Leu Asn Val Leu Asp Thr Pro Phe Val Pro Pro Thr Thr
                220                 225                 230 cca ttt gca ttt caa tac gac ttg tta gca aga gct aag aag gat aag        774
Pro Phe Ala Phe Gln Tyr Asp Leu Leu Ala Arg Ala Lys Lys Asp Lys
            235                 240                 245 aaa aca att gtt ctt cca gaa ggt gag gac gat cgt atc ata acc gct        822
Lys Thr Ile Val Leu Pro Glu Gly Glu Asp Asp Arg Ile Ile Thr Ala
        250                 255                 260 gca aac tac ttg tta caa tca aac gtc gta gat ttg gtg att att ggc        870
Ala Asn Tyr Leu Leu Gln Ser Asn Val Val Asp Leu Val Ile Ile Gly
265                 270                 275                 280 gat aga aac gaa atc ctg gct aga ggt gag aaa tta ggc ttg aaa gcg        918
Asp Arg Asn Glu Ile Leu Ala Arg Gly Glu Lys Leu Gly Leu Lys Ala
                    285                 290                 295 cta gat cag gca aag ttt gtc tcg att gat gac aaa cac ctt ttg gac        966
Leu Asp Gln Ala Lys Phe Val Ser Ile Asp Asp Lys His Leu Leu Asp
                300                 305                 310 aca atg gtt ccg aaa ttg tgt gaa ctt aga gct aag aaa ggt atg acc       1014
Thr Met Val Pro Lys Leu Cys Glu Leu Arg Ala Lys Lys Gly Met Thr
            315                 320                 325 cct gat gta gct ttg aaa act cta cgt gat acg aac tat ttc ggc act       1062
Pro Asp Val Ala Leu Lys Thr Leu Arg Asp Thr Asn Tyr Phe Gly Thr
        330                 335                 340 atg tta atc gtt tta ggg atg gct gac ggt ttg gtg agt ggt gcc att       1110
```

```
Met Leu Ile Val Leu Gly Met Ala Asp Gly Leu Val Ser Gly Ala Ile
345                 350                 355                 360 tct tct acc gca aat acg gta aga cca gca ttg caa ctt ata aag acc      1158
Ser Ser Thr Ala Asn Thr Val Arg Pro Ala Leu Gln Leu Ile Lys Thr
                    365                 370                 375 aaa cca ggt gta tca tcg gtt tct gga gcc ttc ttg atg tgc tta aag      1206
Lys Pro Gly Val Ser Ser Val Ser Gly Ala Phe Leu Met Cys Leu Lys
            380                 385                 390 gat cac gtt tcc gtt ttc gct gat tgt gcc atc aac tta gat ccc gat      1254
Asp His Val Ser Val Phe Ala Asp Cys Ala Ile Asn Leu Asp Pro Asp
        395                 400                 405 cct caa cag ttg gct gat att gca att caa tcc gca gaa aca gct aag      1302
Pro Gln Gln Leu Ala Asp Ile Ala Ile Gln Ser Ala Glu Thr Ala Lys
    410                 415                 420 gcc ttc tca att gac ccg aaa att ggc ttg cta agc tat tct act ctg      1350
Ala Phe Ser Ile Asp Pro Lys Ile Gly Leu Leu Ser Tyr Ser Thr Leu
425                 430                 435                 440 gga tct gga aaa ggt cca gat gtt gat cta gtt gta gag gct act tcc      1398
Gly Ser Gly Lys Gly Pro Asp Val Asp Leu Val Val Glu Ala Thr Ser
                    445                 450                 455 atc gcc caa aat aaa aga ccc gat cta ccg att gtt ggc cct ata cag      1446
Ile Ala Gln Asn Lys Arg Pro Asp Leu Pro Ile Val Gly Pro Ile Gln
            460                 465                 470 ttc gat gcc gca tgg tca aag act gtt gct aga gtc aaa gcg ttt ggt      1494
Phe Asp Ala Ala Trp Ser Lys Thr Val Ala Arg Val Lys Ala Phe Gly
        475                 480                 485 aac cca att gct gga aat gta acg gtg ttt gtg ttt ccc gac cta gat      1542
Asn Pro Ile Ala Gly Asn Val Thr Val Phe Val Phe Pro Asp Leu Asp
    490                 495                 500 gca ggg aac ata tgc tac aaa gca gta cag aga act tct gga gca gtc      1590
Ala Gly Asn Ile Cys Tyr Lys Ala Val Gln Arg Thr Ser Gly Ala Val
505                 510                 515                 520 gcg ata ggt cct gtg ttg caa ggt tta aat agg cct gtt aat gac ttg      1638
Ala Ile Gly Pro Val Leu Gln Gly Leu Asn Arg Pro Val Asn Asp Leu
                    525                 530                 535 agc aga ggt gct tta gtg caa gac att ata aac act atc gcc ttg act      1686
Ser Arg Gly Ala Leu Val Gln Asp Ile Ile Asn Thr Ile Ala Leu Thr
            540                 545                 550 gct ata gaa gcc caa agt aac gaa taacccaagc ttgggctagc tagctag        1737
Ala Ile Glu Ala Gln Ser Asn Glu
        555                 560

<210> SEQ ID NO 76
<211> LENGTH: 560
<212> TYPE: PRT
<213> ORGANISM: Bifidobacterium animalis

<400> SEQUENCE: 76

Met Ser Leu Lys Asn Val Ser Ile Ile Ser Pro Glu Pro Gly Asp Gly
1               5                   10                  15

Arg Asn Val Val Ala Leu Gly Val Asp Met Leu Ala His Thr Ala
            20                  25                  30

Lys Thr Ser Ile Phe Arg Pro Ala Val Gln Ala Asp Glu Asn Leu Thr
        35                  40                  45

Asp Ala Leu Leu Ser Val Val Ser Leu Gln Thr Arg Glu Gln Ala
    50                  55                  60

Val Gly Val Thr Leu His Asp Ala Arg Leu Asp Lys Asp Asn Ala Arg
65                  70                  75                  80

Gln Gln Ile Val Ser Lys Phe Ile Asp Thr Asn Ala Glu Ile Asn Pro
```

```
                    85                  90                  95
Gln Ile Arg Val Ile Val Gly Ser Asp Arg Thr Asn Val Gly Asp Pro
                100                 105                 110
Glu Arg Phe Thr Phe Asn Ala Asp Val Ser Ala Asp Leu Gln Ser Pro
                115                 120                 125
Val Leu Leu Ser Val Ser Ser Met Gly Arg Thr Pro Asp Glu Ile Arg
                130                 135                 140
Glu Thr Ile Asp Ala Cys Arg Glu Val Ala Asn Ala Gly Thr Gln
145                 150                 155                 160
Val Ile Gly Val Phe Ile Thr Asp Cys Thr Asn Ser Ala Leu Pro Thr
                165                 170                 175
Leu Thr Asp Glu Phe Val Ser Tyr Asp Leu Pro Thr Trp Pro Leu Pro
                180                 185                 190
Leu Val Glu Leu Gly Ser Ala Asp Thr Asn Val Lys Ala Ala Leu Asp
                195                 200                 205
Ala Phe Asp Glu His Val Asp Lys Glu Ser Leu Leu Asn Val Leu Asp
                210                 215                 220
Thr Pro Phe Val Pro Pro Thr Thr Pro Phe Ala Phe Gln Tyr Asp Leu
225                 230                 235                 240
Leu Ala Arg Ala Lys Asp Lys Lys Thr Ile Val Leu Pro Glu Gly
                245                 250                 255
Glu Asp Asp Arg Ile Ile Thr Ala Ala Asn Tyr Leu Leu Gln Ser Asn
                260                 265                 270
Val Val Asp Leu Val Ile Ile Gly Asp Arg Asn Glu Ile Leu Ala Arg
                275                 280                 285
Gly Glu Lys Leu Gly Leu Lys Ala Leu Asp Gln Ala Lys Phe Val Ser
                290                 295                 300
Ile Asp Asp Lys His Leu Leu Asp Thr Met Val Pro Lys Leu Cys Glu
305                 310                 315                 320
Leu Arg Ala Lys Lys Gly Met Thr Pro Asp Val Ala Leu Lys Thr Leu
                325                 330                 335
Arg Asp Thr Asn Tyr Phe Gly Thr Met Leu Ile Val Leu Gly Met Ala
                340                 345                 350
Asp Gly Leu Val Ser Gly Ala Ile Ser Ser Thr Ala Asn Thr Val Arg
                355                 360                 365
Pro Ala Leu Gln Leu Ile Lys Thr Lys Pro Gly Val Ser Ser Val Ser
                370                 375                 380
Gly Ala Phe Leu Met Cys Leu Lys Asp His Val Ser Val Phe Ala Asp
385                 390                 395                 400
Cys Ala Ile Asn Leu Asp Pro Asp Pro Gln Gln Leu Ala Asp Ile Ala
                405                 410                 415
Ile Gln Ser Ala Glu Thr Ala Lys Ala Phe Ser Ile Asp Pro Lys Ile
                420                 425                 430
Gly Leu Leu Ser Tyr Ser Thr Leu Gly Ser Gly Lys Gly Pro Asp Val
                435                 440                 445
Asp Leu Val Val Glu Ala Thr Ser Ile Ala Gln Asn Lys Arg Pro Asp
                450                 455                 460
Leu Pro Ile Val Gly Pro Ile Gln Phe Asp Ala Ala Trp Ser Lys Thr
465                 470                 475                 480
Val Ala Arg Val Lys Ala Phe Gly Asn Pro Ile Ala Gly Asn Val Thr
                485                 490                 495
Val Phe Val Phe Pro Asp Leu Asp Ala Gly Asn Ile Cys Tyr Lys Ala
                500                 505                 510
```

```
Val Gln Arg Thr Ser Gly Ala Val Ala Ile Gly Pro Val Leu Gln Gly
        515                 520                 525

Leu Asn Arg Pro Val Asn Asp Leu Ser Arg Gly Ala Leu Val Gln Asp
    530                 535                 540

Ile Ile Asn Thr Ile Ala Leu Thr Ala Ile Glu Ala Gln Ser Asn Glu
545                 550                 555                 560

<210> SEQ ID NO 77
<211> LENGTH: 2199
<212> TYPE: DNA
<213> ORGANISM: Escherichia coli
<220> FEATURE:
<221> NAME/KEY: CDS
<222> LOCATION: (31)..(2172)

<400> SEQUENCE: 77
cgcggatccg cgccgctcga gcggtatata atg agt agg att atc atg tta ata      54
                                Met Ser Arg Ile Ile Met Leu Ile
                                  1               5 ccg aca ggt acc agt gtc gga ctt acc agc gta tcg ttg ggt gtt ata     102
Pro Thr Gly Thr Ser Val Gly Leu Thr Ser Val Ser Leu Gly Val Ile
 10                  15                  20 aga gcc atg gaa cgt aag ggt gtt agg ttg tct gtt ttc aaa ccg att     150
Arg Ala Met Glu Arg Lys Gly Val Arg Leu Ser Val Phe Lys Pro Ile
 25                  30                  35                  40 gca cag cct agg aca ggc ggt gat gct cca gac caa act aca act att     198
Ala Gln Pro Arg Thr Gly Gly Asp Ala Pro Asp Gln Thr Thr Thr Ile
                 45                  50                  55 gta cgt gcc aat tcc tcg acc aca act gct gca gaa ccc ttg aag atg     246
Val Arg Ala Asn Ser Ser Thr Thr Thr Ala Ala Glu Pro Leu Lys Met
             60                  65                  70 tca tat gtg gaa ggc tta tta tct tca aac cag aaa gac gtt ctg atg     294
Ser Tyr Val Glu Gly Leu Leu Ser Ser Asn Gln Lys Asp Val Leu Met
         75                  80                  85 gag gaa ata gta gct aat tat cac gca aat act aaa gac gct gaa gtc     342
Glu Glu Ile Val Ala Asn Tyr His Ala Asn Thr Lys Asp Ala Glu Val
     90                  95                 100 gtt tta gtc gag ggt tta gta ccg acg aga aaa cac caa ttc gct cag     390
Val Leu Val Glu Gly Leu Val Pro Thr Arg Lys His Gln Phe Ala Gln
105                 110                 115                 120 tca ttg aat tac gaa att gcg aag acg ctt aat gct gaa atc gtg ttt     438
Ser Leu Asn Tyr Glu Ile Ala Lys Thr Leu Asn Ala Glu Ile Val Phe
                125                 130                 135 gtc atg tct caa ggg aca gac aca cca gaa cag tta aaa gag agg ata     486
Val Met Ser Gln Gly Thr Asp Thr Pro Glu Gln Leu Lys Glu Arg Ile
            140                 145                 150 gaa ttg acc aga aat agt ttt ggc ggc gcc aag aac act aat att act     534
Glu Leu Thr Arg Asn Ser Phe Gly Gly Ala Lys Asn Thr Asn Ile Thr
        155                 160                 165 gga gtc att gtt aac aaa cta aac gca cca gtt gat gaa caa ggg aga     582
Gly Val Ile Val Asn Lys Leu Asn Ala Pro Val Asp Glu Gln Gly Arg
    170                 175                 180 act aga cca gat ttg tct gaa ata ttc gac gac tcc agc aaa gct aaa     630
Thr Arg Pro Asp Leu Ser Glu Ile Phe Asp Asp Ser Ser Lys Ala Lys
185                 190                 195                 200 gtc aac aat gta gat ccg gca aag ttg cag gag tct agc cca ctt cct     678
Val Asn Asn Val Asp Pro Ala Lys Leu Gln Glu Ser Ser Pro Leu Pro
                205                 210                 215 gtg tta ggc gca gtt cct tgg agt ttt gat cta att gca act cgt gct     726
Val Leu Gly Ala Val Pro Trp Ser Phe Asp Leu Ile Ala Thr Arg Ala
```

```
                220                 225                 230
att gat atg gct agg cat cta aac gca aca atc atc aac gaa ggt gat        774
Ile Asp Met Ala Arg His Leu Asn Ala Thr Ile Ile Asn Glu Gly Asp
        235                 240                 245 ata aac acg agg aga gtc aaa tct gtt act ttc tgt gca aga tcc att        822
Ile Asn Thr Arg Arg Val Lys Ser Val Thr Phe Cys Ala Arg Ser Ile
250                 255                 260 cct cat atg ttg gaa cac ttt aga gct ggc agc ttg ctt gtg acc tca        870
Pro His Met Leu Glu His Phe Arg Ala Gly Ser Leu Leu Val Thr Ser
265                 270                 275                 280 gct gat aga ccc gat gtg ctg gtg gct gca tgt cta gct gct atg aat        918
Ala Asp Arg Pro Asp Val Leu Val Ala Ala Cys Leu Ala Ala Met Asn
            285                 290                 295 gga gtt gag atc gga gca ttg tta tta act ggt gga tat gaa atg gac        966
Gly Val Glu Ile Gly Ala Leu Leu Leu Thr Gly Gly Tyr Glu Met Asp
        300                 305                 310 gcg aga ata tcg aag ttg tgt gag aga gcg ttt gca aca ggt cta ccc       1014
Ala Arg Ile Ser Lys Leu Cys Glu Arg Ala Phe Ala Thr Gly Leu Pro
    315                 320                 325 gtg ttt atg gtt aat aca aac aca tgg caa acc tca ctt agt ttg caa       1062
Val Phe Met Val Asn Thr Asn Thr Trp Gln Thr Ser Leu Ser Leu Gln
330                 335                 340 agt ttt aac ttg gaa gtg cct gtt gac gat cat gag aga att gag aaa       1110
Ser Phe Asn Leu Glu Val Pro Val Asp Asp His Glu Arg Ile Glu Lys
345                 350                 355                 360 gtc caa gaa tac gtt gca aac tat ata aat gcc gac tgg atc gaa tcg       1158
Val Gln Glu Tyr Val Ala Asn Tyr Ile Asn Ala Asp Trp Ile Glu Ser
            365                 370                 375 cta aca gcc acc agt gaa aga tca agg aga cta tct cct cct gcg ttt       1206
Leu Thr Ala Thr Ser Glu Arg Ser Arg Arg Leu Ser Pro Pro Ala Phe
        380                 385                 390 aga tac cag cta act gaa ttg gcc aga aag gca ggt aaa aga atc gtt       1254
Arg Tyr Gln Leu Thr Glu Leu Ala Arg Lys Ala Gly Lys Arg Ile Val
    395                 400                 405 tta cca gaa gga gac gaa ccc aga act gtg aaa gcc gca gct att tgc       1302
Leu Pro Glu Gly Asp Glu Pro Arg Thr Val Lys Ala Ala Ala Ile Cys
410                 415                 420 gca gag cgt ggt att gct acg tgc gta ctg ttg ggt aat cca gct gag       1350
Ala Glu Arg Gly Ile Ala Thr Cys Val Leu Leu Gly Asn Pro Ala Glu
425                 430                 435                 440 atc aat agg gtt gca gcg tct caa gga gta gaa cta ggt gcg ggt ata       1398
Ile Asn Arg Val Ala Ala Ser Gln Gly Val Glu Leu Gly Ala Gly Ile
            445                 450                 455 gaa atc gtc gat cca gaa gtg gtg aga gaa tct tat gtt ggc aga tta       1446
Glu Ile Val Asp Pro Glu Val Val Arg Glu Ser Tyr Val Gly Arg Leu
        460                 465                 470 gtc gaa ctg aga aag aac aag ggg atg aca gag act gtc gct aga gag       1494
Val Glu Leu Arg Lys Asn Lys Gly Met Thr Glu Thr Val Ala Arg Glu
    475                 480                 485 caa tta gaa gat aat gtt gtt ttg ggt act ctg atg ctt gaa cag gat       1542
Gln Leu Glu Asp Asn Val Val Leu Gly Thr Leu Met Leu Glu Gln Asp
490                 495                 500 gaa gtc gat ggt ttg gtt agt gga gct gtt cat acc aca gca aat aca       1590
Glu Val Asp Gly Leu Val Ser Gly Ala Val His Thr Thr Ala Asn Thr
505                 510                 515                 520 att aga cca cca ctg caa ttg ata aag acg gct cct ggc tcc tcg tta       1638
Ile Arg Pro Pro Leu Gln Leu Ile Lys Thr Ala Pro Gly Ser Ser Leu
            525                 530                 535 gtc tcc tcc gta ttc ttt atg ctt ttg cct gaa caa gta tac gtt tat       1686
Val Ser Ser Val Phe Phe Met Leu Leu Pro Glu Gln Val Tyr Val Tyr
```

```
                Val Ser Ser Val Phe Phe Met Leu Leu Pro Glu Gln Val Tyr Val Tyr
                            540                 545                 550 ggg gat tgt gcc att aat cct gat cca acg gcc gaa caa tta gcc gag          1734
Gly Asp Cys Ala Ile Asn Pro Asp Pro Thr Ala Glu Gln Leu Ala Glu
            555                 560                 565 att gcg atc caa agc gcc gat tct gct gca gct ttt ggt atc gag cca          1782
Ile Ala Ile Gln Ser Ala Asp Ser Ala Ala Ala Phe Gly Ile Glu Pro
570                 575                 580 aga gta gct atg ctg tct tac tca aca ggt act tca ggt gct ggt tca          1830
Arg Val Ala Met Leu Ser Tyr Ser Thr Gly Thr Ser Gly Ala Gly Ser
585                 590                 595                 600 gat gtg gaa aag gta aga gaa gca act aga ctt gct caa gaa aag agg          1878
Asp Val Glu Lys Val Arg Glu Ala Thr Arg Leu Ala Gln Glu Lys Arg
                605                 610                 615 cct gat ttg atg att gat ggc ccc tta cag tac gat gcc gcc gtt atg          1926
Pro Asp Leu Met Ile Asp Gly Pro Leu Gln Tyr Asp Ala Ala Val Met
            620                 625                 630 gcc gat gtt gct aaa tct aaa gcc cca aat tcc ccg gta gcg ggt aga          1974
Ala Asp Val Ala Lys Ser Lys Ala Pro Asn Ser Pro Val Ala Gly Arg
        635                 640                 645 gcc act gtt ttc att ttc ccc gat tta aac acg gga aat acc acc tat          2022
Ala Thr Val Phe Ile Phe Pro Asp Leu Asn Thr Gly Asn Thr Thr Tyr
650                 655                 660 aaa gct gta caa cgt tct gct gac tta ata tca att ggt cca atg ctt          2070
Lys Ala Val Gln Arg Ser Ala Asp Leu Ile Ser Ile Gly Pro Met Leu
665                 670                 675                 680 cag ggg atg aga aaa cca gtc aat gac ttg tcc cgt gga gcc ttg gtt          2118
Gln Gly Met Arg Lys Pro Val Asn Asp Leu Ser Arg Gly Ala Leu Val
                685                 690                 695 gac gat att gta tat acc att gca tta act gca ata caa tca gct caa          2166
Asp Asp Ile Val Tyr Thr Ile Ala Leu Thr Ala Ile Gln Ser Ala Gln
            700                 705                 710 caa caa taacccaagc ttgggctagc tagctag                                    2199
Gln Gln <210> SEQ ID NO 78
<211> LENGTH: 714
<212> TYPE: PRT
<213> ORGANISM: Escherichia coli

<400> SEQUENCE: 78

Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
```

-continued

```
            130                 135                 140
Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Gly Tyr Val Ala Asn Tyr
        355                 360                 365

Ile Asn Ala Asp Trp Ile Glu Ser Leu Thr Ala Thr Ser Glu Arg Ser
370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
        435                 440                 445

Gly Val Glu Leu Gly Ala Gly Ile Glu Ile Val Asp Pro Glu Val Val
450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
        515                 520                 525

Lys Thr Ala Pro Gly Ser Ser Leu Val Ser Val Phe Phe Met Leu
530                 535                 540

Leu Pro Glu Gln Val Tyr Val Tyr Gly Asp Cys Ala Ile Asn Pro Asp
545                 550                 555                 560
```

Pro Thr Ala Glu Gln Leu Ala Glu Ile Ala Ile Gln Ser Ala Asp Ser
            565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
            595                 600                 605

Thr Arg Leu Ala Gln Glu Lys Arg Pro Asp Leu Met Ile Asp Gly Pro
    610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
            645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
            675                 680                 685

Asp Leu Ser Arg Gly Ala Leu Val Asp Asp Ile Val Tyr Thr Ile Ala
    690                 695                 700

Leu Thr Ala Ile Gln Ser Ala Gln Gln Gln
705                 710

<210> SEQ ID NO 79
<211> LENGTH: 32
<212> TYPE: DNA
<213> ORGANISM: Artificial
<220> FEATURE:
<223> OTHER INFORMATION: Synthetic DNA

<400> SEQUENCE: 79
atgttaaagg atgaagtaat taaacaaatt ag                                32

<210> SEQ ID NO 80
<211> LENGTH: 32
<212> TYPE: DNA
<213> ORGANISM: Artificial
<220> FEATURE:
<223> OTHER INFORMATION: Synthetic DNA

<400> SEQUENCE: 80
ttacttaaga taatcatata taacttcagc tc                                32

<210> SEQ ID NO 81
<211> LENGTH: 36
<212> TYPE: DNA
<213> ORGANISM: Artificial
<220> FEATURE:
<223> OTHER INFORMATION: Synthetic DNA

<400> SEQUENCE: 81
atgaactcta aaataattag atttgaaaat ttaagg                            36

<210> SEQ ID NO 82
<211> LENGTH: 29
<212> TYPE: DNA
<213> ORGANISM: Artificial
<220> FEATURE:
<223> OTHER INFORMATION: Synthetic DNA

<400> SEQUENCE: 82
ttatgcaggc tcctttacta tataattta                                    29

<210> SEQ ID NO 83
<211> LENGTH: 28
<212> TYPE: DNA
<213> ORGANISM: Artificial
<220> FEATURE:
<223> OTHER INFORMATION: Synthetic DNA

<400> SEQUENCE: 83
atgattaatg ataaaaacct agcgaaag                                       28

<210> SEQ ID NO 84
<211> LENGTH: 24
<212> TYPE: DNA
<213> ORGANISM: Artificial
<220> FEATURE:
<223> OTHER INFORMATION: Synthetic DNA

<400> SEQUENCE: 84
ctaaacagcc atgggtctaa gttc                                           24

<210> SEQ ID NO 85
<211> LENGTH: 32
<212> TYPE: DNA
<213> ORGANISM: Artificial
<220> FEATURE:
<223> OTHER INFORMATION: Synthetic DNA

<400> SEQUENCE: 85
tagggagctc caagaattac tcgtgagtaa gg                                  32

<210> SEQ ID NO 86
<211> LENGTH: 36
<212> TYPE: DNA
<213> ORGANISM: Artificial
<220> FEATURE:
<223> OTHER INFORMATION: Synthetic DNA

<400> SEQUENCE: 86
ataaccgcgg tgttttatat ttgttgtaaa aagtag                              36

<210> SEQ ID NO 87
<211> LENGTH: 37
<212> TYPE: DNA
<213> ORGANISM: Artificial
<220> FEATURE:
<223> OTHER INFORMATION: Synthetic DNA

<400> SEQUENCE: 87
ttaagtcgac attgaattga attgaaatcg atagatc                             37

<210> SEQ ID NO 88
<211> LENGTH: 30
<212> TYPE: DNA
<213> ORGANISM: Artificial
<220> FEATURE:
<223> OTHER INFORMATION: Synthetic DNA

<400> SEQUENCE: 88
ttaaggtacc gcttcaagct tacacaacac                                     30

<210> SEQ ID NO 89
<211> LENGTH: 1097
<212> TYPE: DNA
<213> ORGANISM: Clostridium beijerinckii
<220> FEATURE:
<221> NAME/KEY: CDS

<220> LOCATION: (26)..(1081)

<400> SEQUENCE: 89

```
cgggtttccg cggtctagag ccacc atg aaa ggt ttc gca atg ttg ggt atc      52
                            Met Lys Gly Phe Ala Met Leu Gly Ile
                            1               5 aat aag tta ggc tgg ata gag aaa gaa aga cct gtc gca ggt agc tat     100
Asn Lys Leu Gly Trp Ile Glu Lys Glu Arg Pro Val Ala Gly Ser Tyr
 10              15                  20                  25 gat gcc att gtt cga cca tta gcc gtt tct cct tgc aca tcc gac att     148
Asp Ala Ile Val Arg Pro Leu Ala Val Ser Pro Cys Thr Ser Asp Ile
                 30                  35                  40 cac aca gtg ttt gaa ggt gca tta gga gat agg aag aac atg ata ctg     196
His Thr Val Phe Glu Gly Ala Leu Gly Asp Arg Lys Asn Met Ile Leu
             45                  50                  55 ggt cat gaa gcc gtc gga gaa gta gtt gaa gtt gga agc gaa gta aag     244
Gly His Glu Ala Val Gly Glu Val Val Glu Val Gly Ser Glu Val Lys
         60                  65                  70 gac ttt aag cct ggt gat aga gtg atc gtt cct tgc aca act cca gat     292
Asp Phe Lys Pro Gly Asp Arg Val Ile Val Pro Cys Thr Thr Pro Asp
 75                  80                  85 tgg aga tca tta gaa gtt caa gct gga ttc caa cag cat tct aat ggc     340
Trp Arg Ser Leu Glu Val Gln Ala Gly Phe Gln Gln His Ser Asn Gly
 90                  95                 100                 105 atg ctt gct ggt tgg aaa ttc agt aat ttc aag gat ggc gtg ttt ggt     388
Met Leu Ala Gly Trp Lys Phe Ser Asn Phe Lys Asp Gly Val Phe Gly
                110                 115                 120 gag tac ttt cat gtc aat gat gca gat atg aac cta gct att ctt ccc     436
Glu Tyr Phe His Val Asn Asp Ala Asp Met Asn Leu Ala Ile Leu Pro
            125                 130                 135 aag gat atg cca ttg gag aat gct gtc atg ata acc gac atg atg act     484
Lys Asp Met Pro Leu Glu Asn Ala Val Met Ile Thr Asp Met Met Thr
        140                 145                 150 act ggg ttt cat ggt gct gaa cta gcg gac att cag atg ggt tca tcg     532
Thr Gly Phe His Gly Ala Glu Leu Ala Asp Ile Gln Met Gly Ser Ser
    155                 160                 165 gtt gtt gtg att ggt att ggt gct gtt gga ctt atg ggg att gca ggc     580
Val Val Val Ile Gly Ile Gly Ala Val Gly Leu Met Gly Ile Ala Gly
170                 175                 180                 185 gca aaa ttg cgt ggt gcc ggc cgt atc att ggc gta ggt tcg aga ccc     628
Ala Lys Leu Arg Gly Ala Gly Arg Ile Ile Gly Val Gly Ser Arg Pro
                190                 195                 200 ata tgt gtg gaa gct gcg aaa ttc tat ggt gct aca gac att ttg aac     676
Ile Cys Val Glu Ala Ala Lys Phe Tyr Gly Ala Thr Asp Ile Leu Asn
            205                 210                 215 tac aag aat ggt cac ata gtt gac caa gtc atg aaa ctg acc aat ggg     724
Tyr Lys Asn Gly His Ile Val Asp Gln Val Met Lys Leu Thr Asn Gly
        220                 225                 230 aaa ggc gtt gat agg gtg att atg gct ggt ggt gga tct gaa act ttg     772
Lys Gly Val Asp Arg Val Ile Met Ala Gly Gly Gly Ser Glu Thr Leu
    235                 240                 245 agt caa gcc gtc tct atg gta aaa cca ggt gga atc ata tcc aat atc     820
Ser Gln Ala Val Ser Met Val Lys Pro Gly Gly Ile Ile Ser Asn Ile
250                 255                 260                 265 aac tac cat ggg tca gga gat gcg tta ctt ata ccg aga gtt gag tgg     868
Asn Tyr His Gly Ser Gly Asp Ala Leu Leu Ile Pro Arg Val Glu Trp
                270                 275                 280 gga tgt ggc atg gca cac aaa acg att aag ggt ggt tta tgt cca ggc     916
Gly Cys Gly Met Ala His Lys Thr Ile Lys Gly Gly Leu Cys Pro Gly
            285                 290                 295
```

```
gga aga tta aga gct gaa atg tta aga gat atg gtt gta tat aac agg     964
Gly Arg Leu Arg Ala Glu Met Leu Arg Asp Met Val Val Tyr Asn Arg
        300             305             310 gtt gat ctg tcc aaa cta gtg acg cat gta tat cac ggg ttt gat cat    1012
Val Asp Leu Ser Lys Leu Val Thr His Val Tyr His Gly Phe Asp His
315             320             325 atc gag gaa gca ttg ttg ttg atg aaa gat aaa ccg aaa gac cta atc    1060
Ile Glu Glu Ala Leu Leu Leu Met Lys Asp Lys Pro Lys Asp Leu Ile
        330             335             340             345 aag gcc gta gtc att ttg taa ggatccgtcg acgggg                      1097
Lys Ala Val Val Ile Leu
                350
```

<210> SEQ ID NO 90
<211> LENGTH: 351
<212> TYPE: PRT
<213> ORGANISM: Clostridium beijerinckii

<400> SEQUENCE: 90

```
Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285
```

```
Thr Ile Lys Gly Gly Leu Cys Pro Gly Gly Arg Leu Arg Ala Glu Met
    290                 295                 300
Leu Arg Asp Met Val Val Tyr Asn Arg Val Asp Leu Ser Lys Leu Val
305                 310                 315                 320
Thr His Val Tyr His Gly Phe Asp His Ile Glu Glu Ala Leu Leu Leu
                325                 330                 335
Met Lys Asp Lys Pro Lys Asp Leu Ile Lys Ala Val Val Ile Leu
                340                 345                 350
```

<210> SEQ ID NO 91
<211> LENGTH: 50
<212> TYPE: DNA
<213> ORGANISM: Artificial
<220> FEATURE:
<223> OTHER INFORMATION: Synthetic DNA

<400> SEQUENCE: 91
ggggacaagt ttgtacaaaa aagcaggctc agttcgagtt tatcattatc        50

<210> SEQ ID NO 92
<211> LENGTH: 50
<212> TYPE: DNA
<213> ORGANISM: Artificial
<220> FEATURE:
<223> OTHER INFORMATION: Synthetic DNA

<400> SEQUENCE: 92
ggggacaact ttgtatagaa aagttgggtg ggccgcaaat taaagccttc        50

<210> SEQ ID NO 93
<211> LENGTH: 48
<212> TYPE: DNA
<213> ORGANISM: Artificial
<220> FEATURE:
<223> OTHER INFORMATION: Synthetic DNA

<400> SEQUENCE: 93
ggggacaact tttctataca aagttggctt caagcttaca caacacgg          48

<210> SEQ ID NO 94
<211> LENGTH: 49
<212> TYPE: DNA
<213> ORGANISM: Artificial
<220> FEATURE:
<223> OTHER INFORMATION: Synthetic DNA

<400> SEQUENCE: 94
ggggacaact ttattataca aagttgtcaa gaattactcg tgagtaagg         49

<210> SEQ ID NO 95
<211> LENGTH: 30
<212> TYPE: DNA
<213> ORGANISM: Artificial
<220> FEATURE:
<223> OTHER INFORMATION: Synthetic DNA

<400> SEQUENCE: 95
tagtggatcc gatgattaat gataaaaacc                              30

<210> SEQ ID NO 96
<211> LENGTH: 22
<212> TYPE: DNA
<213> ORGANISM: Artificial
<220> FEATURE:
<223> OTHER INFORMATION: Synthetic DNA

```
<400> SEQUENCE: 96
cctagacttc aggttgtcta ac                                           22

<210> SEQ ID NO 97
<211> LENGTH: 46
<212> TYPE: DNA
<213> ORGANISM: Artificial
<220> FEATURE:
<223> OTHER INFORMATION: Synthetic DNA

<400> SEQUENCE: 97
ggggacaact ttgtataata aagttgggcc gcaaattaaa gccttc                 46

<210> SEQ ID NO 98
<211> LENGTH: 51
<212> TYPE: DNA
<213> ORGANISM: Artificial
<220> FEATURE:
<223> OTHER INFORMATION: Synthetic DNA

<400> SEQUENCE: 98
ggggaccact ttgtacaaga aagctgggta cagttcgagt ttatcattat c           51

<210> SEQ ID NO 99
<211> LENGTH: 35
<212> TYPE: DNA
<213> ORGANISM: Artificial
<220> FEATURE:
<223> OTHER INFORMATION: Synthetic DNA

<400> SEQUENCE: 99
tagggagctc atcacaagtt tgtacaaaaa agctg                             35

<210> SEQ ID NO 100
<211> LENGTH: 33
<212> TYPE: DNA
<213> ORGANISM: Artificial
<220> FEATURE:
<223> OTHER INFORMATION: Synthetic DNA

<400> SEQUENCE: 100
ttaaggtacc atcaccactt tgtacaagaa agc                               33
```

US 9,340,793 B2

RECOMBINANT YEAST AND SUBSTANCE PRODUCTION METHOD USING THE SAME

CROSS REFERENCE TO RELATED APPLICATIONS

This application is a National Stage of International Application No. PCT/JP2011/050974 filed Jan. 20, 2011, the contents of all of which are incorporated herein by reference in their entirety.

TECHNICAL FIELD

The present invention relates to a recombinant yeast prepared through modification to suppress and/or enhance the expression of a predetermined gene or introduction of a predetermined gene, and a substance production method using the recombinant yeast.

BACKGROUND ART

Examples of techniques concerning substance production using yeast are mainly methods for designing substance production pathways using acetyl-CoA as an intermediate. For example, oleic acid, which is a typical fatty acid, requires 9 molecules of acetyl-CoA as a raw material, and carotin, which is a typical diterpene, requires 12 molecules of acetyl-CoA as a raw material. Accordingly, a technique for synthesizing fatty acid useful as a pharmaceutical product or a fine chemical (Patent Document 1), a technique for synthesizing terpenoid (Patent Document 2), and a technique for synthesizing polyketide (Patent Document 3) using acetyl-CoA accumulated within yeast are known. Furthermore, examples of a substance that is synthesized using acetyl-CoA as an intermediate include butanol (Patent Document 4), isopropanol (Patent Document 5) and farnesene (Patent Document 5), which are attracting attention as biofuels.

In yeast, ethanol produced extracellularly is taken up by cells and then acetyl-CoA is synthesized from the incorporated ethanol. When the concentration of ethanol produced by yeast becomes high, the yeast's own growth is inhibited. Therefore, it has been difficult to increase the amount of acetyl-CoA within cells by means such as a means of increasing the ethanol production capacity of yeast or a means of increasing the amount of ethanol to be taken up by yeast.

More specifically, Patent Document 2 discloses a technique for synthesizing farnesene from acetyl-CoA, but the yield thereof is about 25% of the theoretical yield. Moreover, Patent Document 6 discloses a technique for synthesizing 6-methyl salicylate from acetyl-CoA, but the yield is about 20% of the theoretical yield. As described above, substance production from acetyl-CoA is problematic in that productivity is significantly low.

PRIOR PATENT DOCUMENTS

Patent Document 1: JP Patent Publication (Kokai) No. 63-287491 A (1988)
Patent Document 2: WO2008/045555
Patent Document 3: JP Patent Publication (Kokai) No. 2008-22865 A
Patent Document 4: WO2008/137406
Patent Document 5: US2008/0293125
Patent Document 6: US2006/0148052

SUMMARY OF THE INVENTION

Problem to be Solved by the Invention

In view of the above circumstances, an object of the present invention is to provide a recombinant yeast with high substance productivity by introducing a metabolic pathway for synthesis of acetyl-CoA or acetic acid from glucose-6-phosphate into yeast, in particular, and a substance production method using the yeast.

Means for Solving Problem

As a result of intensive studies to achieve the above object, the present inventors have discovered that the productivity of acetic acid, acetyl-CoA, and a substance made from acetyl-CoA can be improved by attenuating a gene involved in the glycolytic system of yeast and introducing a phosphoketolase gene into the yeast, and thus they have completed the present invention. In addition, the term "phosphoketolase" refers to an enzyme that catalyzes a reaction to convert xylulose 5-phosphate into acetylphosphate and glyceraldehyde 3-phosphate.

Specifically, the present invention encompasses the following (1) to (7).
(1) A recombinant yeast, which comprises an attenuated phosphofructokinase gene and an introduced phosphoketolase gene.
(2) The recombinant yeast according to (1), wherein the expression level of a glucose-6-phosphate dehydrogenase gene and/or a D-ribulose-5-phosphate-3-epimerase gene is increased.
(3) The recombinant yeast according to (1), wherein a phosphotransacetylase gene is introduced and/or the expression level of an acetyl-CoA synthetase gene is increased.
(4) The recombinant yeast according to (1), wherein the expression level of an alcohol acetyltransferase gene involved in a reaction for synthesis of ethyl acetate using acetyl-CoA as a substrate is increased.
(5) The recombinant yeast according to (1), which is prepared by introducing an acetoacetic acid decarboxylase gene, a butyrate-acetoacetate CoA-transferase subunit A gene, a butyrate-acetoacetate CoA-transferase subunit B gene, an acetyl-CoA acetyltransferase gene, and an isopropanol dehydrogenase gene, which are involved in a reaction for synthesis of isopropanol using acetyl-CoA as a substrate.
(6) A method for producing a substance, comprising a step of culturing the recombinant yeast of any one of (1) to (5) above in medium.
(7) The method for producing a material according to (6), wherein the substance is 1 type of substance selected from the group consisting of acetic acid, acetyl-CoA, ethyl acetate made from acetyl-CoA, and isopropanol made from acetyl-CoA.

Effects of the Invention

The recombinant yeast according to the present invention has attenuated activity of converting fructose-6-phosphate into fructose-1,6-bisphosphate, and, imparted activity of converting xylulose 5-phosphate into acetylphosphate. Accordingly, through the use of the recombinant yeast according to the present invention, the productivity of acetic acid or a substance made from acetyl-CoA can be improved.

EMBODIMENTS FOR CARRYING OUT THE INVENTION

The present invention will be described in detail as follows with reference to drawings and examples.

The recombinant yeast according to the present invention comprises an attenuated gene that encodes an enzyme involved in a glycolytic system, and an introduced phosphoketolase gene. The recombinant yeast has activity to convert xylulose 5-phosphate to acetylphosphate. Examples of yeast that can be used as a host include, but are not particularly limited to, yeast of the genus *Candida* such as *Candida Shehatae*, yeast of the genus *Pichia* such as *Pichia stipitis*, yeast of the genus *Pachysolen* such as *Pachysolen tannophilus*, yeast of the genus *Saccharomyces* such as *Saccharomyces cerevisiae*, and yeast of the genus *Schizosaccharomyces* such as *Schizosaccharomyces pombe*. In particular, *Saccharomyces cerevisiae* is preferred. A yeast strain to be used herein may be an experimental strain to be used for convenience of experiments or an industrial strain (practical strain) to be employed for practical usefulness. Examples of such an industrial strain include yeast strains to be used for production of wine, sake, and shochu (spirits).

Here, an example of a gene that encodes an enzyme involved in a glycolytic system and is subjected to attenuation is a phosphofructokinase gene.

Furthermore, as an enzyme involved in the glycolytic system, hexokinase, glucose phosphate isomerase, aldolase, triosephosphate isomerase, glyceraldehyde-3-phosphate dehydrogenase, phosphoglycerate kinase, phosphoglyceromutase, enolase, and pyruvate kinase are known in addition to phosphofructokinase. Genes encoding these enzymes other than phosphofructokinase may also be attenuated.

Figure 1:
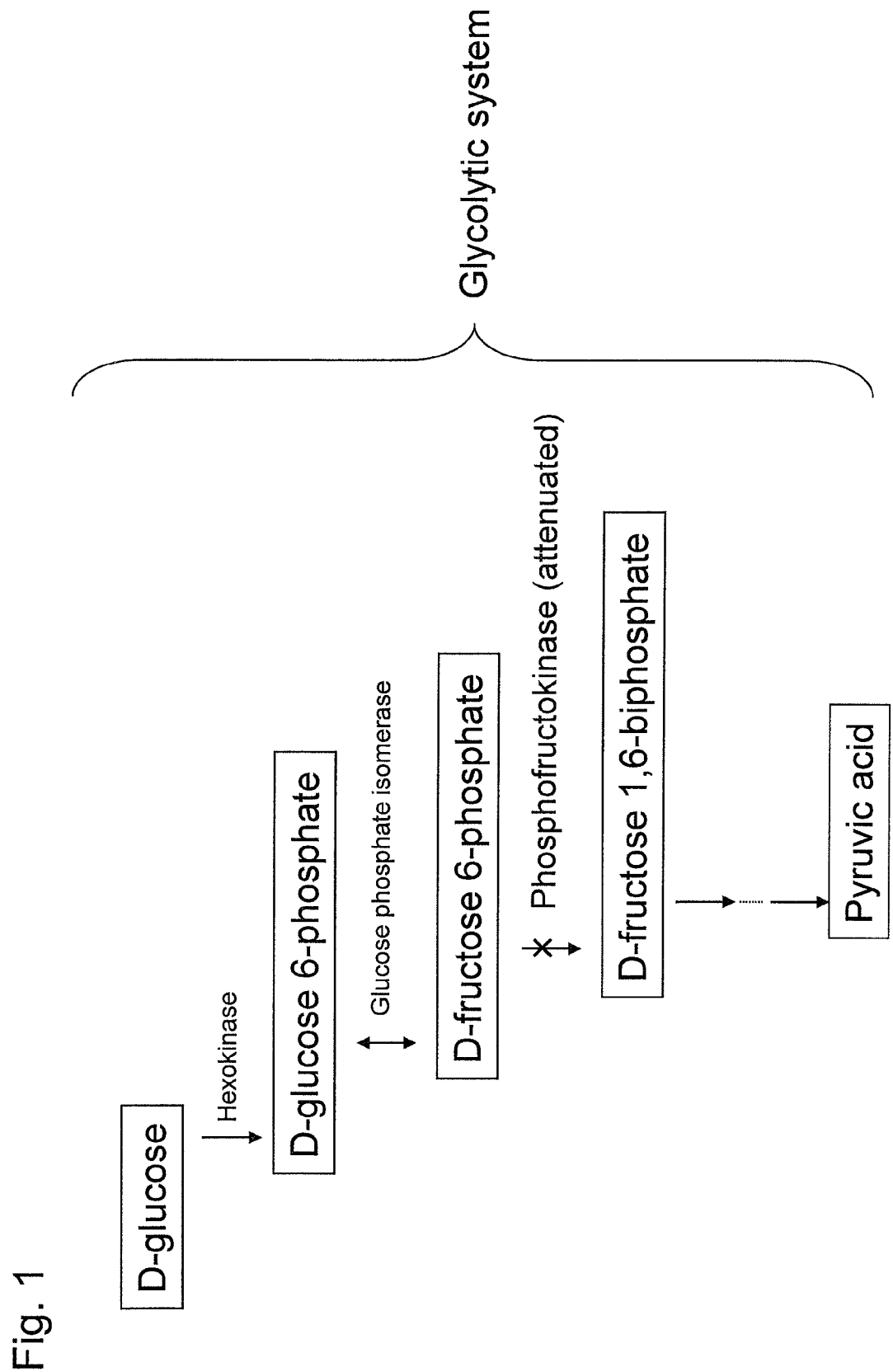
FIG. 1 is a characteristic diagram showing a part of a glycolytic system including a metabolic pathway in which a phosphofructokinase gene to be attenuated in the yeast according to the present invention is involved.

The phosphofructokinase gene encodes an enzyme that converts fructose-6-phosphate into fructose-1,6-bisphosphate in the glycolytic system, as shown in FIG. 1. The expression, "the phosphofructokinase gene is attenuated" means that phosphofructokinase activity is significantly lowered. In other words, the expression means that the amount of fructose-1,6-bisphosphate to be synthesized through the glycolytic system is significantly decreased. Examples of means for attenuating a phosphofructokinase gene include, but are not particularly limited to, disruption or deletion of the phosphofructokinase gene, disruption or deletion of the expression control region of the phosphofructokinase gene, addition of an inhibitor (e.g., citric acid) of phosphofructokinase, and a technique for suppressing the expression of the phosphofructokinase gene with the use of a method using RNA interference such as siRNA or an antisense method.

In addition, as endogenous phosphofructokinase genes of *Saccharomyces cerevisiae*, a PFK1 gene and a PFK2 gene are known (THE JOURNAL OF BIOLOGICAL CHEMISTRY, Vol. 275, No. 52, Issue of December 29, pp. 40952-40960, 2000). When *Saccharomyces cerevisiae* is used as a host for the recombinant yeast according to the present invention, either the PFK1 gene or the PFK2 gene may be attenuated or both genes may be attenuated. Moreover, endogenous phosphofructokinase genes of yeast other than *Saccharomyces cerevisiae* are also known and can be specified referring to existing databases such as Genbank, DDBJ, and EMBL. As described above, phosphofructokinase genes specified by the above techniques and/or means can be attenuated by specifying endogenous phosphofructokinase genes of various types of yeast.

Figure 2:
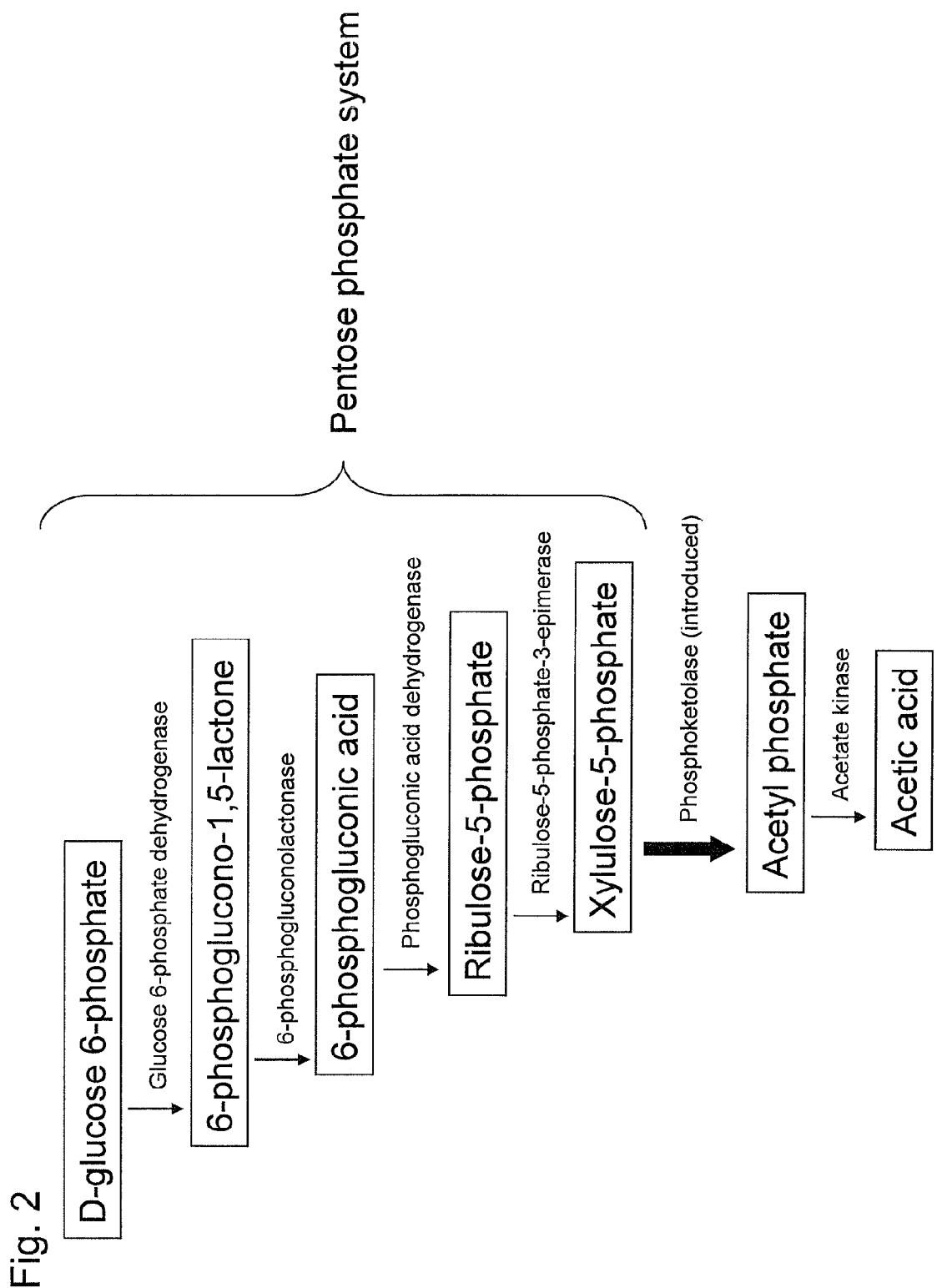
FIG. 2 is a characteristic diagram showing a part of a pentose phosphate system including a metabolic pathway in which a phosphoketolase gene to be introduced into the yeast according to the present invention is involved.

Furthermore, the recombinant yeast according to the present invention acquires the capacity to convert xylulose 5-phosphate into acetylphosphate through exogenous introduction of a phosphoketolase gene (PKT gene). In addition, xylulose 5-phosphate is synthesized as a metabolite resulting from yeast's original pentose phosphate system from ribulose-5-phosphate (FIG. 2). Acetylphosphate synthesized by phosphoketolase is converted into acetic acid by yeast's original acetic acid kinase. Therefore, in the recombinant yeast prepared by attenuating a phosphofructokinase gene and introducing a phosphoketolase gene, the productivity of acetic acid to be secreted to medium is drastically improved.

Examples of phosphoketolase genes to be preferably used herein include, but are not particularly limited to, phosphoketolase genes derived from lactic acid bacteria or bifidobacteria having a metabolic pathway for heterolactic fermentation. Here, the term "heterolactic fermentation" refers to fermentation whereby pyruvic acid generated via the glycolytic system from glucose is metabolized to give not only lactic acid, but also ethanol, acetic acid, and carbon dioxide. Through such heterolactic fermentation, ethanol or acetic acid is synthesized from acetylphosphate that is generated by phosphoketolase.

Figure 3:
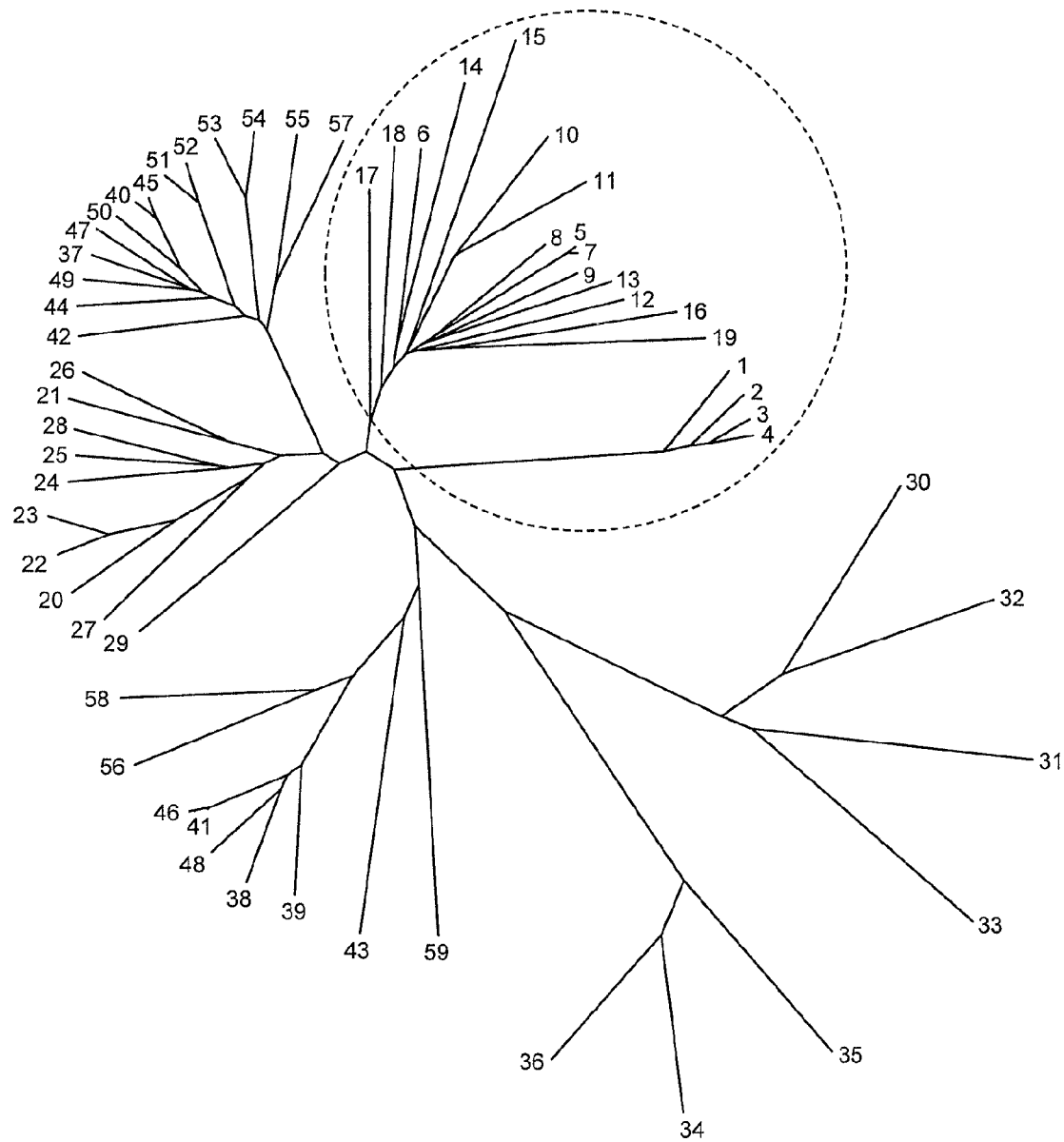
FIG. 3 is a characteristic diagram showing the result of conducting molecular phylogenetic tree analysis of phosphoketolase genes derived from various organisms.

More specifically, as phosphoketolase genes, as shown in FIG. 3, phosphoketolase genes derived from various microorganisms can be used. In addition, Table 1 below shows the relationship between numbers assigned in the molecular phylogenetic tree shown in FIG. 3 and microorganisms.

TABLE 1

| | |
|---|---|
| 1 | *Bifidobacterium_animalis* |
| 2 | *Bifidobacterium_longum* |
| 3 | *Bifidobacterium_adolescentis* |
| 4 | *Bifidobacterium_pullorum* |
| 5 | *Lactobacillus_plantarum_1* |
| 6 | *Lactobacillus_plantarum_2* |
| 7 | *Lactobacillus_pentosus* |

TABLE 1-continued

| | |
|---|---|
| 8 | Lactobacillus_sakei |
| 9 | Lactobacillus_salivarius |
| 10 | Lactobacillus_reuteri |
| 11 | Lactobacillus_johnsonii |
| 12 | Lactobacillus_casei |
| 13 | Bacillus_coagulans |
| 14 | Leuconostoc_mesenteroides_1 |
| 15 | Leuconostoc_mesenteroides_2 |
| 16 | Streptococcus_gordonii |
| 17 | Clostridium_acetobutylicum |
| 18 | Clostridium_butyricum |
| 19 | Mycoplasma_agalactiae |
| 20 | Cellulomonas_flavigena |
| 21 | Methylobacterium_populi |
| 22 | Mycobacterium_gilvum |
| 23 | Mycobacterium_vanbaalenii |
| 24 | Nitrosococcus_oceani |
| 25 | Synechococcus_sp. |
| 26 | Rhizobium_leguminosarum |
| 27 | Nocardioides_sp. |
| 28 | Anabaena_variabilis |
| 29 | Bacteroides_capillosus |
| 30 | Marinobacter_aquaeolei |
| 31 | Acidovorax_sp. |
| 32 | Pseudomonas_aeruginosa |
| 33 | Maricaulis_maris |
| 34 | Cyanothece_sp. |
| 35 | Mariprofundus_ferrooxydans |
| 36 | Nostoc_punctiforme |
| 37 | Aspergullus_oryzae_1 |
| 38 | Aspergullus_oryzae_2 |
| 39 | Aspergullus_nidulans |
| 40 | Aspergillus_fumigatus_1 |
| 41 | Aspergillus_fumigatus_2 |
| 42 | Cryptococcus_neoformans_1 |
| 43 | Cryptococcus_neoformans_2 |
| 44 | Penicillium_chrysogenum |
| 45 | Neosartorya_fischeri_1 |
| 46 | Neosartorya_fischeri_2 |
| 47 | Aspergillus_niger_1 |
| 48 | Aspergillus_niger_2 |
| 49 | Aspergillus_terreus |
| 50 | Aspergillus_clavatus |
| 51 | Sclerotinia_sclerotiorum |
| 52 | Botryotinia_fuckeliana |
| 53 | Phaeosphaeria_nodorum |
| 54 | Pyrenophora_tritici-repentis |
| 55 | Neurospora_crassa_1 |
| 56 | Neurospora_crassa_2 |
| 57 | Podospora_anserina |
| 58 | Magnaporthe_grisea |
| 59 | Ustilago_maydis |

As phosphoketolase genes, phosphoketolase genes classified within the broken-line frame of the molecular phylogenetic tree shown in FIG. 3 are preferably used. Phosphoketolase genes classified in the group are mainly derived from lactic acid bacteria or bifidobacteria having metabolic pathways for heterolactic fermentation. Further specifically, as phosphoketolase genes classified within the broken-line frame of the molecular phylogenetic tree shown in FIG. 3, genes derived from microorganisms belonging to the genus *Bifidobacterium* that are bifidobacteria, microorganisms belonging to the genus *Lactobacillus* that are lactic acid bacteria, or microorganisms belonging to the genus *Leuconostoc* are preferably used. Further specifically, as a phosphoketolase gene classified within the broken-line frame of the molecular phylogenetic tree shown in FIG. 3, a gene encoding phosphoketolase comprising the amino acid sequence shown in any one of SEQ ID NOS: 1 to 19 can be used. The amino acid sequence of SEQ ID NO: 1 is the amino acid sequence encoded by a *Bifidobacterium animalis*-derived phosphoketolase gene. The amino acid sequences shown in SEQ ID NOS: 2 to 19 are the amino acid sequences encoded by phosphoketolase genes derived from *Bifidobacterium longum, Bifidobacterium adolescentis, Bifidobacterium pullorum, Lactobacillus plantarum, Lactobacillus plantarum, Lactobacillus pentosus, Lactobacillus sakei, Lactobacillus salivarius, Lactobacillus reuteri, Lactobacillus johnsonii, Lactobacillus casei, Bacillus coagulans, Leuconostoc mesenteroides, Leuconostoc mesenteroides, Streptococcus gordonii, Clostridium acetobutylicum, Clostridium butyricum*, and *Mycoplasma agalactiae*, respectively.

Specifically, in the present invention, a phosphoketolase gene encoding the amino acid sequence of any one of SEQ ID NOS: 1 to 19 is preferably used. In particular, as phosphoketolase genes, *Bifidobacterium animalis* (SEQ ID NO: 1), *Bifidobacterium longum* (SEQ ID NO: 2), *Bifidobacterium adolescentis* (SEQ ID NO: 3), and *Bifidobacterium pullorum* (SEQ ID NO: 4) are most preferably used.

Furthermore, a phosphoketolase gene may consist of a polynucleotide encoding a protein that consists of an amino acid sequence having a deletion, a substitution, an addition, or an insertion of 1 or several amino acids with respect to the amino acid sequence of any one of SEQ ID NOS: 1 to 19 and has phosphoketolase activity. Here, the term "several amino acids" refers to, for example, 2 to 100, preferably 2 to 80, more preferably 2 to 55, and further preferably 2 to 15 amino acids.

Furthermore, a phosphoketolase gene may consist of a polynucleotide encoding a protein that consists of an amino acid sequence having 80% or more, preferably 85% or more, more preferably 90% or more, and further preferably 98% or more sequence similarity with respect to the amino acid sequence of any one of SEQ ID NOS: 1 to 19, and has phosphoketolase activity. Here, the term "sequence similarity" refers to a value that is calculated to represent similarity between two amino acid sequences when sequence similarity search software such as BLAST, PSI-BLAST, or HMMER is used with default settings.

Here, the term "phosphoketolase activity" refers to activity to convert xylulose-5-phosphate to acetylphosphate. Therefore, whether or not a predetermined protein has phosphoketolase activity can be determined based on the amount of acetylphosphate synthesized, using a reaction solution containing xylulose-5-phosphate as a substrate (e.g., JOURNAL OF BACTERIOLOGY, Vol. 183, No. 9, May 2001, p. 2929-2936).

The recombinant yeast according to the present invention can increase the amount of acetylphosphate synthesized because of the presence of a phosphoketolase gene introduced, by enhancing the expression of an enzyme gene involved in the pentose phosphate system shown in FIG. 2. As a result, it can increase the amount of synthesized acetic acid. Examples of genes to be subjected to enhancement of expression in the pentose phosphate system shown in FIG. 2 include, but are not particularly limited to, a glucose-6-phosphate dehydrogenase gene and a ribulose-5-phosphate-3-epimerase gene. Moreover, the expression of either one of or both of these genes may be enhanced.

Furthermore, an endogenous glucose-6-phosphate dehydrogenase gene of *Saccharomyces cerevisiae* is known as a ZWF1 gene. Also, an endogenous ribulose-5-phosphate-3-epimerase gene of *Saccharomyces cerevisiae* is known as an RPE1 gene. Endogenous glucose-6-phosphate dehydrogenase genes or ribulose-5-phosphate-3-epimerase genes are known for yeast other than *Saccharomyces cerevisiae* and can be specified referring to the existing databases such as Genbank, DDBJ, and EMBL.

Here, the expression "gene expression is enhanced" refers to significant improvement in activity of an enzyme to be encoded by a subject gene, and is meant to include a significant increase in the expression level of such a gene. An example of a technique for enhancing gene expression is a technique for significantly increasing the expression level of the relevant gene. Examples of a technique for increasing the expression level of a specific gene include, but are not particularly limited to, a technique that involves modifying the expression control region of an endogenous gene of a chromosome and a technique that involves introducing a vector having the relevant gene located downstream of a promoter with high activity.

Figure 4:
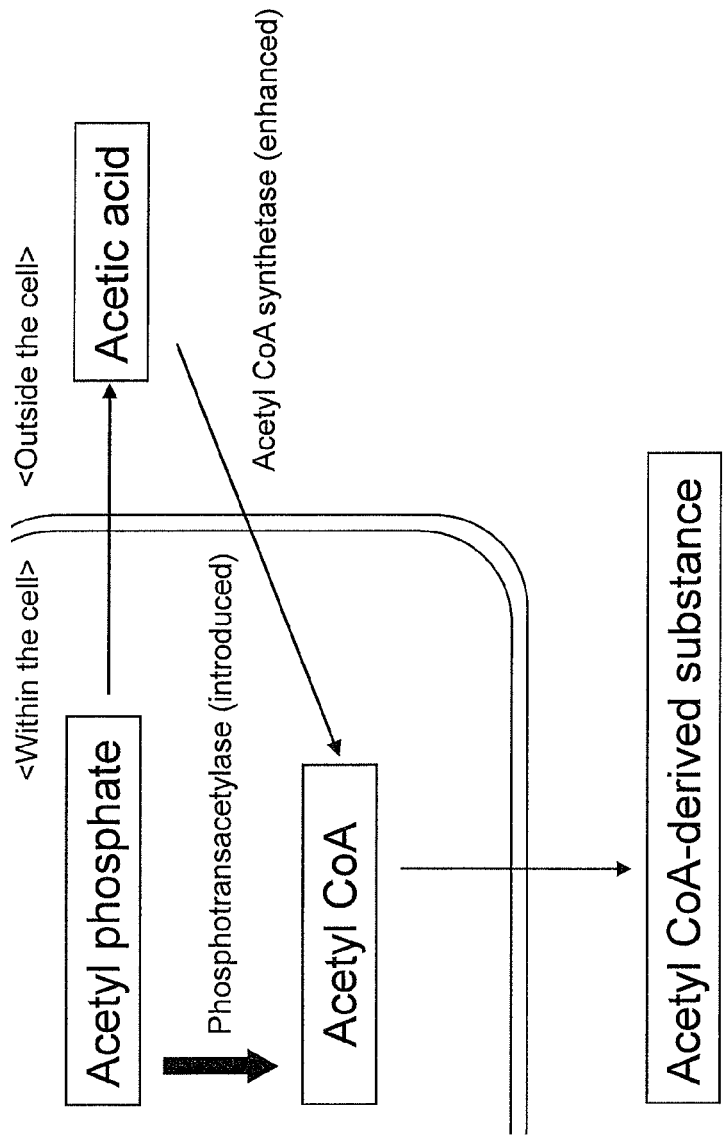
FIG. 4 is a characteristic diagram showing a pathway for synthesis of acetyl-CoA from acetylphosphate and acetic acid and a pathway for synthesis of another substance from acetyl-CoA.

Meanwhile, the recombinant yeast according to the present invention can increase the amount of acetyl-CoA synthesized by further introducing a phosphotransacetylase gene (PTA gene) or further enhancing an acetyl-CoA synthetase gene (ACS gene) as shown in FIG. 4, in addition to attenuation of a phosphofructokinase gene and introduction of a phosphoketolase gene.

A phosphotransacetylase gene is not yeast's original gene and thus is introduced as a foreign gene. Examples of such a phosphotransacetylase gene are not particularly limited, and genes referred to as PTA genes in various bacteria are broadly applicable.

Figure 5:
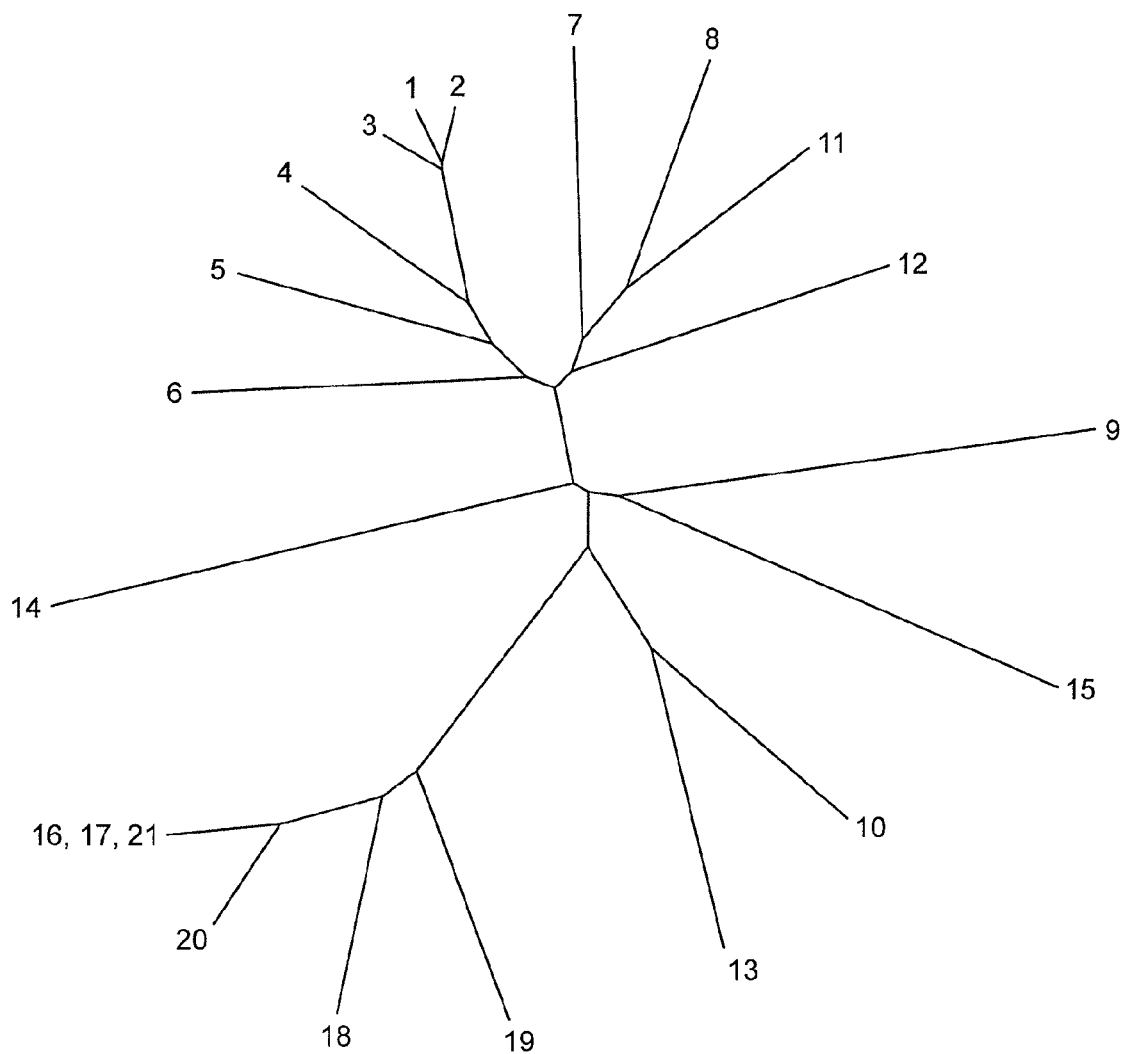
FIG. 5 is a characteristic diagram showing the result of conducting molecular phylogenetic tree analysis of phosphotransacetylase genes derived from various organisms.

More specifically, as phosphotransacetylase genes, as shown in FIG. 5, phosphotransacetylase genes derived from various microorganisms can be used. In addition, Table 2 below shows the relationship between numbers assigned in the molecular phylogenetic tree in FIG. 5 and microorganisms.

TABLE 2

| | |
|---|---|
| 1 | Bacillus_subtilis |
| 2 | Bacillus_amyloliquefaciens |
| 3 | Bacillus_licheniformis |
| 4 | Geobacillus_thermodenitrificans |
| 5 | Listeria_innocua |
| 6 | Staphylococcus_aureus |
| 7 | Lactococcus_lactis |
| 8 | Carnobacterium_sp. |
| 9 | Mycobacterium_vanbaalenii |
| 10 | Clostridium_perfringens |
| 11 | Enterococcus_faecalis |
| 12 | Leuconostoc_mesenteroides |
| 13 | Clostridium_acetobutylicum |
| 14 | Bifidobacterium_animalis_lactis |
| 15 | Corynebacterium_glutamicum |
| 16 | Escherichia_coli_K-12 |
| 17 | Escherichia_coli_53638 |
| 18 | Vibrio_vulnificus |
| 19 | Haemophilus somnus |
| 20 | Yersinia_pestis |
| 21 | Shigella_sonnei |

The origins of the following PTA genes are shown in FIG. 5 and Table 2. The amino acid sequence of a protein encoded by the Bacillus subtilis-derived PTA gene is shown in SEQ ID NO: 20, the amino acid sequence of a protein encoded by the Bacillus amyloliquefaciens-derived PTA gene is shown in SEQ ID NO: 21, the amino acid sequence of a protein encoded by the Bacillus licheniformis-derived PTA gene is shown in SEQ ID NO: 22, the amino acid sequence of a protein encoded by the Geobacillus thermodenitrificans-derived PTA gene is shown in SEQ ID NO: 23, the amino acid sequence of a protein encoded by the Listeria innocua-derived PTA gene is shown in SEQ ID NO: 24, the amino acid sequence of a protein encoded by the Staphylococcus aureus-derived PTA gene is shown in SEQ ID NO: 25, the amino acid sequence of a protein encoded by the Lactococcus lactis-derived PTA gene is shown in SEQ ID NO: 26, the amino acid sequence of a protein encoded by the Carnobacterium sp.-derived PTA gene is shown in SEQ ID NO: 27, the amino acid sequence of a protein encoded by the Mycobacterium vanbaalenii-derived PTA gene is shown in SEQ ID NO: 28, the amino acid sequence of a protein encoded by the Clostridium perfringens-derived PTA gene is shown in SEQ ID NO: 29, the amino acid sequence of a protein encoded by the Enterococcus faecalis-derived PTA gene is shown in SEQ ID NO: 30, the amino acid sequence of a protein encoded by the Leuconostoc mesenteroides-derived PTA gene is shown in SEQ ID NO: 31, the amino acid sequence of a protein encoded by the Clostridium acetobutylicum-derived PTA gene is shown in SEQ ID NO: 32, the amino acid sequence of a protein encoded by the Bifidobacterium animalis_lactis-derived PTA gene is shown in SEQ ID NO: 33, the amino acid sequence of a protein encoded by the Corynebacterium glutamicum-derived PTA gene is shown in SEQ ID NO: 34, the amino acid sequence of a protein encoded by the Escherichia coli K-12-derived PTA gene is shown in SEQ ID NO: 35, the amino acid sequence of a protein encoded by the Escherichia coli 53638-derived PTA gene is shown in SEQ ID NO: 36, the amino acid sequence of a protein encoded by the Vibrio vulnificus-derived PTA gene is shown in SEQ ID NO: 37, the amino acid sequence of a protein encoded by the Haemophilus somnus-derived PTA gene is shown in SEQ ID NO: 38, the amino acid sequence of a protein encoded by the Yersinia pestis-derived PTA gene is shown in SEQ ID NO: 39, and the amino acid sequence of a protein encoded by the Shigella sonnei-derived PTA gene is shown in SEQ ID NO: 40.

In addition, the phosphotransacetylase gene may consist of a polynucleotide encoding a protein that consists of an amino acid sequence having a deletion, a substitution, an addition, or an insertion of 1 or several amino acids with respect to the amino acid sequence of any one of SEQ ID NOS: 20 to 40, and has phosphotransacetylase activity. Here, the term "several amino acids" refers to, for example, 2 to 35, preferably 2 to 25, more preferably 2 to 15, and further preferably 2 to 10 amino acids.

Furthermore, the phosphotransacetylase gene may consist of a polynucleotide encoding a protein that consists of an amino acid sequence having 80% or more, preferably 85% or more, more preferably 90% or more, and further preferably 98% or more sequence similarity with respect to the amino acid sequence of any one of SEQ ID NOS: 20 to 40, and has phosphotransacetylase activity. Here, the term "sequence similarity" refers to a value that is calculated to represent similarity between two amino acid sequences when sequence similarity search software such as BLAST, PSI-BLAST, or HMMER is used with default settings.

Here, the term "phosphotransacetylase activity" refers to activity to transfer CoA to acetylphosphate. Therefore, whether or not a predetermined protein has phosphotransacetylase activity can be determined based on the amount of acetyl-CoA synthesized using a reaction solution containing acetylphosphate and CoA.

Furthermore, the acetyl-CoA synthetase gene shown in FIG. 4 is yeast's original gene. Hence, for enhancement of such an acetyl-CoA synthetase gene, a technique that involves modifying the expression control region of the relevant endogenous gene of a chromosome and a technique that involves introducing a vector having the relevant gene located downstream of a promoter having high activity are applicable. In addition, as endogenous acetyl-CoA synthetase genes of Saccharomyces cerevisiae, an ACS1 gene and an ACS2 gene are known. Endogenous acetyl-CoA synthetase genes of yeast other than Saccharomyces cerevisiae are also known and can be specified referring to existing databases such as Genbank, DDBJ, and EMBL.

As described above, in the recombinant yeast according to the present invention, the amount of acetylphosphate synthesized; that is, the amount of acetic acid synthesized is significantly increased (FIG. 2) or the amount of acetyl-CoA synthesized is significantly increased (FIG. 4). Therefore, the recombinant yeast according to the present invention can be used when acetic acid or acetyl-CoA is a substance to be produced. Alternatively, the recombinant microorganism according to the present invention can be used as a host for further modification to enable production of another substance (in FIG. 4, denoted as a substance made from acetyl-CoA) using acetyl-CoA as a substrate.

Specifically, examples of such a substance made from acetyl-CoA that can be synthesized include, but are not particularly limited to, butanol, alkane, propanol, fatty acid, fatty acid ester, acetone, acetoacetic acid, ethyl acetate, polyketide, amino acid, and terpenoid. When these are substances to be produced, the productivity thereof can be significantly improved using the recombinant yeast according to the present invention.

When isopropanol is a substance to be produced, for example, with reference to APPLIED AND ENVIRONMENTAL MICROBIOLOGY, December 2007, p. 7814-7818, Vol. 73, No. 24, a gene to be further introduced into the recombinant microorganism according to the present invention can be specified. Furthermore, when polyketide is a substance to be produced, with reference to Proc. Natl. Acad. Sci. U.S.A., Vol. 95, pp. 505-509, January 1998, a gene to be further introduced into the recombinant microorganism according to the present invention can be specified. Moreover, when fatty acid is a substance to be produced, for example, with reference to Eur. J. Biochem. 112, p. 431-442 (1980) or MICROBIOLOGY AND MOLECULAR BIOLOGY REVIEWS, September 2004, p. 501-517, a gene (e.g., a FAS gene) to be further introduced to or enhanced in the recombinant microorganism according to the present invention can be specified. Furthermore, when alkane is a substance to be produced, a gene that is involved in aldehyde synthesis from fatty acid and further alkane synthesis from aldehyde and should be further introduced into the recombinant microorganism according to the present invention can be specified with reference to Science vol. 329 30 July pp. 559-562, for example.

Furthermore, the expression of an endogenous alcohol acetyltransferase gene (ATF1 gene) of yeast is further enhanced, so that the amount of ethyl acetate synthesized from acetyl-CoA can be increased. Specifically, when ethyl acetate is a substance to be produced, the expression of such an endogenous ATF1 gene is preferably enhanced.

Also, as described above, when the expression of a predetermined gene is enhanced, an appropriate promoter with high transcriptional activity is used. Examples of such a promoter that can be used herein include, but are not particularly limited to, a glyceraldehyde-3-phosphate dehydrogenase gene (TDH3) promoter, a 3-phosphoglyceratekinase gene (PGK1) promoter, and a high osmotic pressure-responsive 7 gene (HOR7) promoter. Of these, a pyruvate decarboxylase gene (PDC1) promoter is preferred because of its high capacity to cause high-level expression of a gene of interest located downstream thereof. Furthermore, through the use of a gall promoter, a gal10 promoter, a heat shock protein promoter, a MFα1 promoter, a PHO5 promoter, a GAP promoter, an ADH promoter, an AOX1 promoter, or the like, a gene downstream thereof can be strongly expressed.

Also, as a method for introducing the above gene, any conventionally known technique that is known as a method for yeast transformation is applicable. Specifically, for example, gene introduction can be performed by a method described in an electroporation method "Meth. Enzym., 194, p 182 (1990)," a spheroplast method "Proc. Natl. Acad. Sci. U.S.A., 75 p 1929 (1978)," a lithium acetate method "J. Bacteriology, 153, p 163 (1983)," Proc. Natl. Acad. Sci. U.S.A., 75 p 1929 (1978), Methods in yeast genetics, 2000 Edition: A Cold Spring Harbor Laboratory Course Manual, or the like. Examples thereof are not limited to these methods.

When a substance is produced using the above-explained recombinant yeast, the yeast is cultured in a medium containing an appropriate carbon source. More specifically, recombinant yeast pre-cultured according to a conventional method is cultured in a medium so as to cause it to produce a substance of interest. For example, when butanol, alkane, propanol, fatty acid, fatty acid ester, acetone, acetoacetic acid, acetic ester, polyketide, amino acid, and terpenoid are produced as substances of interest, these substances of interest are synthesized in a medium. Hence, after cells are separated from the medium by a means such as centrifugation, such substances can be isolated from the supernatant fraction. To isolate such substances from a supernatant fraction, for example, an organic solvent such as ethyl acetate or methanol is added to the supernatant fraction, and then the resultant is sufficiently stirred. An aqueous layer is separated from a solvent later, and then the substances can be extracted from the solvent layer.

EXAMPLES

The present invention is hereafter described in greater detail with reference to the following examples, although the technical scope of the present invention is not limited thereto.

In these examples, recombinant yeast was prepared by attenuating the endogenous phosphofructokinase gene of wild-type yeast or isopropanol-producing yeast and introducing a phosphoketolase gene into the yeast. Recombinant yeast was further prepared by introducing or enhancing other genes in addition to the aforementioned gene attenuation and gene introduction. These strains were then examined for acetic acid productivity, ethyl acetate productivity, and isopropanol productivity.

[Materials and Methods]
Hosts
ECOS Competent *E. coli* JM109 (Nippon Gene Co., Ltd.), *S. cerevisiae* YPH499 (Stratagene) as wild-type yeast, and a #15-10 strain (disclosed in the reference example described later) as isopropanol-producing yeast were used.
Plasmid
<Preparation of pESCpgkgap-HIS>
PCR was performed under the following conditions.
(Primers)

```
EcoRI-Pgap-F:
                                    (SEQ ID NO: 41)
5'-CACGGAATTCCAGTTCGAGTTTATCATTATCAA-3'

BamHI-Pgap-R:
                                    (SEQ ID NO: 42)
5'-CTCTGGATCCTTTGTTTGTTTATGTGTGTTTATTC-3'
```

(PCR Conditions)
Template: 1 ng of pDI626 plasmid (see JP Patent Publication (Kokai) No. 2005-52046 A)
Primer: 50 pmol primer DNA
Reaction solution: 50 µl of the solution containing 1× Pfu Ultra II reaction buffer (Stratagene), 10 nmol dNTP, and 1 µl of Pfu Ultra II fusion HS DNA polymerase (Stratagene)
Reaction: 95 degrees C. (2 minutes)-(95 degrees C. (30 seconds), 55 degrees C. (30 seconds), 72 degrees C. (2 minutes))×25 cycles-72 degrees C. (3 minutes)-4 degrees C. (stock)

After PCR under the above conditions, a PCR product contained in the reaction solution was purified using a MinElute PCR purification kit (QIAGEN). Subsequently, the PCR product was digested with restriction enzymes Bam HI and EcoR I. Agarose gel electrophoresis was performed, a 686-bp fragment was excised, and the fragment was thus purified using a MiniElute Gel extraction kit (QIAGEN). Furthermore, the resultant was ligated to a pESC-HIS vector digested with restriction enzymes Bam HI and EcoR I. The thus obtained plasmid was designated as pESCgap-HIS.

Next, PCR was performed under the following conditions.
(Primers)

```
MunI-Ppgk1-F:
                                      (SEQ ID NO: 43)
5'-TAGGCAATTGCAAGAATTACTCGTGAGTAAGG-3'

EcoRI-Ppgk1-R:
                                      (SEQ ID NO: 44)
5'-ATAAGAATTCTGTTTTATATTTGTTGTAAAAAGTAG-3'
```

(PCR Conditions)
Template: pDI626PGK plasmid 1 ng
Primer: 50 pmol primer DNA
Reaction solution: 50 µl of the solution containing 1× Pfu Ultra II reaction buffer (Stratagene), 10 nmol dNTP, and 1 µl Pfu Ultra II fusion HS DNA polymerase (Stratagene)
Reaction: 95 degrees C. (2 minutes)-(95 degrees C. (30 seconds), 55 degrees C. (30 seconds), 72 degrees C. (2 minutes))×25 cycles-72 degrees C. (3 minutes)-4 degrees C. (stock)

After PCR under the above conditions, a PCR product contained in the reaction solution was purified using a MinElute PCR purification kit (QIAGEN). Subsequently, the PCR product was digested with restriction enzymes Mun I and EcoR I. Agarose gel electrophoresis was performed, a 718-bp fragment was excised, and the fragment was thus purified using a MiniElute Gel extraction kit (QIAGEN). Furthermore, the resultant was ligated to a pESCgap-HIS vector digested with a restriction enzyme EcoR I and then subjected to BAP treatment. The thus obtained plasmid was designated as pESCpgkgap-HIS.

<Construction of pESCpgkgap-LEU>

After digestion of the above pESCpgkgap-HIS with restriction enzymes Bam HI and Not I, a 1427-bp fragment was excised and ligated to a pESC-LEU vector (Stratagene) digested with restriction enzymes Bam HI and Not I in a similar manner.

<Construction of pESCpgkgap-TRP>

After digestion of the above pESCpgkgap-HIS with restriction enzymes Bam HI and Not I, a 1427-bp fragment was excised and then ligated to a pESC-TRP vector (Stratagene) digested with restriction enzymes Bam HI and Not I in a similar manner.

<Construction of pESCpgkgap-URA>

After digestion of the above pESCpgkgap-HIS with restriction enzymes Bam HI and Not I, a 1427-bp fragment was excised and then ligated to a pESC-URA vector (Stratagene) digested with restriction enzymes Bam HI and Not I in a similar manner.

<Construction of Other Vectors>

Upon construction of a pESC-HIS-ZWF1-RPE1 vector for enhancing the expression of a ZWF1 gene and a RPE1 gene, a pESC-Leu-PKT vector for introducing a PKT gene, a pESC-Leu-PKT-PTA vector for introducing the PKT gene and a PTA gene, a pESC-Trp-ATF1 vector for enhancing the expression of an ATF1 gene, and a vector for disrupting a PFK1 gene and a PFK2 gene, PCR was performed with the following composition under the following conditions. In addition, KOD-Plus-Ver.2 (TOYOBO) was used as DNA polymerase.

TABLE 3

<Composition>

| | |
|---|---|
| 10 × Buffer | 5 ul |
| 2.5 mM dNTP | 5 ul |
| 25 mM MgSO$_4$ | 4 ul |
| fwd primer | 1.5 ul |
| rev primer | 1.5 ul |
| Genome (100 ng/ul) | 1 ul |
| DNA polymerase | 1 ul |
| H$_2$O | 31 ul |

TABLE 4

<PCR conditions>

Figure 6:
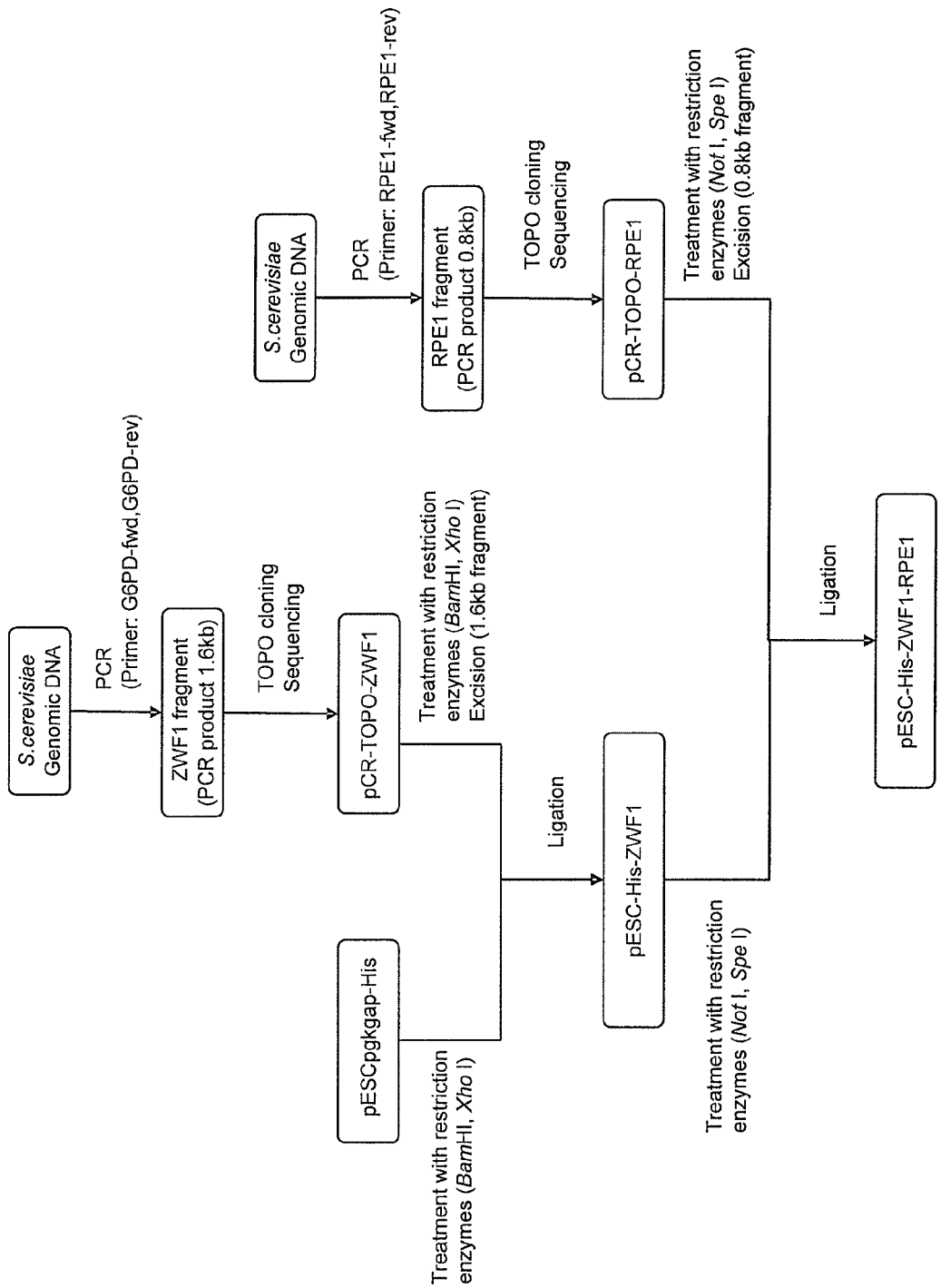
FIG. 6 is a flow chart for construction of a pESC-HIS-ZWF1-RPE1 vector.
Figure 7:
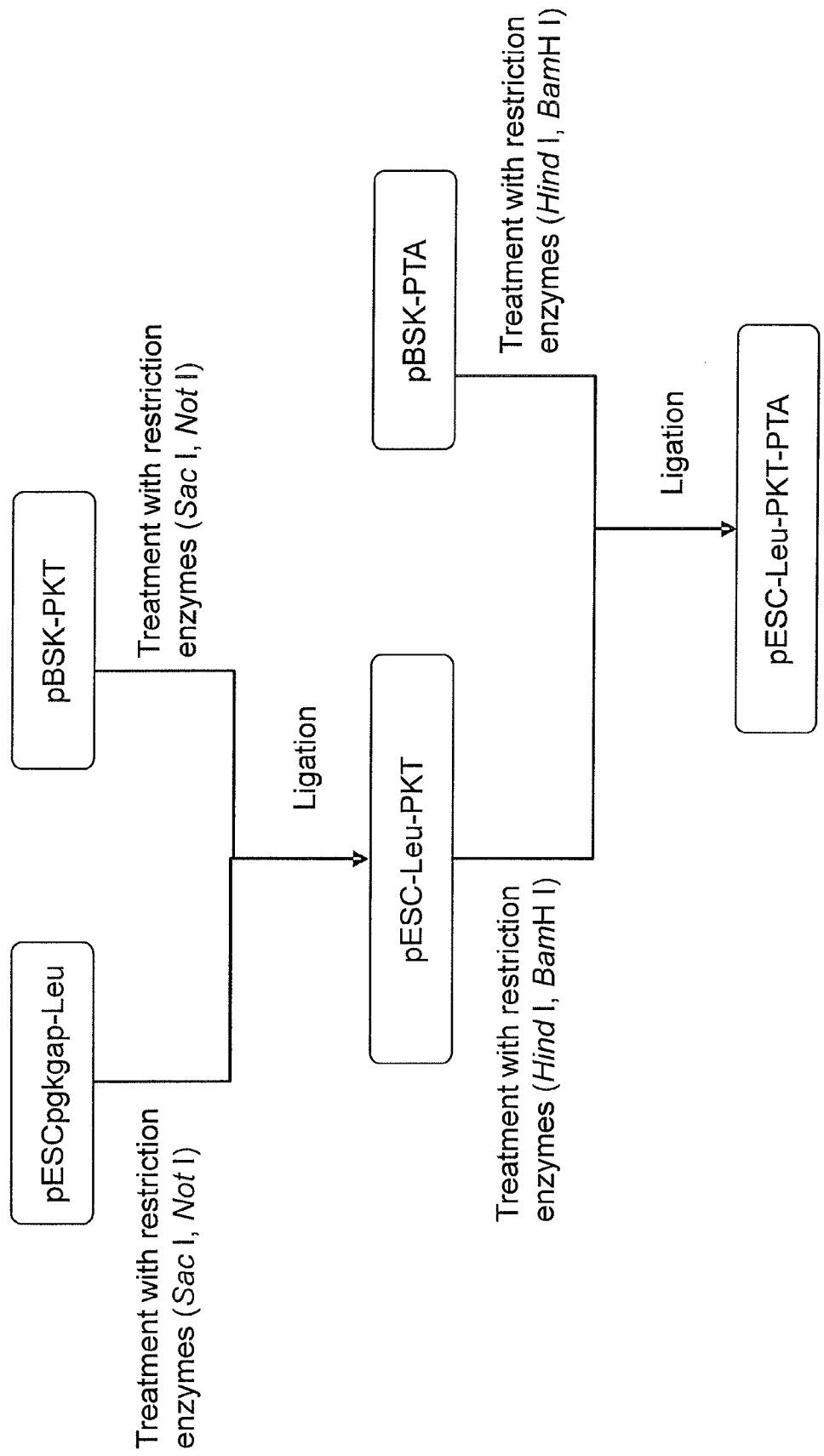
FIG. 7 is a flow chart for construction of a pESC-Leu-PKT vector and a pESC-Leu-PKT-PTA vector.
Figure 8:
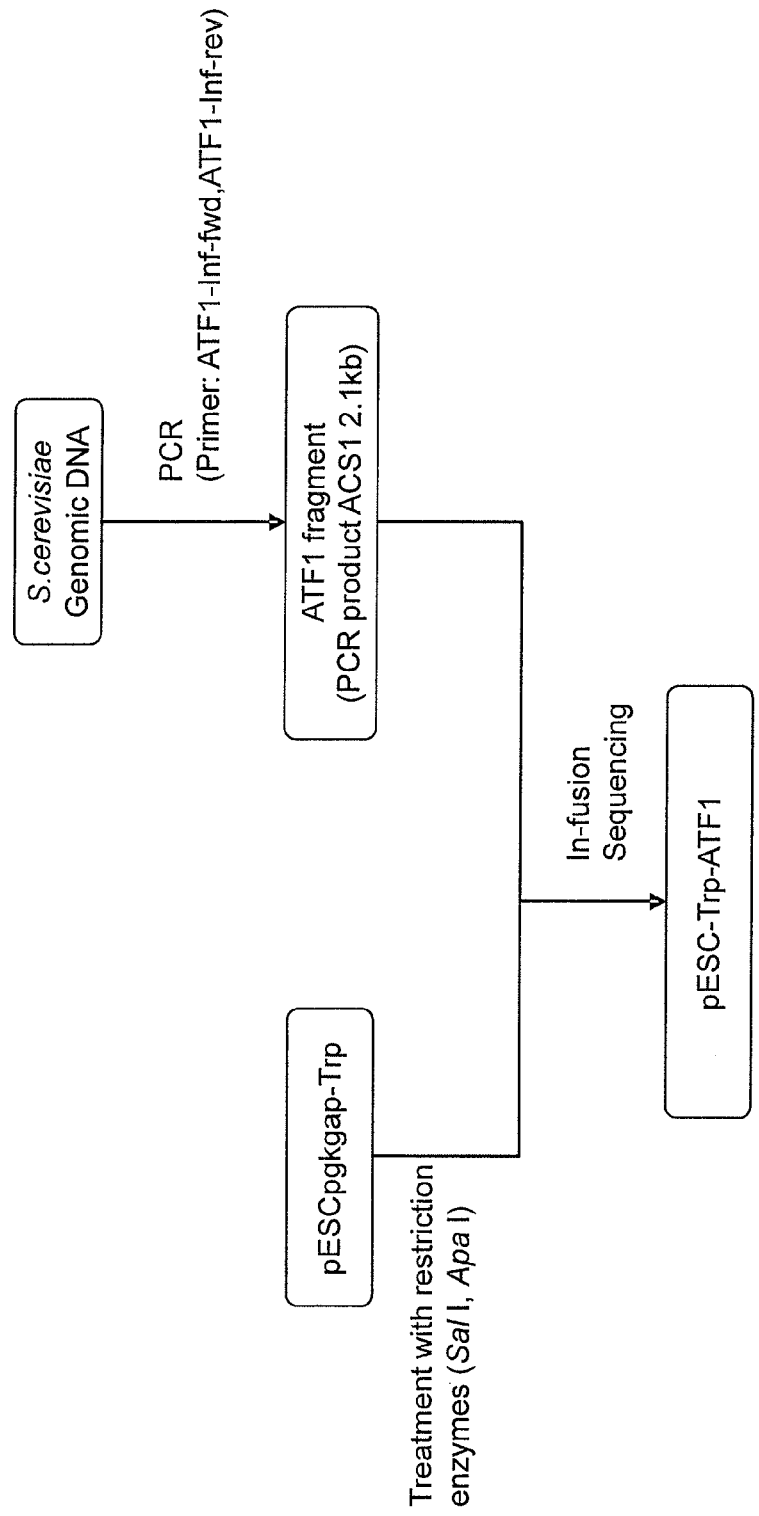
FIG. 8 is a flow chart for construction of a pESC-Trp-ATF1 vector.
Figure 9:
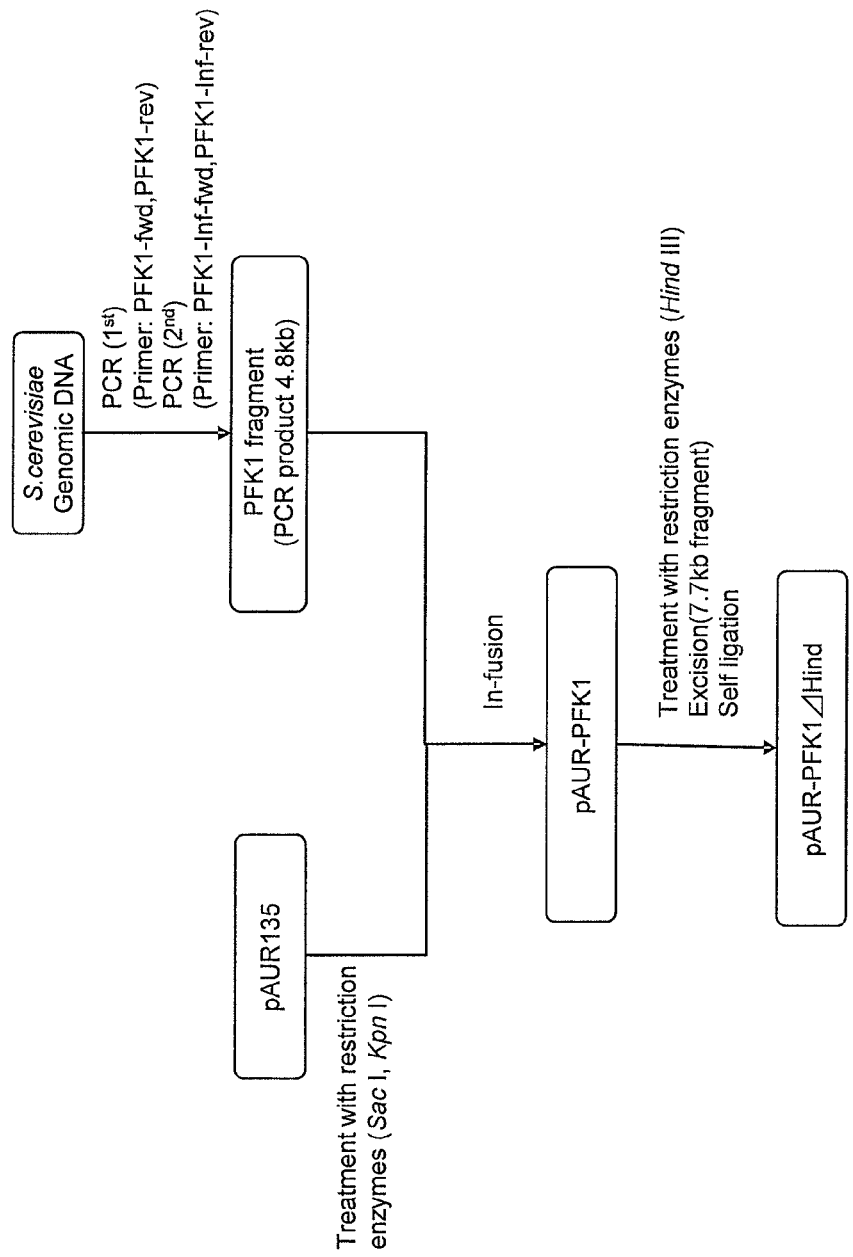
FIG. 9 is a flow chart for construction of a vector for disruption of a PFK1 gene.
Figure 10:
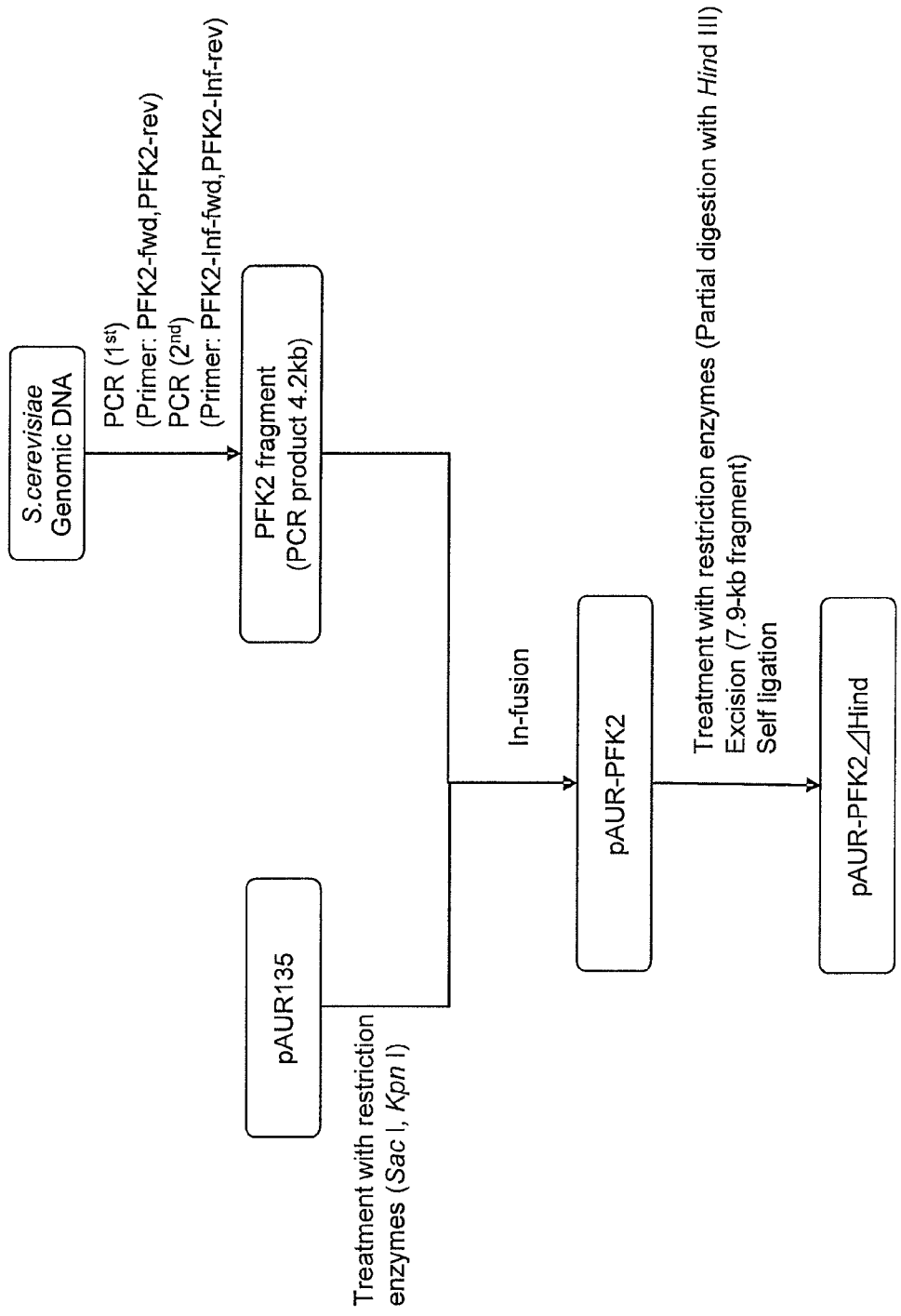
FIG. 10 is a flow chart for construction of a vector for disruption of a PFK2 gene.

94 degrees C., 2 min
->98 degrees C. 10 sec, Tm-5 degrees C. 30 sec, 68 degrees C. 5 min (×30)
->68 degrees C. 5 min FIG. 6 shows a flow chart for construction of the pESC-HIS-ZWF1-RPE1 vector. FIG. 7 shows a flow chart for construction of the pESC-Leu-PKT vector and the pESC-Leu-PKT-PTA vector. FIG. 8 shows a flow chart for construction of the pESC-Trp-ATF1 vector. FIG. 9 shows a flow chart for construction of the vector for disrupting the PFK1 gene. FIG. 10 shows a flow chart for construction of the vector for disrupting the PFK2 gene. Primers used in the flow charts for vector construction shown in FIGS. 6-10 are listed in Table 5.

TABLE 5

| Gene name | Primer | Nucleotide sequence | |
|---|---|---|---|
| ZWF1 | G6PD-fwd | cgcggatccgcggggcccATAAGGCAAGATGAGTGAAGGCCCC | SEQ ID NO: 45 |
| | G6PD-rev | ccgctcgagcgggtcgacGTGCTTGCATTTTTCTAATTATCCT | SEQ ID NO: 46 |
| RPE1 | RPE1-fwd | ggaattccgcggccgcAGGTAAACACACAAGAAAAAATGG | SEQ ID NO: 47 |
| | RPE1-rev | ccttaattaagggactagtcTAAGAAATGCCGCATATGTAC | SEQ ID NO: 48 |
| PFK1 | PFK1-fwd | tcccccggggacgagctcgCTCAGTTTCTTCTTGAAATTTAGCATCGTG | SEQ ID NO: 49 |
| | PFK1-rev | tcccccggggacgagctcgAAACGGAAAGAAAAAAGGCCGAC | SEQ ID NO: 50 |
| | PFK1-Inf-fwd | CTAGAGGATCCCCGGGTACCCTCAGTTTCTTCTTGAAATTTAGCATCGTG | SEQ ID NO: 51 |
| | PFK1-Inf-rvs | CGGCCAGTGAATTCGAGCTCAAACGGAAAGAAAAAAGGCCGAC | SEQ ID NO: 52 |
| PFK2 | PFK2-fwd | tcccccggggacgagctcgTCCGGTCTTTATCTACCATTCATTTATTAC | SEQ ID NO: 53 |
| | PFK2-rev | tcccccggggacgagctcgGGTTTCATGGGGTAGTACTTGTATTA | SEQ ID NO: 54 |
| | PFK2-Inf-fwd | CTAGAGGATCCCCGGGTACCTCCGGTCTTTATCTACCATTCATTTATTAC | SEQ ID NO: 55 |
| | PFK2-Inf-rvs | CGGCCAGTGAATTCGAGCTCGGTTTCATGGGGTAGTACTTGTATTA | SEQ ID NO: 56 |

TABLE 5-continued

| Gene name | Primer | Nucleotide sequence | | |
|---|---|---|---|---|
| ATF1 | ATF1-Inf-fwd | tacgactcactatagggcccTTTGGCCTGGTATTGTCATC | SEQ ID NO: | 57 |
| | ATF1-Inf-rev | tctgttccatgtcgacCGACGATTCTGACCCTTTC | SEQ ID NO: | 58 |
| ACS1 | ACS1-Inf-fwd | GGGCCCGGGCGTCGACAGCAAAACCAAACATATCAA | SEQ ID NO: | 59 |
| | ACS1-Inf-rev | ACCAAGCTTACTCGAGCACACGAAAAAAAAAAGTCG | SEQ ID NO: | 60 |
| ACS2 | ACS2-Inf-fwd | GGGCCCGGGCGTCGACTGTTATACACAAACAGAATA | SEQ ID NO: | 61 |
| | ACS2-Inf-rev | ACCAAGCTTACTCGAGAGAAAAGGAGCGAAATTTTATC | SEQ ID NO: | 62 |

In addition, PCR products were purified using a QIAquick PCR Purification Kit (QIAGEN). Furthermore, in the flow charts for vector construction as shown in FIGS. 6 to 10, a Zero Blunt TOPO PCR cloning kit (Invitrogen) was used for TOPO cloning of PCR products. Also, pAUR135 was purchased from Takara Bio Inc. In the flow charts for vector construction as shown in FIGS. 6 to 10, DNA fragments were excised from agarose gel using a QIAquick Gel Extraction Kit (QIAGEN). In the flow charts for vector construction as shown in FIGS. 6 to 10, vectors were ligated to DNA fragments by ligation reaction using a Ligation-convenience Kit (Nippon Gene Co., Ltd.) or in-fusion reaction using an In-Fusion Dry-Down PCR Cloning Kit (Clontech).

Furthermore, in the flow chart for vector construction as shown in FIG. 7, vectors denoted as pBSK-PKT and pBSK-PTA were constructed by synthesizing 5 types of PKT gene and 3 types of PTA gene, respectively, and then inserting them to the Sma I site of pBluescript IISK(+). In addition, these 5 types of PKT gene and 3 types of PTA gene were all optimized for codons for *Saccharomyces cerevisiae*.

The 5 types of PKT gene were *Bifidobacterium animalis* subsp. *lactis*-derived phosphoketolase genes (SEQ ID NOS: 63 and 64), *Aspergillus oryzae* RIB40-derived phosphoketolase I genes (SEQ ID NOS: 65 and 66), *Aspergillus oryzae* RIB40-derived phosphoketolase II genes (SEQ ID NOS: 67 and 68), *Nostoc punctiforme* ATCC 29133-derived phosphoketolase genes (SEQ ID NOS: 69 and 70), and *Marinobacter aquaeolei* ATCC 700491-derived phosphoketolase genes (SEQ ID NOS: 71 and 72). Furthermore, the 3 types of PTA gene were *Bacillus subtilis* subsp. *subtilis* str.168-derived phosphate acetyltransferase genes (SEQ ID NOS: 73 and 74), *Bifidobacterium animalis* subsp. *lactis* AD011-derived phosphate acetyltransferase genes (SEQ ID NOS: 75 and 76), and *Escherichia coli* K-12 MG1655-derived phosphate acetyltransferase genes (SEQ ID NOS: 77 and 78).

Transformation

*Escherichia coli* was transformed according to the protocols included with ECOS Competent *E. coli* JM109 (Nippon Gene Co., Ltd.). Yeast was transformed according to the protocols included with a Frozen-EZ Yeast Transformation II Kit (Zymo Research). Yeast gene disruption using the vector for disrupting the PFK1 gene and the PFK2 gene was performed according to the protocols included with pAUR135DNA (Takara Bio Inc.).

Acetic Acid Production Test

A transformant was cultured as follows. After active colony formation in an SD-His, Leu agar medium, cells were inoculated to 2 ml of an SD-His, Leu medium in a 15-ml test tube and then cultured overnight at 30 degrees C. (Oriental Giken Inc. IFM, 130 rpm). The thus pre-cultured solution was inoculated to 100 ml of an SD-His, Leu medium in a 500-ml Erlenmeyer flask so that it accounted for 1% of the volume of the medium, and then cultured. The culture solution was centrifuged (6000×g, 15 min, room temperature) and then 1 ml of the supernatant was introduced into a glass vial and thus designated as an analysis sample.

Ethyl Acetate Production Test

A transformant was cultured as follows. After active colony formation in an SD-His, Leu, Trp agar medium, cells were inoculated to 2 ml of an SD-His, Leu, Trp medium in a 15-ml test tube and then cultured overnight at 30 degrees C. (130 rpm). The thus pre-cultured solution was inoculated to 100 ml of an SD-His, Leu, Trp medium in a 500-ml Erlenmeyer flask so that it accounted for 1% thereof, and then cultured. The culture solution was centrifuged (6000×g, 15 min, room temperature) and then 1 ml of the supernatant was introduced into a glass vial so that it was designated as an analysis sample.

Isopropanol Production Test

A transformant was cultured as follows. After active colony formation in an SD-His, Leu, Ura, Trp agar medium, cells were inoculated to 2 ml of an SD-His, Leu, Ura, Trp medium in a 15-ml test tube and then cultured overnight at 30 degrees C. (130 rpm). The thus pre-cultured solution was inoculated to 50 ml of an SD-His, Leu, Ura, Trp medium in a 500-ml Erlenmeyer flask so that it accounted for 1% thereof, and then cultured. The culture solution was centrifuged (6000×g, 15 min, room temperature) and then 1 ml of the supernatant was introduced into a glass vial so that it was designated as an analysis sample.

GC Analysis Conditions

Preparations used herein were acetic acid (NACALAI TESQUE, INC.), ethyl acetate (NACALAI TESQUE, INC.), and isopropanol (NACALAI TESQUE, INC.). The following analytical instrument and analysis conditions were employed for the acetic acid production test, the ethyl acetate production test and the isopropanol production test.

TABLE 6

| <Head space sampler analysis conditions> | |
|---|---|
| Head space | |
| sampler | HP7694(Hewlett-Packard) |
| Zone Temp | |
| Oven | 80° C. |
| Loop | 150° C. |
| TR. LINE | 200° C. |
| Event Time | |
| GC CYCLE TIME | 10 min |
| Vial EQ TIME | 15 min |
| PRESSURIZ. TIME | 0.50 min |
| Loop Fill TIME | 0.2 min |
| Loop EQ TIME | 0.2 min |
| INJECT TIME | 1.00 min |
| Vial Prameter | |
| SHAKE | HIGH |
| Others | |
| Vial pressurization | 15 psi |
| Loop size | 3 ml |

TABLE 6-continued

<GC-MS analysis conditions>

| | |
|---|---|
| GC/MS | HP6890/5973 GC/MS system (Hewlett-Packard, Wilmington, DE) |
| Column | HP-INNOWAX (Agilent: 19091N-213) |
| Inlet temperature | 260° C. |
| Detector temperature | 260° C. |
| | Injection parameter |
| Split ratio | 1/20 |
| Carrier gas | Helium 1.0 ml/min |
| | Oven heating conditions |
| 60° C. | 1 min |
| Heat at 25° C./min to 260° C. | |
| 260° C. | 1 min |

Yeast Metabolome Analysis by CE-TOFMS
<Pre-Treatment>

Cells were cultured (30 degrees C.) in an SD-His, Leu, Ura, Trp medium and then sampling was performed so that the amount of the sample was 15 OD unit. Suction filtration of the resultant was immediately performed by filtration. Next, suction filtration was performed twice with 10 mL of Milli-Q water and then washing was performed. Yeast cells collected on the filter were immersed in 2 mL of methanol containing internal reference material (5 μM) and then 1.6 mL of the resultant was transferred into a centrifugation tube. 1600 μL of chloroform and 640 μL of Milli-Q water were added to the tube and then it was stirred, followed by centrifugation (2,300×g, 4 degrees C., 5 minutes). After centrifugation, aqueous phase was transferred to 6 ultrafiltration tubes (250 μL each) (MILLIPORE, Ultrafree MC UFC3 LCC Centrifugal Filter Unit 5 KDa). The tubes were centrifuged (9,100×g, 4 degrees C., 120 minutes) and thus ultrafiltration was performed. Each filtered fluid was solidified to dryness, dissolved again in 50 μL of Milli-Q water, and then subjected to measurement.

<Measurement>

In this test, anionic metabolite (anion mode) measurement was performed under the following conditions (see references 1) to 3)).
Apparatus: Agilent CE-TOFMS system (Agilent Technologies)
Capillary: Fused silica capillary i.d. 50 μm×80 cm
Measurement conditions:
Run buffer: Anion Buffer Solution (p/n: H3302-1021)
Rinse buffer: Anion Buffer Solution (p/n: H3302-1022)
Sample injection: Pressure injection 50 mbar, 25 sec
CE voltage: Positive, 30 kV
MS ionization: ESI Negative
MS capillary voltage: 3,500 V
MS scan range: m/z 50-1,000
Sheath liquid: HMT Sheath Liquid (p/n: H3301-1020)

REFERENCES, DATA

1) T. Soga, D. N. Heiger: Amino acid analysis by capillary electrophoresis electrospray ionization mass spectrometry. Anal. Chem. 72: 1236-1241, 2000.
2) T. Soga, Y. Ueno, H. Naraoka, Y. Ohashi, M. Tomita et al.: Simultaneous determination of anionic intermediates for *Bacillus subtilis* metabolic pathways by capillary electrophoresis electrospray ionization mass spectrometry. Anal. Chem. 74: 2233-2239, 2002.
3) T. Soga, Y. Ohashi, Y. Ueno, H. Naraoka, M. Tomita et al.: Quantitative metabolome analysis using capillary electrophoresis mass spectrometry. J. Proteome Res. 2: 488-494, 2003.
4) http://vanted.ipk-gatersleben.de/

[Results]
Acetic Acid Production Test

Figure 11:
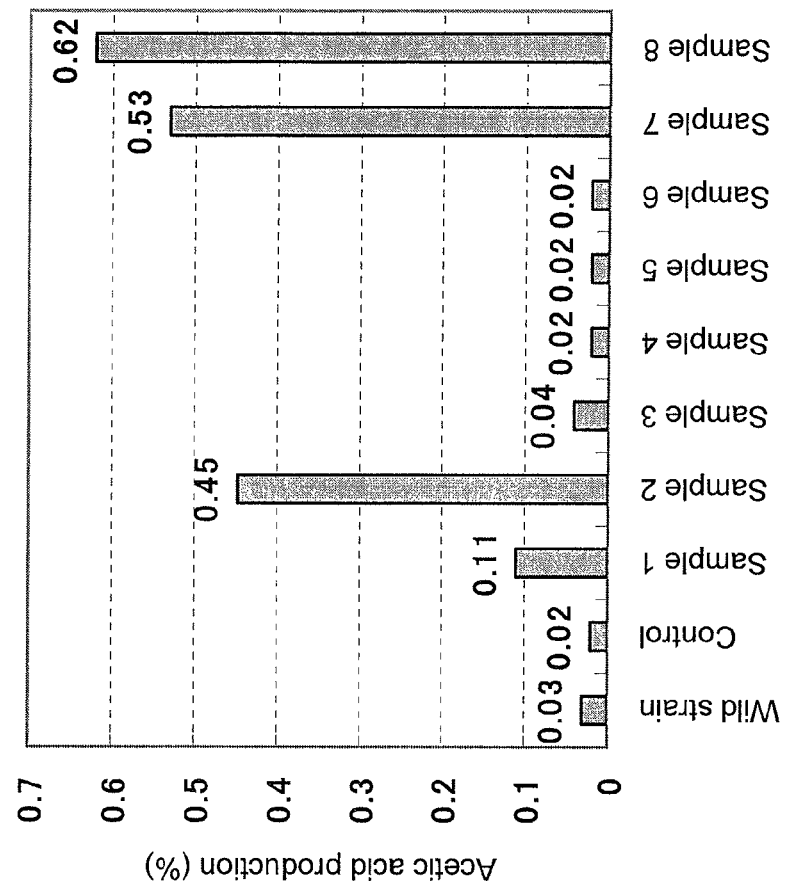
FIG. 11 is a characteristic diagram showing the results of an acetic acid production test.

Yeast strains subjected to the acetic acid production test are listed in Table 7 and the test results are shown in FIG. 11.

TABLE 7

| | Composition | | | | | | | | |
|---|---|---|---|---|---|---|---|---|---|
| Wild-type strain (YPH499) | PFK1 (Disrupted) | PFK2 (Disrupted) | ZWF1 (Enhanced) | RPE1 (Enhanced) | PKT(1) (Introduced) | PKT(2) (Introduced) | PKT(3) (Introduced) | PKT(4) (Introduced) | PKT(5) (Introduced) |
| Control | ○ | | ○ | ○ | | | | | |
| Sample 1 | ○ | | | | ○ | | | | |
| Sample 2 | ○ | | ○ | ○ | ○ | | | | |
| Sample 3 | ○ | | ○ | ○ | | ○ | | | |
| Sample 4 | ○ | | ○ | ○ | | | ○ | | |
| Sample 5 | ○ | | ○ | ○ | | | | ○ | |
| Sample 6 | ○ | | ○ | ○ | | | | | ○ |
| Sample 7 | ○ | ○ | | | ○ | | | | |
| Sample 8 | ○ | ○ | ○ | ○ | | | | | |

In Table 7, PKT(1) denotes a *Bifidobacterium animalis* sub sp. *lactis*-derived phosphoketolase gene, PKT(2) denotes an *Aspergillus oryzae* RIB40-derived phosphoketolase I gene, PKT(3) denotes an *Aspergillus oryzae* RIB40-derived phosphoketolase II gene, PKT(4) denotes a *Nostoc punctiforme* ATCC 29133-derived phosphoketolase gene, and PKT(5) denotes a *Marinobacter aquaeolei* ATCC 700491-derived phosphoketolase gene.

Based on the results shown in FIG. 11, it was revealed that attenuation of an endogenous phosphofructokinase gene of yeast as a host and introduction of a phosphoketolase gene into the yeast can enhance the flux toward the pentose phosphate system rather than toward the glycolytic system (FIG. 2), so that acetic acid can be produced at a high level. It was also revealed that as a phosphoketolase gene, the *Bifidobacterium*-derived gene, and particularly the *Bifidobacterium animalis*-derived gene, is excellent in acetic acid productivity. It was revealed based on the results that as phosphoketolase genes, phosphoketolase genes within the broken-line frame in the phylogenetic tree shown in FIG. 3 are preferable in terms of acetic acid productivity.

Furthermore, it was revealed based on the results shown in FIG. 11 that when a phosphofructokinase gene is attenuated to weaken the flux toward the glycolytic system, both the PFK1 gene and the PFK2 gene are preferably disrupted. Moreover, it was revealed that through enhancement of enzyme genes involved in the pentose phosphate system (FIG. 2), the flux toward the pentose phosphate system (FIG. 2) can be further enhanced and acetic acid can be produced at an even higher level.

Ethyl Acetate Production Test

Figure 12:
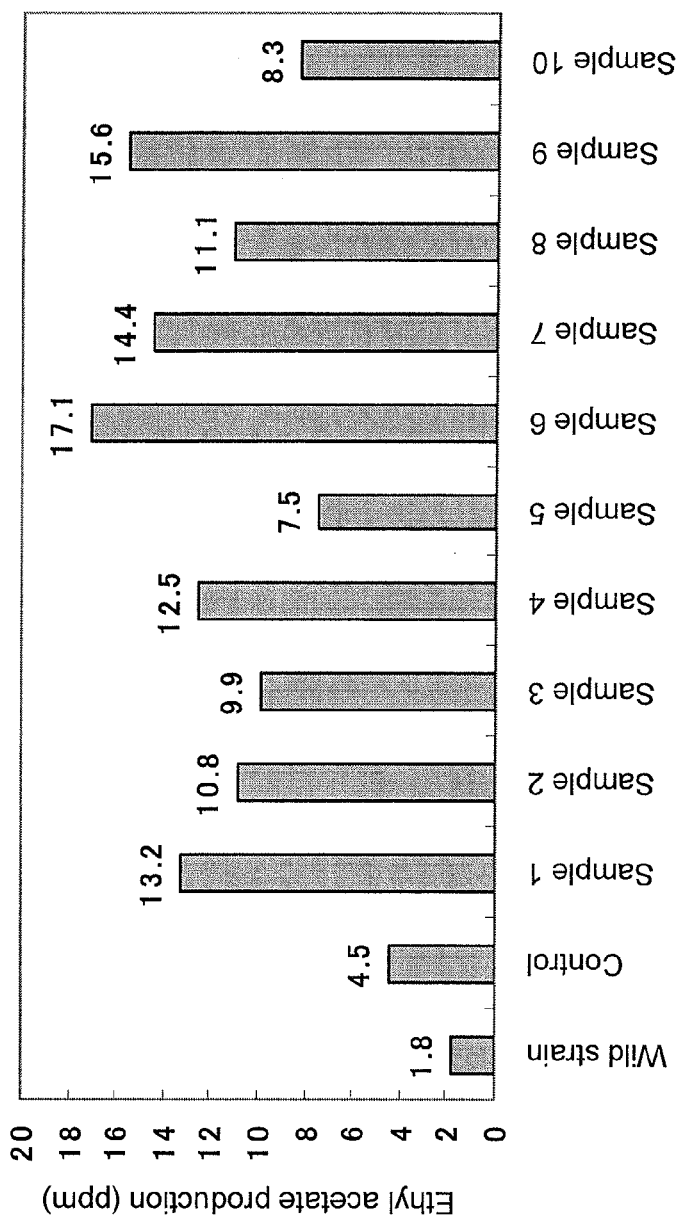
FIG. 12 is a characteristic diagram showing the results of an ethyl acetate production test.

Yeast strains subjected to the ethyl acetate production test are listed in Table 8 and the test results are shown in FIG. 12.

TABLE 8

| Wild-type strain (YPH499) | Composition | | | | | | | | | |
|---|---|---|---|---|---|---|---|---|---|---|
| | PFK1 (Disrupted) | ZWF1 (Enhanced) | RPE1 (Enhanced) | PKT (Introduced) | PTA(1) (Introduced) | PTA(2) (Introduced) | PTA(3) (Introduced) | ACS1 (Enhanced) | ACS2 (Enhanced) | ATF1 (Enhanced) |
| Control | | | | | | | | | | ○ |
| Sample 1 | ○ | | | ○ | ○ | | | | | ○ |
| Sample 2 | ○ | | | ○ | | ○ | | | | ○ |
| Sample 3 | ○ | | | ○ | | | ○ | | | ○ |
| Sample 4 | ○ | | | ○ | | | | ○ | | ○ |
| Sample 5 | ○ | | | ○ | | | | | ○ | ○ |
| Sample 6 | ○ | ○ | ○ | ○ | ○ | | | | | ○ |
| Sample 7 | ○ | ○ | ○ | ○ | | ○ | | | | ○ |
| Sample 8 | ○ | ○ | ○ | ○ | | | ○ | | | ○ |
| Sample 9 | ○ | ○ | ○ | ○ | | | | ○ | | ○ |
| Sample 10 | ○ | ○ | ○ | ○ | | | | | ○ | ○ |

In Table 8, PTA(1) denotes a *Bacillus subtilis* sub sp. *subtilis* str.168-derived phosphate acetyltransferase gene, PTA(2) denotes a *Bifidobacterium animalis* sub sp. *lactis* AD011-derived phosphate acetyltransferase gene, and PTA(3) denotes an *Escherichia coli* K-12 MG1655-derived phosphate acetyltransferase gene. In addition, in this test, a *Bifidobacterium animalis* sub sp. *lactis*-derived phosphoketolase gene was used as a PKT gene.

As shown in FIG. 12, the control strain in which the ATF1 gene had been introduced into the wild-type strain (YPH499 strain) also exhibited more improved ethyl acetate productivity compared with that of the wild-type strain. However, it was understood that through attenuation of an endogenous phosphofructokinase gene of yeast as a host and introduction of a phosphoketolase gene into the host, in addition to further introduction of a phosphoacetyltransferase gene (PTA gene) or enhancement of an acetyl-CoA synthetase gene (ACS gene), ethyl acetate productivity was further improved compared with that of the control. It was demonstrated based on the results and the metabolic overview map shown in FIG. 4 that the amount of acetyl-CoA synthesized was significantly increased through attenuation of the endogenous phosphofructokinase gene and introduction of the phosphoketolase gene in addition to further introduction of the phosphoacetyltransferase gene (PTA gene) or enhancement of the acetyl-CoA synthetase gene (ACS gene). Moreover, it was demonstrated that the thus synthesized acetyl-CoA is accumulated extracellularly at a high level in the form of ethyl acetate by an ATF1 enzyme.

In particular, as a phosphoacetyltransferase gene to be introduced, a *Bacillus subtilis*-derived gene is preferable in view of acetyl-CoA productivity. Also, it was revealed that as an acetyl-CoA synthetase gene to be enhanced, the ACS1 gene is more preferable than the ACS2 gene.

Furthermore, it was revealed based on the results shown in FIG. 12 that when a phosphofructokinase gene is attenuated to weaken the flux toward the glycolytic system, both the PFK1 gene and the PFK2 gene are preferably disrupted. Moreover, it was revealed that through enhancement of enzyme genes involved in the pentose phosphate system (FIG. 2), the flux toward the pentose phosphate system (FIG. 2) can be increased more and ethyl acetate can be produced at an even higher level.

Isopropanol Production Test

Figure 13:
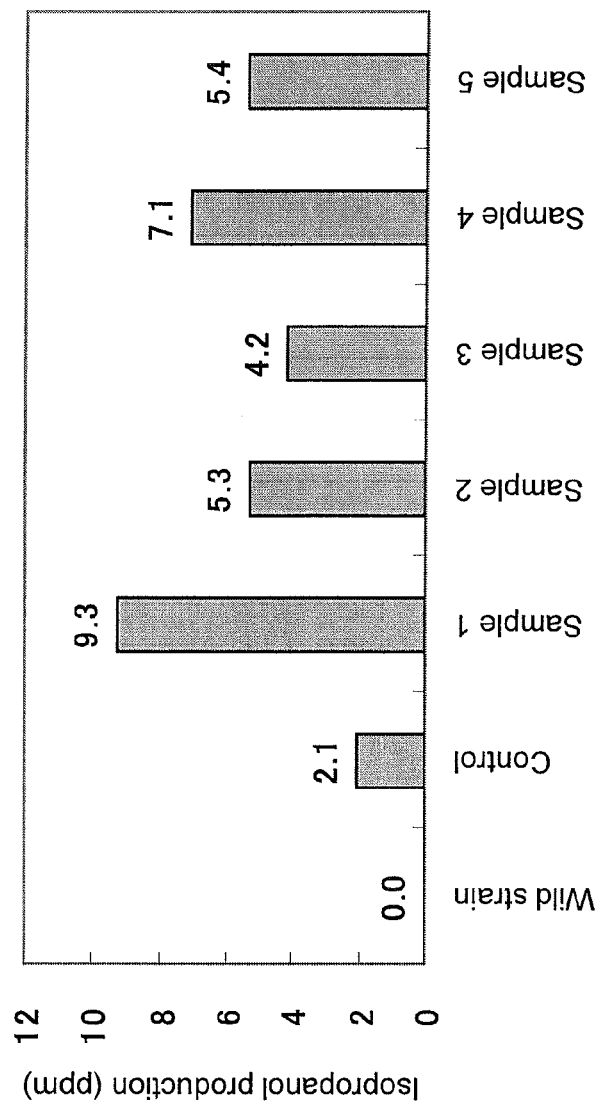
FIG. 13 is a characteristic diagram showing the results of an isopropanol production test.

Yeast strains subjected to the isopropanol production test are listed in Table 9 and the test results are shown in FIG. 13.

TABLE 9

| Wild-type strain (YPH499) | Composition | | | | | | | | | |
|---|---|---|---|---|---|---|---|---|---|---|
| | PFK1 (Disrupted) | ZWF1 (Enhanced) | RPE1 (Enhanced) | PKT (Introduced) | PTA(1) (Introduced) | PTA(2) (Introduced) | PTA(3) (Introduced) | ACS1 (Enhanced) | ACS2 (Enhanced) | ctfA, ctfB, adc, ipdh (Introduced) |
| Control | | | | | | | | | | ○ |
| Sample 1 | ○ | ○ | ○ | ○ | ○ | | | | | ○ |
| Sample 2 | ○ | ○ | ○ | ○ | | ○ | | | | ○ |
| Sample 3 | ○ | ○ | ○ | ○ | | | ○ | | | ○ |
| Sample 4 | ○ | ○ | ○ | ○ | | | | ○ | | ○ |
| Sample 5 | ○ | ○ | ○ | ○ | | | | | ○ | ○ |

In Table 9, PTA genes (1) to (3) denote the same genes as in Table 8.

As shown in FIG. 13, it was understood that the capacity to produce isopropanol can be imparted to yeast through introduction of a ctfA gene, a ctfB gene, an adc gene, and an ipdh gene into the wild-type strain (YPH499 strain). It was also understood that isopropanol productivity was significantly improved compared with that of the control through attenuation of the endogenous phosphofructokinase gene and introduction of the phosphoketolase gene, in addition to further introduction of the phosphoacetyltransferase gene (PTA gene) or enhancement of the acetyl-CoA synthetase gene (ACS gene).

It was demonstrated based on the results and the metabolic overview map shown in FIG. 4 that the amount of acetyl-CoA synthesized was significantly increased through attenuation of the endogenous phosphofructokinase gene and introduction of the phosphoketolase gene, in addition to further introduction of the phosphoacetyltransferase gene (PTA gene) or enhancement of the acetyl-CoA synthetase gene (ACS gene). It was demonstrated that the thus synthesized acetyl-CoA is accumulated extracellularly at a high level as isopropanol because of ctfA, ctfB, adc, and ipdh.

In particular, it was understood that as a phosphoacetyltransferase gene to be introduced, *Bacillus subtilis*-derived gene is preferable in view of acetyl-CoA productivity. Furthermore, it was revealed that as an acetyl-CoA synthetase gene to be enhanced, the ACS1 gene is more preferable than the ACS2 gene.

Metabolome Analysis of Yeast by CE-TOFMS

Figure 14:
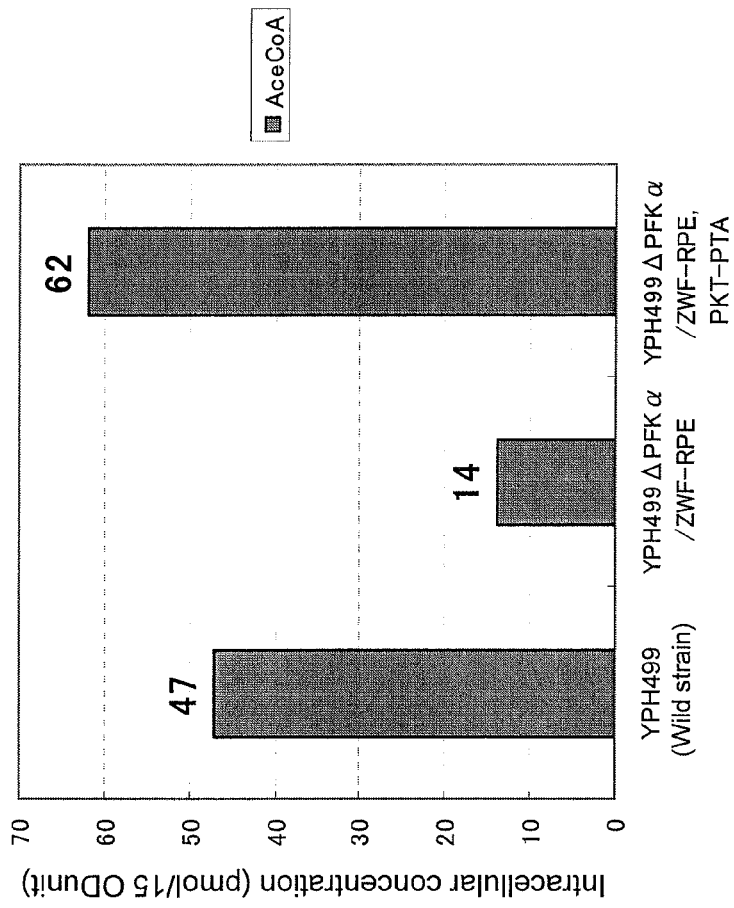
FIG. 14 is a characteristic diagram showing the results of conducting metabolome analysis of yeast by CE-TOFMS.

Metabolome analysis was conducted for: a wild-type strain (YPH499 strain); a strain (denoted as YPH499ΔPFKα/ZWF-RPE) prepared by attenuating an endogenous phosphofructokinase gene of the YPH499 strain and enhancing an enzyme gene involved in the pentose phosphate system (FIG. 2); and a strain (denoted as YPH499ΔPFKα/ZWF-RPE, PKT-PTA) prepared by attenuating the endogenous phosphofructokinase gene of the YPH499 strain, enhancing an enzyme gene involved in the pentose phosphate system (FIG. 2), and introducing a phosphoketolase gene and a phosphoacetyltransferase gene. FIG. 14 shows the results of the metabolome analysis.

In FIG. 14, the amount of acetyl-CoA in the case of the YPH499 strain (wild-type strain) is found by adding up the amount resulting from the ethanol-mediated acetyl-CoA synthetic pathway and the amount resulting from the intramitochondrial acetyl-CoA synthetic pathway. In addition, in yeast's acetyl-CoA synthetic pathway, these two pathways, the ethanol-mediated acetyl-CoA synthetic pathway and the intramitochondrial acetyl-CoA synthetic pathway, are present.

Meanwhile, in the case of the YPH499ΔPFKα/ZWF-RPE strain, the ethanol-mediated acetyl-CoA synthetic pathway becomes unfunctional. This is because NADP is consumed because of the presence of ZWF, and as a result, ALD2 catalyzing the reaction for conversion of aldehyde to acetic acid becomes unfunctional (see acetic acid productivity of the control strain in the acetic acid production test (FIG. 11)). Therefore, the amount of acetyl-CoA synthesized by the YPH499ΔPFKα/ZWF-RPE strain corresponds to the amount of acetyl-CoA generated via the intramitochondrial acetyl-CoA synthetic pathway. In addition, intramitochondrially synthesized acetyl-CoA is consumed within mitochondria, and thus it cannot be used as a raw material for substances such as ethyl acetate and isopropanol. Therefore, unless the amount of acetyl-CoA to be synthesized in the cytosol of yeast cells is increased, the amounts of substances to be synthesized using synthesized acetyl-CoA cannot be increased.

The YPH499ΔPFKα/ZWF-RPE, PKT-PTA strain is a mutant strain prepared by introducing the PKT gene and the PTA gene into the YPH499ΔPFKα/ZWF-RPE strain, so as to construct a novel acetyl-CoA synthetic pathway (see FIG. 2 and FIG. 4). Therefore, the amount of acetyl-CoA synthesized via the above novel acetyl-CoA synthetic pathway can be evaluated by subtracting the amount of acetyl-CoA synthesized by the YPH499ΔPFKα/ZWF-RPE strain from the amount of acetyl-CoA synthesized by the YPH499ΔPFKα/ZWF-RPE, PKT-PTA strain. Specifically, it was concluded from the results shown in FIG. 14 that the amount of acetyl-CoA corresponding to 48 pmol (found by 62−14=48 pmol) could be synthesized via the novel acetyl-CoA synthetic pathway.

REFERENCE EXAMPLE

In the reference example, preparation of the isopropanol-producing yeast (#15-10) used in the above examples is described.

Obtainment of Isopropanol Synthetic Gene

The following 4 genes were cloned from the genome of *Clostridium acetobutylicum* ATCC824 strain to a pT7Blue vector.

adc (Acetoacetic acid decarboxylase)
ctfA (Butyrate-acetoacetate CoA-transferase subunit A)
ctfB (Butyrate-acetoacetate CoA-transferase subunit B)
thiA (Acetyl-CoA acetyltransferase)

Construction of pT7Blue-ADC

PCR was performed under the following conditions.
Primers

```
adc-F:
                                       (SEQ ID NO: 79)
5'-ATGTTAAAGGATGAAGTAATTAAACAAATTAG-3' adc-R:
                                       (SEQ ID NO: 80)
5'-TTACTTAAGATAATCATATATAACTTCAGCTC-3'
```

Reaction Conditions
Template: 0.4 µg of Clostridium genomic DNA
Primer: 50 pmol primer DNA
Reaction solution: 50 µl of the solution containing 1×Pfu Ultra II reaction buffer (Stratagene), 10 nmol dNTP, and 1 µl of Pfu Ultra II fusion HS DNA polymerase (Stratagene)
Reaction: 95 degrees C. (5 minutes)-(95 degrees C. (30 seconds), 60 degrees C. (30 seconds), 72 degrees C. (2 minutes))×30 cycles-72 degrees C. (3 minutes)-4 degrees C. (stock)

The thus amplified 735-bp fragment was blunt-end cloned to a pT7Blue vector using a Perfectly Blunt Cloning Kit (Novagen). The cloned sequence was sequenced, thereby confirming that it was the adc sequence (CA-P0165) of the *Clostridium acetobutylicum* ATCC824 strain. The thus obtained plasmid was designated as pT7Blue-ADC.

Construction of pT7Blue-CTFA

PCR was performed under the following conditions.
Primers

```
ctfA-F:
                                       (SEQ ID NO: 81)
5'-ATGAACTCTAAAATAATTAGATTTGAAAATTTAAGG-3' ctfA-R:
                                       (SEQ ID NO: 82)
5'-TTATGCAGGCTCCTTTACTATATAATTTA-3'
```

Reaction Conditions
Template: 0.4 µg of *Clostridium* genomic DNA
Primer: 50 pmol primer DNA
Reaction solution: 50 µl of the solution containing 1×Pfu Ultra II reaction buffer (Stratagene), 10 nmol dNTP, and 1 µl of Pfu Ultra II fusion HS DNA polymerase (Stratagene)
Reaction: 95 degrees C. (5 minutes)-(95 degrees C. (30 seconds), 60 degrees C. (30 seconds), 72 degrees C. (2 minutes)×30 cycles-72 degrees C. (3 minutes)-4 degrees C. (stock)

The thus amplified 657-bp fragment was cloned to a Perfectly Blunt Cloning Kit (Novagen) in a similar manner. The cloned sequence was sequenced, thereby confirming that it was the ctfA sequence (CA-P0163) of the *Clostridium acetobutylicum* ATCC824 strain. The thus obtained plasmid was designated as pT7Blue-CTFA.

Construction of pT7Blue-CTFB

PCR was performed under the following conditions.
Primers ctfB-F:
(SEQ ID NO: 83)
5'-ATGATTAATGATAAAAACCTAGCGAAAG-3' ctfB-R:
(SEQ ID NO: 84)
5'-CTAAACAGCCATGGGTCTAAGTTC-3'

Reaction Conditions
Template: 0.4 μg of *Clostridium* genomic DNA
Primer: 50 pmol primer DNA
Reaction solution: 50 μl of the solution containing 1× Pfu Ultra II reaction buffer (Stratagene), 10 nmol dNTP, and 1 μl of Pfu Ultra II fusion HS DNA polymerase (Stratagene)
Reaction: 95 degrees C. (5 minutes)-(95 degrees C. (30 seconds), 60 degrees C. (30 seconds), 72 degrees C. (2 minutes))×30 cycles-72 degrees C. (3 minutes)-4 degrees C. (stock)

The thus amplified 666-bp fragment was cloned using a Perfectly Blunt Cloning Kit (Novagen). The cloned sequence was sequenced, thereby confirming that it was the ctfB sequence (CA-P0164) of the *Clostridium acetobutylicum* ATCC824 strain. The thus obtained plasmid was designated as pT7Blue-CTFB.

Construction of pDI626PGKpro

PCR was performed under the following conditions.
Primers

SacI-Ppgk1 FW:
(SEQ ID NO: 85)
5'-TAGGGAGCTCCAAGAATTACTCGTGAGTAAGG-3'

SacII-Ppgk1 RV:
(SEQ ID NO: 86)
5'-ATAACCGCGGTGTTTTATATTTGTTGTAAAAAGTAG-3'

Reaction Conditions
Template: 0.4 μg of yeast YPH499 genomic DNA
Primer: 50 pmol primer DNA
Reaction solution: 50 μl of the solution containing 1× Pfu Ultra II reaction buffer (Stratagene), 10 nmol dNTP, and 1 μl of Pfu Ultra II fusion HS DNA polymerase (Stratagene)
Reaction: 95 degrees C. (5 minutes)-(95 degrees C. (30 seconds), 55 degrees C. (30 seconds), 72 degrees C. (2 minutes))×25 cycles-72 degrees C. (3 minutes)-4 degrees C. (stock)

After purification of the reaction solution using a MinElute PCR purification kit (QIAGEN), the resultant was digested with restriction enzymes Sac I and Sac II. Agarose gel electrophoresis was performed to excise a 712-bp fragment, and then it was purified using a MinElute Gel extraction kit (QIAGEN). The resultant was ligated to a pDI626GAP (APP. Env. Micro., 2009, 5536) vector digested with restriction enzymes Sac I and Sac II in a similar manner. The thus obtained sequence was seqeunced, thereby confirming that a plasmid of interest had been constructed. The thus obtained plasmid was designated as pDI626PGKpro.

Construction of pDI626PGK

PCR was performed under the following conditions.
Primers

SalI-Tpgk1 FW:
(SEQ ID NO: 87)
5'-TTAAGTCGACATTGAATTGAATTGAAATCGATAGATC-3'

KpnI-Tpgk1 RV2:
(SEQ ID NO: 88)
5'-TTAAGGTACCGCTTCAAGCTTACACAACAC-3'

Reaction Conditions
Template: 0.4 μg of the genomic DNA of yeast YPH499
Primer: 50 pmol primer DNA
Reaction solution: 50 μl of the solution containing 1× Pfu Ultra II reaction buffer (Stratagene), 10 nmol dNTP, and 1 μl of Pfu Ultra II fusion HS DNA polymerase (Stratagene)
Reaction: 95 degrees C. (5 minutes)-(95 degrees C. (30 seconds), 55 degrees C. (30 seconds), 72 degrees C. (2 minutes))×25 cycles-72 degrees C. (3 minutes)-4 degrees C. (stock)

After purification of the reaction solution using a MinElute PCR purification kit (QIAGEN), the resultant was digested with restriction enzymes Sal I and Kpn I. Agarose gel electrophoresis was performed to excise a 330-bp fragment, and then it was purified using a MinElute Gel extraction kit (QIAGEN). The resultant was ligated to a pDI626PGKpro vector digested with restriction enzymes Sal I and Kpn I. The thus obtained sequence was sequenced, thereby confirming that a plasmid of interest had been constructed. The thus obtained plasmid was designated as pDI626PGK.

Construction of pDI626PGK-T pDI626PGK was digested with a restriction enzyme Sbf I, and then the reaction solution was purified using a MinElute PCR purification kit (QIAGEN). Subsequently, the resultant was blunt-ended using a Blunting kit (TaKaRaBIO), and then further digested with a restriction enzyme Kpn I. Agarose gel electrophoresis was performed to excise a 3650-bp fragment, and then it was purified using a MinElute Gel extraction kit (QIAGEN). Thus a vector for ligation thereof was constructed. Next, pRS524GAP (APP. Env. Micro., 2009, 5536) was digested with restriction enzymes PmaC I and Kpn I. Agarose gel electrophoresis was performed to excise a 765-bp fragment and then it was purified using a MinElute Gel extraction kit (QIAGEN), so as to prepare an insert. Ligation thereof was performed. Joints of the thus obtained sequence were sequenced, thereby confirming that a plasmid of interest had been constructed. The thus obtained plasmid was designated as pDI626PGK-T.

Construction of pCR2.1-iPDH

A DNA sequence optimized for *Saccharomyces cerevisiae* codons based on the *Clostridium beijerinckii* NRRL B593-derived adh: NADP-dependent alcohol dehydrogenase gene sequence registered in the GenBank (http://www.neb.nih.gov/Genbank/index.html) was synthesized (Operon). A vector portion is pCR2.1 (Invitrogen). In addition, the synthesized DNA sequence is shown in SEQ ID NO: 89, and the amino acid sequence encoded by a coding region contained in the synthesized DNA sequence is shown in SEQ ID NO: 90. The plasmid was designated as pCR2.1-iPDH.

Construction of pDI626PGK-T-iPDH pCR2.1-iPDH was digested with restriction enzymes Sac II and Sal I to excise a 1080-bp fragment. The resultant was ligated to a pDI626PGK-T vector digested with restriction enzymes Sac II and Sal I in a similar manner. The obtained sequence was sequenced, thereby confirming that a plasmid of interest had been constructed. The thus obtained plasmid was designated as pDI626PGK-T-iPDH.

Construction of pENT-ADC

PCR was performed using pDI626-ADC as a template and the following primers.

Primers

```
08-189-adc-attB1-Fw:
                                      (SEQ ID NO: 91)
5'-GGGGACAAGTTTGTACAAAAAAGCAGGCTCAGTTCGAGTTTATCAT
TATC-3'

08-189-adc-attB4-Rv:
                                      (SEQ ID NO: 92)
5'-GGGGACAACTTTGTATAGAAAAGTTGGGTGGGCCGCAAATTAAAGC
CTTC-3'
```

The thus obtained 1809-bp PCR product was introduced into a pDONR221 P1-P4 donor vector by gateway BP reaction. The obtained clone was sequenced, thereby confirming that no mutation was present in any part of the nucleotide sequence of the insert. The thus obtained plasmid was designated as pENT-ADC.

Construction of pENT-CTFA

PCR was performed using pDI626PGK-CTFA as a template and the following primers.

```
08-189-ctfA-attB4r-Fw:
                                      (SEQ ID NO: 93)
5'-GGGGACAACTTTTCTATACAAAGTTGGCTTCAAGCTTACACAACAC
GG-3'

08-189-ctfA-attB3r-Rv:
                                      (SEQ ID NO: 94)
5'-GGGGACAACTTTATTATACAAAGTTGTCAAGAATTACTCGTGAGTA
AGG-3'
```

The obtained 1823-bp PCR product was introduced into a pDONR221 P4r-P3r donor vector by gateway BP reaction. The obtained clone was sequenced, thereby confirming that no mutation site was present in any part of the nucleotide sequence of the insert. The thus obtained plasmid was designated as pENT-CTFA.

Construction of pDI626-CTFB pT7Blue-CTFB was digested with restriction enzymes BamH I and Sal I to excise a 771-bp fragment. The resultant was ligated to a pDI626 vector digested with restriction enzymes BamH I and Sal I in a similar manner. The obtained sequence was sequenced, thereby confirming that a plasmid of interest had been constructed. The thus obtained plasmid was designated as pDI626-CTFB(+A).

PCR was performed under the following conditions using the following primers in order to correct mutation sites in primers.

```
BamHI-ctfB-F:
                                      (SEQ ID NO: 95)
5'-TAGTGGATCCGATGATTAATGATAAAAACC-3' pDI626MCS-seqF:
                                      (SEQ ID NO: 96)
5'-CCTAGACTTCAGGTTGTCTAAC-3'
```

Reaction Conditions
Template: 1 ng of pDI626-CTFB(+A)
Primer: 50 pmol primer DNA
Reaction solution: 50 μl of the solution containing 1× Pfu Ultra II reaction buffer (Stratagene), 10 nmol dNTP, and 1 μl of Pfu Ultra II fusion HS DNA polymerase (Stratagene)

Reaction: 95 degrees C. (2 minutes)-(95 degrees C. (30 seconds), 55 degrees C. (30 seconds), 72 degrees C. (1 minutes)× 20 cycles-72 degrees C. (3 minutes)-4 degrees C. (stock)

After purification of the reaction solution using a MinElute PCR purification kit (QIAGEN), the resultant was digested with restriction enzymes BamH I and Sal I. Agarose gel electrophoresis was performed to excise a 702-bp fragment and then it was purified using a MinElute Gel extraction kit (QIAGEN). The resultant was ligated to a pDI626 vector digested with restriction enzymes BamH I and Sal I. The thus obtained sequence was sequenced, thereby confirming that mutation sites had been corrected. The thus obtained plasmid was designated as pDI626-CTFB.

Construction of pENT-CTFB

PCR was performed using pDI626-CTFB as a template and the following primers.

```
08-189-ctfB-attB3-Fw:
                                      (SEQ ID NO: 97)
5'-GGGGACAACTTTGTATAATAAAGTTGGGCCGCAAATTAAAGCCTT
C-3'

08-189-ctfB-attB2-Rv:
                                      (SEQ ID NO: 98)
5'-GGGGACCACTTTGTACAAGAAAGCTGGGTACAGTTCGAGTTTATC
ATTATC-3'
```

The thus obtained 1737-bp PCR product was introduced into a pDONR221 P3-P2 donor vector by gateway BP reaction. The obtained clone was sequenced, thereby confirming that no mutation site was present in any part of the nucleotide sequence of the insert. The thus obtained plasmid was designated as pENT-CTFB.

Construction of pDEST626(2008)

PCR was performed under the following conditions.

Primers

```
SacI-convA-F:
                                      (SEQ ID NO: 99)
5'-TAGGGAGCTCATCACAAGTTTGTACAAAAAAGCTG-3'

KpnI-convA-R:
                                      (SEQ ID NO: 100)
5'-TTAAGGTACCATCACCACTTTGTACAAGAAAGC-3'
```

Reaction Conditions
Template: 0.5 ng of RfA (Invitrogen; Reading Frame Cassette A of Gateway Vector Conversion System)
Primer: 50 pmol primer DNA
Reaction solution: 50 μl of the solution containing 1× Pfu Ultra II reaction buffer (Stratagene), 10 nmol dNTP, and 1 μl Pfu Ultra II fusion HS DNA polymerase (Stratagene)
Reaction: 95 degrees C. (2 minutes)-(95 degrees C. (30 seconds), 55 degrees C. (30 seconds), 72 degrees C. (1 minute and 30 seconds)×20 cycles-72 degrees C. (3 minutes)-4 degrees C. (stock)

After purification of the reaction solution using a MinElute PCR purification kit (QIAGEN), the resultant was digested with restriction enzymes Sac I and Kpn I. Agarose gel electrophoresis was performed to excise a 1717-bp fragment. After purification using a MinElute Gel extraction kit (QIAGEN), the resultant was ligated to the pDI626GAP vector (APP. Env. Micro., 2009, 5536) digested with restriction enzymes Sac I and Kpn I. The obtained sequence was sequenced, thereby confirming that a plasmid of interest had been constructed.

Construction of pEXP(Ura)-ADC-CTFA-CTFB

The 3 obtained entry clones (pENT-ADC, pENT-CTFA, and pENT-CTFB) were incorporated into a pDEST626

(2008) expression vector by Gateway LR reaction. The thus obtained clones were confirmed by PCR for insert size, thereby confirming correct recombination. Sequencing was performed, thereby confirming that no error was present in the sequence. The thus obtained plasmid was designated as pEXP(Ura)-ADC-CTFA-CTFB.

Preparation of #3-17 Strain

The pEXP(Ura)-ADC-CTFA-CTFB expression vector was cleaved and linearized with restriction enzymes Aat II and BssH II. After ethanol precipitation, the resultant was dissolved in 0.1× TE Buffer and then *Saccharomyces cerevisiae* YPH499 (Stratagene) was transformed using a Frozen EZ yeast transformation kit (Zymoresearch). The obtained clones were subjected to colony PCR, thereby confirming 25 clones into which adc, ctfA, and ctfB genes had been introduced. The strain with the highest acetone production amount was designated as #3-17.

Preparation of #15-10 Strain

The pDI626PGK-T-iPDH expression vector of the ipdh gene that was a synthetic gene expected to convert acetone to isopropanol was cleaved and linearized with restriction enzymes Aat II and BssH II. After ethanol precipitation, the resultant was dissolved in 0.1× TE Buffer, and then the #3-17 acetone-producing yeast was transformed using a Frozen EZ yeast transformation kit (Zymoresearch). The thus obtained 14 clones were subjected to colony PCR, thereby confirming 13 clones in which the ipdh gene had been introduced. The strain with the highest isopropanol production amount was designated as #15-10.

The invention claimed is:

1. A recombinant, non-xylose fermenting *Saccharomyces cerevisiae*, which comprises an attenuated phosphofructokinase gene endogenous to said *Saccharomyces cerevisiae* and an introduced phosphoketolase gene, wherein the expression of a *Saccharomyces cerevisiae* glucose-6-phosphate dehydrogenase gene and/or a *Saccharomyces cerevisiae* D-ribulose-5-phosphate-3-epimerase gene is enhanced, wherein acetic acid production by said recombinant *Saccharomyces cerevisiae* is enhanced compared with the wild-type strain, and wherein said introduced phosphoketolase gene encodes the amino acid sequence of any one of SEQ ID NOs: 1-19.

2. A method for producing a substance selected from the group consisting of acetic acid, acetyl-CoA, and a substance made from acetyl-CoA, comprising a step of culturing the recombinant yeast of claim 1 in medium.

3. The method according to claim 2, wherein the substance is made from acetyl-CoA, and the substance is ethyl acetate or isopropanol.

* * * * *